US007785778B2

(12) United States Patent
Jörgensen et al.

(10) Patent No.: US 7,785,778 B2
(45) Date of Patent: Aug. 31, 2010

(54) PORCINE POLYMORPHISMS AND METHODS FOR DETECTING THEM

(75) Inventors: Claus Böttcher Jörgensen, Rahavevej 1 (DK); Susanna Cirera, Soborg (DK); Alan Archibald, Edinburgh (GB); Leif Andersson, Uppsala (SE); Merete Fredholm, Borgevej (DK); Inger Edfors-Lilia, Kalmar (SE)

(73) Assignee: University of Copenhagen, Copenhagen (DK)

( * ) Notice: Subject to any disclaimer, the term of this patent is extended or adjusted under 35 U.S.C. 154(b) by 858 days.

(21) Appl. No.: 10/536,184

(22) PCT Filed: Nov. 25, 2003

(86) PCT No.: PCT/DK03/00807

§ 371 (c)(1), (2), (4) Date: Dec. 7, 2005

(87) PCT Pub. No.: WO2004/048606

PCT Pub. Date: Jun. 10, 2004

(65) Prior Publication Data

US 2006/0275763 A1 Dec. 7, 2006

Related U.S. Application Data

(60) Provisional application No. 60/428,738, filed on Nov. 25, 2002.

(30) Foreign Application Priority Data

Nov. 25, 2002 (DK) ................................ 2002 01819

(51) Int. Cl.
C12Q 1/68 (2006.01)
C12P 19/34 (2006.01)
C07H 21/02 (2006.01)
(52) U.S. Cl. ........................ 435/6; 435/91.2; 536/23.1
(58) Field of Classification Search ....................... None
See application file for complete search history.

(56) References Cited

U.S. PATENT DOCUMENTS

| 4,136,167 A | 1/1979 | Parry et al. |
| 4,443,549 A | 4/1984 | Sadowski |
| 4,761,372 A | 8/1988 | Maas et al. |
| 6,355,859 B1 | 3/2002 | Bosworth et al. |
| 2001/0053519 A1* | 12/2001 | Fodor et al. ............... 435/6 |

FOREIGN PATENT DOCUMENTS

| EP | 0 060 129 A2 | 9/1982 |
| EP | 0 102 831 A1 | 3/1984 |
| EP | 1 291 424 A1 | 3/2003 |
| WO | WO 86/04604 | 8/1986 |
| WO | WO 94/13811 | 6/1994 |
| WO | WO 98/53101 | 11/1998 |
| WO | WO 00/58476 | 10/2000 |
| WO | WO 01 31006 A2 | 5/2001 |
| WO | WO 2004/043398 A2 | 5/2004 |
| WO | WO 2007/053480 A2 | 5/2007 |

OTHER PUBLICATIONS

Hacker U.T. et al 'Lack of association between an interleukin-1 receptor antagonist gene polymorphism and ulcerative colitis' Gut (1997) 40:623-627.*
Li H. et al. Asian-Aust. J. Anim. Sci. Apr. 2008, vol. 21, No. 4, pp. 489-493.*
Francis D.H. 'Enterotoxigenic *Escherichia coli* infection in pigs and its diagnosis' Journal of Swine Health and Production (2002) vol. 10, No. 4, pp. 171-175.*
Andersson, Leif. Nature Reviews (2001) vol. 2, p. 130-138.*
New England Biolabs catalogue, (Jan. 2000) p. 62.
Susan I. Anderson et al., "A large-fragment porcine genomic library resource in a BAC vector", Mammalian Genome, 11, 811-814, (2000).
Diane R. Baker et al., "Distribution of K88 *Escherichia coli*-adhesive and nonadhesive phenotypes among pigs of four breeds", Veterinary Microbiology 54 (1997), 123-132.
Claude Chevalet et al., "Regional assignment of genetic markers using a somatic cell hybrid panel: a WWW interactive program available for the pig genome", CABIOS, vol. 13, No. 1, 1997, pp. 69-73.
B.P. Chowdhary et al., "FISH on metaphase and interphase chromosomes demonstrates the physical order of the genes for GPI, CRC, and LIPE in pigs", Cytogenet Cell Genet 71: 175-178 (1995).
Francis S. Collins, "Positional cloning moves from perditional to traditional", Nature Genetics, vol. 9, Apr. 1995, pp. 347-350.
Inger EDFORS-LILIA et al., "Performance of Pigs With or Without the Intestinal Receptor for *Escherichia coli* K88", Anim. Prod. 1986, 42: pp. 381-387.
Brent Ewing et al., "Base-Calling of Automated Sequencer Traces Using *Phred*. I. Accuracy Assessment", Genome Research, Dec. 1997, pp. 175-185.
David H. Francis et al., "Expression of Mucin-Type Glycoprotein K88 Receptors Strongly Correlates with Piglet Susceptibility to K88+ Enterotoxigenic *Escherichia coli*, but Adhesion of This Bacterium to Brush Borders Does Not", Infection & Immunity, vol. 66, No. 9, Sep. 1998, pp. 4050-4055.
R.A. Gibbons et al., "Inheritance of Resistance to Neonatal *E. coli* Diarrhoea in the Pig: Examination of the Genetic System", Theor. Appl. Genet. 51, (1977), pp. 65-70.
Philippe A. Grange et al., "Characterization of the Carbohydrate Moiety of Intestinal Mucin-Type Sialoglycoprotein Receptors for the K88ac Fimbrial Adhesin of *Escherichia coli*", Infection & Immunity, vol. 66, No. 4, Apr. 1998, pp. 1613-1621.

(Continued)

Primary Examiner—Stephen Kapushoc
(74) Attorney, Agent, or Firm—Stephen A. Bent; Foley & Lardner LLP

(57) ABSTRACT

Identification of a pig as resistant or non-resistant to enterotoxigenic *E. Coli* (ETEC). Particularly, there is provided methods, probes and DNA molecules involved in identifying a pig as resistant or non-resistant to ETEC. There is also provided methods for breeding pigs using the information of resistance/non-resistance, mixed boar semen, and methods for developing drugs to compensate for non-resistance to ETEC.

10 Claims, 7 Drawing Sheets

OTHER PUBLICATIONS

Figure 1:
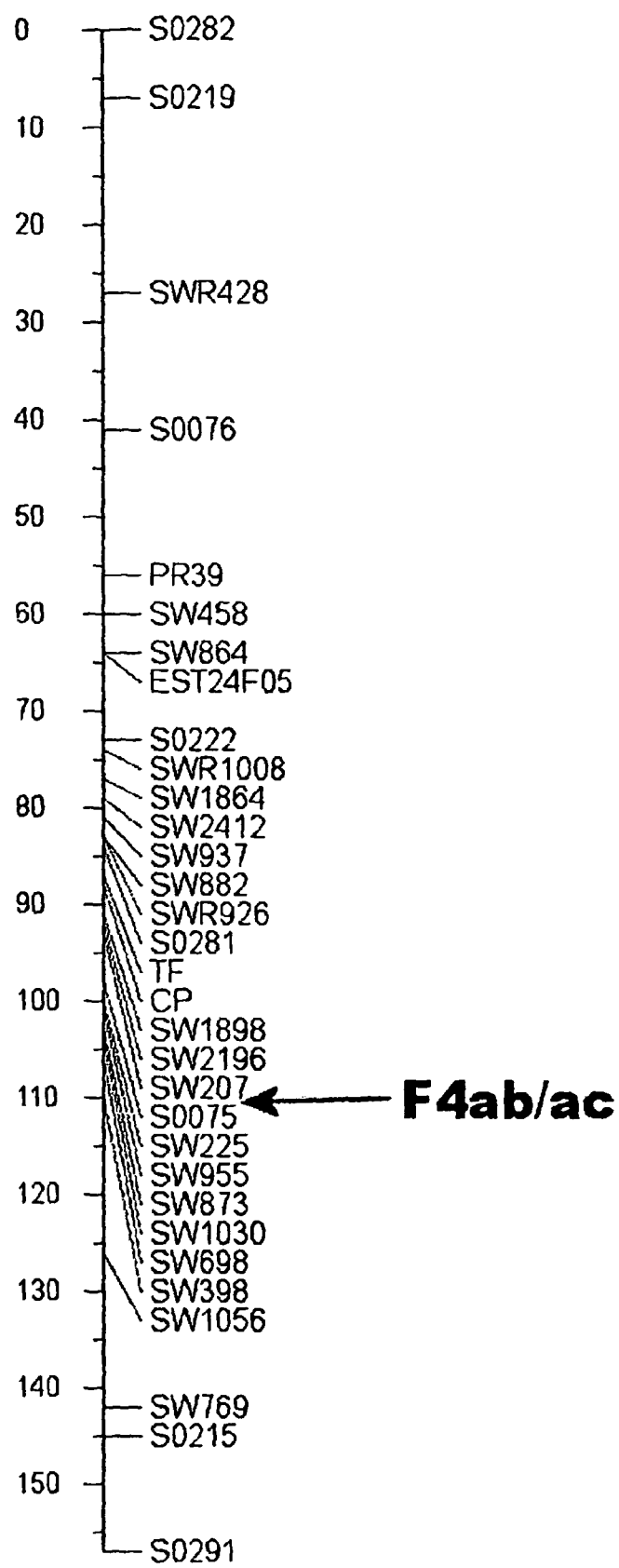

Philippe A. Grange et al., "Transferrin Associated with the Porcine Intestinal Mucosa Is a Receptor Specific for K88ab Fimbriae of *Escherichia coli*", Infection & Immunity, vol. 64, No. 2, Feb. 1996, pp. 606-610.

Phil Green et al., "Documentation for CRI-MAP, version 2.4", (Mar. 26, 1990).

David Gordon et al., "*Coned*: A Graphical Tool for Sequence Finishing", Genome Research, 1998, pp. 195-202.

G. Guérin et al., "Evidence for linkage between K88ab, K88ac intestinal receptors to *Escherichia coli* and transferrin loci in pigs", Animal Genetics, 1993, 24, pp. 393-396.

W. Mathias Howell et al., "Dynamic allele-specific hybridization", Nature Biotechnology, vol. 17, Jan. 1999, pp. 87-88.

E. Iannuccelli et al., "GEMMA: a database to manage and automate microsatellite genotyping", Animal Genetics 27 (Suppl 2), 1996, C002, p. 55.

G.M. Lathrop et al., "Multilocks Linkage Analysis in Humans: Detection of Linkage and Estimation of Recombination", Am. J. Hum. Genet. 37:482-498, 1985.

E. Meijerink et al., "Two α(1,2) fucosyltransferase genes on porcine Chromosome 6q11 are closely linked to the blood group inhibitor (S) and *Escherichia coli* F18 receptor (ECF18R) loci", Mammalian Genome 8, 736-741 (1997).

John W. Metcalfe et al., "Characterization and Identification of a Porcine Small Intestine Mucos Receptor for the K88ab Fimbrial Adhesin", Infection & Immunity, vol. 59, No. 1, Jan. 1991, pp. 91-96.

Denis Milan et al., "IMpRH Server: an RH mapping server available on the WEB" Bioinformatics Applications Note, vol. 16, No. 6, 2000, pp. 558-559.

Nicholas Moniaux et al., "Complete sequence of the human mucin MUC4: a putative cell membrane-associated mucin", Biochem. J. (1999), 338, pp. 325-333.

B. Ojeniyi et al., "Detection of Fimbrial and Toxin Genes in *Escherichia coli* and their Prevalence in Piglets with Diarrhoea. The Application of Colony Hybridization Assay, Polymerase Chain Reaction and Phenotypic Assays", J. Vet. Med. B 41, 49-59 (1994).

M. Van Poucke et al., "Comparative mapping between human chromosome 3 and porcine chromosome 13", Cytogenet Cell Genet. 85:279-284 (1999).

M. Van Poucke et al., "Integation of porcine chromosome 13 maps", Cytogenet Cell Genet 93: 297-303 (2001).

Gary A. Rohrer et al., "A Comprehensive Map of the Porcine Genome", Genome Research, 1996, pp. 371-391.

Steve Rozen et al., "Primer3 on the WWW for General Users and for Biologist Programmers", Methods in Molecular Biology, vol. 132, pp. 365-386, (2000).

R. Sellwood et al., "Adhesion of Enteropathogenic *Escherichia coli* to Pig Intestinal Brush Borders: The Existence of Two Pig Phenotypes", J. Med Microbiol., vol. 8 (1975), pp. 405-411.

H.-F.S. Sun et al., "Human chromosome 3 and pig chromosome 13 show complete synteny conservation but extensive gene-order differences", Cytogenet Cell Genet 85:273-278 (1999).

R.A. Wilson Ph.D. et al., "Fimbriae and enterotoxins associated with *Escherichia coli* serogroups isolated from pigs with colibacillosis", Am J Vet Res, vol. 47, No. 2, Feb. 1986, pp. 213-217.

A. K. Winterø et al., "Evaluation and characterization of a porcine small intestine cDNA library: analysis of 839 clones", Mammalian Genome 7, 509-517 (1996).

M. Yerle et al., "A somatic cell hybrid panel for pig regional gene mapping characterized by molecular cytogenetics", Cytogenet Cell Genet 73:194-202 (1996).

M. Yerle et al., "Construction of a whole-genome radiation hybrid panel for high-resolution gene mapping in pigs", Cytogenet Cell Genet 82:182-188 (1998).

I. Edfors-Lilja et al., "*Escherichia coli* and *Salmonella* Diarrhoea in Pigs", CAB International 2000, Breeding for Disease Resistance in Farm Animals, pp. 253-267.

Philippe Pinion et al., "Localization of 113 anchor loci in pigs: improvement of hte comparative map for humans, pigs & goats", Mammalian Genome 11, 306-315 (2000).

Zhongzhou Chen et al., "Structural Insights into Histone Demethylation by JMJD2 Family Members", Cell 125, May 19, 2006, 691-702.

Paul A.C. Cloos et al., "The putative oncogene GASC1 demethylates tri- and dimethylated lysine 9 on histone H3", Nature, Jul. 20, 2006, United Kingdom, vol. 442, No. 7100, pp. 307-311.

Steven G. Gray et al., "Functional Characterization of JMJD2A, a Histone Deacetylase- and Retinoblastoma-binding Protein", The Journal of Biological Chemistry, vol. 280, No. 31, Issue of Aug. 5, 2005, pp. 28507-28518.

Ying Huang et al., "Recognition of Histone H3 Lysine-4 Methylation by the Double Tudor Domain of JMJD2A", Science, vol. 312, May 5, 2006, pp. 748-751.

Masuko Katoh et al., "Identification and characterization of JMJD2 family genes in silica", International Journal of Oncology 24: 1623-1628, 2004.

Jeesun Kim et al., "Tudor, MBT and chromo domains gauge the degree of lysine methylation", EMBO reports vol. 7, No. 4, 2006, pp. 397-403.

Sarah C. Trewick et al., "Methylation: lost in hydroxylation?", EMBO reports, vol. 6, No. 4, 2005, pp. 315-320.

Yu-ichi Tsukada et al., "Histone demethylation by a family of JmjC domain-containing proteins", Nature, vol. 439, Feb. 16, 2006, pp. 811-816.

Johnathan R. Whetstine et al., "Reversal of Histone Lysine Trimethylation by the JMJD2 Family of Histone Demethylases", Cell 125, 467-481, May 5, 2006.

Zeng-Quan Yang et al., "Identification of a Novel Gene, GASC1, within an Amplicon at 9p23-24 Frequently Detected in Esophageal Cancer Cell Lines", Cancer Research 60, 4735-4739, Sep. 1, 2000.

C.B. Jorgensen et al., "Linkage and comparative mapping of the locus controlling susceptibility towards *E. coli* F4ab/ac diarrhea in pigs", Cytogenct Genome Res, vol. 102, 2003, pp. 157-162.

P. Python et al., "Fine-mapping of the intestinal receptor locus fo renterotoxigenic *Escherichia coli* F4ac on porcine chromosome 13", Animal Genetics, vol. 33, 2002, pp. 441-447.

I. Edfors-Liua et al., "The porcine intestinal receptor for *Escherichia coli* K88ab, K88ac: regional localization on chromosome 13 and influence of IgG response to the K88 antigen" Animal Genetics, vol. 26, 1995, pp. 237-242.

\* cited by examiner

```
AACTGTTGTGTCAGAGACTGAGCCACCTCCCCTTGGGAACCCACGTCC
CCATCCATCTCTGTCTTCCATCTTTGCCACTGACAGACGCTGCTGGTG
CCTTGGGTGAGAGGTTAATTCCAGCCAATCGAAAGTCAGGAAGGCAGAT
TTCAACCTTATATTTGGGTTCAGCTTCCCACTTTGCCACATCCCAGCTCT
GTGACTTTGGGCAATGACTTATCTATTTGTACCTCAGTTTCTGTATCTGT
AGAATGGGTAATAAAATAGATCCCTTCATGGGGTTGTGTAATATACAA
AATAATGCATACTGAGTGCTGGTATAATAAATGTTGGCTGTTATTGTTAA
GCTCTGAAAAGTCAAGTGAGTCAGTCGTCAGTGGAAGTCCTAGAAG
TCAAGGCTCTCGGGGATTATTATCACATGCACGGAGACCTTGATAGGAAAG
AGAACGGCAGAGTGAATAGGGGTCTTTTAATTTGAAACAGCAAGAAGTGG
```

Fig. 6

```
ACTGTTGTGTCAGAGACTGAGCCACCTCCCCTTGGGAACCCACGTCC
CATCCATCTCTGTTCTCCATCTTTGCCACTGACACAGACGCTGGTG
CTTGGGTGAGAGGTTAATTTCCAGCCAATCGAAAGTCAGGAAGGCAGAT
TCAACCTTATATTTGGGTTCAGCTTCCCACTTTGCCACATCCCAGCTCT
TGACTTTGGGCAATGACTTATCTATTTGTACCTCAGTTTCTGTATCTCT
GAATGGGTAATAAAATAGATCCCTTCATGGGGTTGTTGTTATTGTTAA
ATAATGCATACTGAGTGCTGGTATAATAAATGTTGGCTGTTATTGTTAA
CTCTGAAAAGTCAAGTGAGGTCAGCTACTGTCAGTGGAAGTCCTAGAAG
CAAGGCTCTGGGGATTATTATCACATGCACGGAGACCTTGATAGGAAAG
GAACGGCAGAGTGAATAGGGGTCTTTTAATTTGAAACAGCAAGAAGTGG
```

Fig. 7

PORCINE POLYMORPHISMS AND METHODS FOR DETECTING THEM

FIELD OF THE INVENTION

The present invention relates in its broadest aspect to identification of a pig as resistant or non-resistant to enterotoxigenic E. coli (ETEC). Particularly, there is provided methods, probes and DNA molecules involved in identifying a pig as resistant or non-resistant to ETEC. The present invention further relates to methods for breeding pigs using the information of resistance/non-resistance, mixed boar semen, and methods for developing drugs to compensate for non-resistance to ETEC.

TECHNICAL BACKGROUND AND PRIOR ART

In breeding of pigs a major problem is to keep the newborn, and in particular post weaning young pigs, disease-free. In that respect intestinal disorders are among the most widespread and serious problems, and swine breeding and production farms all over the world suffer sizeable losses of livestock each year from outbreak of these diseases. Further losses arise from the costs of medication, growth retardation and other consequences of the diseases, which may be more substantial than direct damage due to mortality.

It is known that the causative agents responsible for a significant number of the diarrhoeas in young pigs are enterotoxigenic strains of E. coli ETEC. Several ETEC have been isolated from infected animals and types of E. coli strains, such as E. coli F18, and E. coli F4 (formerly known as K88), are among the major lethal strains found in young pigs.

The designations F18 and F4 refer to fimbriae types of the ETEC and are used to distinguished the different strains. The adhesive fimbriae mediate the colonisation of E. coli in the intestine. Colonisation depends on the adherence of the bacteria to the enterocytes and subsequent proliferation and toxin production of the ETEC will cause the diarrhoea.

The disease develops after the ETECs are introduced into the intestinal tract of the piglets. The ETEC bacteria adhere to the wall of the small intestine through their surface protein antigens (fimbriae), multiply there in large numbers and transfer their toxins directly to the intestinal epithelial cells. Due to the effect exerted by the toxins, the fluid-absorbing activity of intestinal epithelial cells will cease and the cells will secrete a large volume of fluid into the intestinal lumen resulting in the development of more or less severe diarrhoeas.

In the art, efforts have been made in order to control diarrhoea in animals, such as pigs, caused by ETEC. U.S. Pat. No. 4,443,549 describes a method of producing monoclonal antibodies against adhesion of a pathogenic bacterium, which adhesion mediates attachment of the bacterium to mucocutaneous tissue. The antibodies may be used in a pharmaceutical composition suitable for oral administration to animals.

U.S. Pat. No. 4,761,372 discloses a plasmid comprising genes coding for an immunogenic, non-toxic, heat labile enterotoxin and/or a non-toxic, heat stable enterotoxin and an E. coli containing this plasmid for use as a live vaccine for vaccinating humans and animals against diarrheal diseases.

Additionally, WO 00/58476 describes a method of producing a live, orally applicable E. coli vaccine for the prevention of postweaning diarrhoea in pigs. An enterotoxin-free strain of E. coli which produces two adhesive fimbriae (F4 and F18) are administered to the young pigs in an attempt to provide local protection.

However, not all pigs succumb to E. coli infections. Susceptibility to adhesion, i.e. expression of receptors in pigs for binding of particular fimbriae, has been shown to be genetically controlled by the host. The mechanism for resistance appears to be that intestinal borders in resistant animals are not colonised by E. coli i.e., the bacteria do not adhere to the intestinal walls of resistant animals.

An attempt to detect E. coli resistance is reported in WO 98/53101. The application relates to a method for differentiating between pigs that are either resistant or susceptible to F18 E. coli related diseases. The differentiation is performed using a DNA test for DNA polymorphisms in the alpha (1,2) fucosyltransferase 1 (FUT1) gene on the porcine chromosome 6.

Enterotoxigenic Escherichia coli cells (ETEC) that expresses the F4ab or F4ac fimbriae (formerly know as K88ab and K88ac) are major causes of diarrhoea and death in neonatal and young pigs (Wilson and Francis, 1986). In Denmark, ETEC F4 is present in about 25% of the reported diarrhoea cases (Ojeniyi et al., 1994).

In 1975 Sellwood and co-workers published a paper describing the existence of two pig phenotypes in relation to ETEC F4, namely resistant pigs and susceptible pigs, respectively. In 1977, Gibbons et al. showed that ETEC F4ac resistance was inherited as an autosomal recessive Mendelian trait and linkage to the transferrin locus (TF) was suggested and later confirmed (Guérin et al. 1993). Linkage mapping of the porcine loci responsible for susceptibility towards ETEC F4ac and F4ab led to the hypothesis that a potential candidate gene was located on pig chromosome 13 (Edfors-Lilja et al., 1995), but no candidate gene was found or suggested. This means that the only available diagnostic test for this type of ETEC F4 resistance is the adhesion test developed by Sellwood et al. in 1975. Since the adhesion test either demands major intestinal surgery or slaughter of the pig and the fact that it is very laborious makes it difficult to incorporate it into breeding programs.

The prerequisites that need to be fulfilled in order to incorporate a diagnostic test into a breeding program is that it needs to be quick, easy to use and allowing precise genotyping of live animals; however, so far no suitable method fulfils this need.

SUMMARY OF THE INVENTION

The present invention relates to the applications of newly discovered genetic. polymorphisms linked to resistance to E. coli and located in the region between and including the markers SW2196 and SW225 on the porcine chromosome (SSC) 13.

Some of the advantages of the present invention include ease of use, non-invasive testing and fast test result. Seen from a broader perspective the advantages of the various aspects of the present invention are e.g. an environmentally safer meat production with a reduced consumption of antibiotics, better economy of the meat production and healthier animals in the production.

Accordingly, in a first aspect the present invention pertains to an isolated nucleic acid (NA) molecule, comprising an allele of a genetic polymorphism linked to resistance to enterotoxigenic E. coli (ETEC), said genetic polymorphism being located in the region between and including the markers SW2196 and SW225 on the porcine chromosome 13.

Another aspect of the invention provides a NA probe, which comprises a NA sequence that is homologous to a fragment of the above NA molecule.

Yet another aspect of the present invention relates to a method for identifying if a pig is resistance to ETEC, the method comprising:
i) obtaining a sample from said pig, said sample comprising genetic material,
ii) determining by use of said sample if the pig is homozygous for an allele of a genetic polymorphism linked to resistance to ETEC, said genetic polymorphism being located in the region between and including the markers SW2196 and SW225 on the porcine chromosome 13, and
iii) identifying the pig as resistant to ETEC if the pig is homozygous for the allele of genetic polymorphism linked to resistance.

A further aspect of the present invention relates to the use of the isolated NA molecule and/or the NA probe, as a probe for detecting a porcine allele of a genetic polymorphism linked to resistant to ETEC.

Still another aspect of the present invention relates to the use of a pair of NA molecules for primers in a PCR-based method, said PCR-based method being used in a method for identifying whether a pig is resistant or non-resistant to ETEC, said pair of NA molecules being selected from the group consisting of SEQ ID NO: 18 and SEQ ID NO: 19, SEQ ID NO: 20 and SEQ ID NO: 21, SEQ ID NO: 22 and SEQ ID NO: 23, SEQ ID NO: 24 and SEQ ID NO: 25, SEQ ID NO: 26 and SEQ ID NO: 27, SEQ ID NO: 28 and SEQ ID NO: 29, SEQ ID NO: 30 and SEQ ID NO: 31, SEQ ID NO: 32 and SEQ ID NO: 33, SEQ ID NO: 34 and SEQ ID NO: 35, SEQ ID NO: 36 and SEQ ID NO: 37, SEQ ID NO: 38 and SEQ ID NO: 39, SEQ ID NO: 40 and SEQ ID NO: 41, SEQ ID NO: 42 and SEQ ID NO: 43, SEQ ID NO: 44 and SEQ ID NO: 45, SEQ ID NO: 46 and SEQ ID NO: 47, SEQ ID NO: 48 and SEQ ID NO: 49, SEQ ID NO: 50 and SEQ ID NO: 51, SEQ ID NO: 52 and SEQ ID NO: 53, SEQ ID NO: 54 and SEQ ID NO: 55, SEQ ID NO: 56 and SEQ ID NO: 57, SEQ ID NO: 58 and SEQ ID NO: 59, SEQ ID NO: 60 and SEQ ID NO: 61, SEQ ID NO: 62 and SEQ ID NO: 63, SEQ ID NO: 64 and SEQ ID NO: 65 and their complementary sequences.

Another aspect of the present invention provides a kit for determining if a pig is homozygous, heterozygous or non-carrier of an allele of a genetic polymorphism being linked to resistance to ETEC, said kit comprising a first component selected from the group consisting of a NA probe, a NA molecule, a pair of PCR-primers, a restriction enzyme and any combination thereof.

Yet another aspect of the present invention relates to a method for breeding pigs that are resistant to ETEC, the method comprising
i) selecting a first pig, said pig identified as resistant to ETEC using the method described herein; and
ii) breeding said first pig with a second pig, to obtain a pig progeny that is more resistant to ETEC than progeny from randomly chosen parent pigs.

In a still further aspect, the invention provides an isolated NA molecules for the use as an antisense-NA, a iRNA, a Ribosyme, an ETC for genetic medicine, gene therapy or cinetoplastic DNA repair.

The present invention also pertains to a method for producing pork meat, the method comprising i) obtaining a pig progeny as defined herein, and ii) preparing pork meat from the pig progeny.

In one interesting aspect, the invention relates to a method for screening a potential drug candidate for treatment of non-resistance to ETEC, the method comprising
i) selecting a test population of pigs that are identified as non-resistant to ETEC, said identification being performed using the method described herein;

ii) administering the potential drug candidate to the test population, and
iii) evaluation the efficacy of the potential drug candidate on the test population.

In a further aspect, the present invention provides a mixed boar semen, comprising semen from at least two boars, said boars being identified as resistant to ETEC using the method described herein.

DETAILED DESCRIPTION OF THE INVENTION

DEFINITIONS

The term "nucleic acid molecule" or "NA molecule" refers in the present context to an oligomer or polymer of ribonucleic acid (RNA) or deoxyribonucleic acid (DNA) or mimetics thereof. This term includes molecules composed of naturally-occurring nucleobases, sugars and covalent internucleoside (backbone) linkages as well as molecules having non-naturally occurring nucleobases, sugars and covalent internucleoside (backbone) linkages which function similarly or combinations thereof. Such modified or substituted nucleic acids are often preferred over native forms because of desirable properties such as, for example, enhanced cellular uptake, enhanced affinity for nucleic acid target and increased stability in the presence of nucleases and other enzymes, and are in the present context described by the terms "nucleic acid analogues" or "nucleic acid mimics". Preferred examples of nucleic acid mimetics are peptide nucleic acid (PNA-), Locked Nucleic Acid (LNA-), xylo-LNA-, phosphorothioate-, 2'-methoxy-, 2'-methoxyethoxy-, morpholino- and phosphoramidate-containing molecules or the like.

As used herein, the term "ETEC" refers to bacteria from genus *Escherichia* and species *Escherichia coli* which are enterotoxigenic and/or enteropathogenic *E. coli* (ETEC) bacteria. The ETEC are distinguished by their fimbriae type and the ETEC group includes but are not limited to *E. coli* F4 (formerly known as K88) such as *E. coli* F4ab/F4ac, *E. coli* F4ab, *E. coli* F4ac, *E. coli* F4ad, *E. coli* 0149, *E. coli* F5 (formerly known as K99), *E. coli* F6 (formerly known as 987P), *E. coli* F41, *E. coli* F18, *E. coli* F18ab, *E. coli* F107, F18ac, *E. coli* 2134P, *E. coli* Av24, and any combinations thereof.

The term "allele of the genetic polymorphism linked to resistance to ETEC" relates to the NA sequence that is observed in connection with resistance to ETEC and the term "allele of the genetic polymorphism linked to non-resistance to ETEC" is a nucleotide sequence that is observed in connection with non-resistance to ETEC.

The term "NA sequence" may be employed to designate a nucleic acid molecule. More precisely, the expression "NA sequence" encompasses the nucleic material itself and is thus not restricted to the sequence information (i.e. the succession of letters chosen among the four bases) that biochemically characterises a specific DNA or RNA molecule.

The term "homology" indicates a quantitative measure of the degree of homology between two amino acid sequences of equal length or between two nucleotide sequences of equal length. If the two sequences to be compared are not of equal length, they must be aligned to the best possible fit. The sequence identity can be calculated as $((N_{ref}-N_{dif})100)/(N_{ref})$, wherein $N_{dif}$ is the total number of non-identical residues in the two sequences when aligned, and wherein $N_{ref}$ is the number of residues in one of the sequences. Hence, the DNA sequence AGTCAGTC will have a sequence identity of 75% with the sequence AATCAATC ($N_{dif}=2$ and $N_{ref}=8$). A gap is counted as nonidentity of the specific residue(s), i.e. the DNA sequence AGTGTC will have a sequence identity of 75% with the DNA sequence AGTCAGTC (Ndif=2 and Nref=8). Sequence identity can alternatively be calculated by the BLAST program, e.g. the BLASTP program (Pearson & Lipman (1988), available at the NCBI webpage. In one embodiment of the invention, alignment is performed with the global align algorithm with default parameters as described by Huang & Miller (1991).

The term "homologous" means that one single-stranded nucleic acid sequence may hybridise to a complementary single-stranded nucleic acid sequence. The degree of hybridisation may depend on a number of factors including the amount of identity between the sequences and the hybridisation conditions such as temperature and salt concentration.

The term "lod score" has the following meaning: In order to determine if an allele of genetic polymorphism is linked to resistance to ETEC, a lod score can be applied. A lod score, which is also sometimes referred to as $Z_{max}$, indicates the probability (the logarithm of the ratio of the likelihood) that a genetic marker locus and a specific gene locus are linked at a particular distance. Lod scores may e.g. be calculated by applying a computer programme such as the MLINK programme of the UNKAGE package (Lathrop et al., 1985). A lod score greater than 3.0 is considered to be significant evidence for linkage between the genetic polymorphism and the resistance to ETEC or gene locus.

The term "fragment" relates to a subset of larger NA molecule, wherein said subset comprises at least 10 nucleotides, such as at least 11, 12, 13, 14, 15, 16, 17, 18, 19, 20, 21, 22, 23, 24, 25, 30, 35, 40, 50, 60, 70, 80, 90, 100, 150, 200, 250, 300, 400, 500, 1000, 2000, 5000 such as at least 10000 nucleotides. When a fragment of a NA molecule is used as a primer for a PCR-based method it is preferred that the subset comprises from 10-30 nucleotides and even more preferred from 15-23 nucleotides, such as 15, 16, 17, 18, 19, 20, 21, 22 or 23 nucleotides.

The term "genetic polymorphism" relates to a variable nucleotide sequence (polymorphic) that may be present in porcine genomic DNA on a chromosome. Genetic polymorphisms include polymorphisms selected from the group consisting of a single nucleotide polymorphism (SNP), a variable number tandem repeat polymorphism, an interspersed repetitive DNA, insertions, duplications, deletions, amplifications, rearrangements, a combination of SNP's, short tandem repeats, dinucleotide repeats, interspersed repetitive DNA and any combination of these. Variable nucleotide sequence may e.g. be distinguishable by nucleic acid amplification and observation of a difference in size or sequence of nucleotides due to the polymorphism.

The term "pig" comprises all members of the family Suidae species Sus scrofa. Today a large number of relatively well characterised breeds of pigs exists and many of these breeds are susceptible to variable degrees to enterotoxigenic or enteropathogenic E. coli strains. It is evident that a method according to present invention wherein the pig is selected from the group of pigs consisting of a descender of Sus scrofa could result in a breed wherein the animals were resistant to ETEC. At present, there are 10 breeds of swine, which are recognised and can be registered as pure-bred in the United States. These are Berkshire, Chester White, Duroc, Hampshire, Landrace, Poland China, Spot, Yorkshire, Hereford and Tamworth.

In the highly industrialised animal production of today four breeds being Landrace, Yorkshire, Duroc and Hampshire are particular important. Individuals from all four breeds may be non-resistant to ETEC and all populations could benefit from a breeding programme comprising the method disclosed in the present invention.

Other examples of pig breeds are Landrace, Hampshire, Duroc, Yorkshire, Danish Yorkshire, Danish Duroc, Landrace, Danish Landrace, White Danish Landrace, Blackspotted (Sortbroget) Danish Landrace, Hampshire, Danish Hampshire, Poland China, Hereford American Landrace, American Yorkshire, Arapawa Island, Ba Xuyen, Bantu, Bazna, Beijing Black, Belarus Black Pied, Belgian Landrace, Berkshire, British Landrace, British Lop, Bulgarian White, Cantonese, Chester White, Czech Improved White, Dermantsi Pied, Dutch Landrace, Fengjing, Finnish Landrace, French Landrace, German Landrace, Gloucestershire Old Spots, Guinea Hog, Hezuo, Iberian, Italian Landrace, Jinhua, Kele, Krskopolje, Kunekune, Lacombe, Large Black, Large Black-white, Large White, Lithuanian Native, Meishan, Middle White, Minzhu, Mong Cai, Mukota, Mora Romagnola, Moura, Mulefoot, Neijiang, Ningxiang, Norwegian Landrace, Ossabaw Island, Oxford Sandy and Black, Philippine Native, Pietrain, Red Wattle, Saddleback, Spots, Swedish Landrace, Swallow Belied Mangalitza, Tamworth, Thuoc Nhieu, Tibetan, Turopoije, Vietnamese Potbelly, Welsh and Wuzhishan.

It should further be noted that the method of the present invention may be used to identify resistant animals from any crossbreeding of any of the pig families and breeds mentioned above.

The term "genetic material" should in the present context be interpreted in its broadest aspect and may comprise one or more components selected from the group consisting of genomic DNA, such as chromosomes, mRNA, and fragments and/or digests of these molecules.

The term "genomic DNA" should be interpreted in its broadest aspect and may comprise one or more components selected from the group consisting of genomic DNA, such as chromosomes, and fragments and/or digests of these molecules.

DESCRIPTION

It should be emphasised that all terms, embodiments and features described herein may be used with all of the aspects mentioned herein.

In a first aspect of the present invention there is provided an isolated nucleic acid (NA) molecule, comprising an allele of a genetic polymorphism linked to resistance to enterotoxigenic E. coli (ETEC), said genetic polymorphism being located in the region between and including the markers SW2196 and SW225 on the porcine chromosome 13. In an useful embodiment, the genetic polymorphism is located in the region flanked by and including the markers SW207 and S0075.

In one embodiment of the present invention, the allele of a genetic polymorphism linked to resistance to ETEC renders a pig, which is homozygous with respect to said allele, resistant to ETEC.

In one embodiment of the present invention, a pig which is homozygous with respect to said allele of a genetic polymorphism linked to resistance to ETEC, is resistant to ETEC.

In a preferred embodiment of the present invention, the ETEC is E. coli F4 and/or E. coli F4 ab/ac.

In preferred embodiments, the isolated NA molecule may comprise an allele of the genetic polymorphism that is linked to resistance to ETEC with a lod score of at least 3.0 including at least 4.0, 5.0, 6.0, 7.0, 8.0 or 9.0, 10 such as at least 50.

In a preferred embodiment of the invention, the isolated NA molecule comprises an allele of the genetic polymorphism that is linked to resistance to ETEC. The isolated NA molecule may also comprise a NA sequence, which is located in the porcine MUC4 gene.

In certain preferred embodiments of the present invention, the isolated NA molecule comprises a NA sequence which is identical or has at least 90% homology, such as at least 95% or at least 99% homology to a sequence selected from the group of sequences consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 67, SEQ ID NO: 68, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, their complementary sequences and any fragments thereof.

In further preferred embodiments of the present invention, the isolated NA molecule comprises a NA sequence which is identical or has at least 90% homology, such as at least 95% or 99% homology to a sequence selected from the group of sequences consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 67, SEQ ID NO: 68, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 5 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, their complementary sequences and fragments thereof.

In an especially preferred embodiment of the present invention, the isolated NA molecule comprises a NA sequence which is identical or has at least 90% homology, such as at least 95% or 99% homology to a sequence selected from the group of sequences consisting of SEQ ID NO: 6, SEQ ID NO: 8, SEQ ID NO: 82, SEQ ID NO: 83, SEQ ID NO: 87 and SEQ ID NO: 88, their complementary sequences and fragments thereof.

In a suitable embodiment, the isolated NA molecule comprises a NA sequence that distinguishes pigs, which are resistant to ETEC from pigs, which are non-resistant to ETEC.

In another embodiment of the present invention, the isolated NA molecule is a NA molecule, which is in complete or nearly complete linkage disequilibrium with any of the NA molecules described above.

Alleles at two or more neighbouring loci show linkage disequilibrium when they occur together in frequencies significantly different from those predicted from the individual allele frequencies. Complete linkage disequilibrium generally occurs when two NA sequences (e.g. a genetic polymorphism and the porcine MUC4 gene) are physically very close to each other on the chromosome and where the opportunities for recombination have been limited. Where the two NA sequences are in linkage equilibrium then it is essential to determine the linkage phase (i.e. how the alleles are associated) in each pedigree before the markers can be used to predict genotypes at the gene of interest. Genetic polymorphisms that are In partial, but not complete, linkage disequilibrium with the gene of interest may have some utility in predictive tests.

In a preferred embodiment of the invention, the NA molecule comprise a site for a genetic polymorphism such as e.g. A1059G in SEQ ID NO: 6, T1125G in SEQ ID NO: 6, A1134G in SEQ ID NO: 6, C1138G in SEQ ID NO: 6, C1849G in SEQ ID NO: 8, C2129T in SEQ ID NO: 8, A4847G in SEQ ID NO: 82, T4913G in SEQ ID NO: 82, A4922G in SEQ ID NO: 82, C4926G in SEQ ID NO: 82, A1659T in SEQ ID NO: 83, T1666G in SEQ ID NO: 83, C1684A in SEQ ID NO: 83, T1740A in SEQ ID NO: 83, C1795T in SEQ ID NO: 83, T1820G in SEQ ID NO: 83, C1912T in SEQ ID NO: 83, G2997A in SEQ ID NO: 83, G3277C in SEQ ID NO: 83 or any of their complementary sequences.

The NA molecule may be selected so as to comprise a site for genetic polymorphism such as the variation found at position 1726 of SEQ ID NO: 83 where the nucleotides 10 AACGTG in are present in a resistant pig and a 6 basepair deletion is observed in an ETEC susceptible pig; the variation found at position 2009 of SEQ ID NO: 83, where pigs either dislay a T or a deletion of the T; the variation found at position 332 of SEQ ID NO: 87, where a SNP shifting between G and A is present; or the variation found at position 3530 of SEQ ID NO: 88, where a SNP shifting between G and 15 A is present. Without being bound by theory, these three genetic polymorphisms are believed to be associated to resistance ETEC.

The invention provides in a second aspect a NA probe, which comprises a NA sequence that is homologous to a fragment of an isolated NA molecule as described above.

The NA probe may be specific for an allele of at least one SNP selected from the group of SNPs consisting of A1059G in SEQ ID NO: 6, T1125G in SEQ ID NO: 6, A1134G in SEQ ID NO: 6, C1138G in SEQ ID NO: 6, C1849G in SEQ ID NO: 8, C2129T in SEQ ID NO: 8, A4847G in SEQ ID NO: 82, T4913G in SEQ ID NO: 82, A4922G in SEQ ID NO: 82, C4926G in SEQ ID NO: 82, A1659T in SEQ ID NO: 83, T1666G in SEQ ID NO: 83, C1684A in SEQ ID NO: 83, T1740A in SEQ ID NO: 83, C1795T in SEQ ID NO: 83, T1820G in SEQ ID NO: 83, C1912T in SEQ ID NO: 83, G2997A in SEQ ID NO: 83, 30 G3277C in SEQ ID NO: 83 and their complementary sequences.

A NA probe may be specific for an allele of at least one genetic polymorphism comprising the variation found at position 1726 of SEQ ID NO: 83 where the nucleotides AACGTG in are present in a resistant pig and a 6 basepair deletion is observed in an ETEC susceptible pig.

A NA probe may be specific for an allele of at least one genetic polymorphism comprising the variation found at position 2009 of SEQ ID NO: 83, where pigs either dislay a T or a deletion of the T; the variation found at position 332 of SEQ ID NO: 87, where a SNP shifting between G and A is present; and the variation found at position 3530 of SEQ ID NO: 88, where a SNP shifting between G and A is present. Without being bound by theory, these three genetic polymorphisms are believed to be associated to resistance ETEC.

In an preferred embodiment of the present invention, the NA probe is capable of hybridising to a part of the allele which comprises the genetic polymorphism or to a NA sequence which is complementary to the part of the allele which comprises the genetic polymorphism.

The NA probe may be specific for an allele of a genetic polymorphism linked to resistance to ETEC, said allele of a genetic polymorphism linked to resistance to ETEC being linked to resistance to ETEC at a lod score of at least 3.0 including at least 4.0, 5.0, 6.0, 7.0, 8.0 or 9.0, 10 such as at least 50.

The NA probe may also in an interesting embodiment comprise a NA sequence that is homologous to the NA sequence of SEQ ID NO: 66 or its complementary sequence.

In useful embodiments, the NA probe comprises at least 10 nucleotides, such as at least 11, 12, 13, 14, 15, 16, 17, 18, 19, 20, 21, 22, 23, 24, 25, 30, 35, 40, 50, 60, 70, 80, 90, 100, 150, 200, 250, 300, 400, such as at least 500 nucleotides. A presently preferred NA probe comprises from 10 to 30 nucleotides, such as from 15 to 23 nucleotides. In further useful embodiments, the NA probe comprises 15 nucleotides such as 16, 17, 18, 19, 20, 21, 22 or 23 nucleotides.

In a further aspect of the present invention there is provided a method for identifying if a pig is resistance to ETEC, the method comprising
  i) obtaining a sample from said pig, said sample comprising genetic material;
  ii) determining by use of said sample if the pig is homozygous for an allele of a genetic polymorphism linked to resistance to ETEC, said genetic polymorphism being located In the region between and including the markers SW2196 and SW225 on the porcine chromosome 13; and
  iii) identifying the pig as resistant to ETEC if the pig is homozygous for the allele of genetic polymorphism linked to resistance.

In one embodiment of the invention, the method further comprises identifying if the pig is non-resistance to ETEC and a carrier or a non-carrier of resistance, said method further comprises
  iv) determining by use of said sample if the pig is heterozygous or non-carrier of the allele of the genetic polymorphism linked to resistance to ETEC; and
  v) identifying
    a) the pig as non-resistant to ETEC and a non-carrier of resistance, if the pig is a non-carrier of the allele of the genetic polymorphism linked to resistance; or that
    b) the pig as non-resistant to ETEC but a carrier of resistance if the pig is heterozygous for the allele of the genetic polymorphism linked to resistance to ETEC.

In another embodiment of the invention, the genetic polymorphism is not located within the porcine chromosome 6. In a further embodiment, the genetic polymorphism is not located in the porcine alpha-(1,2) fucosyl-transferase gene (FUT1 gene).

In a preferred embodiment, the genetic polymorphism is located in the region flanked by and Including the markers SW2196 and SW225, such as the region flanked by and including the markers SW207 and S0075.

The most commonly used genetic markers for linkage mapping in pigs are microsatellites (e.g. SW2196, SW225, SW207 and S0075 and the other markers of Table 1 below), where the core of the marker is a tandemly-repeated sequence of two (usually) or a small number of nucleotides, where different alleles are distinguished by having different numbers of repeats. For microsatellites (and for many of the other possible marker types), the polymerase chain reaction (PCR) is used to amplify a small DNA sample and provides the first step in Identifying alternative alleles (i.e. genotyping). Unique PCR primers are used to ensure that only alleles of the specific marker of interest are amplified from the DNA sample of an individual animal. The PCR products are then separated by electrophoresis and can be visualised, for example via use of radioactive or fluorescent labels. The use of PCR on DNA-based markers means that genotyping can be performed on very small samples of DNA, which can be relatively easily collected at any time. Hence animals can be genotyped as soon as they are born using DNA isolated from blood, ear notches or other material.

The genetic polymorphism may be any genetic polymorphism located in the region between and including the markers SW2196 and SW225 on the porcine chromosome 13, wherein the allele of the genetic polymorphism linked to resistance to ETEC is linked to resistance to ETEC at a lod score of at least 3.0, including at least 4.0, 5.0, 6.0, 7.0, 8.0, 9.0 or 10.0, such as at least 50.

In another embodiment, the genetic polymorphism is located in the porcine MUC4 gene and/or in the adjacent genomic sequences at 3' and/or 5' end of the MUC4 gene. The adjacent genomic sequences may be the at less than 500 kb (kilobases) such as less than 300 kb or even less than 100 kb.

In a presently preferred embodiment of the invention the genetic polymorphism is located in a genomic sequence corresponding to SEQ ID NO: 6 and/or SEQ ID NO: 8. These sequences are believed to be a part of the porcine MUC4 gene. However, the genetic polymorphism may also be located in a genomic sequence corresponding to a nucleotide sequence selected from the group of SEQ ID NO: 1, SEQ ID NO: 2, SEQ ID NO: 3, SEQ ID NO: 4, SEQ ID NO: 5, SEQ ID NO: 7, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, any fragments thereof and any combinations thereof.

In an embodiment of the present invention, the genetic polymorphism is located in the porcine MUC4 gene.

Also, the genetic polymorphism comprises genetic polymorphisms that is in complete or nearly complete linkage disequilibrium with genetic polymorphisms mentioned above. The genetic polymorphisms according to the present invention may be identified as described in the Examples, e.g. in Example 6.

The terms "resistant to ETEC" or "resistance to ETEC" relates in the present context to a pig being resistant to one or more levels of *E. coli* infection, e.g. resistant to intestinal adhesion by ETEC, resistant to intestinal colonisation by ETEC, resistant to intestinal disorders, such as diarrhoea, caused by ETEC and any combination thereof. A pig resistant to a certain ETEC strain will be less susceptible to intestinal adhesion by ETEC and/or intestinal colonisation by ETEC and/or intestinal disorders caused by ETEC than a pig, which is non-resistant, when the two pigs are exposed to a similar dose of ETEC. In an useful embodiment of the present invention, the resistant pig is not susceptible to the ETEC at all.

In the case of intestinal adhesion, resistance vs. non-resistance is determined using the Adhesion test as described in Sellwood et al., 1975.

Briefly described, the Adhesion test may be performed in the following fashion: Epithelial cells from the upper part of the small intestine are obtained from specimens collected after slaughter of the pig. The adhesion test is performed by incubating the epithelial cells with e.g. *E. coli* F4ab and *E. coli* F4ac, respectively. Samples containing e.g. 10 to 20 epithelial cells may be examined for adhesion of both *E. coli* F4ab and *E. coli* F4ac by interference contrast microscopy. The results may be scored from 1 to 4, where 1=no bacteria adhering to the intestinal cells and 4=bacteria adhering to the whole brush border of all cells. If the score is 1, then the animal is considered to be resistant to intestinal adhesion by the respective ETEC (in this case to *E. coli* F4ab and *E. coli* F4ac). Alternatively, the pig may be considered to be resistant to intestinal adhesion by ETEC if the score is either 1 or 2.

In the case of intestinal colonisation by ETEC, resistance vs. non-resistance may be determined e.g. using an ETEC cell count in a faeces sample from the pig or by determining the concentration of ETEC related fimbrie in the faeces sample. A resistant, infected pig will have a significantly lowered number of ETEC or concentration of ETEC related fimbrie in the faeces sample than a non-resistant, infected pig.

In the case of intestinal disease by ETEC, resistance vs. non-resistance may be determined e.g. by feeding the pig a dose of ETEC and observe whether it develops an intestinal disease caused by the ETEC. If the pig develops the disease it is non-resistant. If the pig does not develop the disease it may either mean that the pig is resistant or that the pig is non-resistant, but for some reason it has not developed the intestinal disease. Administering drugs or special diets that compensate for non-resistance to the pig, might result in that a non-resistant pig does not develop the intestinal disease upon ETEC exposure.

The pig may either be male or female, and may have any age at the time of either determination and/or use of the identification of resistance or non-resistance. Thus, the pig may be selected from the group consisting of a boar, a sow, a suckling piglet, a weaned pig, a grower pig and a finisher pig. At the time of either determination and/or use of the identification of resistance or non-resistance, the pig may be unborn or have an age of 1 day to 1 month, 1-2 months, 2-3 months, 3-4 months, 4-5 months, 5-6 months, 6-7 months, 7-8 months, 8-9 months, 9-10 months, 10-11 months, 11-12 months, 12-14 months, 14-16 months, 16-18 months, 18-20 months, 20-24 months, 2-3 years, 3-4 years, 3-4 years, 4-5 years, 5-6 years, 6-7 years, 7-8 years or 8-10 years.

In an embodiment of the invention, the pig has a known pedigree, e.g. with known ancestors at least 1 generation back, such as at least 2 generations back, including at least 3, 4, 5, 6, 7, 8, 9, 10, or 15, such as at least 20 generations back. The pig may be a highly inbred animal and may have a pedigree certificate.

In a presently preferred embodiment of the invention, the genetic polymorphism is a SNP or a combination of SNPs. The SNP may e.g. be a single nucleotide G/C polymorphism.

A presently preferred SNP may be selected from the group consisting of A1059G in SEQ ID NO: 6, T1125G in SEQ ID NO: 6, A1134G in SEQ ID NO: 6, C1138G in SEQ ID NO: 6, C1849G in SEQ ID NO: 8, C2129T in SEQ ID NO: 8, A4847G in SEQ ID NO: 82, T4913G in SEQ ID NO: 82, A4922G in SEQ ID NO: 82, C4926G in SEQ ID NO: 82, A1659T in SEQ ID NO: 83, T1666G in SEQ ID NO: 83, C1684A in SEQ ID NO: 83, T1740A in SEQ ID NO: 83, C1795T in SEQ ID NO: 83, T1820G in SEQ ID NO: 83, C1912T in SEQ ID NO: 83, G2997A in SEQ ID NO: 83 and G3277C in SEQ ID NO: 83.

When referring to a SNP, the used syntax is "XpositionY in SEQ ID NO: ZZ", where position is the nucleotide number of the SNP in SEQ ID NO: ZZ and where X is the nucleotide of the non-resistant haplotype and Y is the nucleotide in the resistant haplotype. For example A1059G in SEQ ID NO: 6, means that there is a SNP in nucleotide number 1059 of the nucleotide sequence of SEQ ID NO:6, and further that nucleotide number 1059 is an adenosine monophosphate group if the pig is non-resistant and that nucleotide number 1059 is a guanosine monophosphate group if the pig is resistant.

When making a more general reference to a SNP the syntax "X/Y SNP" is used. This refers to SNP where the non-resistant pig has a X nucleotide at the SNP position and the resistant pig has a Y nucleotide at the SNP position. Thus, a G/C SNP means a guanosine monophosphate group if the pig is resistant and a cytosine monophosphate group if the pig is non-resistant.

According to the present invention the SNP may be any single nucleotide polymorphism, such as a G/C single nucleotide polymorphism, a G/A single nucleotide polymorphism, a T/C single nucleotide polymorphism, a G/T single nucleotide polymorphism, an A/T single nucleotide polymorphism or a C/A single nucleotide polymorphism.

In an embodiment of the present invention, the method further comprising
  in step ii), determining in the sample if the pig in addition to the allele of the first genetic polymorphism linked to resistance to ETEC, is homozygous, heterozygous or non-carrier for an allele of an at least second genetic polymorphism linked to resistance to ETEC, and
  in step iii) identifying the pig as resistant to ETEC if the pig is homozygous for the first allele of the genetic polymorphism linked to resistance to ETEC and/or for the at least second allele of the genetic polymorphism linked to resistance to ETEC.

The at least second genetic polymorphism may comprise at least 3 genetic polymorphisms, such as at least 4, 5, 6, 7, 10, 20, 30 or at least 50 genetic polymorphisms.

In preferred embodiments, the at least second genetic polymorphism is a genetic polymorphism selected from the group consisting of a single nucleotide polymorphism (SNP), a variable number tandem repeat polymorphism, an interspersed repetitive DNA, insertions, deletions, amplifications, rearrangements, a combination of SNP's, short tandem repeats, dinucleotide repeats, interspersed repetitive DNA and any combination of these.

The at least second polymorphism may be a SNP selected from the group consisting of A1059G in SEQ ID NO: 6, T1125G in SEQ ID NO: 6, A1134G in SEQ ID NO: 6, C1138G in SEQ ID NO: 6, C1849G in SEQ ID NO: 8, C2129T in SEQ ID NO: 8, A4847G in SEQ ID No: 82, T4913G in SEQ ID NO: 82, A4922G in SEQ ID NO: 82, C4926G in SEQ ID NO: 82, A1659T in SEQ ID NO: 83, T1666G in SEQ ID NO: 83, C1684A in SEQ ID NO: 83, T1740A in SEQ ID NO: 83, C1795T in SEQ ID NO: 83, T1820G in SEQ ID NO: 83, C1912T in SEQ ID NO: 83, G2997A in SEQ ID NO: 83 and G3277C in SEQ ID NO: 83.

In another embodiment of the invention, the at least second genetic polymorphism is located in the porcine FUT1 gene.

According to the method of the present invention, the sample obtained from the pig may be selected from the group consisting of a material comprising DNA and/or RNA, blood, saliva, tissue, throat swap, semen, and combinations thereof.

The method according to the invention includes providing a sample comprising genetic material. Such material comprises porcine DNA material, which may be provided by any conventional method or means. The porcine DNA material may e.g. be extracted, isolated and purified from blood (e.g., fresh or frozen), tissue samples (e.g., spleen, buccal smears), hair samples containing follicular cells and semen. The sample may comprise blood, partly or fully hydrolysed blood, saliva, tissue, throat swap, semen or combinations thereof.

The determination whether the pig is homozygous, heterozygous or non-carrier of the allele of the genetic polymorphism linked to resistance to ETEC may be performed using a technique selected from the group consisting of allele specific PCR, mini sequencing, primer extension, pyrosequencing, PCR-RFLP, allele-specific rolling circle amplification, ARMS (Amplification Refracting Mutation System), hybridisation e.g. to DNA arrays, DASH (Dynamic Allele-Specific Hybridisation), melting curve measurement, and primer extension followed by MALDI-TOF mass spectrometry and any combinations thereof.

The below Example 4 illustrates the use of PCR and DASH, respectively, for determining whether the pig is homozygous, heterozygous or non-carrier of the allele of the genetic polymorphism linked to resistance to ETEC.

A number of methods exist that can be used to detect single base mutations and other types of polymorphisms. Detailed description of useful methods may be found in Ausubel et al. (2000) and in Sambrook et al. (1989). Among the more important methods are: DNA sequencing; single strand conformation polymorphism (SSCP) method; denaturing gradient gel electrophoresis (DGGE) method; dideoxy fingerprinting, restriction endonuclease fingerprinting and constant denaturing gel electrophoresis (CDGE). Mutations can also be detected by specific hybridisation of oligonucleotides to the nucleic acid to be analysed.

The determination of whether the pig is homozygous, heterozygous or non-carrier of the allele of the genetic polymorphism linked to resistance to ETEC may be performed using a method which comprises at least one of the following steps
  a) obtaining a sample from the pig, said sample comprising genetic material;
  b) extracting genomic DNA from said sample;
  c) amplifying at least a fragment of the genomic DNA to obtain an amplification product;
  d) contacting the amplification product with a restriction enzyme;
  e) separating the resulting fragments by gel electrophoresis;
  f) determining the respective numbers and lengths of fragments; and
  g) determining from the number and lengths which polymorphism is present.

The method of determination may be performed in the sequence a), b), c), d), e), f) and g).

The restriction enzyme may be an enzyme such as Aat II, Bam HI, BgI II, Cla I (Bsu 151), Dpn I, Eco RI, Eco RV, Esp I (Bpu 1102I), Hind III, Nco I, Nde I, Not I, Pae I (Sph I), Pau I, Pst I, Pvu I, Sac I, Sal I, Sma I, Xba I or Xho I.

The restriction enzyme XbaI is preferred when the allele of the genetic polymorphism linked to resistance to ETEC is the SNP C1849G.

In preferred embodiments, the ETEC is selected from the group consisting of *E. coli* F4ab/F4ac, *E. coli* O149, *E. coli* F4, *E. coli* F18, *E. coli* F5, *E. coli* F6, *E. coli* 987P, *E. coli* F41, *E. coli* F18ab, *E. coli* F107, *E. coli* F18ac, *E. coli* 2134P and *E. coli* Av24, and any combinations of these organisms.

The present invention further relates to the use of the isolated NA molecule as described herein and/or the NA probe as described herein, as a probe for detecting an allele of a genetic polymorphism linked to resistant to ETEC.

A further aspect of the present invention relates to the use of a pair of NA molecules for primers in a PCR-based method, said PCR-based method being used in a method for identifying whether a pig is resistant or non-resistant to ETEC, said pair of NA molecules being selected from the group consisting of SEQ ID NO: 18 and SEQ ID NO: 19, SEQ ID NO: 20 and SEQ ID NO: 21, SEQ ID NO: 22 and SEQ ID NO: 23, SEQ ID NO: 24 and SEQ ID NO: 25, SEQ ID NO: 26 and SEQ ID NO: 27, SEQ ID NO: 28 and SEQ ID NO: 29, SEQ ID NO: 30 and SEQ ID NO: 31, SEQ ID NO: 32 and SEQ ID NO: 33, SEQ ID NO: 34 and SEQ ID NO: 35, SEQ ID NO: 36 and SEQ ID NO: 37, SEQ ID NO: 38 and SEQ ID NO: 39, SEQ ID NO: 40 and SEQ ID NO: 41, SEQ ID NO: 42 and SEQ ID NO: 43, SEQ ID NO: 44 and SEQ ID NO: 45, SEQ ID NO: 46 and SEQ ID NO: 47, SEQ ID NO: 48 and SEQ ID NO: 49, SEQ ID NO: 50 and SEQ ID NO: 51, SEQ ID NO: 52 and SEQ ID NO: 53, SEQ ID NO: 54 and SEQ ID NO: 55, SEQ ID NO: 56 and SEQ ID NO: 57, SEQ ID NO: 58 and SEQ ID NO: 59, SEQ ID NO: 60 and SEQ ID NO: 61, SEQ ID NO: 62 and SEQ ID NO: 63, SEQ ID NO: 64 and SEQ ID NO: 65 and their complementary sequences.

The present invention is not restricted to using the pairs mentioned herein, thus the NA sequences in SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64 and SEQ ID NO: 65 may all be used for primers in a PCR-based process, said PCR-based process being a step in a method for identifying whether a pig is resistant or non-resistant to ETEC.

Also, the pair of NA molecules for primers in a PCR-based method may comprise a NA molecules being selected from the group consisting of SEQ ID NO: 18 and SEQ ID NO: 19, SEQ ID NO: 20 and SEQ ID NO: 21, SEQ ID NO: 22 and SEQ ID NO: 23, SEQ ID NO: 24 and SEQ ID NO: 25, SEQ ID NO: 26 and SEQ ID NO: 27, SEQ ID NO: 28 and SEQ ID NO: 29, SEQ ID NO: 30 and SEQ ID NO: 31, SEQ ID NO: 32 and SEQ ID NO: 33, SEQ ID NO: 34 and SEQ ID NO: 35, SEQ ID NO: 36 and SEQ ID NO: 37, SEQ ID NO: 38 and SEQ ID NO: 39, SEQ ID NO: 40 and SEQ ID NO: 41, SEQ ID NO: 42 and SEQ ID NO: 43, SEQ ID NO: 44 and SEQ ID NO: 45, SEQ ID NO: 46 and SEQ ID NO: 47, SEQ ID NO: 48 and SEQ ID NO: 49, SEQ ID NO: 50 and SEQ ID NO: 51, SEQ ID NO: 52 and SEQ ID NO: 53, SEQ ID NO: 54 and SEQ ID NO: 55, SEQ ID NO: 56 and SEQ ID NO: 57, SEQ ID NO: 58 and SEQ ID NO: 59, SEQ ID NO: 60 and SEQ ID NO: 61, SEQ ID NO: 62 and SEQ ID NO: 63, SEQ ID NO: 64 and SEQ ID NO: 65 and their complementary sequences.

It will be understood, that the present invention is not restricted to using the pairs mentioned herein, thus the NA sequences in SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64 and SEQ ID NO: 65 may all be used for primers in a PCR-based process, said PCR-based process being a step in a method for identifying whether a pig is resistant or non-resistant to ETEC.

At least one primer of the pairs of primers may comprise a NA sequence or a fragment of a NA sequence, said NA sequence being selected from the group consisting of SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64 and SEQ ID NO: 65.

A useful primer may comprise a fragment of a NA sequence selected from the group consisting of SEQ ID NO: 1, SEQ ID NO: 2, SEQ ID NO: 3, SEQ ID NO: 4, SEQ ID NO: 5, SEQ ID NO: 7, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ-ID NO: 195, SEQ ID NO: 196, SEQ ID NO: 197, and their complementary sequences.

Preferred primers may comprise a fragment of a NA sequence selected from the group consisting of SEQ ID NO: 1, SEQ ID NO: 2, SEQ ID NO: 3, SEQ ID NO: 4, SEQ ID NO: 5, SEQ ID NO: 7, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101.

A useful pair of primers may comprise two primers as defined above. Preferably, one of these primers is complementary to the NA sequences of the mentioned SEQ ID NO:s.

In a preferred embodiment the primer pairs SEQ ID NO: 62 and SEQ ID NO: 63 or SEQ ID NO: 64 and SEQ ID NO: 65, are used as the amplify parts of the porcine MUC4 gene.

In accordance with the present invention there is also provided a kit for determining if a pig is homozygous, heterozygous or non-carrier of an allele of a genetic polymorphism linked to resistance to ETEC, said kit comprising a first component selected from the group consisting of a NA probe as described herein, a NA molecule as described herein, a pair of PCR-primers as described herein, a restriction enzyme and any combination thereof.

Useful primers may comprise a primer as described herein, such as a pair of PCR-primers may be selected from the group consisting of SEQ ID NO: 18 and SEQ ID NO: 19, SEQ ID NO: 20 and SEQ ID NO: 21, SEQ ID NO: 22 and SEQ ID NO: 23, SEQ ID NO: 24 and SEQ ID NO: 25, SEQ ID NO: 26 and SEQ ID NO: 27, SEQ ID NO: 28 and SEQ ID NO: 29, SEQ ID NO: 30 and SEQ ID NO: 31, SEQ ID NO: 32 and SEQ ID NO: 33, SEQ ID NO: 34 and SEQ ID NO: 35, SEQ ID NO: 36 and SEQ ID NO: 37, SEQ ID NO: 38 and SEQ ID NO: 39, SEQ ID NO: 40 and SEQ ID NO: 41, SEQ ID NO: 42 and SEQ ID NO: 43, SEQ ID NO: 44 and SEQ ID No: 45, SEQ ID NO: 46 and SEQ ID NO: 47, SEQ ID NO: 48 and SEQ ID NO: 49, SEQ ID NO: 50 and SEQ ID NO: 51, SEQ ID NO: 52 and SEQ ID NO: 53, SEQ ID NO: 54 and SEQ ID NO: 55, SEQ ID NO: 56 and SEQ ID NO: 57, SEQ ID NO: 58 and SEQ ID NO: 59, SEQ ID NO: 60 and SEQ ID NO: 61, SEQ ID NO: 62 and SEQ ID NO: 63, SEQ ID NO: 64 and SEQ ID NO: 65 and their complementary sequences.

The kit may further comprise at least a second component selected from the group consisting of a restriction enzyme, a pH-buffer, a gel, a washing buffer and an incubation buffer, or any combination thereof.

The kit may even further comprise an at least third component selected from the group consisting of a restriction enzyme, a pH-buffer, a gel, a washing buffer, an incubation buffer, and any combination thereof.

In a further aspect, the present invention relates to a method for breeding pigs that are resistant to ETEC, the method comprising
 i) selecting a first pig, said pig identified as resistant to ETEC using a method described herein; and
 ii) breeding said first pig with a second pig, to obtain a pig progeny that has a greater probability of being resistant to ETEC than progeny from randomly chosen parent pigs.

Also, the method may be performed by breeding a first pig, which is identified as resistant to ETEC using a method described herein, with a second pig. The pig progeny obtained thereby will have a greater probability of being resistant to ETEC than progeny from randomly chosen parent pigs. The resistance/non-resistance of the second pig need not to be known.

However, In a preferred embodiment, the second pig is a pig chosen among pigs that are identified as resistant to ETEC using a method of identification as described herein.

In accordance with the present Invention, it may be useful to use a physical marking of a pig for identifying the pig as resistant or non-resistant to ETEC. The physical marking could comprise a sign to be read by the human eye, a barcode, a marking device capable of transmitting the information of resistance/non-resistance wireless to a receiving device.

In yet a further aspect, the present invention relates to an isolated NA molecules as described herein for the use as: an antisense-NA, an iRNA, a Rribosyme, an ETC for genetic medicine, gene therapy or cinetoplastic DNA repair.

In accordance with the present invention, there is also provided a method for producing pork meat, comprising the steps of i) obtaining a pig progeny with improved resistance as described herein, and ii) preparing pork meat from the pig progeny.

In accordance with the present invention, it may be useful to use a physical marking of a pig for identifying the pig as resistant or non-resistant to ETEC. The physical marking could comprise a sign to be read by the human eye, a barcode, a marking device capable of transmitting the information of resistance/non-resistance wireless to a receiving device.

In further aspect, the invention relates to the use of a genetic polymorphism to treat pigs that are non-resistant to ETEC, said genetic polymorphism being located in the region between and including the markers SW2196 and SW225 on the porcine chromosome 13. In a useful embodiment, the genetic polymorphism is located in the region flanked by and including the markers SW207 and S0075.

In a still further aspect, the present invention relates to a method for screening a potential drug candidate for treatment of non-resistance to ETEC, the method comprising the steps of
 i) selecting a test population of pigs that are determined as non-resistant to ETEC as described herein;
 ii) administering the potential drug candidate to the test population; and
 iii) evaluation the efficacy of the potential drug candidate on the test population.

In accordance with the present invention, the porcine MUC4 protein may be used as a drug to make a non-resistant pig resistance to ETEC.

Also encompassed by the present invention is a mixed boar semen, comprising semen from at least two boars, said boars being identified as resistant to ETEC using a method as defined herein. The number of boars contributing to the mix may be at least 3 such as at least 4, 5, 6, 7, 8, 10, 12, 15, 20, 25 such as at least 100 boars.

It will be understood, that the information of the presence or absence of the genetic polymorphism in a pig may conveniently be stored on a data storage medium. Such information of resistance/non-resistance in a data processing system may be used e.g. to control feeding, medication or breeding of the pigs.

Yet another aspect of the present invention provides a method for identifying if a pig is resistant or non-resistant to enterotoxigenic or enteropathogenic E. coli (ETEC), the method comprising:
 i) obtaining a sample from said pig, said sample comprising genetic material;
 ii) determining in said sample the presence or absence of a marker linked to resistance to ETEC, and
 iii) inferring that the pig is resistant to ETEC, if the marker linked to resistance to ETEC is present in the sample.

In a useful embodiment of the invention, the marker comprises one or more of the components selected from the group consisting of a protein, a hormone and a genetic polymorphism. The marker may be considered present in the sample if the component is present in the sample. Also, the marker may be considered present in the sample if the concentration of the component in the sample is e.g. above a certain threshold, below a certain threshold, within a certain concentration interval or outside a certain concentration interval.

When the marker comprises a protein, this protein may be porcine MUC4, or a porcine mucin-like protein. The protein may also well be a transferrin receptor protein or a protein with a transferrin-receptor-like activity.

Also encompassed by the present invention is a probe specific for the marker linked to resistance to ETEC.

The probe may comprise a binding element selected from the group consisting of a polyclonal antibody, a monoclonal antibody, a receptor, a ligand. In a preferred embodiment the probe is an antibody or a ligand specific for the MUC4 protein.

The invention is further illustrated in the following non-limiting examples and in the figures, wherein FIG. 1. illustrates the linkage map showing the location of the F4ab/F4ac locus (in bold)

Figure 2:
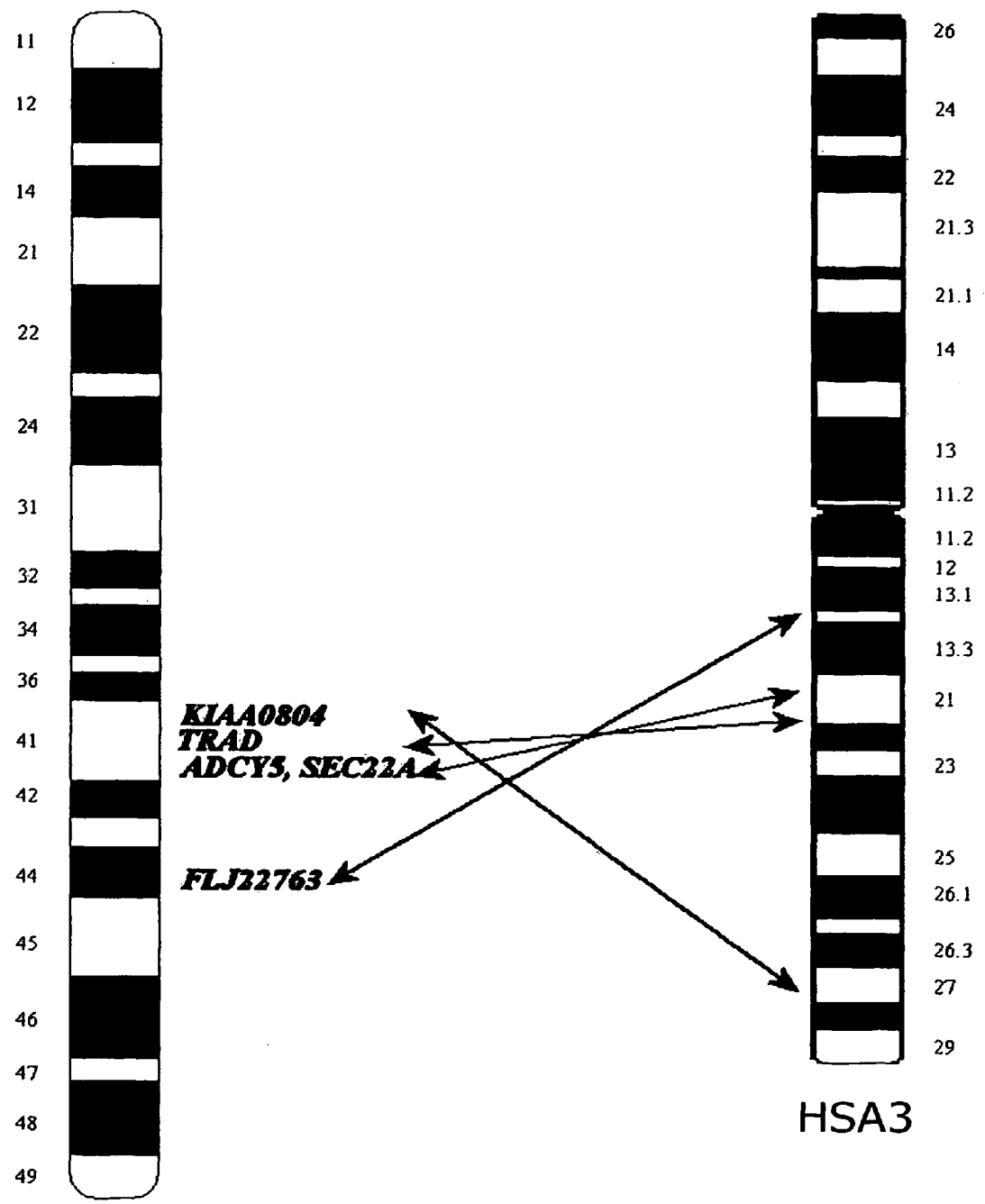
Figure 3:
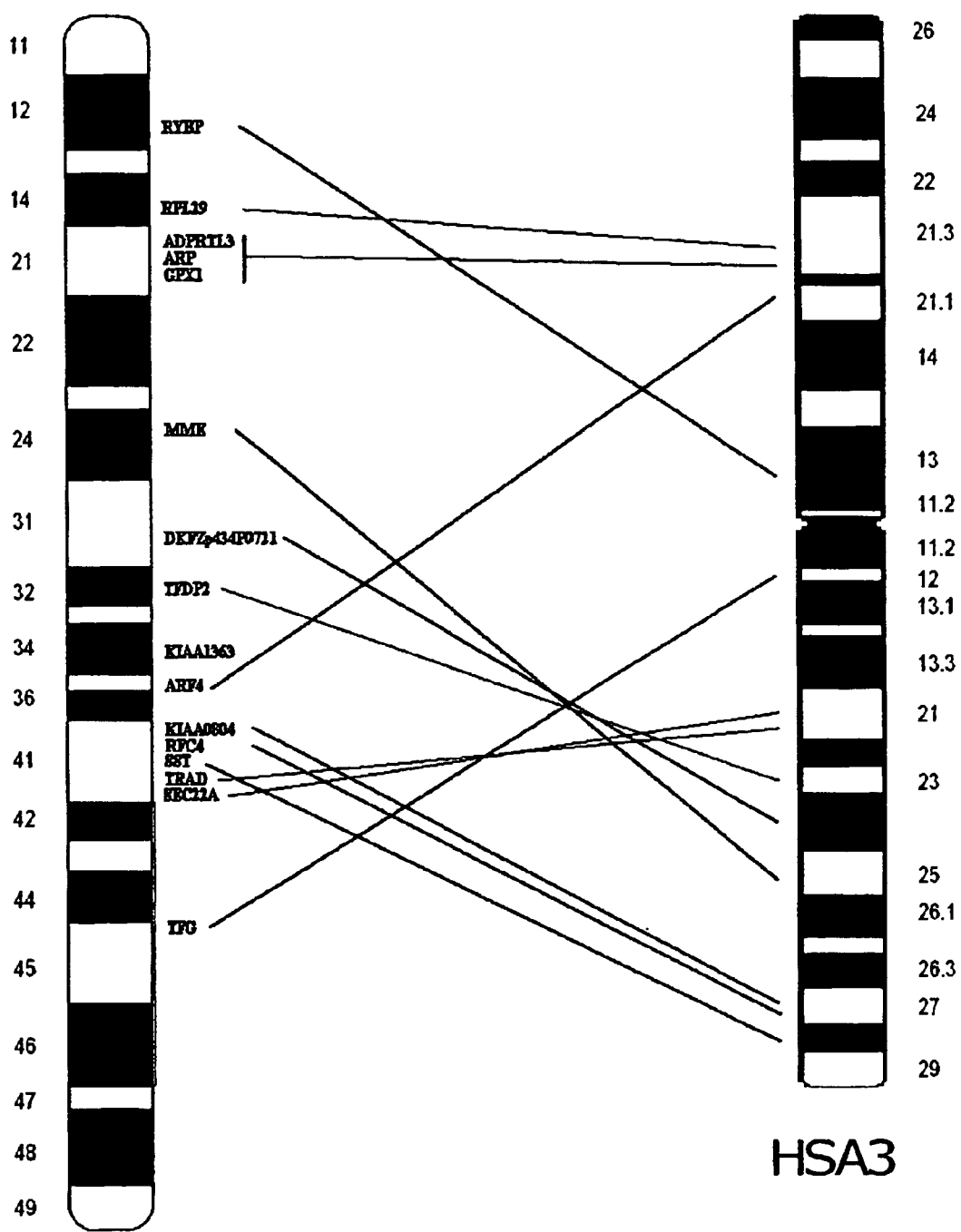
Figure 4:
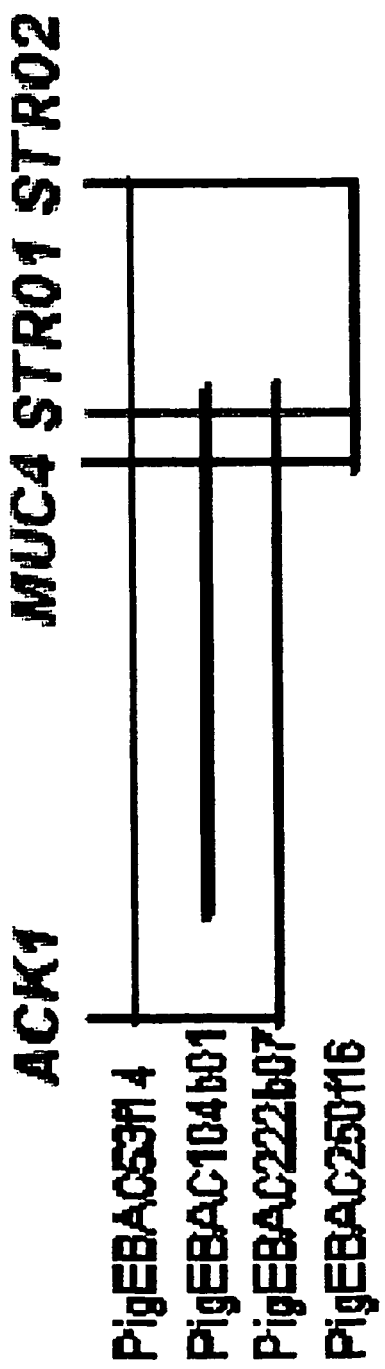
Figure 5:
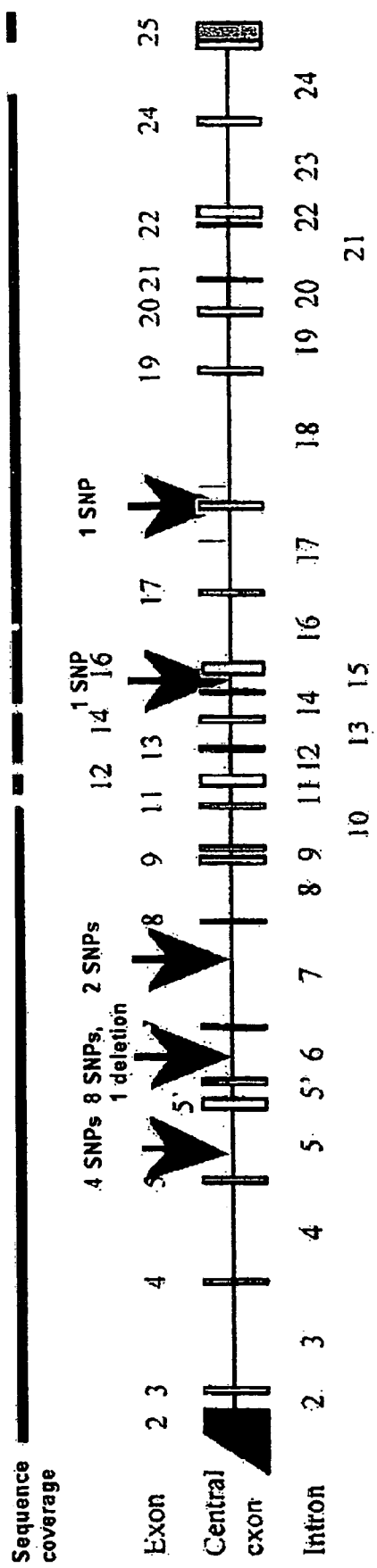

FIG. 2. shows a comparative mapping of the porcine chromosome 13 (SSC13) and the human chromosome 3 (HSA3) with the BAC sequences;

FIG. 3. shows a comparative map between SSC13 and HSA3 using the mapping results in this application;

FIG. 4. illustrates contig of the MUC4 pigEBACs;

FIG. 5. illustrates the sequencing status along with the SNP information using the human Mucin 4 genme as scaffold. The aligned porcine sequences are indicated by the solid lines over exons, vertical bars indicate exons;

FIG. 6. shows the sequence surrounding the XbaI polymorphism (SEQ ID NO:. 67). The SNP of the resistant allele is shown in bold and underlined; and FIG. 7. shows the sequence surrounding the XbaI polymorphism (SEQ ID NO:. 68). The SNP of the sensitive allele is shown in bold and underline.

EXAMPLES

Example 1

Identification of the Gene Responsible for Resistance Towards *E. coli* ETEC F4ab/F4ac Diarrhoea

1.1. Introduction

In order to characterise the gene responsible for resistance towards *E. coli* F4ab/F4ac diarrhoea it was decided to rely on the so-called 'positional candidate gene cloning' strategy (Collins 1995). The starting point was the work described by Edfors-Lilja and co-workers in 1995. This study was significantly expanded by increasing the DNA-marker density on the pig chromosome 13 (SSC13) linkage map in the same intercross pedigree that was used in the Edfors-Lilja analysis. In addition the gene mapping in the chromosomal area where the gene responsible for resistance towards ETEC F4ab/F4ac is localised were significantly improved.

In the following the work is described that was carried out in order to identify candidate genes and resulted in the identification of polymorphisms in a candidate gene showing strong linkage disequilibrium with ETEC F4ab/F4ac status in pigs.

1.2 Linkage Analysis

Animals

In the linkage analysis we used the pedigree described by Edfors-Lilja et al. (1995). The parental generation comprised two European Wild boars each mated to four Swedish Yorkshire sows. The F1 generation was intercrossed (four sires and 22 dams) to generate 200 F2 offspring. In order to obtain large full-sib families, the maitings were repeated, and the offspring were consequently born in two parities.

Adhesion Test

Epithelial cells from the upper part of the small intestine were obtained from specimens collected after slaughter of all animals. The adhesion test was performed by incubating the epithelial cells with *E. coli* F4ab and *E. coli* F4ac, respectively. Samples containing 10 to 20 cells were examined for adhesion of both *E. coli* F4ab and *E. coli* F4ac by interference contrast microscopy. The results were scored from 1 to 4, where 1=no bacteria and 4=bacteria adhering to the whole brush border of all cells (Edfors-Lilja et al., 1996).

Genotyping

Microsatellite markers (i.e. markers where the core of the marker is a tandemly-repeated sequence of two (usually) or a small number of nucleotides, where different alleles are distinguished by having different numbers of repeats) were used as genetic markers for linkage mapping.

In the present work 60 microsatellites markers from the porcine chromosome 13 (SSC13) were selected from the USDA linkage map (Rohrer et al. 1996)

One PCR primer from each of the 60 markers were fluorescently labelled with either 6-FAM, HEX or TET (Applied Biosystems, Foster City, Calif., USA) and Polymerase Chain Reaction (PCR) was carried out in a PE9600 thermocycler (Applied Blosystems, Foster City, Calif., USA) or an ABI877 (Applied Blosystems, Foster City, Cailf., USA) using 10 μl reaction volume containing 25 ng genomic DNA, 1×PCR buffer, 1.5-2.0 mM $MgCl_2$, 200 μM of each dNTP, 0.35 μM of each primer, and 0.25 units AmpliTaq Gold DNA polymerase (Applied Biosystems, Foster City, Calif., USA). Thermocycling conditions were: pre-denaturation for 10 min at 95° C., followed by 10 cycles with decreasing annealing temperatures (15 sec at 95° C., 30 sec at 64°-55° C., 60 sec at 72° C.), 25 cycles of reaction with a fixed annealing temperature (15 sec at 89° C., 30 sec at 55° C., 60 sec at 72° C.), and extension at 72° C. for 1 hour.

PCR products were loaded on 4.25% polyacrylamide denaturing sequencing gel, and run on an ABI PRISM 377 DNA sequencer. The PCR products were analyzed using the GeneScan 2 software (Applied Biosystems, Foster City, Calif., USA). Markers that amplified well, that were easy to score and showed heterozygosity in the F1-generation of the pedigree were selected for the linkage mapping in all 236 animals. In alphabetical order the following markers were used:

CP, EST24F05, PR39, S0075, S0076, S0215, 50219, S0222, S0281, S0282, S0291, SW1030, SW1056, SW1864, SW1898, SW207, SW2196, SW225, SW2412, SW398, SW458, SW698, SW769, SW864, SW873, SW882, SW937, SW955, SWRlOO8, SWR428, SWR926, and TF.

Detailed descriptions of the genetic markers can be found on the Web site of the USDA Meat Animal Research Center and in the pig genome database (ArkDB database) available on a website hosted at Roslin Institute.

Alleles were assigned and genotyping data was managed using the GEMMA software (Iannuccelli, 1996). The genotyping data were used for the construction of a SSC13 linkage map. The linkage analysis was performed using CRIMAP version 2.4 (Green et al. 1990). Initially, the option TWOPOINT was used to find linkage between the markers with a lod score higher than three. Subsequently, the option BUILD was used to construct the framework map and the remaining markers were incorporated using the option ALL. Finally, the genotypes were checked using the option CHROMPIC and the data was scrutinized for any unlikely double-recombinants.

The results of the linkage analysis map is shown in Table 1.

When the data for the F4ab/F4ac locus (the location of the gene conferring resistance/susceptibility to ETEC F4 induced disease) are added the most likely position for this locus is proximal to S0075 and it is supported by a lod score of 1.91 in comparison to the next best order where ETEC F4ab/F4ac locus is located distal to S0075. So the conclusion from the linkage analysis is the following position of F4ab/F4ac is CEN-SW207-F4ab/F4ac-S0075-TEL. The linkage map showing the position of the F4ab/F4ac locus is shown in FIG. 1

TABLE 1

The generated linkage map (sex averaged)

| Marker | Recombination | cM | Kosambi cM |
|---|---|---|---|
| S0282 | | | 0.0 |
| S0219 | 0.07 | 6.7 | 6.7 |
| SWR428 | 0.20 | 21.8 | 28.5 |
| S0076 | 0.14 | 14.3 | 42.9 |
| PR39 | 0.15 | 15.6 | 58.4 |
| SW458 | 0.04 | 4.4 | 62.9 |
| SW864 | 0.04 | 3.8 | 66.7 |
| EST24F05 | 0.00 | 0.0 | 66.7 |
| S0222 | 0.09 | 9.2 | 75.9 |
| SWR1008 | 0.01 | 0.9 | 76.8 |
| SW1864 | 0.03 | 3.3 | 80.1 |
| SW2412 | 0.02 | 2.1 | 82.1 |
| SW937 | 0.02 | 1.6 | 83.7 |
| SW882 | 0.02 | 1.5 | 85.2 |
| SWR926 | 0.00 | 0.0 | 85.2 |
| S0281 | 0.01 | 0.6 | 85.8 |
| TF | 0.03 | 2.5 | 88.4 |
| CP | 0.01 | 1.1 | 89.4 |
| SW1898 | 0.03 | 2.9 | 92.4 |
| SW2196 | 0.01 | 1.0 | 93.4 |
| SW207 | 0.01 | 1.2 | 94.6 |
| S0075 | 0.05 | 4.9 | 99.4 |
| SW225 | 0.02 | 2.2 | 101.6 |
| SW955 | 0.01 | 0.8 | 102.5 |
| SW873 | 0.02 | 1.8 | 104.3 |
| SW1030 | 0.01 | 0.5 | 104.8 |
| SW698 | 0.02 | 2.0 | 106.8 |
| SW398 | 0.04 | 3.8 | 110.6 |
| SW1056 | 0.16 | 16.7 | 127.3 |
| SW769 | 0.16 | 17.1 | 144.4 |
| S0215 | 0.03 | 3.4 | 147.8 |
| S0291 | 0.12 | 12.3 | 160.1 |

1.3 Cytogenetic Mapping

To obtain a physical map of the region containing the gene responsible for resistance owards *E. coli* F4ab/F4ac diarrhoea microsatellites markers surrounding the F4ab/F4ac locus were used to screen a pig BAC library (Anderson et al. 2000). The pig BAC library is a collection of large fragments of pig genomic DNA (average size=150,000 base pairs) in which each fragment is maintained in a bacterial artificial chromosome (BAC) cloning vector immortalised in a clone of *E. coli* bacteria.

In the present study the Roslin pigE BAC library, which consists of approximately 100,000 independent BAC clones stored as individual clones in 96-well and 384-well microplates was used. This library provides an approximately five fold coverage of the pig genome. The BAC clones were identified using PCR primers from markers Sw207, S0283, S0075, Sw1876 and Sw225 on DNA pools from the BAC clones.

DNA was extracted from the marker-positive BAC clones using the Qiagen Plasmid Midiprep kit (Qiagen, Germany) and the BACs were individually labelled with biotin-14-dATP or digoxigenin-11-dUTP (Boehringer-Mannheim, Germany) both single-colour and dual-colour fluorescent in situ hybridisation (FISH) analysis to porcine metaphase and interphase chromosomes (as described in Chowdhary et al., 1995).

The physical order of the markers were shown to be in accordance with the linkage data namely CEN-Sw207-50283-S0075-Sw1876-Sw225-TEL. BACs containing markers Sw207, S0283 and S0075 were all hybridising to pig chromosome 13 band q41 indicating that this is the candidate region. Primers for amplifying the markers mentioned herein are listed in Table 2.

TABLE 2

Sequences related to the invention

| SEQ ID NO: | Description of sequence |
|---|---|
| 1 | Genomic pig DNA showing similarity to the human Mucin 4 gene exon 2 (GenBank acc. No. AJ430032). |
| 2 | Genomic pig DNA showing similarity to the human Mucin 4 gene intron 3, exon 4 (GenBank acc. No. AJ430033). |
| 3 | Genomic pig DNA showing similarity to the human Mucin 4 gene exon 4 (GenBank acc. No. AJ430033). |
| 4 | Genomic pig DNA showing similarity to the human Mucin 4 gene intron 4, exon 5 (GenBank acc. No. AJ430034). |
| 5 | Genomic pig DNA showing similarity to the human Mucin 4 gene exon 5, intron 5 (GenBank acc. No. AJ430034). |
| 6 | Genomic pig DNA showing similarity to the human Mucin 4 gene exon 5, intron 5 (GenBank acc. No. AJ430034). Variation found at position 1059: G in resistant, A in susceptible Variation found at position 1125: G in resistant, T in susceptible Variation found at position 1134: G in resistant, A in susceptible Variation found at position 1138: G in resistant, C in susceptible |
| 7 | Genomic pig DNA showing similarity to the human Mucin 4 gene intron 6 (GenBank acc. No. AJ430034). |
| 8 | Genomic pig DNA showing similarity to the human Mucin 4 gene intron 7, exon 8, intron 8 (GenBank acc. No. AJ430034). Variation found at position 1849: G in resistant, C in susceptible Variation found at position 2129: T in resistant, C in susceptible |
| 9 | Genomic pig DNA showing similarity to the human Mucin 4 gene exon 17 (GenBank acc. No. AJ430034). |
| 10 | Genomic pig DNA showing similarity to the human Mucin 4 gene intron 17 (GenBank acc. No. AJ430034). |

TABLE 2-continued

Sequences related to the invention

| SEQ ID NO: | Description of sequence |
|---|---|
| 11 | Genomic pig DNA showing similarity to the human Mucin 4 gene intron 18 (GenBank acc. No. AJ430034). |
| 12 | Genomic pig DNA showing similarity to the human Mucin 4 gene exon 20 (GenBank acc. No. AJ430034). |
| 13 | Genomic pig DNA showing similarity to the human Mucin 4 gene exon 22 (GenBank acc. No. AJ430034). |
| 14 | Genomic pig DNA showing similarity to the human Mucin 4 gene exon 23 (GenBank acc. No. AJ430034). |
| 15 | Genomic pig DNA showing similarity to the human Mucin 4 gene intron 23 (GenBank acc. No. AJ430034). |
| 16 | Genomic pig DNA showing similarity to the human Mucin 4 gene exon 24 (GenBank acc. No. AJ430034). |
| 17 | Porcine cDNA sequence showing similarity to Homo sapiens MUC4 gene, 3' flanking region (Genbank acc. no. AJ010901). |
| 18 | upper primer related to gene ADPRLT3 |
| 19 | lower primer related to gene ADPRLT3 |
| 20 | upper primer related to gene ARF4 |
| 21 | lower primer related to gene ARF4 |
| 22 | upper primer related to gene ARP |
| 23 | lower primer related to gene ARP |
| 24 | upper primer related to gene DKFZp434P0721 |
| 25 | lower primer related to gene DKFZp434P0721 |
| 26 | upper primer related to gene GPX1 |
| 27 | lower primer related to gene GPX1 |
| 28 | upper primer related to gene KIAA0804 |
| 29 | lower primer related to gene KIAA0804 |
| 30 | upper primer related to gene KIAA1363 |
| 31 | lower primer related to gene KIAA1363 |
| 32 | upper primer related to gene MME |
| 33 | lower primer related to gene MME |
| 34 | upper primer related to gene RFC4 |
| 35 | lower primer related to gene RFC4 |
| 36 | upper primer related to gene RPL29 |
| 37 | lower primer related to gene RPL29 |
| 38 | upper primer related to gene RYBP |
| 39 | lower primer related to gene RYBP |
| 40 | upper primer related to gene SEC22A |
| 41 | lower primer related to gene SEC22A |
| 42 | upper primer related to gene SST |
| 43 | lower primer related to gene SST |
| 44 | upper primer related to gene TFDP2 |
| 45 | lower primer related to gene TFDP2 |
| 46 | upper primer related to gene TFG |
| 47 | lower primer related to gene TFG |
| 48 | upper primer related to gene TRAD |
| 49 | lower primer related to gene TRAD |
| 50 | sense primer NAU 491 |
| 51 | primer NAU 483 |
| 52 | upper ACK1 primer |
| 53 | lower ACK1 primer |
| 54 | upper MUC4 primer |
| 55 | lower MUC4 primer |
| 56 | upper STR01 primer |
| 57 | lower STR01 primer |
| 58 | upper STR02 primer |
| 59 | lower STR02 primer |
| 60 | SSMUC4_ex4U primer |
| 61 | SSMUC4_ex8L primer |
| 62 | Muc4_in7u primer |
| 63 | Muc4_in7l primer |
| 64 | Biotin labelled forward primer flanking the position 1849 SNP |
| 65 | reverse primer flanking the position 1849 SNP |
| 66 | probe specific for C allele of 1849 SNP |
| 67 | Sequence surrounding the XbaI polymorphism. Variant base in XbaI polymorphism is G in the resistant, non-digested, type. |
| 68 | Sequence surrounding the XbaI polymorphism. Variant base in XbaI polymorphism is C in the non-resistant, XbaI-digested, type. |
| 69 | Upstream primer for the SW2196 microsatellite marker (Alexander et al. (1996) Animal Genetics 27: 137-148) |
| 70 | Downstream primer for the SW2196 microsatellite marker (Alexander et al. (1996) Animal Genetics 27: 137-148) |
| 71 | Upstream primer for the SW207 microsatellite marker (Rohrer et al. (1994) Genetics 136: 231-45). |

TABLE 2-continued

Sequences related to the invention

| SEQ ID NO: | Description of sequence |
|---|---|
| 72 | Downstream primer for the SW207 microsatellite marker (Rohrer et al. (1994) Genetics 136: 231-45). |
| 73 | Upstream primer for the S0283 microsatellite marker (Davies et al. (1994) Mammalian Genome 5: 707-711). |
| 74 | Downstream primer for the S0283 microsatellite marker (Davies et al. (1994) Mammalian Genome 5: 707-711). |
| 75 | Upstream primer for the S0075 microsatellite marker (Winterø and Fredholm (1995) Animal Genetics 26: 125-126). |
| 76 | Downstream primer for the S0075 microsatellite marker (Winterø and Fredholm (1995) Animal Genetics 26: 125-126). |
| 77 | Upstream primer for the SW1876 microsatellite marker (Alexander et al. (1996) Animal Genetics 27: 137-148). |
| 78 | Downstream primer for the SW1876 microsatellite marker (Alexander et al. (1996) Animal Genetics 27: 137-148). |
| 79 | Upstream primer for the SW225 microsatellite marker (Rohrer et al. (1994) Genetics 136: 231-45). |
| 80 | Downstream primer for the SW225 microsatellite marker (Rohrer et al. (1994) Genetics 136: 231-45). |
| 81 | Genomic pig DNA showing similarity to the human Mucin 4 gene, exon 1 (GenBank acc. No. AJ000281). |
| 82 | Genomic pig DNA showing similarity to the human Mucin 4 gene, exon 1, intron 1, exon 2, intron 2, exon 3, intron 3, exon 4, intron 4, exon 5, intron 5, exon 6 (GenBank acc. Nos. AJ000281, AJ430032, AJ430033, AJ430034) Variation found at position 4847: G in resistant, A in susceptible Variation found at position 4913: G in resistant, T in susceptible Variation found at position 4922: G in resistant, A in susceptible Variation found at position 4926: G in resistant, C in susceptible |
| 83 | Genomic pig DNA showing similarity to the human Mucin 4 gene, intron 4, exon 5, intron 5, exon 6, intron 6, exon 7, intron 7, exon 8, intron 8, exon 9, intron, 9, exon 10, intron 10, exon 11, intron 11 (GenBank acc. No. AJ430034). Variation found at position 1659: T in resistant, A in susceptible Variation found at position 1666: G in resistant, T in susceptible Variation found at position 1684: A in resistant, C in susceptible Variation found at position 1726: AACGTG in resistant, 6 bp deletion in susceptible Variation found at position 1740: A in resistant, T in susceptible Variation found at position 1795: T in resistant, C in susceptible Variation found at position 1820: G in resistant, T in susceptible Variation found at position 1912: T in resistant, C in susceptible Variation found at position 2009: T/deletion, not in linkage disequilibrium Variation found at position 2997: A in resistant, G in susceptible Variation found at position 3277: C in resistant, G in susceptible |
| 84 | Genomic pig DNA showing similarity to the human Mucin 4 gene, intron 11, exon 12, intron 12 (GenBank acc. No. AJ430034). |
| 85 | Genomic pig DNA showing similarity to the human Mucin 4 gene, intron 11, exon 12, intron 12, exon 13, intron 13, exon 14, intron 14 (GenBank acc. No. AJ430034). |
| 86 | Genomic pig DNA showing similarity to the human Mucin 4 gene, intron 13, exon 14, intron 14 (GenBank acc. No. AJ430034). |
| 87 | Genomic pig DNA showing similarity to the human Mucin 4 gene, intron 14, exon 15, intron 15 (GenBank acc. No. AJ430034). Variation found at position 332 G/A, Not in linkage disequilibrium. |
| 88 | Genomic pig DNA showing similarity to the human Mucin 4 gene, intron 15, exon 16, intron 16, exon 17, intron 17, exon 18, intron 18, exon 19, intron 19 (GenBank acc. No. AJ430034).. Variation found at position 3530 G/A, Not in linkage disequilibrium |
| 89 | Genomic pig DNA showing similarity to the human Mucin 4 gene, intron 19, exon 20, intron 20, exon 21, intron 21, exon 22, intron 22, exon 23, intron 23 (GenBank acc. No. AJ430034). |
| 90 | Genomic pig DNA showing similarity to the human Mucin 4 gene, intron 22, exon 23, intron 23, exon 24, intron 24(GenBank acc. No. AJ430034). |
| 91 | Genomic pig DNA showing similarity to the human Mucin 4 gene, exon 25, 3?*** region (GenBank acc. No. AJ430034). |
| 92 | contig2 |
| 93 | contig3 |
| 94 | contig4 |
| 95 | contig9 |
| 96 | contig10 |
| 97 | contig15 |
| 98 | contig20 |
| 99 | contig21 |
| 100 | contig23 |
| 101 | contig24 |
| 102 | contig25 |
| 103 | contig26 |
| 104 | contig27 |

TABLE 2-continued

Sequences related to the invention

| SEQ ID NO: | Description of sequence |
|---|---|
| 105 | contig28 |
| 106 | contig29 |
| 107 | contig30 |
| 108 | contig31 |
| 109 | contig32 |
| 110 | contig33 |
| 111 | contig34 |
| 112 | contig35 |
| 113 | contig36 |
| 114 | contig37 |
| 115 | contig38 |
| 116 | contig39 |
| 117 | contig40 |
| 118 | contig41 |
| 119 | contig42 |
| 120 | contig44 |
| 121 | contig45 |
| 122 | contig49 |
| 123 | contig50 |
| 124 | contig51 |
| 125 | contig52 |
| 126 | contig53 |
| 127 | contig54 |
| 128 | contig55 |
| 129 | contig56 |
| 130 | contig57 |
| 131 | contig58 |
| 132 | contig59 |
| 133 | contig60 |
| 134 | contig61 |
| 135 | contig62 |
| 136 | contig63 |
| 137 | contig64 |
| 138 | contig65 |
| 139 | contig66 |
| 140 | contig67 |
| 141 | contig68 |
| 142 | contig69 |
| 143 | contig70 |
| 144 | contig71 |
| 145 | contig72 |
| 146 | contig73 |
| 147 | contig75 |
| 148 | contig76 |
| 149 | contig77 |
| 150 | contig78 |
| 151 | contig79 |
| 152 | contig80 |
| 153 | contig81 |
| 154 | contig82 |
| 155 | contig84 |
| 156 | contig85 |
| 157 | contig86 |
| 158 | contig88 |
| 159 | contig89 |
| 160 | contig90 |
| 161 | contig92 |
| 162 | contig93 |
| 163 | contig94 |
| 164 | contig97 |
| 165 | contig98 |
| 166 | contig100 |
| 167 | contig101 |
| 168 | contig102 |
| 169 | contig103 |
| 170 | contig104 |
| 171 | contig105 |
| 172 | contig106 |
| 173 | contig107 |
| 174 | contig108 |
| 175 | contig109 |
| 176 | contig110 |
| 177 | contig111 |
| 178 | contig112 |

TABLE 2-continued

Sequences related to the invention

| SEQ ID NO: | Description of sequence |
|---|---|
| 179 | contig113 |
| 180 | contig114 |
| 181 | contig115 |
| 182 | contig116 |
| 183 | contig117 |
| 184 | contig118 |
| 185 | contig119 |
| 186 | contig120 |
| 187 | contig121 |
| 188 | contig122 |
| 189 | contig123 |
| 190 | contig126 |
| 191 | contig127 |
| 192 | contig129 |
| 193 | contig131 |
| 194 | contig132 |
| 195 | 40_11.60T7.ab1 |
| 196 | bac104001a21.g1_A02_02.ab1 |
| 197 | bac104001b18.g1_H03_15.ab1 |

1.4 Comparative Mapping

To facilitate the search for the gene responsible for resistance towards *E. coli* F4ab/F4ac diarrhoea, Is was decided to take advantage of the vast amount of sequence information presented by the sequence of the total human genome.

In order to exploit this information a comparative mapping of the genes on the relevant part of the porcine chromosome 13 (SSC13) and the human chromosome 3 (HSA3) was performed.

DNA from the FISH verified BACs were digested using Sau3AI and the fragments were ligated into the BamHI site of pUC19 and transformed into *Epicurian Coli* XL1-BLUE cells (Stratagene). The transformants were plated out on LB ampicillin plates and around 100 subclones were picked at random. Plasmid DNA was isolated from the subclones using a Qiaprep spin miniprep kit (Qiagen, Germany). The inserts cloned in the plasmid vectors were sequenced using T3 and T7 primers and BigDye terminator sequencing (Applied Biosystems, Foster City, Calif. USA) and electrophoresed on an ABI377 (Applied Biosystems, Foster City, Calif. USA). The generated sequences were BLASTed against the non-redundant nucleotide database at the NCBI website.

The genes identified in the shot-gun sequencing of the BACs are listed in Table 3.

TABLE 3

Genes identified in the isolated BAC clones.

| Marker | BAC id. | Cytogenetic position on Ssc13 | Identified genes | HSA3 position |
|---|---|---|---|---|
| Sw207 | PigEBAC169o10 | q41 | KIAA0804 | 181 Mbp (q28) |
| S0283 | PigEBAC177o11 | q41 | TRAD | 121 Mbp (q21.3) |
| S0075 | PigEBAC169f15 | q41 | ADCY5, SEC22A | 120 Mbp (q21.2) |
| Sw1876 | PigEBAC242a21 | na | none | |
| Sw225 | PigEBAC76g23 | q44 | FLJ22763 | 106 Mbp (q13) |

The human data were taken from the Entrez Genome view build 30 at the NCBI website. Details of the human genes (e.g. TRAD) found in these searches of the DNA sequence database can be found on several Web sites including the NCBI website. Note that SSC13 is the porcine chromosome 13 and that HAS3 is the human chromosome 3.

Based on the matches between the sequences derived from the pig BAC clones and the human genomic sequence a comparative map between SSC13 and HSA3 was drawn, see FIG. 2.

1.5 Comparative Fine Mapping

In order to further improve the comparative map between SSC13 and HSA3, the sequences obtained by shotgun-sequencing that showed similarity to KIAA0804, TRAD and SEC22A were selected. In addition expressed sequence tags (ESTS) predicted to map to SSC13 on the basis of sequence similarity to genes and ESTs known to map to the homologous human chromosome (HSA3) were selected from our resource of porcine small intestine ESTs (Winterø et al., 1996; Winterø & Fredholm, unpublished).

Criteria for selection were that the 5' cDNA sequences of the respective clones had significant sequence identity (expectation values $<e^{-6}$) with the human orthologous genes using BLAST network service against the non-redundant nucleotide database.

Primers were designed in the 3' UTR region of the selected clones (see Table 4) in order to increase pig specificity. Primer3 (Rozen and Skaletsky, 2000) was used for designing primers. A pig somatic cell hybrid panel (Yerle et al., 1996) and a pig radiation hybrid panel (IMpRH) (Yerle et al., 1998) were used for regional assignment and mapping. PCR conditions were optimized using pig, mouse and hamster genomic DNA. The PCR was performed on 10 ng and 25 ng of DNA from each hybrid line for the somatic and radiation panels, respectively. The PCR conditions were: 0.35 µM of each primer, from 2 to 4 mM of 10 $Mg^{2+}$ and 0.05 units of Hot-StartTaq (Qiagen, Germany) in a 10 µl reaction volume, during 35 cycles with touch down (TD) 60 or 64. The PCR was performed using 15 min. initial denaturation at 95° C. and subsequently 95° C. for 15 sec. in the additional cycles. Extension was carried out at 72° C. for 1 min. The touchdown was performed by lowering the annealing temperature by 1° C. after each cycle in the first 10 cycles, starting at 64° C. or 60° C. for TD64 and TD60, respectively. The last 25 cycles were performed at annealing temperatures 54° C. or 50° C. for TD64 and TD60, respectively.

The amplification products were resolved in 2% agarose gels and manually scored. The PCR results were directly introduced into the SCH and RH data analysis programs described in Milan et al. (2000). Regional assignment was achieved by using the computer program developed by Chevalet et al. (1997). The results of the radiation hybrid PCR products were analysed with the IMpRH mapping tool developed by Milan et al. (2000). The genes and their localisations are shown in Table 4.

A comparative map between SSC13 and HSA3 using the mapping results from 4 is shown in FIG. 3.

When previously reported comparative data were added (Sun et al. 1999; Van Poucke et al. 1999, Pinton et al. 2000, Van Poucke et al. 2001) to the data generated in this study a comprehensive comparative map between SSC13 and HSA3 was compiled. When zooming in on the candidate region (SCC13q41) it became evident that the candidate regions on HSA3 are q21 and q28-qtel.

1.6 Candidate Genes

When scanning the literature for possible candidate genes for the ETEC F4ab/F4ac status in pigs there have been several reports of proteins associated with susceptibility towards ETEC F4ab/F4ac (Metcalfe et al., 1991; Grange and Mouricout, 1996; Francis et al., 1998; Grange et al., 1998). One report indicates that it is a 74-kDa glycoprotein that belongs to the transferrin family (Grange and Mouricout, 1996), one group suggests glycoproteins of 40 kDa (Metcalfe et al., 1991) and more recent studies points to mucin-type sialoglycoproteins (Francis et al. 1998; Grange et al. 1998). When we considered these reports it became clear that the search for a gene should concentrate on either transferrin-like-genes or mucin-like genes. If the linkage and comparative data was added one gene from the candidate regions of HSA3 became the positional candidate, namely Mucin 4 (MUC4) at Hsa3q29.

TABLE 4

List of genes selected for hybrid cell mapping

| Gene symbol (E-value) | Clone (labid.) | Accession number (GenBank) | Human cytogenetic position | Pig cytogenetic position | PCR primers Upper | Lower |
|---|---|---|---|---|---|---|
| ADPRTL3 (6e-13) | C16b04 | AJ508800 | 3p22.2-21.1 | 13q21-q22 | 5'-CCCAGCCATGCTAGGACTAA (SEQ ID NO: 18) | 5'-AGATTCGCCTCTGAGGTGTC (SEQ ID NO: 19) |
| ARF4 (1e-133) | c11f10 | AJ508808 | 3p21.1 | 13(q21-q22 or q23-1/2q41) | 5'-ACCAAAAGCAACATGCAACA (SEQ ID NO: 20) | 5'-CAGGGAATGCTCCAAAACAC (SEQ ID NO: 21) |
| ARP (2e-74) | c15g08 | AJ508798 | 3p21.1 | 13(q21-q22 or q23-1/2q41) | 5'-TAGTGTAAACCCGCAACAGA (SEQ ID NO: 22) | 5'-AACAGTTCATCTGTGTCTTC (SEQ ID NO: 23) |
| DKFZp434-P0721 (2e-43) | c18g08 | AJ508802 | 3q24 | 13q23-1/2q41 | 5'-ACAGCATGAAAAGTGCCTGA (SEQ ID NO: 24) | 5'-TCCATATCTGTGTCTCATAAA-AA (SEQ ID NO: 25) |
| GPX1 (1e-6) | c17d11 | AJ508799 | 3p21.3 | 13(q21-q22 or q23-1/2q41) | 5'-TAGTGAGGAACTGTGGTCTG (SEQ ID NO: 26) | 5'-ATATCGAGCCTGACATCGAA (SEQ ID NO: 27) |
| KIAA0804 (3e-49) | PigEBAC 169o10 | AY156078 | 3q27 | 13q41 | 5'-CTATGTGCCCATGTGCATTC (SEQ ID NO: 28) | 5'-AACCTGAGAGCATCGGTCAC (SEQ ID NO: 29) |
| KIAA1363 (1e-64) | c03b02 | AJ508807 | 3q26.2-q27 | 13q23-1/2q41 | 5'-TCAAGAGGGGCTCAACACTT (SEQ ID NO: 30) | 5'-TGGAATCATGTACGCAAAGC (SEQ ID NO: 31) |
| MME (2e-77) | c14c07 | AJ508801 | 3q25.1-25.2 | 13q23-1/2q41 | 5'-CATATCCACTCCAGGGACAC (SEQ ID NO: 32) | 5'-ACCAAGACAGTTATGAACCA (SEQ ID NO: 33) |
| RFC4 (7e-30) | c18a04 | AJ508811 | 3q27 | 13(1/2q46-q49) | 5'-CGGTGCTTTGGTCATTTTTA (SEQ ID NO: 34) | 5'-TGCTTAGCTGATGGTGCTGA (SEQ ID NO: 35) |
| RPL29 (3e-80) | c11b05 | AJ508797 | 3q21.3-p21.2 | 13q21-q41 | 5'-GACAGATCCTGAGGCAGGTT (SEQ ID NO: 36) | 5'-CAGGTTCTGCCGGCCAAAGT (SEQ ID NO: 37) |
| RYBP (7e-43) | c17g07 | AJ508795 | 3p12.3 | 13q23-1/2q41 | 5'-AAGCAGAGCAGGTCAATTAAGG (SEQ ID NO: 38) | 5'-TATTCAGCGGCACAGTAAGC (SEQ ID NO: 39) |
| SEC22A (2e-60) | PigEBAC 169f15 | AY156080 | 3q21.2 | 13q41 | 5'-CCAGCCGGTGTAGTAGACAAG (SEQ ID NO: 40) | 5'-CCCTTTTAAGGTGTGGAGCTT (SEQ ID NO: 41) |
| SST (1e-131) | c09c04 | AJ508810 | 3q28 | 13(1/2q41 or 1/2q46-q49) | 5'-TTTGGAGGAGAGGAATTGGA (SEQ ID NO: 42) | 5'-TGGAGCCTGAAGATTTGTCC (SEQ ID NO: 43) |
| TFDP2 (3e-83) | c13g02 | AJ508806 | 3q23 | 13q23-1/2q41 | 5'-ATAGTAAAACGCGGGTTTGC (SEQ ID NO: 44) | 5'-GCTGAAGTGGCCTTAGCAAC (SEQ ID NO: 45) |
| TFG (6e-64) | c17b07 | AJ508803 | 3q11-q12 | 13q42-1/2q46 | 5'-AGATGACTGAACTTCAACCTAG-CA (SEQ ID NO: 46) | 5'-AGCAGCTTCCTAGTTACTTTGG (SEQ ID NO: 47) |
| TRAD (5e-76) | PigEBAC I77o11 | AY156082 | 3q21.3 | 13q41 | 5'-CAGGAAGAGCCCCCTAAATC (SEQ ID NO: 48) | 5'-CAGCAAAGGCAGAAACCTTC (SEQ ID NO: 49) |

Example 2

Cloning the Dorcine MUC4 Gene

2.1 Screening Pig BACs containing MUC4

In order to investigate if the MUC4 gene indeed is the gene responsible for resistance towards *E. coli* ETEC F4ab/F4ac diarrhoea, large portions of the gene were cloned and sequenced.

Plasmid S1325 containing a 3229 bp RACE PCR fragment of the human MUC4 cDNA (Moniaux et al., 1999) was obtained from prof. J.P. Aubert. The fragment was synthetised using total RNA from human colon mucosa. Advantage™ RT-for-PCR kit (Clontech, Heidelberg, Germany) was used to synthesize first-strand cDNA from 1 µg of RNA using the oligo (dT)-anchor primer of the 5'/3'-RACE kit (Boehringer Mannheim, Roche Diagnostics, Meylan, France). Expand long PCR was performed using Expand™ Long Template PCR System (Boehringer Mannheim) with the sense primer NAU 491 (5'-AGCAGGCCGAGTCTTGGATTA-3', SEQ ID NO:. 50), and as antisense primer the PCR anchor primer of the 5'/3'-RACE kit was used. The PCR amplification reaction mixture (50 µl) contained 5 µl of cDNA, 10 mM sodium dNTPs, 0.4 µM of each primer, 5 µl of 10×Expand™ Long Template PCR buffer 3, 0.75 mM MgC12 and 2.5 units of enzyme mixture. The PCR was performed using a Perkin-Elmer Thermal Cycler Gene Amp® PCR System 9700. PCR parameters were 94° C. for 2 min, followed by 30 cycles at 94° C. for 30 s, annealing at 60° C. for 45 s and elongation at 71° C. for 4 min, of which the 20 last cycles had their elongation time extended by 40 s for each new cycle, followed by a final elongation at 71° C. for 15 min. Nested PCR was carried out using NAU 483 (5'-25 CTGTTTCTCTACCA-GAGCGGT-3', SEQ ID NO:. 51) and the PCR anchor primer. The amplified product was electrophoresed on 1% TBE (1 ×TBE=45 mM Tris/borate/1 mM EDTA) agarose gel and stained with ethidium bromide. The band was cut out, purified using QIAquick Gel Extraction Kit (Qiagen), and subcloned into the Original TA Cloning® Kit (Invitrogen, Leek, The Netherlands). The insert was purified and randomly labelled using 32P-dCTP.

High density gridded filters of a Pig BAC library (Anderson et al., 2000) provided by UK HGMP Resource Centre was hybridised with the human MUC4 probe.

Four positive BAC clones were selected and these are listed in Table 5.

TABLE 5

Mucin 4 positive Pig EBAC clones
Clone name

PigEBAC53f14
PigEBAC104b01
PigEBAC222b07
PigEBAC250f16

2.2 Contig of MUC4 Pig E BAC clones

The ends of the four MUC4 pig E BAC clones along with subclones from each of the four MUC4 pig E BAC clones were sequenced using BigDye terminator chemistry and sequence tagged sites (STSS) were derived. The STSs are listed in Table 6.

TABLE 6

STSs used for BAC contig

| Name | Upper primer | SEQ ID NO: | Lower primer | SEQ ID NO: |
|---|---|---|---|---|
| ACK1 | 5'-CGTGACGACCTCAACGTTAC | 52 | 5'-CTGCCGATCTTCAGGTC | 53 |
| MUC4 | 5'-CTACTCCAACCCTCCCCTCA | 54 | 5'-GAAATCAGCATCATCCCAGAA | 55 |
| STR01 | 5'-CACACATGTTCATACAGTGCTGA | 56 | 5'-CCAGGCACTTCTGGCTCTTA | 57 |
| STR02 | 5'-CAATGTGCCAATTTCCACTG | 58 | 5'-ATACGGGGAGTTTGGGGTTA | 59 |

This allowed a partial determination of how the BAC clones overlap. The contig is shown in FIG. 4.

From the BAC end sequence it was shown that PigEBAC250f16 contained a 5'-truncation of the MUC4 gene. PigEBACs 53f14 and 222b07 contained a gene upstream to MUC4, namely ACK1 and thus these clones are good candidates for containing the entire pig genomic MUC4 sequence. Due to its the smaller size clone 222b07 was selected for further sequencing.

2.3 Shotgun Sequencing of PigEBAC222b07

BAC DNA was prepared using the Qiagen Large-construct kit (Qiagen, Germany) and the BAC DNA was subcloned using the TOPO shotgun subcloning kit (Invitrogen, Calif., USA). Clones were plated on LB ampicillin plates and 1536 clones were picked into four 384-well plates. Plasmid preparations were performed using Qiaprep spin miniprep kit (Qiagen, Germany). The inserts were sequenced using T3 and T7 primers and BigDye terminator sequencing (Applied Biosystems, Foster City, Calif., USA) and electrophoresed on an ABI3100 (Applied Biosystems, Foster City, Calif., USA).

The generated tracefiles were base called and quality checked using PHRED (Ewing et al., 1998), vector sequences were masked out using CROSS MATCH, sequences were assembled into contigs using PHRAP and viewed using CONSED (Gordon et al. 1998). All generated sequences (ie. contigs and singlet) The sequences were BLAST-searched against the non-redundant nucleotide database at the NCBI website. In addition FASTA33 searches using the human MUC4 genomic sequences (GenBank accession AJ430032, AJ430033, AJ430034) was performed.

Around 1200 subclones have been sequenced and sequences from all 25 exons of the porcine MUC4 have been identified by comparison of the pig sequences with the sequence of the human MUC4 gene. We have full sequence information from all exons except exons 1 and 25. Further, we have sequence information on all introns, and we have full information except from introns 1, 11, 14, 16, 19 and 24 (See Table 2, "Sequences related to the invention").

Example 3

Identifying Polymorphisms in the MUC4 Gene Linked to Resistance towards *E. coli* ETEC F4ab/F4ac Diarrhoea To identify possible genetic variations in the porcine MUC4 gene that links to resistance towards *E. coli* ETEC F4ab/F4ac diarrhoea the sequence information obtained in example 2 was exploited as described.

After having generated the sequences of exons 4 and 8 the following PCR primers were designed:

```
SSMUC4_ex4U:
5'-GAC TTC ACC TCG CCA CTC TT      (SEQ ID NO:. 60)

SSMUC4_ex8L:
5'-CGA TAC TTC TCC CAC ACT GG      (SEQ ID NO:. 61)
```

Using these primers on pig genomic DNA we generated an approximately 4 kb long range PCR product using Elongase (Invitrogen, Calif., USA). Initial denaturation was 94° C. for 2 min and 35 cycles 94° C. 30 s, 60° C. 1 min, 68° C. 10 min. After amplification different restriction enzymes were tested on amplified fragments from animals with known F4ab/F4ac genotype and a XbaI polymorphism was discovered.

3.1 Linkage Analysis with MUC4

The pedigree used in the linkage analysis was genotyped for the XbaI polymorphism and complete co-segregation with the F4ab/F4ac was shown. Multi-point analysis firmly localised MUC4 to the interval between Sw207 and S0075, showing no recombination with the F4ab/F4ac locus.

3.2 Linkage Disequilibrium

In the 10 parental animals of the linkage mapping pedigree 18 chromosomes have known F4ab/F4ac status (ie. The chromosomal region is known to be either susceptible or resistant). The haplotypes surrounding the F4ab/F4ac locus show maximal linkage disequilibrium with MUC4. The probability of such observation using Fisher's exact test is P=0.00005. None of the other markers in the region are showing the same degree of linkage disequilibrium.

3.3 RT-PCR

Complementary DNA was synthesised from RNA isolated from mucosal tissue of jejunum, ileum and colon. The SSMUC4_ex4U/SSMUC4_ex8L primers were used in PCR on 5 ng of cDNA from the different tissues in a total volume of 20:1 using 1×PCR buffer, 200:M of each dNTP, 0.4:M of each primer and 0.25 units HotStarTaq (Qiagen, USA).

Thermocycling was performed using 15 min initial denaturation at 95° C. and subsequently 95° C. for 15 s in the additional cycles. Extension was carried out at 72° C. for 1 min. Touchdown was performed lowering the annealing temperature by 1° C. after each cycle in the first 10 cycles, starting at 60° C. The last 25 cycles were performed at annealing temperature 50° C.

Electrophoresis in 2% agarose gel revealed a RT-PCR product of around 600 bp in all three tissues.

The result clearly showed that Mucin 4 was expressed in jejunum, ileum and colon in pigs.

3.5 Characterisation of the XbaI-Polymorphism

By using PCR and sequencing of PCR products, genomic sequences were generated of pigs with known F4ab/F4ac genotypes from the used pedigree. Seventeen polymorphisms in the genomic sequence of the MUC4-gene were found. In the region exon 5 to exon 8 two MUC4-haplotypes, which differ by at least 14 single nucleotide substitutions and a 6 bp deletion, can be described. One of these haplotypes is consistent with the resistance allele towards *E. coli* F4ab/F4ac diarrhoea and the other haplotype with the susceptibility towards *E. coli* F4ab/F4ac diarrhoea in our family material. In FIG. 5. the current sequencing status is shown using the genomic organisation of the human MUC4 as a scaffold.

In Tables 7A-D the differences between the two haplotypes are shown.

TABLE 7A

Positions of polymorphisms. The positions are related to the two sequences of SEQ ID NO: 6 and SEQ ID NO: 8. The polymorphisms of SEQ ID NO: 6 are present in a part of the sequence that shows similarity of intron 5 of the human MUC4 gene. The polymorphisms of SEQ ID NO: 8 are present in a part of the sequence that shows similarity of intron 7 of the human MUC4 gene.

| | Sequence | | | | | |
|---|---|---|---|---|---|---|
| | SEQ ID NO: 6 | | | | SEQ ID NO: 8 | |
| | Position in sequence | | | | | |
| | 1059 | 1125 | 1134 | 1138 | 1849 | 2129 |
| Resistant haplotype | G | G | G | G | G | T |
| Susceptible haplotype | A | T | A | C | C | C |

TABLE 7B

Positions of polymorphisms. The positions are related to the sequences of SEQ ID NO: 82. The polymorphisms are present in a part of SEQ ID NO: 82 that shows similarity of intron 5 of the human MUC4 gene.

| | Sequence SEQ ID NO 82 | | | |
|---|---|---|---|---|
| | Position in sequence | | | |
| | 4847 | 4913 | 4922 | 4926 |
| Resistant haplotype | G | G | G | G |
| Susceptible haplotype | A | T | A | C |

TABLE 7C

Positions of polymorphisms. The positions are related to the sequences of SEQ ID NO: 83. The polymorphisms are present in a part of SEQ ID NO: 83 that shows similarity of intron 6 of the human MUC4 gene.

| | Sequence SEQ ID NO: 83 Position in sequence | | | | | | | | |
|---|---|---|---|---|---|---|---|---|---|
| | 1659 | 1666 | 1684 | 1726 | 1740 | 1795 | 1820 | 1912 | 2009 |
| Resistant haplotype | T | G | A | AACGTG | A | T | G | T | T/deletion not in linkage disequilibrium |
| Susceptible haplotype | A | T | C | deletion | T | C | T | C | |

TABLE 7D

Positions of polymorphisms. The positions are related to the sequences of SEQ ID NO:s 83, 87 and 88. The two polymorphisms of SEQ ID NO: 83 are present in a part of the sequence that shows similarity of intron 7 of the human MUC4 gene. Accordingly, the polymorphisms of SEQ ID NO: 87 are present in parts of the sequences related to intron 15 and Exon 18, respectively.

| | Sequence/SEQ ID NO: | | | |
|---|---|---|---|---|
| | Intron 7/ SEQ ID NO: 83 | | Intron 15/ SEQ ID NO: 87 | Exon 18/ SEQ ID NO: 88 |
| | Position in sequence | | | |
| | 2997 | 3277 | 332 | 3530 |
| Resistant haplotype | A | C | G/A not in linkage disequilibrium | G/A not in linkage disequilibrium |
| Susceptible haplotype | G | G | | |

EXAMPLE 4

DNA-Based Assays that Discriminate between the Resistant and Susceptible Alleles in the MUC4-Gene In order to facilitate the validation of the MUC4 polymorphism different tests to discriminate between the resistant and susceptible alleles in the MUC4-gene were developed. The first SNP discovered was at the 1849 position in sequence #8 (intron 7). This SNP results in an XbaI restrictionsite in the resistant allele. The SNP was discovered using long-range PCR-RFLP (see Example 3) and after further characterisation a simple PCR-based test to allow more rapid genotyping was developed. Furthermore, a Dynamic allele-specific hybridisation assay to allow genotyping of crude DNA preparations was developed. The consensus sequence around the position 1849 SNP is shown in FIGS. 6 and 7.

4.1 PCR-RFLP

In the PCR-RFLP assay we performed PCR on 25 ng genomic DNA from pig in a total volume of 20:1 using 1×PCR buffer, 200:M of each dNTP, 0.4:M of each primer and 0.25 units HotStarTaq (Qiagen, USA). The primer sequences are as follows:

```
Muc4_in7u:
5'-GTG CCT TGG GTG AGA GGT TA-3'    (SEQ ID NO:. 62)

Muc4_in7l:
5'-CAC TCT GCC GTT CTC TTT CC-3'    (SEQ ID NO:. 63)
```

Thermocycling was performed using 15 min initial denaturation at 95° C. and subsequently 95° C. for 15 s in the additional cycles. Extension was carried out at 72° C. for 1 min. Touchdown was performed lowering the annealing temperature by 1° C. after each cycle in the first 10 cycles, starting at 60° C. The last 25 cycles were performed at annealing temperature 50° C. The PCR product obtained from pig genomic DNA is 367 bp and 10 µl of the PCR product is used for XbaI digest as recommended by the supplier (New England Biolabs, Mass., USA). After digest with XbaI the fragments are:

| Resistant allele | 367 bp |
|---|---|
| Susceptible allele | 151 bp, 216 bp |

The following patterns are observed from the three different genotypes:

| Resistant | 367 bp |
|---|---|
| Susceptible heterozygote | 151 bp, 216 bp, 367 bp |
| Susceptible homozygote | 151 bp, 216 bp |

4.2 Dynamic Allele-Specific Hybridisation (DASH) Assay

DASH was carried out as described in Howell et al. (1999) and by the use of primers flanking the position 1849 SNP, the conditions were as follows:

```
Biotin labelled forward primer:
                                    (SEQ ID NO:. 64)
5'-biotin-GGCAATGACTTATCTATTTGTACC-3'

Reverse primer:
                                    (SEQ ID NO:. 65)
5'-GTATATTACAACAACCCCATGAAGG-3'

Probe specific for the C allele:
                                    (SEQ ID NO:. 66)
5'-CCATTCTAGAGATACAG-3'
```

PCR was performed in 20 µl using the following reagents:

| | |
|---|---|
| Water | 13.52 µl |
| MgCl$_2$ (25 mM) | 0.80 µl |
| 10 × PCR buffer | 2.00 µl |
| Biotin-labelled forward primer (2.5 pmol/µl) | 0.80 µl |
| Non-labelled revers primer (15 pmol/µl) | 0.80 µl |
| Taq polymerase (5 units/µl) | 0.08 µl |
| DNA (10-25 ng/µl) | 1.00 µl |
| dNTP mix (4 mM each) | 1.00 µl |
| Total | 20.00 µl |

Thermocycling was performed using 15 min initial denaturation at 95° C. and subsequently 95° C. for 15 s in the additional cycles. Extension is carried out at 72° C. for 1 min. Touchdown was performed lowering the annealing temperature by 1° C. after each cycle in the first 10 cycles, starting at 60° C. The last 25 cycles were performed at annealing temperature 50° C.

After PCR 10 µl of HEN buffer (0.1 M HEPES, 50 mM NaCl, 10 mM EDTA pH=8.0) and 10 µl of PCR product were added to each well of a streptavidin coated microtiter plate and incubated for 16 hours at +4° C. The PCR mixture was removed and 50 µl of 0.1 M NaOH was added and incubated for 1-5 min. and removed. The plate was then washed with 50 µl of HEN buffer. DASH buffer (1 µl SybrGreen (Molecular Probes, Oreg., USA) in 10 ml HEN buffer) (49 µl) and 1 µl of the allele specific probe (30 pmol/µl) was added to each well. Samples was heated to 85° C. and let to cool down to between 20° C. and 25° C. in less than 10 min. Samples was washed with 50 µl HEN buffer and 50 µl DASH buffer was added. DASH was performed using heat rate set at 0.03 and heat range 35° C. to 90° C.

4.3 Validation

The tests were verified on the pig pedigree material and as described previously that maximal linkage disequilibrium between F4ab/F4ac and MUC4 were found. In addition 13 unrelated pigs were tested with score 4 (i.e. strong adhesion) in the adhesion test and they all had at least one copy of the susceptible haplotype. Twenty piglets with *E. coli* O149, F4ac diarrhoea have also been genotyped in the MUC4 locus and all carried the susceptible haplotype. Nine resistant animals were tested and all animals showed either no or weak adhesion. In order to test previous report that the Chinese pig breed Meishan is resistant two sows were tested and both were shown to be homozygous for the resistant haplotype.

Example 5

Population Studies

The long range PCR-RFLP test was used in a limited number of animals from the four main commercial breeds in Denmark. The estimated frequencies of the *E. coli* F4ab/F4ac susceptibility allele are shown in Table 8.

TABLE 8

Frequencies of the position 1849 C allele (ETEC F4ab/F4ac susceptible)

| | No. Animals | f(pos 1849 C) |
|---|---|---|
| Duroc | 17 | 0.06 |
| Hampshire | 9 | 0.00 |
| Landrace | 14 | 0.96 |
| Yorkshire | 19 | 0.58 |
| Total | 59 | 0.44 |

Conclusion

The F4ab/F4ac locus has been firmly positioned by linkage analysis and Mucin 4 was a strong positional candidate gene. Expression analysis by the use of RT-PCR clearly showed that MUC4 is expressed in intestinal mucosa in the pig. Polymorphisms in introns 5 and 7 of Mucin 4 have been discovered and two haplotypes of the gene are presented. The difference between the two haplotypes shows at least 14 substitutions and this indicate haplotypes with different origins, ie. Asian and European. The two founder wild boars in the family material are homozygous resistant for ETEC F4ab/F4ac and they share the same haplotype for the MUC4-gene. Two of the Yorkshire sows were heterozygous ETEC F4ab/F4ac susceptible and these two sows had both the resistant and susceptible haplotypes. The remaining Yorkshire sows were homozygous and all had the same haplotype of the MUC4-gene. Sequencing of unrelated commercial pigs has not contributed extra haplotypes. Genotyping of Chinese Meishan pigs was in agreement with this breed being resistant towards *E. coli* F4ab/F4ac.

Example 6

Identification of New Genetic Polymorphisms

Given the technical means that are provided with the present invention new genetic polymorphisms are easily identified by the following procedure.

Shot-gun sequencing is continued and the entire PigEBAC222b07 is assembled into one contig. The entire genomic sequence of porcine Mucin 4 will be revealed and PCR primers flanking each of the 25 exons is designed. The 25 exons are sequenced in animals with the different Mucin 4 genotypes. Comparisons of the exon sequences will reveal coding SNPs and these is tested in the pedigree used for linkage mapping and in additional unrelated animals.

Regions flanking the Mucin 4 gene will also be sequenced and SNPs in these region is tested for linkage disequilibrium.

The region showing maximal linkage disequilibrium will be characterised using SNPs flanking the Mucin 4 region on pig chromosome 13.

Real time RT-PCR will be used to evaluate MUC4 expression profiles in all three different Mucin 4 haplotypes.

Transfection studies and the use of transgenic animals using different porcine Mucin 4 gene variants will be used to prove the association between Mucin 4 variants and ETEC F4ab/F4ac status.

REFERENCES

Anderson S I, Lopez-Corrales N L, Gorick B, Archibald A L. (2000). A large-fragment porcine genomic library resource in a BAC vector. *Mammalian Genome.* 11(9): 811-814

Ausubel et al. (2000). Current protocols in molecular biology. John Wiley and Sons, Inc., N.Y.

Chevalet C, Gouzy J, SanCristobal-Gaudy M (1997) Regional assignment of genetic markers using a somatic cell hybrid panel: a WWW interactive program available for the pig genome. *Comput Appl Biosci.* 13, 69-73

Chowdhary B P, de la Sena C, Habitz I, Eriksson L, Gustavsson I. (1995). FISH on metaphase and interphase chromosomes demonstrates the physical order of the genes fro GPI, CRC, and LIPE in pigs. *Cytogenetics and Cell Genetics* 71, 175-178.

Collins F S (1995) Positional cloning moves from perditional to traditional. *Nature Genetics* 9: 347-350.

Edfors-Lilja I, Gustafsson U, Duval-Iflah Y, Ellegren H, Johansson M, Juneja R K, Marklund L, Andersson L. (1995) The porcine intestinal receptor for *Escherichia coli* K88ab, K88ac: regional localization on chromosome 13 and influence of IgG response to the K88 antigen. *Animal Genetics* 26(4): 237-42.

Edfors-Lilja I, Petersson H, Gahne B (1996). Performance of pigs with or without the itesinal receptor for *Escherichia coli* K88. Animal production 42, 381-387

Ewing B, Hillier L, Wendl M C, Green P (1998) Base-calling of automated sequencer traces using phred. I. Accuracy assessment. *Genome Research* 8, 175-85.

Francis D H, Grange P A, Zeman D H, Baker D R, Sun R, Erickson A K. (1998) Expression of mucin-type glycoprotein K88 receptors strongly correlates with piglet susceptibility to K88+ enterotoxigenic *Escherichia coli*, but adhesion of this bacterium to brush borders does not. *Infection and Immunity* 66, 4050-4055.

Gibbons R A, Sellwood R, Burrows M, Hunter P A. (1977). Inheritance of resistance to neonatal diarrhoea in the pig: examination of the genetic system. *Theoretical and applied genetics* 81: 65-70.

Grange P A, Erickson A K, Anderson T J, Francis D H (1998) Characterization of the carbohydrate moiety of intesinal mucin-type sialoglycoprotein receptors for the K88ac fimbrial adhesin of *Escherichia coil. Infection and Immunity* 66, 1613-1621.

Grange P A, Mouricout, M A. (1996) Transferrin associated with the porcine intestinal mucosa is a receptor specific for K88ab flmbriae of *Escherichia coil*. Infection and Immunity 64, 606-610.

Green, P., Falls, K., Crooks, S. (1990). *Documentation for CRI-MAP, version* 2.4 (Mar. 26, 1990).

Gordon D, Abajian C, Green P. (1998) Consed: a graphical tool for sequence finishing. *Genome Research* 8, 195-202.

Guérin G, Duval-Iflah Y, Bonneau M, Bertaud M, Guillaume P, Ollivier L (1993). Evidence for linkage between K88ab, K88ac intesinal receptors to *Escherichia coli* and transferrin loci in pigs. *Animal Genetics* 24, 393-396.

Howell W M, Jobs M, Gyllensten U and Brookes A J (1999) Dynamic Allele-Specific Hybridisation : A New Method for Scoring Single Nucleotide Polymorphisms. *Nature Biotech* 17, 87-88

Iannuccelli E., Woloszyn N, Arhainx J, Gellin J, Milan D. (1996). GEMMA: a database to manage and automate microsatellite genotyping. *Animal Genetics* 27, S2, 55.

Lathrop G M, Lalouel J M, Julier C, Ott J (1985) Multilocus linkage analysis in humans: detection of linkage and estimation of recombination. Am J Hum Genet 37, 482-498

Metcalfe J W, Krogsfelt K A, Krivan H C, Cohen P S, Laux D C. (1991) Characterization and identification of a porcine small intestine mucus receptor for the K88ab fimbrial adhesin. *Infection nad immunity* 59, 91-96.

Milan D, Hawken R, Cabau C, Leroux S, Genet C (2000) IMpRH server: an RH mapping server available on the Web. *Bioinformatics* 16, 558-559.

Moniaux N, Nollet S, Porchet N, Degand P, Laine A, Aubert J P. (1999) Complete sequence of the human mucin MUC4: a putative cell membrane-associated mucin. *Biochemical Journal* 338, 325-33.

Ojeniyi B, Ahrens P, Meylin A. (1994). Detection of fimbrial and toxin genes in *Escherichia coli* and their prevalence in piglets with diarrhoea. The application of colony hybridzation assay, polymerase chain reaction and phenotypic assays. *Journal of veterinary medicine series B.* 41: 49-59.

Pinton P, Schibler L, Cribiu E, Gellin J, Yerle M (2000) Localization of 113 anchor loci in pigs: improvement of the comparative map for humans, pigs, and goats. *Mammalian Genome* 11, 306-315.

Van Poucke M, Tömsten A, Mattheeuws M, Van Zeveren A, Peelmann U, Chowdhary B P. (1999). Comparative mapping between human chromosome 3 and porcine chromosome 13. *Cytogenetics and Cell Genetics* 85, 279-284.

Van Poucke, Yerle M, Tuggle C, Piumi F, Genet C, Van Zeveren, Peelman U. (2001) Integration of porcine chromosome 13 maps. *Cytogenetics and Cell Genetics* 93: 297-303.

Rohrer G A, Alexander U, Hu Z, Smith TP, Keele J W, Beattie C W. (1996) A comprehensive map of the porcine genome. *Genome Research* 6(5):371-91

Rozen S, Skaletsky H (2000) Primer3 on the WWW for general users and for biologist programmers. *Methods Mol Biol.* 132, 365-386.

Sambrook et al. 1989. Molecular Cloning, A Laboratory Manual, 2nd Edition. Cold Spring Harbor Laboratory Press, Cold Spring Harbor, N.Y.

Sellwood R, Gibbons R A, Jones G W, Rutter J M. (1975). Adhesion of enteropathogenic *escherichia coli* to pig intestinal brush borders: the existence of two pig phenotypes. *Journal of medical microbiology* 8: 405-411.

Sun H-F S, Ernst C W, Yerle M, Pinton P, Rothschild M F, Chardon P, Rogel-Gaillard C, Tuggle C K (1999). Human chromosome 3 and pig chromosome 13 show complete synteny conservation but extensive gene-order differences. *Cytogenetics and Cell Genetics* 85, 273-278.

Wilson R A, Francis D H. (1986) Fimbrial and enterotoxins associated with *E. coli* serotypes isolated from clinical cases of porcine colibacillosis. *American Journal of Veternary Research.* 47:213-217.

Winterø A K, Fredholm M, Davies W (1996) Evaluation and characterization of a porcine small intestine cDNA library: analysis of 839 clones. *Mammalian Genome* 7, 509-517.

Yerle M, Echard G, Robic A, Mairal A, Dubut-Fontana C et al. (1996) A somatic cell hybrid panel for pig regional gene mapping characterized by molecular cytogenetics. *Cytogenet Cell Genet* 73, 194-202.

Yerle M, Pinton P, Robic A, Alfonso A, Palvadeau Y et al. (1998) Construction of a whole-genome radiation hybrid panel for high-resolution gene mapping in pigs. *Cytogenet Cell Genet* 82, 182-188.

The invention claimed is:

1. A method for identifying if a pig is resistant or non-resistant to an *E. coli* pathogen carrying fimbriae F4ac or F4 ab, the method comprising
   i) obtaining a sample from said pig, said sample comprising genomic material,
   ii) detecting in said genetic material the genotype of alleles of a genetic polymorphism indicative of resistance or susceptibility to said *E. coli* pathogen;
   iii) determining that said pig is resistant to said *E. coli* pathogen if the pig is homozygous for an allele of the genetic polymorphism indicative of resistance to ETEC;
   iv) determining that said pig is non-resistant to said *E. coli* pathogen and a non-carrier of resistance to said *E. coli* pathogen if the pig is homozygous for an allele of the genetic polymorphism indicative of non-resistance to said *E. coli* pathogen; and
   v) determining that said pig is non-resistant to said *E. coli* pathogen and a carrier of resistance to said *E. coli* pathogen if the pig is heterozygous and contains both an allele of the genetic polymorphism indicative of resistance to ETEC and an allele of the genetic polymorphism indiciative of non-resistance to said *E. coli* pathogen,
   wherein the allele of a genetic polymorphism indicative of resistance to ETEC is selected from the group consisting of: G at position 1849 of SEQ ID NO: 8; T at position 2129 of SEQ ID NO: 8; A at position 2997 of SEQ ID NO: 83; and C at position 3277 of SEQ ID NO: 83, and
   wherein the allele of a genetic polymorphism indicative of non-resistance to ETEC is selected from the group consisting of: C at position 1849 of SEQ ID NO: 8; C at position 2129 of SEQ ID NO: 8; G at position 2997 of SEQ ID NO: 83; and G at position 3277 of SEQ ID NO: 83.

2. A method according to claim 1, wherein the pig is selected from the group of pigs consisting of *sus scrota* (Suidae), Yorkshire, Danish Yorkshire, Danish Duroc, Landrace, Danish Landrace, White Danish Landrace, Blackspotted Danish Landrace, Hampshire, Danish Hampshire, Poland China, Hereford and any cross-breedings thereof.

3. A method according to claim 1, wherein the pig is selected from the group consisting of a boar, a sow, a suckling piglet, a weaned pig, a grower pig and a finisher pig.

4. A method according to claim 1, wherein the sample is selected from the group consisting of a material comprising DNA and/or RNA, blood, saliva, tissue, throat swab, semen, and combinations thereof.

5. The method according to claim 1, wherein the steps of determining if the pig is resistant, non-resistant, or a non-resistant carrier of resistance to said *E. coli* pathogen can be performed using a technique selected from the group consisting of allele specific PCR, mini sequencing, primer extension, pyro-sequencing, PCR-RFLP, allele-specific rolling circle amplification, ARMS (Amplification Refracting Mutation System), hybridisation e.g. to DNA arrays, DASH (Dynamic Allele-Specific Hybridisation), melting curve measurement, primer extension followed by MALDI-TOF mass spectrometry and any combinations thereof.

6. A method according to claim 1, further comprising at least one of the following steps:
   (i) extracting genomic DNA from said sample;
   (ii) amplifying at least a fragment of extracted genomic DNA to obtain an amplification product;
   (iii) contacting an amplification product with a restriction enzyme;
   (iv) separating restriction fragments by gel electrophoresis;
   (v) determining number and lengths of restriction fragments; and
   (vi) detecting the presence of a polymorphism based on number and lengths of restriction fragments.

7. The method according to claim 6, wherein the restriction enzyme is XbaI.

8. A method for breeding pigs that are resistant to ETEC, the method comprising:
   (i) determining that a first pig is resistant to ETEC using the method according to claim 1;
   (ii) selecting said first pig; and
   (iii) breeding said first pig with a second pig to obtain progeny that is more likely to be resistant to ETEC than progeny from randomly chosen parent pigs.

9. A method for breeding pigs that are resistant to ETEC, the method comprising:
   (i) determining that a first pig is resistant to ETEC using the method according to claim 1;
   (ii) selecting said first pig;
   (iii) determining that a second pig is resistant to ETEC using the method according to claim 1;

(iv) breeding said first pig with said second pig to obtain progeny that is more likely to be resistant to ETEC than progeny from randomly chosen parent pigs.

10. A method for producing pork meat, comprising the steps of:

(i) obtaining pig progeny according to the method of claim 8 or claim 9; and
(ii) preparing pork meat from the pig progeny.

* * * * *

SEQUENCE LISTING

<160> NUMBER OF SEQ ID NOS: 197

<210> SEQ ID NO 1
<211> LENGTH: 712
<212> TYPE: DNA
<213> ORGANISM: Sus scrofa

<400> SEQUENCE: 1

```
cccacagcag cgccatcgca gctgtgagct cctcgacacc tttatcttcc acaagtggac     60
accctcttac agaaggcgct tcccgggaga catccccttc gggggaccca acctcttcat    120
ccgcgtccag acccaccccc acacctgcaa caacatcagc cgtgtcgaca gcacctgctt    180
ctacagatgg cacttccccc acttccagcc taagcaacac accccaaca acatcacggg    240
tggtcacatc cccagttaca accgacacca ctgtgggagg cccaggggac acgtccccac    300
ccggcacaag aaccatcact ccaggcacct catcagtctc agcgacaact ggaccagggc    360
cccagtcaac ctcaccctct ccaccacct ctgctgaggg gacagcagca tcttctctgg    420
tccaccagac tcagagcatg gagaccacca gagaaaccca cagcagcgcc atcgcagctg    480
tgagctcctc gacaccttta tcttccacaa gtggacaccc tcttacagaa ggcgcttccc    540
gggagacatc cccttcgggg gacccaacct cttcatccgc gtccagaccc accccacac    600
ctgcaacaac atcagccgtg tcgacagcac ctgcttctac agatggcact tcccccactt    660
ccagcctaag caacacaccc caacaacat acgggtggt cacatccca gt              712
```

<210> SEQ ID NO 2
<211> LENGTH: 449
<212> TYPE: DNA
<213> ORGANISM: Sus scrofa

<400> SEQUENCE: 2

```
gccctaatga catcagggcc catgagaact tcctgcttct ctttgtactg gcccaggcgt     60
tccccctcttc ccctacgggc cgcaggctgg agactggcag tttgtgagaa ggacggtgga    120
cttcacctcg ccactcttca agccccagat tggcttcccc ctcggttcct ctctccggga    180
ttgcctctac gtgagtcctt ggctgcagcc cgaaggcggg gggcggggg catgacctgc    240
attcctcagg cctttcttct ccctccaggg ctcagagatg gccctgtgat catggccata    300
actgtgactg tgattgacag ggaaaacgga agcaacgctt gtcaggcacc tgctgtgccc    360
cagttgctgc ctcagtttgc accatcttta acgatgggca ccacccgagg aaaacaggga    420
gctaggcgag gcccttacc cacgtggac                                      449
```

<210> SEQ ID NO 3
<211> LENGTH: 555
<212> TYPE: DNA
<213> ORGANISM: Sus scrofa

<400> SEQUENCE: 3

```
ttccccagtt tgaagaaaaa cagctatcag aacacccca cattattctg cacctattac     60
ggtactcaca attctgtgaa atgttaaaag acaaaatgcc tctaatgcag taaagtaatt    120
gcaagatcgt tcacagaat gagacttgtt tcctaagatg ttatgtctct aggtaaactt    180
gaagaccgcc ccgccacac acacacactg cccctgcta gaattgtca taagatcccc      240
taccgaggcc cttgggctcc ggtttgagaa actttgtccc aaacattct caaaggggcc    300
tcctcctttc catactggca gccttcacct ggtcttgctt ggaaaacctc agtgatatct    360
```

```
acctgctgc cctggcctcc tgcaagttca tcctccatcc cagccatgag gacactgttc    420
ctaaatgcaa atctagccac attctccctg gttcctgtca tctacaagat tccttcacat    480
aacaaccttg cttctcaaca cctttcacct tactgctggc agccccaaat gctatgggga    540
tctctgtccc atgca                                                     555

<210> SEQ ID NO 4
<211> LENGTH: 566
<212> TYPE: DNA
<213> ORGANISM: Sus scrofa

<400> SEQUENCE: 4
agggtcctgg cctgtaaagc ctctgagggg agggttggag taggagaaaa tctggtactc     60
tgactctggg aaaatgattt ggccgttatc tgtgaactga acacaaaagt tctcctggtt    120
agcattcagg gtgggaggtg gggaaggagc ctcggcttgg ggacagctcc tggactgatg    180
caagaccctg aagggccctg ctgggtagaa ccagagagat gccaacaacc tctggaaggt    240
ctcatccatc tccctgcatg ctgggacagc tctgtatat agttctcaca caaatactct    300
tcaccctcag cacattttt ttatgtcctg agtctttcct aaggtggtag ttttgtcctg    360
tctcagtggc acccgtctag agaccagccc atcccagagc agagtaaagc ctctcagccc    420
accctgaagc ttgtgccaca tcaattaggg ctaaaggata ccctgacccc attgctgagt    480 caccctttg tagtgtgtcc tgaccagccc tctcgagggc cacgactgct gttctgctct    540 cccccagag acatgggcta cttgga                                         566

<210> SEQ ID NO 5
<211> LENGTH: 453
<212> TYPE: DNA
<213> ORGANISM: Sus scrofa

<400> SEQUENCE: 5
ctggtggctc cattctggga tgatgctgat ttctccaggc aaggaaccac gttttaccag     60
gtgggccttt caaagctcag cattcagggt cctccagcag ccagcaagga cagacagagg    120
gctgtgtgga gggccttgca agtgttactg ctgtcagagc ctaggctcag tgtgggcagg    180
gactaaaact taaatgtgag gatgaggagg aagcagatga ggacaaaatc atggaagac     240 tgaaggtgcc agggatgggg attggggatc catcgtttga ttttaggatg aggttgtagc    300
agggtccctc ctaataaggc tgagttaagc aaggcccctg cattgggctg atgattccat    360
tcagtgggag ctattgtgta atgaaagcta ccacgtgccc ctgccaagga ccaggcacta    420
tagaaggtcc aaagatggag aaacatgtgc ctg                                 453

<210> SEQ ID NO 6
<211> LENGTH: 1491
<212> TYPE: DNA
<213> ORGANISM: Sus scrofa
<220> FEATURE:
<221> NAME/KEY: variation
<222> LOCATION: (1059)
<223> OTHER INFORMATION: Variation found at position 1059: G in
      resistant, A in susceptible
<220> FEATURE:
<221> NAME/KEY: variation
<222> LOCATION: (1125)
<223> OTHER INFORMATION: Variation found at position 1125: G in
      resistant, T in susceptible
<220> FEATURE:
<221> NAME/KEY: variation
<222> LOCATION: (1134)
```

<223> OTHER INFORMATION: Variation found at position 1134: G in
resistant, A in susceptible
<220> FEATURE:
<221> NAME/KEY: variation
<222> LOCATION: (1138)
<223> OTHER INFORMATION: Variation found at position 1138: G in
resistant, C in susceptible

<400> SEQUENCE: 6

| | | | | | |
|---|---|---|---|---|---|
| cgggtgccac | tgagacagga | caaaactacc | accttaggaa | agactcagga | cataaaaaaa | 60 |
| atgtgctgag | ggtgaagagt | atttgtgtga | aactatata | cagaggctgt | cccagcatgc | 120 |
| agggagatgg | atgagacctt | ccagaggttg | ttggcatctc | tctggttcta | cccagcaggg | 180 |
| cccttcaggg | tcttgcatca | gtccaggagc | tggccccaag | ccgaggctcc | ttccccacct | 240 |
| cccgccctga | atgctaacca | ggagaacctt | tgtgttcagt | tcacagataa | tggccaaatc | 300 |
| attttcccag | agtcagagta | ccagattttc | tcctactcca | accctcccct | cagaggcttt | 360 |
| acaggccggg | accctgtggc | cctggtggct | ccattctggg | atgatgctga | tttctccagg | 420 |
| caaggaacca | cgttttacca | ggtgggcctt | tcaaagctca | gcattcaggg | tcctccagca | 480 |
| gccagcaagg | acagacagag | ggctgtgtgg | agggccttgc | aagtgttact | gctgtcagag | 540 |
| cctaggctca | gtgtgggcag | ggactaaaac | ttaaatgtga | ggatgaggag | gaagcagatg | 600 |
| aggacaaaat | catgggaaga | ctgaaggtgc | cagggatggg | gattgggat | ccatcgtttg | 660 |
| attttaggat | gaggttgtag | caaggtccct | cctaacaagg | ctgagttaag | caaggcccct | 720 |
| gcactgggct | gatgattcca | ttcagtggga | gctattgtgt | aatgaaagct | accacaggca | 780 |
| aaggtacgtc | gtgcccctgc | caaggaccag | gcactgtaga | aggtccaaag | atggagaaac | 840 |
| atgtgcctgt | cctcaaagag | cctccagtgg | atacagggt | ggtacagatg | ggcacaggtg | 900 |
| gctgcacaat | ccaagccagt | ctgcgctaag | cgaggcacaa | gttcaagtcc | agaagttact | 960 |
| ggcctcgact | ctccactcca | catacccag | gtttccctgc | agcccgaacc | tgatttgatc | 1020 |
| ttaaggtcag | aggtgctaac | tgtgaaaatg | tgggcctgrg | acggggagg | atggaagata | 1080 |
| tgggcagact | caaatgagca | ggatcaccat | gcagaaagtg | ggggktcgcc | cagragtstt | 1140 |
| gagctgggat | ccttgtttct | tgtctgaatc | tgccttcttt | tctaggagta | tgagacgctc | 1200 |
| tatgatgaat | acaaccagct | agtgtgggag | gtggagtatt | ggattaaaat | gttaacaaac | 1260 |
| acctggaact | acaaagccag | gtggacacta | aaggtcacgt | gggtccacgc | ccctgcctat | 1320 |
| cctgcccaga | agaccctcag | ggtgagtgga | ccagtgggca | gctccctggg | aaccatctgg | 1380 |
| aagtcagaca | tcctagaatc | ctaggcaggg | gccactcttc | taaaatcctt | tctgactctt | 1440 |
| acagaacctc | ccactagccc | agagcactgg | gtattaggag | gttgaaacat | a | 1491 |

<210> SEQ ID NO 7
<211> LENGTH: 305
<212> TYPE: DNA
<213> ORGANISM: Sus scrofa

<400> SEQUENCE: 7

| | | | | | |
|---|---|---|---|---|---|
| tgaatcaggt | agtcaaaata | catatttttt | taaaagaacg | aaatgaggaa | gatgatggtt | 60 |
| agaaaagtta | agtgacttgc | ttcaaggtca | cccagctagc | aaatgacaaa | gccaggcctg | 120 |
| aaacagaggt | ttttctgact | ctgcactcca | gctcttgacc | aaaacgcatc | cactggaagc | 180 |
| aggcacacca | catgtccccc | cctatctggg | gcctcaccac | cctgatagtc | acaaagttct | 240 |
| tccttgtgtc | tggtctaaag | tcactcattt | cttcattggc | tcaacaagct | cattgcttac | 300 |
| ctact | | | | | | 305 |

<210> SEQ ID NO 8
<211> LENGTH: 2222
<212> TYPE: DNA
<213> ORGANISM: Sus scrofa
<220> FEATURE:
<221> NAME/KEY: variation
<222> LOCATION: (1849)
<223> OTHER INFORMATION: Variation found at position 1849: G in
      resistant, C in susceptible
<220> FEATURE:
<221> NAME/KEY: variation
<222> LOCATION: (2129)
<223> OTHER INFORMATION: Variation found at position 2129: T in
      resistant, C in susceptible

<400> SEQUENCE: 8

```
tgaaatttct tttctttagg ggtcaccgga cagtaatcaa atcatggagg aggcccgtgg      60
ggcctagagt actggccttc ttaccagagg gggagctctt tgacagcaaa catagtcttt     120
ttcatttctc atacttctgg ctcttagcac agtgtcctac acccagcagg tactcaataa     180
acgaagactg aatagatgtc agatcccctg gagctcctct tggtagattc cattgaagaa     240
tgaagtctca ttactgttct gggacaggac acttggagaa ttgtcctagc tgcccattca     300
ttcctcacct cctgccatgc ccctgtcctc acttccagga tcagggcccc cactcatagc     360
tctcctgtgt ttggctccgc caggaggag gaagcagcct caaatgactt tgtgctgtgt      420
gagggcacgg gaggtaacca ctccctgggc agtgccacat ctggattgca ccatgggaag     480
tcagttgtgc tggaaacacc ctttgggatg gtggagatgc aagggagctg ccctctggga     540
ctgtcatggc acatggaggg gaggacagaa ggggacttgg gtccctcaag tgtgataagg     600
tggtgctttt acctgatgtg ggatccagga actggtctgg acgatacttc tcccacactg     660
gctgcaatgt cagttggctg tttttgaaat acccatctcc actgtaggca aaaggaagaa     720
tcttcagcca ctgtcacaca gtttttcctc tcagtcagca agttactcat tcatacagct     780
ggtcagtcag ctggtcaccc actcagtcca gccagtcatt agttatcagc tgttcagtcg     840
tttcgtcagc cagccagaat catagacccg gtgccaagca ggagtgggga agggaggctt     900
ggggcaggaa taggagactc taattgattc cacatctgat ggtgaactgt aggaaacggg     960
tcatgagaca ggggtgtgag aacaacaggt caggcccccct tcctgttagt ttcccttcaa    1020
ctaggaattg gagaaggggt gctgcagggc acagctggct gtgagggtta aaagccagtc    1080
tctcggtcat ggattcaacc cccagttcca ctacttagta gcttggtgat catgggcaag    1140
ttaatttaac ctctttgatt cttagttttc acctctgtgt caaaggggtg acagtattgt    1200
gaagattcaa agcagtaaca ctggtaaatc cctcagcacc gagtgaggac caggcaatgg    1260
gtgtgcccca cccccacccc tggaaggaag gagcaaagcc cacagcctca gggtgcacgc    1320
ctcagagcag ccactcctga tcttttctcc tctctgacac aggacagatg acgcacttgg    1380
gtgtgacacc ttccgtgggt gcactcagaa tggtgtgaaa ttcctagctg gtcggataat    1440
tctacttctt tttccttcag ggctcatcac taagcaagtg aaagcaatgt aattacaggc    1500
gcaatcctga atacactcta agagaaaaac atttgtagca attagcagta acaaattaca    1560
tgcgaccttc acagccagtg gcgcacatgg caaggttgag aactgttgtg tcagagactg    1620
agccacctcc tcccttggga acccacgtcc ccatccatct ctctgttctc catctttgcc    1680
actgacagac gctgctggtg ccttgggtga gaggttaatt tccagccaat cgaaagtcag    1740
gaaggcagat ttcaacctta tatttgggtt cagcttccca ctttgccaca tcccagctct    1800
```

```
gtgactttgg gcaatgactt atctatttgt acctcagttt ctgtatctst agaatgggta    1860
ataaaataga tctccttcat ggggttgttg taatatacaa ataatgcat actgagtgct     1920 ggtataataa atgttggctg ttattgttaa gctctgaaaa gtcaagtgag gtcagctact    1980
gtcagtggaa gtcctagaag tcaaggctct ggggattatt atcacatgca cggagacctt    2040
gataggaaag agaacggcag agtgaatagg ggtcttttaa tttgaaacag caagaagtgg    2100
gaactggagt cagcgtgaat cagaagcayg ggcagggagg attttggcgt atccttgggg    2160
aatggagttc gtgtgcagct gcaagccctg ctttgcaccg cctcctgctg tctactcaat    2220
gc                                                                   2222

<210> SEQ ID NO 9
<211> LENGTH: 450
<212> TYPE: DNA
<213> ORGANISM: Sus scrofa

<400> SEQUENCE: 9
taaaaagaca aaaagacaaa aaaaaattta ttctaataac ttggtgattg cataaagatg     60
attttgcaat attacaagaa tgagaagaaa tgatctttga atcagcctgg agtcagtcga    120
gctagctggc cagatcacta ttaatctctg ggggaatct atttgattta tatggatcat     180
tcctgggtaa tgttggtcct agatattcca atgaaaggtg acatgaagtt gcacagagta    240
taataacgca aaattaccca aagcttgact cagacctcaa ccactaactg ccccagccga    300
gcattcttac cagagagctt gaagtcagtg cagttgtgtc tgagagtgaa tgtgacgttc    360
tcagagctgc tggtgtaatt aacaaggctg gcctgtccca tataggtttt caccacatca    420
ggacccttga tggagggcgg gtactgatct                                     450

<210> SEQ ID NO 10
<211> LENGTH: 424
<212> TYPE: DNA
<213> ORGANISM: Sus scrofa

<400> SEQUENCE: 10
ctccatgaga tgaaggtggt tgccccccac ctccccaaag cccccaaagg gtaaccctgc     60
ctggacctgc actaggatgg gatatggggg gcggggagcc atggagggtg aaggccagga    120
tcttcccaac acttactcag gctacacttc aggccagact gacctcagct tcacagcagc    180
ctcatccctc acccacttgc tctcatttcc tggacctttg accagacccc aggctacagg    240
gaaatactgc tgtgtatcaa taaggactct tctgattcaa cctgtcttat gttttcaag    300 aaaataggga agtctcctta aaacagtgga ttgaaaagag ctgatgggtg ggagcagatg    360
agagtcactt ccaggacctc cctcttcagg ataggagccc agtggaggag tgagtctcct    420
gatg                                                                 424

<210> SEQ ID NO 11
<211> LENGTH: 155
<212> TYPE: DNA
<213> ORGANISM: Sus scrofa

<400> SEQUENCE: 11
gcatggccat taaaaaaaaa aaggcagata gggccagatt catggactta ggccaagtat     60
cttggctaga aacttgaatg gagaaggatt ttctctaaac tgccaaagag atgcttcgtt    120
tagttggaag agagcaaaaa ggaaaaatag gattt                               155
```

<210> SEQ ID NO 12
<211> LENGTH: 1011
<212> TYPE: DNA
<213> ORGANISM: Sus scrofa

<400> SEQUENCE: 12

| | | | | | |
|---|---|---|---|---|---|
| cttcaatgaa | atctagaaac | cactgcatct | tctgagcaca | gcccagattg | gagaagcaca | 60 |
| gccttataaa | ggccaaaaag | gggatggaag | tgaggaaagc | aggctggtgg | gcctttctcc | 120 |
| tcccagcctt | ttgggtcctt | tcctgatggg | gagggtctaa | caacactcca | ttccctcagc | 180 |
| agaagtggga | gaaccctac | ctggcagagg | aaaaagggtt | gtctggcaaa | gaaatgtctg | 240 |
| gaaaagggag | aaagatggtt | tggggttcag | agtggcccac | ccgcagaaca | cagtttaagt | 300 |
| gagcttttgca | gggaaaaagc | caaccctgtc | ctgggagcag | ctttctctgg | ctggcggctg | 360 |
| ccagtgtggt | gtagcagact | gtctgttccc | tctgcagctc | tcaacagctt | tttcaactgt | 420 |
| tggaacaaga | cctgtcctga | gaattactgc | tacaaccagg | gtcgctgcta | catctcccag | 480 |
| tctctgacct | gcgagcccgc | ctgcacctgc | cccccagcct | tcatggaaga | cacccgctgc | 540 |
| ttcctggctg | gaaaaaattt | cactccaacc | atccttccag | gtacagccag | atgccctgcc | 600 |
| atccccactc | cacacgtctc | ttaacttggg | ggaagatggg | ggactctggg | ggccaggctc | 660 |
| agtccctcaa | actcacagga | cagaactcca | aatctctctc | gtgtgctcgt | aagttgtagg | 720 |
| ctgtgggagt | gagtggggg | cagctgtcac | accacaaacc | acaggtctga | gcagtctgct | 780 |
| gagaaaagac | tgaaggggac | ctcacagctc | agcgagacaa | gagtcaggcc | agccttgatc | 840 |
| acagggtgag | gtcagcagac | ctggccattt | ctgattcttc | tggtgacctt | ctatgactgt | 900 |
| agaagagggc | agtcttcttg | ggctgtcctc | cttggctaag | tctgggtaaa | cctgtgaggt | 960 |
| gactatgaat | ctgcttcttc | cctctccaga | gcttcccccg | aggctcatcc | a | 1011 |

<210> SEQ ID NO 13
<211> LENGTH: 342
<212> TYPE: DNA
<213> ORGANISM: Sus scrofa

<400> SEQUENCE: 13

| | | | | | |
|---|---|---|---|---|---|
| attcgccctt | caaaaaaaaa | agaagaataa | gaaggaggag | gaggaaacac | ggatgaatac | 60 |
| atgcacaaaa | gtgggaaagg | tctcctctct | ggactggacc | tcaccccat | ttccaccccc | 120 |
| accccaaccc | ccaccctctg | ccctaggtgg | cttatagact | ggggaacctg | gatgtgcggg | 180 |
| cctttctccg | gaacagacaa | gtggaacgag | tgtaagtggg | actgccccca | cctgggcccc | 240 |
| ggtccttacc | tacacccctc | accctcggc | ccctcactgt | gcccctctca | cacagtgaac | 300 |
| tcccagcaat | accggcctca | ggaaacttcc | ttcaatactg | ga | | 342 |

<210> SEQ ID NO 14
<211> LENGTH: 846
<212> TYPE: DNA
<213> ORGANISM: Sus scrofa

<400> SEQUENCE: 14

| | | | | | |
|---|---|---|---|---|---|
| taaacgaatt | cgcccttttc | gctggcaagt | ttgccaacct | acctcattcc | ccttctggga | 60 |
| taattagagt | ctgtcagagc | tgaaagggac | ctcagacatc | ccacctcctt | ttccagatga | 120 |
| gcgtgttgag | gccttgactg | gggatggact | tttgcacagg | gtcacgctct | ttcaaggagg | 180 |
| tgatagttct | gccccctgggc | caggtctcca | gccttcaact | ttatatctcc | aggtggaggc | 240 |
| aaaggcaaag | gcaaaaacaa | tgtccttgtt | tatatttata | aaataaatgt | taaccaaatc | 300 |

| | |
|---|---:|
| attaacaatt ttatagaaag aaaaccatta gcagcaatgg tcaggaaagc agcagttgga | 360 |
| gcagttgctc tgtgaaactg tacacgtggg gattcatcaa gcagtacttt gtgctcctgt | 420 |
| tcctgaatct agaaggctgg tgggtaaaag gttcccaatt tctcttaaaa atgacaaaca | 480 |
| aaacccccct aaatttactt ccttcttatc tgtggcctgc tgtagaatac acttcagcca | 540 |
| tgggtttgtg tgggcctgag atctgtggca ggctccctct gcttacccgc tccctcagct | 600 |
| atccttgctg ctgtccaaga gatagtgact caccagccat cacactgagc acatctctcc | 660 |
| tggagatggg ttggaagacc acattgttcc tgggctcctc acttctcttc cacctcctct | 720 |
| gtgaggcctg ggataagaat gcctccacca ctgcgtccag cagcctggta ttcaggaagt | 780 |
| caatgacagg gccccagggg cggtactgga actccgagat gactttccag taaagggcga | 840 |
| attcgt | 846 |

<210> SEQ ID NO 15
<211> LENGTH: 603
<212> TYPE: DNA
<213> ORGANISM: Sus scrofa

<400> SEQUENCE: 15

| | |
|---|---:|
| catgccaaat gccacagaag gtgctgtgtt acctgagcct agggccaagc aagagcttct | 60 |
| tctagaatcc aggctaagct ccctcccttc caggggcaac aatgagaaat cctccaaact | 120 |
| actatggtat gtgtggtagg gaggcagtgt tggggataag ggaataaata ctccagactt | 180 |
| gactgtgcct tttcttagag aaaacaaatc aacaaaaccc ccacaatttt tattatgcaa | 240 |
| gtacaatatg ttttgtgttt aggacacaga agttaacaga aaaaaaatca cctgtattct | 300 |
| aatccccaga gacaaatccc ctttgcacat actctgctaa attctctttt atgcatagga | 360 |
| cacttcatat atcaataaag ggatcaaatc atacctaatg tttgataacc tctccattac | 420 |
| tttaactgtg aacatattac cttgtacatt gtattcacat tctgatttga tatattattt | 480 |
| tatgtcttaa atagtgtgtt ttaatatatt ttaaatagaa tgttttaaa tattttttaaa | 540 |
| tattttaaat agaatagtga ctgttaaact gaaggcttac tatgtcaggc actgtgctaa | 600 |
| ata | 603 |

<210> SEQ ID NO 16
<211> LENGTH: 433
<212> TYPE: DNA
<213> ORGANISM: Sus scrofa

<400> SEQUENCE: 16

| | |
|---|---:|
| tcgattacag agggaaccac cctacatttt caggcgctgt gaggtaccat ggcatttcca | 60 |
| gactccttgc agcttggatt ctctggcact gcccctccacc tcctgccccc acctgctca | 120 |
| cctgcattgg ggcccctcgg gtaggtgctg gcactggcct ccattctcac agtagcccct | 180 |
| gctgcacggg gacacacagg tgaagcctct ctccgggctt aaaaccaggt tgtagtcctt | 240 |
| gtagccgtta cattggaagt aatttttcag tgtgctcaca ttcactgtca gataggacac | 300 |
| aagcaaaatg gaaccaatg gatttacacc aaatctatac cttttctgtc aagaattcca | 360 |
| ttttaggcac tcatcctgag aaatagttgg aaacacacaa aaactacata tattcacgga | 420 |
| aatctgtagc agc | 433 |

<210> SEQ ID NO 17
<211> LENGTH: 568
<212> TYPE: DNA
<213> ORGANISM: Sus scrofa

<400> SEQUENCE: 17

```
ccacactggc tgcaatgtca gttggctgtt tttgaaatac ccatctccac tggagaagcc        60
catgacgacg gggttgccta ggtgttgggt cacatcccac tgcatgccac cgctttggta       120
gagaaacaag gcgtaggacc tgctcccatc cgtggaaagg atggcctggt aggtgttggt       180
cctgagggtc ttctgggcag gataggcagg ggcgtggacc cacgtgacct ttagtgtcca       240
cctggctttg tagttccagg tgtttgttaa cattttaatc caatactcca cctcccacac       300
tagctggttg tattcatcat agagcgtctc atactcctgg taaaacgtgg ttccttgcct       360
ggagaaatca gcatcatccc agaatggagc caccagggcc acagggtcct ggcctgtaaa       420
gcctctgagg ggagggttgg agtaggagaa aatctggtac tctgactctg ggaaaatgat       480
ttggccgtta tctgtgaagt agaggcaatc ccggagagag gaaccgaggg ggaagccaat       540
ctggggcttg aagagtggcg aggtgaag                                          568
```

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      upper primer related to gene ADPRLT3

<400> SEQUENCE: 18

```
cccagccatg ctaggactaa                                                    20
```

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      lower primer related to gene ADPRLT3

<400> SEQUENCE: 19

```
agattcgcct ctgaggtgtc                                                    20
```

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      upper primer related to gene ARF4

<400> SEQUENCE: 20

```
accaaaagca acatgcaaca                                                    20
```

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      lower primer related to gene ARF4

<400> SEQUENCE: 21

```
cagggaatgc tccaaaacac                                                    20
```

<210> SEQ ID NO 22
<211> LENGTH: 20
<212> TYPE: DNA

```
<213> ORGANISM: Artificial Sequence
<220> FEATURE:
<223> OTHER INFORMATION: Description of Artificial Sequence: Synthetic
      upper primer related to gene ARP

<400> SEQUENCE: 22
tagtgtaaac ccgcaacaga                                              20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      lower primer related to gene ARP

<400> SEQUENCE: 23
aacagttcat ctgtgtcttc                                              20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      upper primer related to gene DKFZp434P0721

<400> SEQUENCE: 24
acagcatgaa aagtgcctga                                              20

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      lower primer related to gene DKFZp434P0721

<400> SEQUENCE: 25
tccatatctg tgtctcataa aaa                                          23

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      upper primer related to gene GPX1

<400> SEQUENCE: 26
tagtgaggaa ctgtggtctg                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      lower primer related to gene GPX1

<400> SEQUENCE: 27
atatcgagcc tgacatcgaa                                              20

<210> SEQ ID NO 28
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      upper primer related to gene KIAA0804

<400> SEQUENCE: 28
ctatgtgccc atgtgcattc                                                   20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      lower primer related to gene KIAA0804

<400> SEQUENCE: 29
aacctgagag catcggtcac                                                   20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      upper primer related to gene KIAA1363

<400> SEQUENCE: 30
tcaagagggg ctcaacactt                                                   20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      lower primer related to gene KIAA1363

<400> SEQUENCE: 31
tggaatcatg tacgcaaagc                                                   20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      upper primer related to gene MME

<400> SEQUENCE: 32
catatccact ccagggacac                                                   20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      lower primer related to gene MME

<400> SEQUENCE: 33
accaagacag ttatgaacca                                                   20

<210> SEQ ID NO 34
<211> LENGTH: 20
<212> TYPE: DNA
<213> ORGANISM: Artificial Sequence
<220> FEATURE:
```

-continued

<223> OTHER INFORMATION: Description of Artificial Sequence: Synthetic
      upper primer related to gene RFC4

<400> SEQUENCE: 34
cggtgctttg gtcattttta                                                    20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      lower primer related to gene RFC4

<400> SEQUENCE: 35
tgcttagctg atggtgctga                                                    20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      upper primer related to gene RPL29

<400> SEQUENCE: 36
gacagatcct gaggcaggtt                                                    20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      lower primer related to gene RPL29

<400> SEQUENCE: 37
caggttctgc cggccaaagt                                                    20

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      upper primer related to gene RYBP

<400> SEQUENCE: 38
aagcagagca ggtcaattaa gg                                                 22

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      lower primer related to gene RYBP

<400> SEQUENCE: 39
tattcagcgg cacagtaagc                                                    20

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic upper primer related to gene SEC22A

<400> SEQUENCE: 40
ccagccggtg tagtagacaa g                                        21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      lower primer related to gene SEC22A

<400> SEQUENCE: 41
cccttttaag gtgtggagct t                                        21

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      upper primer related to gene SST

<400> SEQUENCE: 42
tttggaggag aggaattgga                                          20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      lower primer related to gene SST

<400> SEQUENCE: 43
tggagcctga agatttgtcc                                          20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      upper primer related to gene TFDP2

<400> SEQUENCE: 44
atagtaaaac gcgggtttgc                                          20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      lower primer related to gene TFDP2

<400> SEQUENCE: 45
gctgaagtgg ccttagcaac                                          20

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      upper primer related to gene TFG

<400> SEQUENCE: 46
agatgactga acttcaacct agca                    24

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      lower primer related to gene TFG

<400> SEQUENCE: 47
agcagcttcc tagttacttt gg                      22

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      upper primer related to gene TRAD

<400> SEQUENCE: 48
caggaagagc ccctaaatc                          20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      lower primer related to gene TRAD

<400> SEQUENCE: 49
cagcaaaggc agaaaccttc                         20

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      sense primer NAU 491

<400> SEQUENCE: 50
agcaggccga gtcttggatt a                       21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      primer NAU 483

<400> SEQUENCE: 51
ctgtttctct accagagcgg t                       21

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      upper ACK1 primer

```
<400> SEQUENCE: 52
cgtgacgacc tcaacgttac                                              20

<210> SEQ ID NO 53
<211> LENGTH: 17
<212> TYPE: DNA
<213> ORGANISM: Artificial Sequence
<220> FEATURE:
<223> OTHER INFORMATION: Description of Artificial Sequence: Synthetic
      lower ACK1 primer

<400> SEQUENCE: 53
ctgccgatct tcaggtc                                                 17

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      upper MUC4 primer

<400> SEQUENCE: 54
ctactccaac cctcccctca                                              20

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      lower MUC4 primer

<400> SEQUENCE: 55
gaaatcagca tcatcccaga a                                            21

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
      upper STR01 primer

<400> SEQUENCE: 56
cacacatgtt catacagtgc tga                                          23

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      lower STR01 primer

<400> SEQUENCE: 57
ccaggcactt ctggctctta                                              20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      upper STR02 primer

<400> SEQUENCE: 58
```
caatgtgcca atttccactg                                              20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      lower STR02 primer

<400> SEQUENCE: 59
atacggggag tttggggtta                                              20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      SSMUC4_ex4U primer

<400> SEQUENCE: 60
gacttcacct cgccactctt                                              20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      SSMUC4_ex8L primer

<400> SEQUENCE: 61
cgatacttct cccacactgg                                              20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      Muc4_in7u primer

<400> SEQUENCE: 62
gtgccttggg tgagaggtta                                              20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      Muc4_in7l primer

<400> SEQUENCE: 63
cactctgccg ttctctttcc                                              20

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence: Synthetic
      Biotin labeled forward primer flanking the
      position 1849 SNP
<220> FEATURE:
<221> NAME/KEY: modified_base

```
<222> LOCATION: (1)
<223> OTHER INFORMATION: biotinylated-G

<400> SEQUENCE: 64
ggcaatgact tatctatttg tacc                                          24

<210> SEQ ID NO 65
<211> LENGTH: 25
<212> TYPE: DNA
<213> ORGANISM: Artificial Sequence
<220> FEATURE:
<223> OTHER INFORMATION: Description of Artificial Sequence: Synthetic
      1849 SNP reverse primer

<400> SEQUENCE: 65
gtatattaca acaccccat gaagg                                          25

<210> SEQ ID NO 66
<211> LENGTH: 17
<212> TYPE: DNA
<213> ORGANISM: Artificial Sequence
<220> FEATURE:
<223> OTHER INFORMATION: Description of Artificial Sequence: Synthetic
      probe specific for C allele

<400> SEQUENCE: 66
ccattctaga gatacag                                                  17

<210> SEQ ID NO 67
<211> LENGTH: 500
<212> TYPE: DNA
<213> ORGANISM: Sus scrofa
<220> FEATURE:
<221> NAME/KEY: variation
<222> LOCATION: (249)
<223> OTHER INFORMATION: variant base in XbaI polymorphism, G in the
      resistant, non-cutting, type

<400> SEQUENCE: 67
aactgttgtg tcagagactg agccacctcc tcccttggga acccacgtcc ccatccatct    60
ctctgttctc catctttgcc actgacagac gctgctggtg ccttgggtga gaggttaatt   120
tccagccaat cgaaagtcag gaaggcagat ttcaacctta tatttgggtt cagcttccca   180
ctttgccaca tcccagctct gtgactttgg gcaatgactt atctatttgt acctcagttt   240
ctgtatctgt agaatgggta ataaaataga tctccttcat ggggttgttg taatatacaa   300
aataatgcat actgagtgct ggtataataa atgttggctg ttattgttaa gctctgaaaa   360
gtcaagtgag gtcagctact gtcagtggaa gtcctagaag tcaaggctct ggggattatt   420
atcacatgca cggagacctt gataggaaag agaacggcag agtgaatagg ggtcttttaa   480
tttgaaacag caagaagtgg                                              500

<210> SEQ ID NO 68
<211> LENGTH: 500
<212> TYPE: DNA
<213> ORGANISM: Sus scrofa
<220> FEATURE:
<221> NAME/KEY: variation
<222> LOCATION: (249)
<223> OTHER INFORMATION: variant base in XbaI polymorphism, C in the
      non-resistant, XbaI-cutting, type

<400> SEQUENCE: 68
aactgttgtg tcagagactg agccacctcc tcccttggga acccacgtcc ccatccatct    60
```

-continued

```
ctctgttctc catctttgcc actgacagac gctgctggtg ccttgggtga gaggttaatt      120
tccagccaat cgaaagtcag gaaggcagat ttcaaccta tatttgggtt cagcttccca       180
ctttgccaca tcccagctct gtgactttgg gcaatgactt atctatttgt acctcagttt      240
ctgtatctct agaatgggta ataaaataga tctccttcat ggggttgttg taatatacaa      300
aataatgcat actgagtgct ggtataataa atgttggctg ttattgttaa gctctgaaaa      360
gtcaagtgag gtcagctact gtcagtggaa gtcctagaag tcaaggctct ggggattatt      420
atcacatgca cggagacctt gataggaaag agaacggcag agtgaatagg ggtcttttaa      480
tttgaaacag caagaagtgg                                                  500
```

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: Synthetic
      upstream primer for the SW2196 marker

<400> SEQUENCE: 69

```
gctctgtatt gagtacccct gg                                               22
```

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      downstream primer for the SW2196 marker

<400> SEQUENCE: 70

```
acttggttgg attgctgagc                                                  20
```

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      upstream primer for the SW207 marker

<400> SEQUENCE: 71

```
cgcttcacaa aataagttgg g                                                21
```

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: Synthetic
      downstream primer for the SW207 marker

<400> SEQUENCE: 72

```
gttgttactc ccaaaaaggt gc                                               22
```

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: Synthetic
      upstream primer for the S0283 marker

<400> SEQUENCE: 73

| agcagcccta gaaatagcaa gcgc | 24 |

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic
      downstream primer for the S0283 marker

<400> SEQUENCE: 74

| ctctctgttc ctggcacctg gg | 22 |

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      upstream primer for the S0075 marker

<400> SEQUENCE: 75

| ggatccaagt gccagcaatg | 20 |

<210> SEQ ID NO 76
<211> LENGTH: 18
<212> TYPE: DNA
<213> ORGANISM: Artificial Sequence
<220> FEATURE:
<223> OTHER INFORMATION: Description of Artificial Sequence: Synthetic
      downstream primer for the S0075 marker

<400> SEQUENCE: 76

| ttgtccaccc tgggaggg | 18 |

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      upstream primer for the SW1876 marker

<400> SEQUENCE: 77

| tgtcactgct gtggcttagg | 20 |

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      downstream primer for the SW1876 marker

<400> SEQUENCE: 78

| ctggctactc caagacattg g | 21 |

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      upstream primer for the SW225 marker

<400> SEQUENCE: 79

| aggacccacc aagagttacc | 20 |

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      downstream primer for the SW225 marker

<400> SEQUENCE: 80
tgctggtaat gggtgattag g                                             21

<210> SEQ ID NO 81
<211> LENGTH: 3235
<212> TYPE: DNA
<213> ORGANISM: Sus scrofa
<220> FEATURE:
<221> NAME/KEY: modified_base
<222> LOCATION: (22)
<223> OTHER INFORMATION: a, c, t, g, unknown or other
<220> FEATURE:
<221> NAME/KEY: modified_base
<222> LOCATION: (24)..(26)
<223> OTHER INFORMATION: a, c, t, g, unknown or other
<220> FEATURE:
<221> NAME/KEY: modified_base
<222> LOCATION: (44)
<223> OTHER INFORMATION: a, c, t, g, unknown or other
<220> FEATURE:
<221> NAME/KEY: modified_base
<222> LOCATION: (51)..(55)
<223> OTHER INFORMATION: a, c, t, g, unknown or other
<220> FEATURE:
<221> NAME/KEY: modified_base
<222> LOCATION: (57)
<223> OTHER INFORMATION: a, c, t, g, unknown or other
<220> FEATURE:
<221> NAME/KEY: modified_base
<222> LOCATION: (2049)
<223> OTHER INFORMATION: a, c, t, g, unknown or other

<400> SEQUENCE: 81
taggcagggg cctaaaaaaa gnannnttcg tctgagacct gatnggaagg nnnnntnctc     60
tccccttaaa aaaagcctg catgccctgc tcttccttcc tgattatgcc tgttattccc    120
aatagatcaa aatggttgac ctgaagctcc aaagtctcca ggtgcagccc ttacgtcctc    180 aagggggtcac aatttctcct ccccaacttc tgctctcacc ccactatcca cctcagttcc    240
cttcagcaac ttcccaggtt gcctccggct ttctggcccc tgccctgttg cgcccctac    300 tggaaagagg aaatccacca ttcggtgacg gtctagcctg tactcagcgg agccccgcac    360
tccatcccac aggttgcgta tgggggtggg ggggttctga tttccacccc tcgccttaca    420
ttgttccccc cacttcccat gtctcttagg gtctcctcag atttcactct ttctcctctt    480
catacagccc ccaaattgct ccctcttgac cccttcttc cccatgctgc cctgcccttt    540
cttctggaat gacccagcta ttccctctgt ggcagtctga cggggcagcc caggatccca    600
ggcgcgaggg aggccctca tttccaggat gccctggttt ctattcctct gcatgcctct    660
cccatccctc ccccaacttg gcacaggctg actaggaaca gagcaatggg tgtatcggta    720
tttttattat tttatttttt cctggtgggg aaggggtg gagattgagg aaagaaaaga    780
cacgtaaggg tgattggcac aaggcccgc cttcttttgt cctccttccc aggtacttgg    840
gcccctcagg gaaatacacc tgtttcagac cagcagcccg tggggacagg ttcacctgtg    900
ttcctcacac caccacttca gtcctaagga gcctccctgg gggagcttga gggactcttt    960
ctggagccat gaggggggtc caccagagga gggtcccctg ggtgtttctg agctgcttat   1020

```
gttcctgcct cctttggcca gaggtcctgg gtaagtgatg tacccggggc agccttctgg    1080
gggtgagggt ggctgacttc acagagtgcc tccggggagc tgaggcctgg catcaagaga    1140
aagggggggg tgtgaatgga cagagatggg acaaggcggg gtggggggga cgctagagaa    1200
atagaaggag gagaaggtag agactggaga gaagcaggga gatgccgggg tgcaggagtg    1260
gcctagtttg gggaaacccc gttagggcaa ccagggctta ttttgtggaa agagatgggt    1320
aggcaaaact agaaagagag agcactgagg agagggaatg aagcagaaaa agaggaagct    1380
ggggaagaga actgggagaa aaacttatag acagatgtag agtcagaggt caagacaggt    1440
gagaaacaga tgaaccaaag caaaattgat acagagagag gaagaaatca gaggagacag    1500
gcagaactga aaggaaggga gcaggagagg agagaatggc cgggcttgga gaaacaaggc    1560
aggaccagaa acttggcagc cccagtgttg gcctcggctt cctctacatc cccttcctcc    1620
ccgggtgtgg agctgggagc agagccagaa ggaagacccc tttggagaag cccccacccc    1680
ccaccccgag gtcctccagt tctctccccg ccaccttcca agctgcggcc ctgggcccca    1740
ggaccggggt tcattctatg tttctggatg tctgagtctt ctgaggtctc tgggggccca    1800
ggagagggtg agcggtcagg aacccaaacc aaagataaaa tcacagctcc tccggctcct    1860
cagcaggcct ggcgaatcat ttccagggga gtgagtcaga gaaactcact ctcttacaga    1920
tagtaagggg cacaatgtca gggacgtgga ggattctgcc ttccttgaaa tgtttaaggg    1980
cccagccaag ggaaaacaga acacccaccg cctccaccag cctgtaaccc aaccaccccc    2040
tccctcctna ctcattgcac agtgaggaaa aggaagccaa aaggcgcctt cagaactgca    2100
gtagccaatc cctcaggtct attcctgggg gtaaaataga aagatgtaga ctaaagagtg    2160
tctgtgggag tcatgacgat gggcaatgag gagaaggtgg cttggattta gggaccttgg    2220
gcacagtctt ggctttgcca ctaagggatc tggtcccatg accaggttct atcgcacctc    2280
tgtccaggcc tcagttcccc tgtggaaaaa gcagggtggt ggattgcatg acctctggat    2340
tactaaattc ttaggttttg atgttctgtg atttaacgtt atcactaaaa ttgttcagta    2400
ctggctcctc gcttggccct gcattagggt ggtcaagccc aggaggagcc aggaagtgtg    2460
tggagaggag cccaaagggg caaggactgg gatgggagtg gccaggggaa ggcagtaggg    2520
agcgatgggg tatgagcaag aggaggacct ttaaggtgga agggagtaac cgttatggtc    2580
ctgaagcccc tcacaggtgc cctggagctg agtcctgtac cttgtgaaag ggcacagagt    2640
aggagttccc gtcgtggcgc agtggttaac gaatcctacc aggaaccatg aggttgtggg    2700
ttcgatccct ggcctcgctc agtgggttaa ggatctggta ttgccgtgag ctgtggtgta    2760
ggttgcagac acggctcata tcccacgttg ctatggctct ggcgtagggc ggtggctaca    2820
gctccgatta gacccctacc ctgggtacct ccatatgcca tgggagcggc cctagaaaag    2880 gaaaataaa taaataaata aataaaaata atataatttt taaaaaaagg gggcacagag    2940
tgcagcagga ccaggaaagg agaggggagt gggatgagag gtggtgcccc agggatgtgg    3000
ccaagcaccc tgaggacctt ggagggaaaa gtcatcccta tagaatgggc agtgagcccc    3060
ctacatctgc tgcggtgggt atgggttccg ggaaagggaa gctggtcagt tccattccca    3120
tggatccctg acagggagct tatgggtacc tgcctatgtt cgaacctagg gtctgtttcc    3180
agacttgctg ccagcatcct tgcccaggcc tggtcagccc tggacaaagg gcgat         3235

<210> SEQ ID NO 82
<211> LENGTH: 5277
<212> TYPE: DNA
```

```
<213> ORGANISM: Sus scrofa
<220> FEATURE:
<221> NAME/KEY: variation
<222> LOCATION: (4847)
<223> OTHER INFORMATION: Variation found at position 4847: G in
      resistant, A in susceptible
<220> FEATURE:
<221> NAME/KEY: variation
<222> LOCATION: (4913)
<223> OTHER INFORMATION: Variation found at position 4913: G in
      resistant, T in susceptible
<220> FEATURE:
<221> NAME/KEY: variation
<222> LOCATION: (4922)
<223> OTHER INFORMATION: Variation found at position 4922: G in
      resistant, A in susceptible
<220> FEATURE:
<221> NAME/KEY: variation
<222> LOCATION: (4926)
<223> OTHER INFORMATION: Variation found at position 4926: G in
      resistant, C in susceptible

<400> SEQUENCE: 82
gcggtttacg aatcgccctt ctttacttcc acaagtggac accctcttac agaaggcgct    60
tcccgggaga catccccttc ggggacccca acctcttcat ccgcgtccag acccaccccc   120
acacctgcaa caacatcagc cgtgtcgaca gcacctgctt ctacagatgg cacttccccc   180
acttccagcc taagcaacac acccccaaca acatcacggg tggtcacatc cccagttaca   240
accgacacca ctgtgggagg cccaggggac acgtccccac ccggcacaag aaccatcact   300
ccaggcacct catcagtctc agcgacaact ggaccagggc cccagtcaac ctcaccctct   360
tccaccacct ctgctgaggg gacagcagca tcttctctgg tccaccagac tcagagcatg   420
gagaccacca gagaaaccca cagcagcgcc atcgcagctg tgagctcctc gacacccttta   480 tcttccacaa gtggacaccc tcttacagaa ggcgcttccc gggagacatc cccttcgggg   540
gacccaacct cttcatccgc gtccagaccc accccacac ctgcaacaac atcagccgtg   600
tcgacagcac ctgcttctac agatggcact ccccccactt ccagcctaag caacacaccc   660
ccaacaacat cacgggtggt cacatcccca gttacaaccg acaccactgt gggaggccca   720
ggggacacgt ccccacccgg cacaagaacc atcactccag gcacctcatc agtctcagcg   780
acaactggac cagggcccca gtcaacctca ccctcttcca ccacctctgc tgagggggaca   840 gcagcatctt ctctggtcca ccagactcag agcatggaga ccaccagaga aacccacagc   900
agcgccatcg cagctgtgag ctcctcgaca ccttttatctt ccacaagtgg acaccctctt   960
acagaaggcg cttcccggga gacatcccct tcaggtgaaa caagctcttc agccacattt  1020
agaccgaccc ccatatctgt gtcgtgtttc catacataaa ccagtatttc ttcttttttct  1080 gcatcagctc ctggccacaa agtcaccttg agctccactg ccctattcac aggtcacccc  1140
acttctctgt ctctcatgag cccttttccc ttatccactg tgtcttcaag atccacagtg  1200
aaggctggga catcaggtag gtcgtaaccc tggggtctta gtctcttgca cttgcccagt  1260
tggctcaatt cagtgcagaa gagtgcttga gagaggacat tcaattagca ctgccaggct  1320
ggaggtcagg tccagaaggt tatgaaatca gttggggttt ggtgggtgat agcctcacca  1380
tcctctttac cccaggtggc agctgcttct cctcaggcag tggttttggt gtgactagaa  1440
gacagttttc tagctgtctc ttccaggttc taaagtctat gactctgttt aactctgcta  1500 cccctgact gttagactca ctcctgtctt ctctccctgc ctgcctagga acaatcacca  1560
ccttgcagaa gacagacagc aagacaagca cagcagcatc tctaccctca accacctccc  1620
aggctcttac aacttccact gctcacactt ccacaggcac tcgctcaaca gctgcccag  1680
```

```
tccctcccaa gccgaagaaa ggtgagtgaa tccatagagc tgggtcctct tcaccctggg    1740
tcaaagagga tggagctata tgtggaggtt atagttgtgg cagctggact ggatctacca    1800
atgaggatct ttgtggggag gtaggggac cagttctgtg gatcgctcca ctgccctggg     1860
tgtggcaagt ccagctgctc tctgtgtccc cttgataggg gtggtgtaac tgagtgcttt    1920
gtctcagcct gcttgcttac agactctcga gtcagaaagg ccttacagtg aacaatgtga    1980
catcatcagt gttgggtgct gagggctgac tttgcacatg gtgctaggct aagagctgga    2040
gataaaaaaa tgattgagtc actgtttagt gagacagcct tgctgcctca gtaggtgcga    2100
ttagaggcat aaacccaggg tattaggtac acacaatgga aggccccaag ggaatattgg    2160
ggtgtgggtt caaggtgaaa aggagtctcc ctggaaaggg tgaataggat ctgcggggag    2220
gggaagtgcc ccaagcaggc aggagggcct gaatagctag aataaaggct cggacaggaa    2280
gagcagtcct agtattgcat gggacagaga tccccatagc atttgggcct gccagcagta    2340
aggtgaaagg tgttgagaag caaggttgtt atgtgaagga atcttgtaga tgacaggaac    2400
cagggagaat gtggctagat ttgcatttag gaacagtgtc ctcatggctg ggatggagga    2460
tgaacttgca ggaggccagg gcagcagggt agatatcact gaggttttcc aagcaagacc    2520
aggtgaaggc tgccagtatg gaaggagga ggccccttg agaaatgttt gggacaaagt     2580
ttctcaaacc ggagcccaag ggcctcggta ggggatctta tgacaaattc tagcagggg    2640
cagtgtgtgt gtgtggcggg ggcggtcttc aagtttacct agagacataa catcttagga   2700
aacaagtctc attctgtgaa acgatcttgc aattacttta ctgcattaga ggcattttgt    2760
cttttaacat ttcacagaat tgtgagtacc gtaataggtg cagaataatg tggggtgtt    2820
ctgatagctg ttttttcttca aactggggaa ggcgagagt accatgtaag ggagtgaaag   2880
aggagatggg ttaaatgcaa gtggagaggg ggagagagaa gtccttgacg gctcttgctt    2940
aagcgaacag gtccaagggt ggaggagcag cttggggaca ctcttgcggg acccctgcca    3000
gccctaatga catcagggcc catgagaact tcctgcttct ctttgtactg gcccaggcgt    3060
tccctcttc ccctacgggc cgcaggctgg agactggcag tttgtgagaa ggacggtgga    3120
cttcacctcg ccactcttca agccccagat tggcttcccc ctcggttcct ctctccggga    3180
ttgcctctac gtgagtcctt ggctgcagcc cgaaggcggg gggcggggg catgacctgc     3240
attcctcagg cctttcttct ccctccaggg ctcagagatg gccctgtgat catggccata    3300
actgtgactg tgattgacag ggagaacgga agcaacgctt gtcaggcacc tgctgtgccc    3360
cagttgctgc ctcagtttgc accatcttta acgatgggca ccagctgagg aagacaggga    3420
gctaggcgag gcccttacc cacgtggaca gaagtgtggc cacctcagta gagaggtcct    3480
ggggcccagt aagctctcca ctgttttcat gggtcctttt ttacaagtag gaagctctgc    3540
tgggaaaacc tgtatgatgc tgttcacacg gtctctcatt gtttcctggt tcccctagtcc   3600
aagtagccca tgtctctggg gggagagcag aacagcagtc gtggccctcg agagggctgg    3660
tcaggacaca ctacaaaagg gtgactcagc aatggggtca gggtatcctt tagccctaat    3720
tgatgtggca caagcttcag ggtgggctga gaggctttac tctgctctgg gatgggctgg    3780
tctctagacg ggtgccactg agacaggaca aaactaccac cttaggaaag actcaggaca    3840
taaaaaaat gtgctgaggg tgaagagtat ttgtgtgaga actatataca gaggctgtcc     3900
cagcatgcag ggagatggat gagaccttcc agaggttgtt ggcatctctc tggttctacc    3960
cagcagggcc cttcagggtc ttgcatcagt ccaggagctg tccccaagcc gaggctcctt    4020
```

```
ccccacctcc caccctgaat gctaaccagg agaacttttg tgttcagttc acagataacg    4080
gccaaatcat tttcccagag tcagagtacc agatttctc ctactccaac cctccctca      4140 gaggctttac aggccaggac cctgtggccc tggtggctcc attctgggat gatgctgatt    4200
tctccaggca aggaaccacg ttttaccagg tgggccttc aaagctcagc attcagggtc    4260
ctccagcagc cagcaaggac agacagaggg ctgtgtggag ggccttgcaa gtgttactgc    4320
tgtcagagcc taggctcagt gtgggcaggg actaaaactt aaatgtgagg atgaggagga    4380
agcagatgag gacaaaatca tgggaagact gaaggtgcca gggatgggga ttggggatcc    4440
atcgtttgat tttaggatga ggttgtagca aggtccctcc taacaaggct gagttaagca    4500
aggcccctgc actgggctga tgattccatt cagtgggagc tattgtgtaa tgaaagctac    4560
cacaggcaaa ggtacgtcgt gccctgcca aggaccaggc actgtagaag gtccaaagat     4620
ggagaaacat gtgcctgtcc tcaaagagcc tccagtggga tacagggtgg tacagatggg    4680
cacaggtggc tgcacaatcc aagccagtct gcgctaagcg aggcacaagt tcaagtccag    4740
aagttactgg cctcgactct ccactccaca taccccaggt ttccctgcag cccgaacctg    4800
atttgatctt aaggtcagag gtgctaactg tgaaaatgtg ggcctgrgac ggggaggat     4860 ggaagatatg ggcagactca aatgagcagg atcaccatgc agaaagtggg ggktcgccca    4920
gragtsttga gctgggatcc ttgtttcttg tctgaatctg ccttcttttc taggagtatg    4980
agacgctcta tgatgaatac aaccagctag tgtgggaggt ggagtattgg attaaatgtt    5040
aacaacacct ggactacaaa gccaggtgga cactaaggtc acgtgggtca cgcccctgct    5100
atctgccaga gacctcaggt gagtgacagt ggcactcctg ggacattgaa tcaactctaa    5160
tctagcaggg catctctaat cttcgatcta gactcactac caacctggat agagtgacta    5220
gatgctagca atgcgcatgc atcatgtcac aatctcaata acagatctgg caagtaa       5277
```

<210> SEQ ID NO 83
<211> LENGTH: 7904
<212> TYPE: DNA
<213> ORGANISM: Sus scrofa
<220> FEATURE:
<221> NAME/KEY: variation
<222> LOCATION: (1659)
<223> OTHER INFORMATION: Variation found at position 1659: T in
    resistant, A in susceptible
<220> FEATURE:
<221> NAME/KEY: variation
<222> LOCATION: (1666)
<223> OTHER INFORMATION: Variation found at position 1666: G in
    resistant, T in susceptible
<220> FEATURE:
<221> NAME/KEY: variation
<222> LOCATION: (1684)
<223> OTHER INFORMATION: Variation found at position 1684: A in
    resistant, C in susceptible
<220> FEATURE:
<221> NAME/KEY: variation
<222> LOCATION: (1726)..(1731)
<223> OTHER INFORMATION: Variation found at position 1726: AACGTG in
    resistant, 6 bp deletion in susceptible
<220> FEATURE:
<221> NAME/KEY: variation
<222> LOCATION: (1740)
<223> OTHER INFORMATION: Variation found at position 1740: A in
    resistant, T in susceptible
<220> FEATURE:
<221> NAME/KEY: variation
<222> LOCATION: (1795)
<223> OTHER INFORMATION: Variation found at position 1795: T in
    resistant, C in susceptible
<220> FEATURE:
<221> NAME/KEY: variation

```
<222> LOCATION: (1820)
<223> OTHER INFORMATION: Variation found at position 1820: G in
      resistant, T in susceptible
<220> FEATURE:
<221> NAME/KEY: variation
<222> LOCATION: (1912)
<223> OTHER INFORMATION: Variation found at position 1912: T in
      resistant, C in susceptible
<220> FEATURE:
<221> NAME/KEY: variation
<222> LOCATION: (2009)
<223> OTHER INFORMATION: Variation found at position 2009: T / deletion,
      not in linkage disequilibrium
<220> FEATURE:
<221> NAME/KEY: variation
<222> LOCATION: (2997)
<223> OTHER INFORMATION: Variation found at position 2997: A in
      resistant, G in susceptible
<220> FEATURE:
<221> NAME/KEY: variation
<222> LOCATION: (3277)
<223> OTHER INFORMATION: Variation found at position 3277: C in
      resistant, G in susceptible

<400> SEQUENCE: 83
tgcagtttac gaatcgccct tgttccacg  gtctctcatt gtttcctggt tccctagtcc      60
aagtagccca tgtctctggg gggagagcag aacagcagtc gtggccctcg agagggctgg     120
tcaggacaca ctacaaaagg gtgactcagc aatggggtca gggtatcctt tagccctaat     180
tgatgtggca caagcttcag ggtgggctga gaggctttac tctgctctgg gatgggctgg     240
tctctagacg ggtgccactg agacaggaca aaactaccac cttaggaaag actcaggaca     300
taaaaaaaat gtgctgaggg tgaagagtat ttgtgtgaga actatataca gaggctgtcc     360
cagcatgcag ggagatggat gagaccttcc agaggttgtt ggcatctctc tggttctacc     420
cagcagggcc cttcagggtc ttgcatcagt ccaggagctg gccccaagcc gaggctcctt     480
ccccacctcc cgccctgaat gctaaccagg agaacctttg tgttcagttc acagataatg     540
gccaaatcat tttcccagag tcagagtacc agattttctc ctactccaac cctcccctca     600
gaggctttac aggccgggac cctgtggccc tggtggctcc attctgggat gatgctgatt     660
tctccaggca aggaaccacg ttttaccagg tgggcctttc aaagctcagc attcagggtc     720
ctccagcagc cagcaaggac agacagaggg ctgtgtggag ggccttgcaa gtgttactgc     780
tgtcagagcc taggctcagt gtgggcaggg actaaaactt aaatgtgagg atgaggagga     840
agcagatgag gacaaaatca tgggaagact gaaggtgcca gggatgggga ttggggatcc     900
atcgtttgat tttaggatga ggttgtagca gggtccctcc taataaggct gagttaagca     960
aggcccctgc attgggctga tgattccatt cagtgggagc tattgtgtaa tgaaagctac    1020
cacgtgcccc tgccaaggac caggcactat agaaggtcca aagatggaga acatgtgcc     1080 tgtcctcaag gagcctccag tgggacacag ggcgatacag atgggcacag gtggctgcac    1140
aatccaagcc agtctgtgct aagcgaggca caagttcaag tccagaagtt actggcctcg    1200
actctccact ccacataccc caggtttccc tgcagcccga acctgaattg atcttaaggt    1260
cagaggtgct aactgtgaaa atgtgggcct gggatggggg aggatggaag atatgggcag    1320
actcaaatga gcaggatcac catgcagaaa gtgggggggtc gcccaggagt gttgagctgg    1380
gatccttgtt tcttgtctga atctgccttc ttttctagga gtatgagacg ctctatgatg    1440
aatacaacca gctagtgtgg gaggtggagt attggattaa aatgttaaca acacctggaa    1500
actcaaaagc caggtggaca ctaaaggtca cgtgggtcca cgcccctgcc tatcctgccc    1560
agaagaccct cagggtgagt ggaccagtgg gcagctccct gggaaccatc tggaagtcag    1620
```

```
acatcctaga atcctaggca ggggccactc ttctaaaawc ctttckgact cttacagaac   1680
ctcmcactag cccagagcac tgggtattag gaggttgaaa catagaacgt ggaatgtccw   1740
taagtcaaaa atggctggca attggcaatt ctatatggct caacctaata ttttyatcca   1800
catattagaa acgaggagtk ccctggtggc tcagcaggtt aaggatctgg cattgtcact   1860
gctgtggctc tggttgctgc cgtggcacag gttcgatccc tgatctgaca aytttctgaa   1920
tgccaagggt acaacctaaa taaataaata gaaatagaaa gaaaatagcc agaaaatata   1980
actgtgaatc aggtagtcaa aatacatatt tttttaaaag aacgaaatga ggaagatgat   2040
ggttagaaaa gttaagtgac ttgcttcaag gtcacccagc tagcaaatga caaagccagg   2100
cctgaaacag aggtttttct gactctgcac tccagctctt gaccaaaacg catccactgg   2160
aagcaggcac accacatgtc cccccctatc tggggcctca ccaccctgat agtcacaaag   2220
ttcttccttg tgtctggtct aaagtcactc atttcttcat tggctcaaca agctcattgc   2280
ttacctactt tgcacaagca cagtgctggc cccggccttc agagaacctc cactctcacc   2340
tgtgtggtcc tccacgccat ccaggtggag gggacatttg acaatatacc ttaaatatcc   2400
ctgaggaagt tccttaggcc tcccccagct ctccaacgtc cgctgatcac tcaggttgct   2460
gaagctttct catacaaacc ctcttctcac tgaattctgg cctagagtcc tttggctccc   2520
ttcctgggga agaagtccca aagaaggcaa atccaccatg gcaggtgctt ggacagtcag   2580
agtgaaatct ctgcataatt ccaaatttgc ccatatttta agcccacacc ttagctctgg   2640
gtaggccagg aaacagtgat atgggtgtca tgcccaggct gtgtgacagg taatgggaca   2700
taccagatct ctcacgggca tccctatgct tgtctccaac caatcccag accaacacct   2760 accaggccat cctttccacg gatgggagca ggtcctacgc cttgtttctc taccaaagcg   2820
gtggcatgca gtgggatgtg acccaacacc taggcaaccc cgtcgtcatg ggcttctcca   2880
ggtaggacag agtggggctg tctgcattga gtagacagca ggaggcggtg caaagcaggg   2940
cttgcagctg cacacgaact ccattcccca aggatacgcc aaaatcctcc ctgcccrtgc   3000
ttctgattca cgctgactcc agttcccact tcttgctgtt tcaaattaaa agaccctat   3060 tcactctgcc gttctctttc ctatcaaggt ctccgtgcat gtgataataa tccccagagc   3120
cttgacttct aggacttcca ctgacagtag ctgacctcac ttgacttttc agagcttaac   3180
aataacagcc aacatttatt ataccagcac tcagtatgca ttattttgta tattacaaca   3240
accccatgaa ggagatctat tttattaccc attctasaga tacagaaact gaggtacaaa   3300
tagataagtc attgcccaaa gtcacagagc tgggatgtgg caaagtggga agctgaaccc   3360
aaatataagg ttgaaatctg ccttcctgac tttcgattgg ctggaaatta acctctcacc   3420
caaggcacca gcagcgtctg tcagtggcaa agatggagaa cagagagatg gatggggacg   3480
tgggttccca agggaggagg tggctcagtc tctgacacaa cagttctcaa ccttgccatg   3540
tgcgccactg gctgtgaagg tcgcatgtaa tttgttactg ctaattgcta caaatgtttt   3600
tctcttagag tgtattcagg attgcgcctg taattacatt gctttcactt gcttagtgat   3660
gagccctgaa ggaaaaagaa gtagaattat ccgaccagct aggaatttca caccattctg   3720
agtgcaccca cggaaggtgt cacacccaag tgcgtcatct gtcctgtgtc agagaggaga   3780
aaagatcagg agtggctgct ctgaggcgtg caccctgagg ctgtgggctt tgctccttcc   3840
ttccaggggt gggggtgggg cacacccatt gcctggtcct cactcggtgc tgagggattt   3900
accagtgtta ctgctttgaa tcttcacaat actgtcaccc ctttgacaca gaggtgaaaa   3960
```

```
ctaagaatca aagaggttaa attaacttgc ccatgatcac caagctacta agtagtggaa   4020
ctgggggttg aatccatgac cgagagactg gcttttaacc ctcacagcca gctgtgccct   4080
gcagcacccc ttctccaatt cctagttgaa gggaaactaa caggaagggg gcctgacctg   4140
ttgttctcac acccctgtct catgacccgt ttcctacagt tcaccatcag atgtggaatc   4200
aattagagtc tcctattcct gccccaagcc tcccttcccc actcctgctt ggcaccgggt   4260
ctatgattct ggctggctga cgaaacgact gaacagctga taactaatga ctggctggac   4320
tgagtgggtg accagctgac tgaccagctg tatgaatgag taacttgctg actgagagga   4380
aaaactgtgt gacagtggct gaagattctt ccttttgcct acagtggaga tgggtatttc   4440
aaaaacagcc aactgacatt gcagccagtg tgggagaagt atcgtccaga ccagttcctg   4500
gatcccacat caggtaaaag caccacctta tcacacttga gggacccaag tccccttctg   4560
tcctcccctc catgtgccat gacagtccca gagggcagct cccttgcatc tccaccatcc   4620
caaagggtgt ttccagcaca actgacttcc catggtgcaa tccagatgtg gcactgccca   4680
gggagtggtt acctcccgtg ccctcacaca gcacaaagtc atttgaggct gcttctcctc   4740
cctgggcgga gccaaacaca ggagagctat gagtggggc cctgatcctg gaagtgagga   4800
caggggcatg gcaggaggtg aggaatgaat gggcagctag gacaattctc caagtgtcct   4860
gtcccagaac agtaatgaga cttcattctt caatggaatc taccaagagg agctccaggg   4920
gatctgacat ctattcagtc ttcgtttatt gagtacctgc tgggtgtagg acactgtgct   4980
aagagccaga agtatgagaa atgaaaaaga ctatgtttgc tgtcaaagag ctccccctct   5040
ggtaagaagg ccagtactct aggccccacg ggcctcctcc atgatttgat tactgtccgg   5100
tgacccctaa agaaaagaaa tttcagtttc caaatgtgac agaacaaagg atattctggc   5160
attaaaaatc tgccatgtaa agtatgaagc attaatccag ttctgattgc tctgtggcaa   5220
caacttctga taaacagaag ttaagtcaaa tcatgggtgc catcttgtgg agaaagctgt   5280
cctattagac tagggcccctt ctatccagtt tgtgcttgta gggggcgcaa taggatagtg   5340
tgtgtgtgtg tgtgtgtgtg tgtgtgtgtg cgtgtgcatg agcgtgcatg taaggcccct   5400
ctatccagat gcatctgctt gtgacgtggg gatgcaatag gagtgtgtgt gtgtgtgtgt   5460
gtgtgtgttg ggggagagta tctggtgtgt ttcccctgat accaggccac agtggagaca   5520
atgcacagat gatcataaac aatgattact ctttccaaa cctcatcaaa actgtagtta   5580
gcttgatact ttcttttaca cggggtcagg gtcaaaatca aatacattat atcctattgt   5640
attttactgg actctggagc ccacactcag ggtttggctc tgagttggat tacaggtgag   5700
gccctcctgc ccagcacttg tctcaaggtt tcgctgtaag atccaaactc ttgaggtttt   5760
ggaggtcaca tcaaagggcc tttggggagg cactactgcc agtctgactg ggtccattcc   5820
tagaagagct gtccagggca gggggagtga catacagagg gtgcatttat gagtttgtt   5880 tgttcccaaa actaaagcag agcctgtggc ccaggccctg agatcacccc cttttcctct   5940 gctcccagg cctccggggg ctgcagatct ataagctaca caaggaagac aagcccaact   6000
atcgtctctg gtgcctgcgg tggttgaaga gacagtctca ctggtccggc tggggctgga   6060
accaggtctc ctgcccctgc tcctggcagc agggactatg ggacttaaga tttcagccca   6120
tcaacatagg tgacacctcc ttcatagtat cctgtggtgc cccactgtcc ctcacaagcc   6180
tgcccaccct cccttтgggcc ttgcctgacc cgtctcttcc agggcaccct cagttcctcc   6240
ccagaagcac cccctaccgt tgatgcacac accaaaggca tcctgggcct gagtgtgtct   6300
ggcttgttgc aggctggtgg ggcatcgtca acaggcagct gtgcagcttc tcctcctggc   6360
```

```
gtgggagtgt gtgctgcagc tacgggccct ggggagagct tcttgaaggc tggagattgc    6420
agagtccttg gcagtttggt atgtgtgtcc acagagaact tgagcccagc ttttctggag    6480
ctttctgttc ttccctgtca gagaccagcc agcagtgaga cccacagaag gaaggctctt    6540
gtcccatttc ctcccagcta ccttccccct ctggccttca atttcctgat ctggtaacat    6600
gaggaaattt ccaacatccc ttccagctga caccctaggg atttatgatg gagtccctct    6660
tgtcccatct ccacttcgcc aaaagcccca gcccagagtc gggcatcttc tagggaagaa    6720
aggggcctgg tctggccctg tccatcggaa cccagattag cagctgtgca ggggaagact    6780
tggagtcgcc tcctgcagag accctccaaa gcagctagag aggacagcgt tggggggcca    6840
gggtcatgcg tgtccttctc acctcctcct tgtaatcaca gcctccttag tccccacacc    6900
accagccatg ccctcctgct cccacagcac tttgagactc agcaccccac ccttcaagaa    6960
aggaagggcc ctgggagttc ccactgtggt tcagtggtaa tgaacctgac tagtatccat    7020
gaggacacag gttcaatccc tggcctcact cagtgggtta acaatctggt gttgctgtaa    7080
gctgtggtgt aggtcgcaga cacgacttgg atctggtgtt gctgtggctg tggtgtagac    7140
ctgcagctgc agctccgatt tgaccccag cctgggaacc tctatatgcc gcaggtgcgg    7200
ctctaaaaag acaacaacaa cgacaacaaa gaaagaaaga aaggaagggt cctgtgcctg    7260
gcccactagg ggctttgcta cacatggctc caaatacccca aagggagac agtcactggt    7320 caatggcttc aggtcattga gcagggtggg ttctgaactg aggtgtgccc gattcctaaa    7380
ccatacccct gccaccgttt catcctgcca gaactgccca gtgctacttc ctgcaggttc    7440
tccatctccc ccaacacgct gctcttcttc acagaccaag aactggagcc ccagaactgg    7500
tgctgccgct tcaatgacaa gccctccttc tgtgccctgt atgagctaat gcggccccga    7560
atcggctgca gtgggtacca gccccgagg cctggtgagc tgctggagcc tggctccagg    7620
acagggcaga gacagagcat caggggaagg gtagcctctc aggacctgac caaggcagca    7680
caagcttcct ggggcagggc tgtggccaca cgggaggatg gagatgggtc cagtgtgtgg    7740
agatggcaaa cgagaaattt tatatgtggc cttgggggag ggaggtgtt gggggtggga    7800 aaatgaagat gcggtggggc gcccaagggc aggaggaatt ctggggaggg gtctgtgctc    7860
catgagcacc tccccaggct ggagtctcct gagcaaacat ccat                    7904
```

<210> SEQ ID NO 84
<211> LENGTH: 712
<212> TYPE: DNA
<213> ORGANISM: Sus scrofa

<400> SEQUENCE: 84

```
cctccccaca tcggagtctc aagaaaaaca tcctgtctgg ggccagtaag gaatcccagg     60
cccttccctg gtccactctg ccaatgtggt atctcctctt ttccagcctg gatgtttggg    120 gaccccaca tcaccacctt ggatggtgcc aattacacct tcaatgggct gggggacttc    180
ctgctggtcc gggcccagga cagaaactcc tccttccagc tgcagggtcg aactgcccag    240
accctctcag cccgggccac caacttcatt gcctttgctg catattacag ctccagcagc    300
ctggacccca tcacggtgag ccttcagctg gcaattgagt cccaggagga aaagagaag    360 gaagaaggc aggggcaga ggtgagggag gatgcatcct gctggcacag cagtcccaga    420
gtcaaccctg gaaacatagg attagggtct tggctccacc agctgtgaga ctgaagaagg    480
acctactttt cagtgcctcc cagttttttct tagggtaaat ggggacgatc tactacctca    540
```

```
cagggggctgt tgtgagatta aaactaacta gacccggcca ggcctctacc agtgctgctc      600
actcatcgcc ctccagcacg tccttctcag cccaggtcta gtctcgagct ctcctgcctt      660
gacacgcagc ggctagcccg catcctcagt caggtctgac cagccacggt cg             712
```

<210> SEQ ID NO 85
<211> LENGTH: 1302
<212> TYPE: DNA
<213> ORGANISM: Sus scrofa
<220> FEATURE:
<221> NAME/KEY: modified_base
<222> LOCATION: (98)
<223> OTHER INFORMATION: a, c, t, g, unknown or other

<400> SEQUENCE: 85

```
aaaaaggcgg gcccggggat ttgaattccg ccccccctaaa ggggcgaatt gaattttagg      60
ggcccggaaa ttccgccctt caattccctt tcagggtnca aaggcccctt aagcccaatg     120
acacaatcca ggttctgctc aatacccaga ctgtaacatt tgagactaac catgcaggtg     180
ccgaaggtag gctggggatg gccgtcagct gccctctcct gcttccctgg gtcgggtcac     240
tggggagcag ggtgctgggg tggagaggca gcagcatcgg gcagagcaga gtggtcgcca     300 ccctgctgt ccttccagca gctgtgcctg agcagcttct tcactggagc cgagcattga      360
gcttttcctc cgcacttctc tccttcctcc agggctgtga cggcctctct gggcaatgcc     420
agggagaact ggttgggggg gcgggtgcca tgagggtgtc ctgtgagctt ggtttgcggc     480
tactggtgta ggacctggga gggcatctcc cagctgctct cagcctcctc tccacatctt     540
gaaccttcac tactgccaag tcttgggcct ctaggactcc aacactggct gtttcatcat     600
ctgtctcccc accttctagg ccaggagatg ttcaacacct ctggagtcat aatgatccgc     660
aatggctcca cggtgtcagc cagctttgat ggggcggtga ccatctcagt gatcgctctc     720
gcccaaatcc tccatgcctc ctgcggcctc ccaaaggagt atcagaacca cacagagggc     780
ctcatgggta aggagcgggc aggcccctgc ctctgcagca ccagctcaga ccccggcct      840 ccaggcagct ccccctcccg tgggtctgcg gatactccgg gtggagtttc cttttcagc      900 ctcctgggag cagagccctg agggtacaga gcagcaggga gggaggggggg acccttcag     960 ctacctttga ggctcacttc ccatccttct gaagctctgg ttccagggca gccaagaatg    1020
aatcaatagt gggctctggc agttcccgtt gtggctcaac agtttaagga cccagtattg    1080
tctttgtgag aatgtgggtt tgaacctggg ccccactttg ctaattaagg actggcattg    1140
cacatgttgt tggtgcccct tttcttatcc accctactct tggtacttttt ctattcagtg   1200 gttgccctat atatggaaat aacactatcg actcctcacg cccaggtcgg agaatgcgca    1260
attaggtctg tggtaaactg attctaatag tatattagtc tc                       1302
```

<210> SEQ ID NO 86
<211> LENGTH: 937
<212> TYPE: DNA
<213> ORGANISM: Sus scrofa
<220> FEATURE:
<221> NAME/KEY: modified_base
<222> LOCATION: (1)
<223> OTHER INFORMATION: a, c, t, g, unknown or other
<220> FEATURE:
<221> NAME/KEY: modified_base
<222> LOCATION: (101)
<223> OTHER INFORMATION: a, c, t, g, unknown or other
<220> FEATURE:
<221> NAME/KEY: modified_base
<222> LOCATION: (180)
<223> OTHER INFORMATION: a, c, t, g, unknown or other

```
<220> FEATURE:
<221> NAME/KEY: modified_base
<222> LOCATION: (329)
<223> OTHER INFORMATION: a, c, t, g, unknown or other

<400> SEQUENCE: 86
naaatttcca ccagaaacac tatggcccat atagcccaag ttcagaatta acccttcata      60
aagggctatt cctcgcggtt taaaggaatt cggcttctct nttcacatct taaactttaa     120
taatggcaag ttctgggctc ctaggactca aaacactggc tgtttattca tctgtctccn     180
ccacctttag gcccagagga tgttcaacac cctctggagt catattgatc cgcaatggct     240
ccacggtgtc agccagcttg aatggggcgg tgaccatctc agtgatcgct ctcgcccaaa     300
tcctccatgc ctcctgcggc ctcccaagng agtatcagaa ccacacagag ggcctcatgg     360
gtaaggagcg ggcaggcccc tgcctctgca gcaccagctc agaccccgg cctccaggca     420 gctccccctc ccgtgggtct gcggatactc cgggtggagt ttccttttc agcctcctgg     480 gagcagagcc ctgagggtac agagcagcag ggagggaggg gggacccctt cagctacctt     540
tgaggctcac ttcccatcct tctgaagctc tggttccagg gcagccaaga aggaatcaat     600
agtgggctct gggagttccc gttgtggctc agcagtttaa ggacccagtg ttgtctttgt     660
gagaatgcgg gtttgaaccc tggcctcact cagtgagtta aggactggca ttgccacaag     720
cagctgcagc gcctattcta ttcaaccct agcctgggaa cttccatata ctgcaggtgt     780
ggccataaaa agagaaaaaa aaagaatgg gctctgactg ccttgggtgg cggggggggg     840
gggaggaaag gggactgatg gagagtttga gttggtaggg gtaaactatc acattcagaa     900
tggataagca agggcgaatt cgcggccgct aaatcaa                             937

<210> SEQ ID NO 87
<211> LENGTH: 738
<212> TYPE: DNA
<213> ORGANISM: Sus scrofa
<220> FEATURE:
<221> NAME/KEY: variation
<222> LOCATION: (332)
<223> OTHER INFORMATION: Variation found at position 332 G/A, Not in
      linkage disequilibrium
<220> FEATURE:
<221> NAME/KEY: modified_base
<222> LOCATION: (417)..(418)
<223> OTHER INFORMATION: a, c, t, g, unknown or other
<220> FEATURE:
<221> NAME/KEY: modified_base
<222> LOCATION: (420)..(421)
<223> OTHER INFORMATION: a, c, t, g, unknown or other
<220> FEATURE:
<221> NAME/KEY: modified_base
<222> LOCATION: (425)
<223> OTHER INFORMATION: a, c, t, g, unknown or other
<220> FEATURE:
<221> NAME/KEY: modified_base
<222> LOCATION: (672)
<223> OTHER INFORMATION: a, c, t, g, unknown or other
<220> FEATURE:
<221> NAME/KEY: modified_base
<222> LOCATION: (674)
<223> OTHER INFORMATION: a, c, t, g, unknown or other
<220> FEATURE:
<221> NAME/KEY: modified_base
<222> LOCATION: (678)..(679)
<223> OTHER INFORMATION: a, c, t, g, unknown or other
<220> FEATURE:
<221> NAME/KEY: modified_base
<222> LOCATION: (691)
<223> OTHER INFORMATION: a, c, t, g, unknown or other
<220> FEATURE:
<221> NAME/KEY: modified_base
```

<222> LOCATION: (697)
<223> OTHER INFORMATION: a, c, t, g, unknown or other
<220> FEATURE:
<221> NAME/KEY: modified_base
<222> LOCATION: (708)..(709)
<223> OTHER INFORMATION: a, c, t, g, unknown or other
<220> FEATURE:
<221> NAME/KEY: modified_base
<222> LOCATION: (712)
<223> OTHER INFORMATION: a, c, t, g, unknown or other
<220> FEATURE:
<221> NAME/KEY: modified_base
<222> LOCATION: (719)
<223> OTHER INFORMATION: a, c, t, g, unknown or other
<220> FEATURE:
<221> NAME/KEY: modified_base
<222> LOCATION: (721)
<223> OTHER INFORMATION: a, c, t, g, unknown or other

<400> SEQUENCE: 87

| | | | | | |
|---|---|---|---|---|---|
| catactgcgg | tttacgattc | gcctatccag | gatggaggac | tcctgctctg | tctctcaggg | 60 |
| ttctggaacg | gcaacccaga | tgatgacttc | aggatgccca | atggctctac | tctttcccca | 120 |
| cggagctccg | aggagaccct | ttttcagtat | ggaatgacct | gtgagtctgg | tcctcagagt | 180 |
| cctcgggtag | atgggcaggg | ctgctgcatg | gtctccctca | ggcctgtggg | aaccagacct | 240 |
| ctgtcctttg | tgagagaggg | gtagaaagga | agagatctaa | agatgctggt | gctaccccca | 300 |
| gatttgtccc | ctctgtcccc | aacccacctg | crcctctcta | cctgggagag | gggacaaggg | 360 |
| aggtgggtgg | ccctcagtca | ctagagtgag | gatttccaga | ctcagaagct | ggaaatnntn | 420 |
| nctcnagtga | ctgagggcca | cccacctccc | ttgtcccctc | tcccaggtag | agaggcgcag | 480 |
| gtgggttggg | gacagagggg | acaaatctgg | gggtagcacc | agcatcttta | gatctcttcc | 540 |
| tttctacccc | tctctcacaa | aggacagagg | tctggttccc | acaggcctga | gggagaccat | 600 |
| gcagcggctt | tgcccatcta | gccgaggact | aagaggacca | gactcccagg | tcattcatac | 660 |
| tggaaagggg | tncntcgnng | gtcggtgggg | naggagngag | ccttgggnnt | cnggaggcnt | 720 |
| ntcggggtgc | cgttcaaa | | | | | 738 |

<210> SEQ ID NO 88
<211> LENGTH: 6041
<212> TYPE: DNA
<213> ORGANISM: Sus scrofa
<220> FEATURE:
<221> NAME/KEY: variation
<222> LOCATION: (3530)
<223> OTHER INFORMATION: Variation found at position 3530 G/A, Not in linkage disequilibrium

<400> SEQUENCE: 88

| | | | | | |
|---|---|---|---|---|---|
| ttttcagtcc | ctgccccaac | cccaaaccat | ataagggtaa | ggggtggaca | caacagaaat | 60 |
| acagccagag | gcccaccctg | gtaacaccac | catcatgcct | tgtgtgtttt | agggagatc | 120 |
| aacggaacca | gcctccttgg | caagaggaat | gaccatgtgt | cttataactt | cacccctgtc | 180 |
| ttcctttcac | aacttcgggg | aaacaagtcc | ttgaataaaa | gtttgacttc | caggtgtaat | 240 |
| ggagatgaac | aatgcatcta | tgatgccctg | gccacagaaa | atgcaaacct | ggagagcac | 300 |
| actatgcggc | tctttcgaag | ctaccagcaa | atgaatgcta | ccttgagtga | gtggcgtgag | 360 |
| gctcggggag | gtgtgtgcag | agttaggggg | cagatgagga | gcccctcttc | caagacaccc | 420 |
| cttaagctac | acattttttt | cctaaagtta | ttcaacattt | taatcccctc | ctaaacataa | 480 |
| cataaatttt | tggggggcca | cacccatggc | atgtggaagt | tcccaagcgg | ggaatcgaac | 540 |
| ctgccccaca | gcagtgaccc | aagctgctgc | agtgacaatg | caggatcctt | aacctgttgc | 600 |

```
accaccaaga gaactcctaa gctacacatt ttttaattta gccgattatt ttgctcatgt      660
tgtccctctg ctcaaatcct cccctgactc cccagctcac tctatcctta tgacaacctt      720
caaatcaaag ccctgtgcac tccagcccca ctgcctctcc acactcttct cctagaactt      780
ctagaacctc gctccctcca ctgcatcccc actgcttctt catgttcttc aaacacgcca      840
ggctcgcccc cgactctgag actctgcaca tgttctgttc tctttgccta gaataccttc      900
ccccagacac ccacaggtcg ctcctcacct ccttcaagtc tctattaaat gccaccctct      960
cagcagtgcc tttcttggct aacttgtcta aagtttcacc ttcactcaca cttcctattt     1020
gccttccctg atttatttt tctctttagc atctataact atctaatgta ttttctaatt     1080
gtagcaggtc tttttattat ttgttcattg ctatgccctt acgacctaga acaatgccag     1140
ccatagagta ggtgctcaat aaatatttgc taagtgacta actgaatgaa tgaatgaaca     1200
acagaatgga ataccaggg ctccaaatcc agagaccagt ggaaaacttt tactctctca     1260
ttctacttcc tgacaatgta atatccacct agatataacc ctcagtgttt ccagctctcc     1320
tccaaaggta aaattccaca atggcctgaa cagctctgtc ctctgatcac ttcataccat     1380
gccctgcata actttctcac caggaaagaa cctgaaatga atcttgtttg gggagaaaat     1440
aaagagagag taaagatttg ctgggtggg caatacaaca atgacctgct ctgcatagat     1500
gcaagagcag gtgcatagat tatttcctgc ttctggaggt gggtcccagc cctgggaatg     1560
cctcacacaa gcgagaagac tagagagaga gaaaggaggc ccagaaggca ggaaatatcc     1620
tgccccagac cctgacccct tctttgtgtc tcagatcagt acccgccctc catcaagggt     1680
cctgatgtgg tgaaaaccta tgggacag gccagccttg ttaattacac cagcagctct     1740
gagaacgtca cattcactct cagacacaac tgcactgact tcaagctctc tggtaagaat     1800
gctcggctgg ggcagttagt ggttgaggtc tgagtcaagc tttgggtaat tttgcgttat     1860
tatactctgt gcaacttcat gtcacctttc attggaatat ctaggaccaa cattacccag     1920
gaatgatcca tataaatcaa atagattccc cccagagatt aatagtgatc tggccagcta     1980
gctcgactga ctccaggctg attcaaagat catttcttct cattcttgta atattgcaaa     2040
atcatcttta tgcaatcacc aagttattag aataaatttt ttttgtctt tttgtctttt     2100 taggactgca ctggtggcat atggaggttt ccaggctagg ggtcaaatca gagctgtagc     2160
tgccaaccta caccacagcc acagcaacat gggatcctta acccactgag caaggccagg     2220
gatctaaccc acaacctcat ggttcctagt tggattcgtt tccactgcgc cacaacggga     2280
actcctagaa taaatatagc aattaaaaag tactaattta aaatatttgc acatctatta     2340
aaagaaggat atcatatgga acaagattta aagaaataca aataccttca tttggtaact     2400
ttctcacaat tttgatgttt gtcaaccatg tttacctaac tttgcccctc cttgcctgct     2460
tttctgtact gggcccaagc agtttcactt tccctctcag taatggtgtg gagaccccat     2520
ttcagaacgg gaaccatgat ctgggtcaag agtcaaagca cacaggttac agcttgcctt     2580
ttagggccag ccctaattaa gctggtgact gctctttgct aagccagagc ccttagggac     2640
cttgctctga gcacctctct gcctctcttt ctctgtgcat aagaagagac agcattgtct     2700
gcaccctgtg ctccatgtgg catgctccct agtgcctaat caatggcatc aggagactca     2760
ctcctccact gggctcctat cctgaagagg gaggtcctgg aagtgactct catctgctcc     2820
cacccatcag ctcttttcaa tccactgttt taaggagact tccctatttt cttgaaaaac     2880
ataagacagg ttgaatcaga agagtcctta ttgatacaca gcagtatttc cctgtagcct     2940
```

```
ggggtctggt caaaggtcca ggaaatgaga gcaagtgggt gagggatgag gctgctgtga    3000
agctgaggtc agtctggcct gaagtgtagc ctgagtaagt gttgggaaga tcctggcctt    3060
caccctccat ggctccccccc ccccatatc ccatcctagt gcaggtccag gcagggttac    3120
cctttggggg ctttggggag gtgggggggca accaccttca tctcatggag ttctacccta    3180
gaatcactta gttgggctgg tgccacctcc aggttggagc gtgatccaac agaaactaga    3240
aaccagcctt gctcaaggaa atgcctagta agattggagg ggtggtctga caggggtggg    3300
ggacgtccag catcagcact tggggtatta gatgccagga tgtgtcaggc agcagaggag    3360
atgaggctcc cagctctcaa aatgatctgt cttccctggg ggcagagaat gggacgttgc    3420
tatggacacc acagtcactg aaaccatgtc ctctggagat tctggcaaga agtgccaagg    3480
atgacttgtc atctgtactc aagccaagaa tggtggtctg cacttgccar gcagagagcc    3540
agtgtttata taaccagaac gatcgggtgg gcaattcctc cctggaggtg agtgtgggag    3600
agggtgggag gtcggtctct gtgttgaggg aagggaagtg ggaattgaag ggatgttgtc    3660
attcagcccc tctgtcctaa tgtgtgtgtt gggaggtggg tggagctgtg gtaggtgagt    3720
agggcagata ccaattttgg gccacaaaca taagaaatag gactttcttt agtgcttata    3780
ggtcaactga attttttacct cccagctccc atccagccaa gctagcagga aacttccacc    3840
tcagcctttc tttgagttgc tcagtggttt ctagctccat ggttctggaa cgagacaatg    3900
aagtgtgggg tgggaggagg tccatgtggc ccctgggggg cctgagtctc catggatcac    3960
agcttcttca tcccatcaga tgtagggaga tgctctgtgg cttctgggcc ttacttggat    4020
acaggaaacc tcctttaaag tggcttaggg tcccatgtgc ctagaagcag tgcacagcca    4080
tttctttggg gcctcatcgt catcttggga agagaggtac aggcccccctc tgattttaac    4140
acctgtaaaa tcctattttt ccttttttgct ctcttccaac taaacgaagc atctctttgg    4200
cagtttagag aaaatccttc tccattcaag tttctagcca agatacttgg cctaagtcca    4260
tgaatctggc cctatctgcc tttttttttt taatggccat gcccacagtg tatgggtgtg    4320
accattaaaa aaaaaaaaaa aaaaacactt ctgggccagg gattgaatct gagccacagc    4380
tccggcaata ccaaatcctt taactcactg tgcctgtctg gagattgaac ccacacctct    4440
gcagtgaccc aagctgctgc agccagattc ttatctcact gcactacagc aggaactccc    4500
cctacctgct tcttaaaaaa aaaaaaaaat gttgttgttg tgaaagggga gctggaaaag    4560
acaggttttg actggcaata ctgcaccccca ttcttcaacc ccttacatac acacacaccc    4620
tccttatgaa acatgaacac agaattctga cttgaaaggg acagaggtgg gggagtccag    4680
gaggcagaaa aagaaaaaaa aaaatcagaa tggagaaagg agggattaaa atcaatacat    4740
tattttggat ttcccaagat atcccttctt ggcagtagga agtgttgaag ggctccattt    4800
cagggagctt tccagagccg tctcagtaga ggagttagag agacccggag cttggtaaag    4860
tttccgaagg gtttccctcc ctgtgccctt gctctggtgg ccatgtgctc tttcagaagg    4920
ttctatcttg gagttcccat tgtggctcag cagaaacgag tctgactagc attcaagagg    4980
acacagcttc gatccctggc cttgttcaat ggggttaaag atccagcatt gccctgagct    5040
gtggtgtagg tcgcagctgt agctctgatt ggatccctag cctgggaacc tccatatgtc    5100
acagatgcag ccctaaaaag acgaaaaaaa aaaagaaaaa gaaagaaaac aaacaaacaa    5160
acacaagaag aagaaggcgg ctctgtcttc ttcgaagtca gcaagggaag ggagagcagg    5220
acactacagc ttgtgtggga tacagctctc cagaaagaat agaatattta tttatttcgc    5280
ccctgcctta ttctagaaag gaattcagtc caggagagaa ggtgtgagag ggaagaggct    5340
```

| | |
|---|---:|
| tgaggtccca gggcaggggc caggcagagg gctccgggga aatgatggcc cagggaggcc | 5400 |
| acccagcttg gaggatgatc ggcctttggg cagggatgtg gaggcccagg gtctgatcca | 5460 |
| aaaggtgctc agtgatactg acagaagaca aggacctgag tccatgggtt ctcagaccag | 5520 |
| aggagttggt acagctacac ccagaagccc ttgatggttc ggcttcctgg cggcccagtg | 5580 |
| atcagcaacc cattccagat ggccggctgc aagtgtgacg ggaacacctt tggccgctac | 5640 |
| tgcaaccact ccaaggaccc ctgtgatgag ccgtgcttcc cgaatgtgaa gtgcatttcc | 5700 |
| gggaagggct gcgaggcctg cccgacaaca ctgactgggg atggacgtca ctgtgcacgt | 5760 |
| gagctgggga cagggccttg gcaggaggag gttctgggga tggggcctaa acagccaggg | 5820 |
| aaaaccattt ctccccccctt tccagcaagc ctttagaatg ttcgataaag ggggctatgg | 5880 |
| taaggaggta agaggggag gggagggtat gaggccaaag gaggagagat ggtccaggca | 5940 |
| tgggggaggg gccagagtac agcagtccca aggcaacgat gaagggcgca ttcgcggccg | 6000 |
| ctgcgactag aaggcttgta ggaggctgta ggtcttggcg t | 6041 |

<210> SEQ ID NO 89
<211> LENGTH: 4254
<212> TYPE: DNA
<213> ORGANISM: Sus scrofa

<400> SEQUENCE: 89

| | |
|---|---:|
| tttttgattt accggccgcg aattcgccct ttgctcagtg ggttaaggat ccagcgttgc | 60 |
| cgtgagctgt ggtgtaggtt gcagacgcgg ctcggatcct gcgttgctgt ggctctggcg | 120 |
| taggccagtg gctgcagctc cgattcgacc cctagcctgg gaacctccat atgccgcgag | 180 |
| agcagcccaa agaaatagca aaaagaccaa aaaaaaaaaa aaaaaaaaaa aaagactgga | 240 |
| gacaggaggg gacttccagc agcacccagg ggaccagagg taagctggct cctggaggtt | 300 |
| tccagagatg caaggcccag ggcctctgca ttctccagtc aggacactgg cggcagggtg | 360 |
| gggtgggggg gtctgccatg ggcatctagc agcaggaatg ccttgtcttc cctttgagtc | 420 |
| ctccatccac catctgttcc ttgacctctg agcactggga gtcatgggtg gcatcatggt | 480 |
| gacatcttca ctgagccccc taaaacactc aaatgaaatc tagaaaccac tgcatcttct | 540 |
| gagcacagcc cagattggag aagcacagcc ttataaaggc caaaagggg atggaagtga | 600 |
| ggaaagcagg ctggtgggcc tttctcctcc cagccttttg ggtcctttcc tgatggggag | 660 |
| ggtctaacaa cactccattc cctcagcaga agtgggagaa cccctacctg gcagaggaaa | 720 |
| aagggttgtc tggcaaagaa atgtctggaa agggagaaa gatggtttgg ggttcagagt | 780 |
| ggcccacccg cagaacacag tttaagtgag cttttgcaggg aaaaagccaa ccctgtcctg | 840 |
| ggagcagctt tctctggctg gcggctgcca gtgtggtgta gcagactgtc tgttccctct | 900 |
| gcagctctca acagcttttt caactgttgg aacaagacct gtcctgagaa ttactgctac | 960 |
| aaccagggtc gctgctacat ctcccagtct ctgacctgcg agcccgcctg cacctgcccc | 1020 |
| ccagccttca tggaagacag ccgctgcttc ctggctggaa aaaatttcac tccaaccatc | 1080 |
| cttccaggta catccagatg ccctgccatc cccactccac acgtctctta acttggggga | 1140 |
| agatggggga ctctggggc caggctcagt ccctcaaact cacaggacag aactccaaat | 1200 |
| ctctctcgtg tgctcgtaag ttgtaggctg tgggagtgag tggggggcag ctgtcacacc | 1260 |
| acaaaccaca ggtctgagca gtctgctgag aaaagactga aggggacctc acagctcagc | 1320 |
| gagacaagag tcaggccagc cttgatcaca gggtgaggtc agcagacctg gccatttctg | 1380 |

```
attcttctgg tgaccttcta tgactgtaga agagggcagt cttcttgggc tgtcctcctt    1440
ggctaagtct gggtaaacct gtgaggtgac tatgaatctg cttcttccct ctccagagct    1500
tcccccaagg ctcatccagc tcttgctcag tgaaaaagaa aatgcctccc aagcagatgt    1560
caatgccacg gtcagtgctg caggctagct ctgggtgggg aggcggttct tggcagattc    1620
ttatccatgg cttgtacatt ctgcatctca tcatccatct agactcaact gccagaggtg    1680
gctagagcct cctgccccag gggggtgggg gtgagggagg cagggaggcg caggacagag    1740
acctccaaag ggctgtgaat gaccatctca caatgaacag aatctggggg cagggagagg    1800
ggggcaagtc aacacagcct cgcctctcct tctgagcatc cctcgagacc tgctcttggg    1860
cactatatgg aagaaacaca agagggcatt tcacctccag gaagccttcc ctgaattccc    1920
caagagaact gggggctcct tcttcttggc tcccacaccc ctgttgattc tgcagtcaca    1980
ggcaaagtag cacaattgtt gagttactga ggctctagaa tcctacctgg gttcacatcc    2040
tggcagtacc actcactaga gcaggtatga tcattagaca aattatttga tctcccatat    2100
ataaaaacag aagtaataat agtactcatg tcaatgggtt gtgtcaaagt tgaaatgata    2160
atatatgtaa agcacttagc acagtgcctg aaacacaata cattcaaaaa ttaccaaaat    2220
aactattgtt tctgctgcta ctgctactac tactacaaca gcagcattct gggatctcta    2280
tggtaaaggc tgttgacatg gatctttgag tatgggcagc attctgggat ctctatggta    2340
aaggctgttg acatggatct tgagtatgg gctgtttcta actcacactg acacacacac    2400 ccccccacc ccaacgcaca catctgacca tcccccaggt ctggctaaat ataattgatg    2460
ttcattcaga tatggggaga gggtgagtgg gtgagtcagg gatcagaggc aaggtagggg    2520
ctgttcattt catattctcg ctttgtgagt ggaactgggg tgaggttatg taaagtccta    2580
cactcaccaa caaacttcta ttaagtaggg acccatgcca gtcaccagtc gaggcttgtg    2640
gggcggggat gcagaaatag ataagaaaca ttctgagatt tcccatcatg gctcagtggt    2700
taacaagtcc gactaagaac catgggggttg tgggtttgat ccctggcctt gctcagtggg    2760
ttaaggatcc ggcattgccg tgagctgtgg tgtaggttgc agacatggct cgggtcccac    2820
gttgctgtgg ctctagcgta ggccagtggc tacagctccc attcgacccc tagcctggga    2880
acctccatat gctgcgggag cagcccaaga aatggcaaaa agacgaacaa aaaaaaaatt    2940
ctggtggtcc tggggctcac attcaaagaa agaaactggg gtggaggggt gttcccattg    3000
tggctcagtg gtaacgaact gaactagtat ccataaggat gcgagtttga tccctggccc    3060
tcctcagtgg gttaaggatc tggcgttgcc gtgagctgta gtgtagactg acagctgcag    3120
ctccgattca accccctagcc tgggaacttt ctatatgcca tgggtgtggc cctaaaaaaa    3180
aagacaaaaa aaaagaaga ataagaagga ggaggaggaa acacggatga atacatgcac    3240
aaaagtggga aaggtctcct ctctggactg gacctcaccc ccatttccac cccaccccca    3300
acccccaccc tctgccctag gtggcttata gactgggaa cctggatgtg cgggcctttc    3360
tccggaacag acaagtggaa cgagtgtaag tgggactgcc cccacctggg cccggtcct    3420 tacctacacc cctcacccct cggccccctca ctgtgcccct ctcacacagt gaactcccag    3480
caataccggc ctcaggaaac ttccttcaat actgaaagt catctcggag ttccagtacc    3540
gccctggggg ccctgtcatt gacttcctga ataccaggct gctggacgca gtggtggagg    3600
cattcttatc ccaggcctca cagaggaggt ggaagagaag tgaggagccc aggaacaatg    3660
tggtcttcca acccatctcc aggagagatg tgctcagtgt gatggctggt gagtcactat    3720
ctcgtggaca gcagtaagga tagctgaggg agcgggtaag cagagggagc ctgccacaga    3780
```

| | |
|---|---:|
| tctcaggccc acacaaaccc atggctgaag tgtattctac agcaggccac agacaagaag | 3840 |
| gaagtaaatt tagggggggtt ttgtttgtca tttttaagag aaattgggaa ccttttaccc | 3900 |
| accagccttc tagattcagg aacaggagca caaagtactg cttgatgaat ccccacgtgt | 3960 |
| acagtttcac agagcaactg ctccaactgc tgctttcctg accattgctg ctaatggttt | 4020 |
| tctttctata aaattgttaa tgatttggtt aacatttatt ttataaatat aaacaaggac | 4080 |
| attgtttttg cctttgcctt cgcctccacc tggagatata agttgaagg ctggagacct | 4140 |
| ggcccagggg cagaactatc acctccttga aagagcgtga ccctgtgcaa aagtccatcc | 4200 |
| ccagtcaagg cctcaacacg agaagggcga attcgcggcc gctaaattca atct | 4254 |

<210> SEQ ID NO 90
<211> LENGTH: 3461
<212> TYPE: DNA
<213> ORGANISM: Sus scrofa

<400> SEQUENCE: 90

| | |
|---|---:|
| cccgccctca tgtgcccctc tcacacagtg actcccagca ataccggcct caggaaactt | 60 |
| ccttcaatac tggaaagtca tctcggagtt ccagtaccgc cctggggggcc ctgtcattga | 120 |
| cttcctgaat accaggctgc tggacgcagt ggtggaggca ttcttatccc aggcctcaca | 180 |
| gaggaggtgg aagagaagtg aggagcccag gaacaatgtg gtcttccaac ccatctccag | 240 |
| gagagatgtg ctcagtgtga tggctggtga gtcactatct cttggacagc agcaaggata | 300 |
| gctgagggag cgggtaagca gagggagcct gccacagatc tcaggcccac acaaacccat | 360 |
| ggctgaagtg tattctacag caggccacag ataagaagga agtaaattta gggggggtttt | 420 |
| gtttgtcatt tttaagagaa attgggaacc ttttacccac cagccttcta gattcaggaa | 480 |
| caggagcaca agtactgct tgatgaatcc ccacgtgtac agtttcacag agcaactgct | 540 |
| ccaactgctg ctttcctgac cattgctgct aatggttttc tttctataaa attgttaatg | 600 |
| atttggttaa catttatttt ataaatataa acaaggacat tgttttttgcc tttgcctttg | 660 |
| cctccacctg gagatataaa gttgaaggct ggagacctgg cccaggggca gaactatcac | 720 |
| ctccttgaaa gagcgtgacc ctgtgcaaaa gtccatcccc agtcaaggcc tcaacacgct | 780 |
| catctggaaa aggaggtggg atgtctgagg tcccttttcag ctctgacaga ctctaattat | 840 |
| cccagaaggg gaatgaggta ggttggcaaa cttgccagcg aaggaaagga atagcccacc | 900 |
| ctgtcttatg agtggggcag agaacaggac agtggccatg ccaaatgcca cagaaggtgc | 960 |
| tgtgttacct gagcctaggg ccaagcaaga gcttcttcta gaatccaggc taagctccct | 1020 |
| cccttccagg ggcaacaatg agaaatcctc caaactacta tggtatgtgt ggtagggagg | 1080 |
| cagtgttggg gataagggaa taaatactcc agacttgact gtgccttttc ttagagaaaa | 1140 |
| caaatcaaca aaaccccccac aattttttatt atgcaagtac aatatgtttt gtgtttagga | 1200 |
| cacagaagtt aacagaaaaa aaatcacctg tattctaatc cccagagaca aatcccctttt | 1260 |
| gcacatactc tgctaaattc tctttttatgc ataggacact tcatatatca ataagggggat | 1320 |
| caaatcatac ctaatgtttg ataacctctc cattactttta actgtgaaca tattaccttg | 1380 |
| tacattgtat tcacattctg atttgatata ttattttatg tcttaaatag tgtgttttaa | 1440 |
| tatatttttaa atagaatgtt tttaaatatt tttaaatatt ttaaatagaa tagtgactgt | 1500 |
| taaactgaag gcttactatg tcaggcactg tgctaaatac tgtgcatata ttacctcatt | 1560 |
| taaactttac agtaaggtag tttccttttta aaaataagga aggaagttcc cgttgtggct | 1620 |

```
cagcagtaac aagcccaact agtatccatg aggatgcagg ttgaattcct ggcctccatc      1680
agtgggttaa ggatctggtg ttgccatgag ctgtggtgta ggtcgcagac acgtttggat      1740
cctgtgttgc tgtggctgtg gctgtagcat agactgccag ctatagctcc tattcaaccc      1800
ctagccaggg aacttccata tgccacaggt gtgaccctaa aaagcaaaat aaataaataa      1860
aataaaagga aatataaaat aaaaaatata aggaaactta taaataacg taaaatataa       1920 aataaagaaa taaagaaact gaaggaattc tcttgtggca cagcaggtga aggatccagt      1980
gtagtcactg tagaggctta ggttgctgct gtggtgcagg ttcaatccct ggcctaggaa      2040
cttccacatg ctataggcag accaaaattt aaacaaaaaa attttttttt cttttttgcca     2100 tttgggccgc tccctcggca tatgtaggtt cccaggctag ggttgaatc agagctgtaa      2160 ctgccggcct acaccagagc cacagcaatg caggatccga gccgtgtctg caatctacac     2220
cacagctcac agcaatgccg aatccttaac ccactgagca aggccaggga tcgaacccga     2280
aaccccatcg ttcccagtcg gattcattaa ccactgagcc accacaggaa ctccaataaa     2340 gattttttaat aaaaaaataa ggaaattgag gctgaaagag ttaagaaact tccccaaaat    2400
aacacaacta gttagtagta gagtttgaat ttcaactcag gtctagtaga gttcaaagca     2460
tatgctctta accaatgcac ttttcatact gtggtcctca tccattgcac aatattcttt     2520
atttaacaaa accacttctg ggagctctcg ttgtggctca gcgtgttaag aacctgacta     2580
gtatccaaaa ggtttcgggg tctatccctg gcctcgccca gtgggttggg gatccagtat     2640
tgcagcaagc tgtggtatag gttgcagatg cagctcagat ctggcattgc tgtggctgtg     2700
gctgtggctt tggctggcag ctgcagctcc aattcaaccc ctagcctggg aacttccata     2760
tgccactagt gtggccctaa aaaacaaaca aagccacttc tgcttattgt tgctcttata     2820
aaccatgctg ctacagattt ccgtgaatat atgtagtttt tgtgtgtttc caactatttc     2880
tcaggatgag tgcctaaaat ggaattcttg acagaaaagg tatagatttg gtgtaaatcc     2940 attggttttcc attttgcttg tgtcctatct gacagtgaat gtgagcacac tgaaaaatta     3000
cttccaatgt aacggctaca aggactacaa cctggttttc agcccggaga gaggcttcac     3060
ctgtgtgtcc ccgtgcagca ggggctactg tgagaatgga ggccagtgcc agcacctacc     3120
cgagggcccc caatgcaggt gagcagggtg ggggcaggag gtggagggca gtgccagaga     3180
atccaagctg caaggagtct ggaaatgcca tggtacctca cagcgcctga aaatgtaggg     3240
tggttccctc tgtaatcgag agaaggggga tcagagaaaa agggacagag gaaaagaaga     3300
tatgagtgcc tacatttgtg gagaataaag atgctatata acctttgcac ctcaaaccag     3360
caaatggata gatagatatg accatttttaa aacgcaactt agaaatgata aggaatctga    3420
ctacggtacc cagtaattaa gaagggcaat tcgtaaactg c                          3461

<210> SEQ ID NO 91
<211> LENGTH: 1402
<212> TYPE: DNA
<213> ORGANISM: Sus scrofa

<400> SEQUENCE: 91
tcgcccttcg ctgtgagcac ctgagcatga aacttggcgc cttcttcgga atcctctttg       60
gggctctggg cgccctcttg ctgatggggg tcgcctttgtt cgtgttcctg cacttcagat     120
acttctctgg gacccattac tccctggacg gagacctgag gcctgaaagc tgaggccttg      180
ccccacacag gtggctctgt cctaggatac ctcagggccc accccagtcc cacccgcaca      240 cacttttca ggcgccttgg tttggtccag attggaaaga gaaagtgac tgatggcagt        300
```

```
tcaggattct tcaagaagaa tgaaaaacag gaatgaataa aaacagtcat aaaaacaaga      360
ccatacctta tcagtataat agacacaggc tgacaggaag aggccatata ggcctgctac      420
ataaatggta gattctcaca cagacacaca aagaagacac acctacagaa cacgtatgtg      480
cacacaccag agttgaaggg gtgatggctc taaattaaaa accagaatac atttacacac      540
aaaactctct ggtttacttc taattaaagt ctatttaact aaaaatccct ctgacttttt      600
gtgtctccca aagccatgga tttcattcat gattttcctc tggtggctga agggcttggc      660
acagcgggta gaagagcgga ggtgagctgg attcagccct gcatcagctc tcagttactg      720
catattggaa agctcggttg ctccagccca gacctggatc cttgcttcct cctccatctc      780
actttcttcc actcccccca tcacaagcca aggcctggcc ctctgaggag gatgataaag      840 acaccccat atggagtttt cccaaccatc tcccagtaac ccctcctggc ttgctggtct      900
ctgcccatca gtttcaagag gataaatttt tttttttttt tggcttttta gggcctcacc      960
tgtgggatat ggaggttccc aggctagggg tcaaatcaga gctgcagctg ctggcctacg     1020
ccacagccag agcaatgtag ggtctgagcc gagtctgtga cctacaccac agctcatggc     1080
aatgctggat ccttaaccca ctgagtgagg gatcaaacct gcaacctcat ggatcctagt     1140
ggggttcggt agccactgag ccacaaagga aactcctcag gaggataaac attcagtgct     1200
ttttcttgtc tagagtgttc cctggaggag ggattaaatc atttcagctc ctttttcagg     1260
agctacctca cctttagatc cagggtaccc gacatctgtt acaccttctc tggtctttcc     1320
tggtccccag ttggagactt ctgattgtgc ctcatagccc tcaatccac tctgtctgtt     1380 tgttcccaaa aacctgatca gt                                              1402

<210> SEQ ID NO 92
<211> LENGTH: 764
<212> TYPE: DNA
<213> ORGANISM: Sus scrofa
<220> FEATURE:
<221> NAME/KEY: modified_base
<222> LOCATION: (9)..(10)
<223> OTHER INFORMATION: a, c, t, g, unknown or other
<220> FEATURE:
<221> NAME/KEY: modified_base
<222> LOCATION: (566)
<223> OTHER INFORMATION: a, c, t, g, unknown or other
<220> FEATURE:
<221> NAME/KEY: modified_base
<222> LOCATION: (637)
<223> OTHER INFORMATION: a, c, t, g, unknown or other
<220> FEATURE:
<221> NAME/KEY: modified_base
<222> LOCATION: (691)
<223> OTHER INFORMATION: a, c, t, g, unknown or other
<220> FEATURE:
<221> NAME/KEY: modified_base
<222> LOCATION: (764)
<223> OTHER INFORMATION: a, c, t, g, unknown or other

<400> SEQUENCE: 92
cctgcaggnn ccctagaggt gagctgcagg agtcgccctt ctcatttaat cctcccaact       60
accctataaa gtagatacca ttatcatttc cagtctataa agaagtaatg aaagtacaga      120
gaaattgaaa taacttgcct agtgacatag ctggtaaaca atggagcctg gagccaaata      180
cagccagtct gtttccaaaa accccacttt ttttttcttt tttagggcca tatctgtggc      240
atttggaagt tccagcaac actggtatcc gagccgcatc tgcaacctat gccacagctt      300
gcagcagtgc cagacccctta atccactgaa cctgcatcct catggatagt agttgggttt      360
```

```
ttaacccact gagccacaat gggaactcct ccaaaatacc actcttaatg actatgttat      420
gccaaaatga atgctaatga cagagttcta gaagatcaga gaaggggag atcagtgggg       480 ccagagtgat caggggtggc ctcagatcct cttggttctg gagctggctc ccagaagcag      540
gggtggcttt aatcttctga gaggangaaa gaagaccctc tgggacagaa aagaagggtc     600
agtgcagcag gagcaaaaac acaaagctgg atctganatt agtgtttaga cagtatgaaa     660
cataagaggg gggtctttgg gtttaattat nttattattt tattttggg cttggggccc       720 ggaccgtggc ttatggaaat cccagctagg ggtgtatcaa aatn                      764

<210> SEQ ID NO 93
<211> LENGTH: 314
<212> TYPE: DNA
<213> ORGANISM: Sus scrofa

<400> SEQUENCE: 93
aactccagga gggggctctt aggggaggtg gttaagcaaa tatagtggag gactggaggg      60
caagcacaac caggatctga gtgggagcta gtggctggtc taggaaggac tggacagatt     120
tagacatacg cagccctcag gcagcagca cagatggttc tggagccaaa gccacttggt      180
ttcttactgg ctctactgcc ccaccctag tcttccgaac caaaaatctc gggctgcctg      240
tggagtccat ggcctatggc ccctcctagt gtatccctcc agtgaattta agggcgaatt     300
cgcggcccct aaat                                                       314

<210> SEQ ID NO 94
<211> LENGTH: 573
<212> TYPE: DNA
<213> ORGANISM: Sus scrofa

<400> SEQUENCE: 94
gcacgaggag agagtgcacg ggtggcagcc ggaggaccct gcgcgatggc caagtttctt      60
tcccaggacc aaattaatga gtacaaggaa tgcttctccc tgtacgacaa gcagcagcga     120
gggaagatta aggccactga cctcctgact gtgatgaggt gcctggggc cagcccgacg      180 ccggtggagg cacagaggca cctgcagact cacaagatag acaaaaatgg agagctggat     240
ttctctactt tcctgaccat cctgcacatg caaatgaaac aagaggatcc aaagaaggaa     300 attctttttgg ccatgctgat ggcagacaag gagaagaaag gatacatcat ggcatctgaa     360
ctgcggtcca aactcatgaa actggggggag aagctcaccc acaaggaagt ggatgatctt     420
ttcaaggaag cagatattga acctaatggc aaagtgaagt atgacgaatt catccacaag     480
gtcaccattc ccgtgcagga ctactgaatc aggaaggag agagcctccc ctgggctgag     540
aactcaactg atgcattttt aaagaaatg tgt                                   573

<210> SEQ ID NO 95
<211> LENGTH: 671
<212> TYPE: DNA
<213> ORGANISM: Sus scrofa
<220> FEATURE:
<221> NAME/KEY: modified_base
<222> LOCATION: (8)
<223> OTHER INFORMATION: a, c, t, g, unknown or other
<220> FEATURE:
<221> NAME/KEY: modified_base
<222> LOCATION: (19)
<223> OTHER INFORMATION: a, c, t, g, unknown or other
<220> FEATURE:
<221> NAME/KEY: modified_base
<222> LOCATION: (24)..(25)
<223> OTHER INFORMATION: a, c, t, g, unknown or other
```

```
<220> FEATURE:
<221> NAME/KEY: modified_base
<222> LOCATION: (481)
<223> OTHER INFORMATION: a, c, t, g, unknown or other

<400> SEQUENCE: 95
tgggtggnaa atcggactng gagnntttta aatttctat atgacctaaa gtgaggaaag      60
aaattatcaa acccttctta aaagctcaat ccatatttgt ggagctcctg atttaaaaac    120
catccatgtt aggatacaaa attaatatac agaaatctct tgcattccta tacactaaca    180
atgaaagatc agaaagagaa attaaggaaa caatcccatt tatcactgca tcaaaaagaa    240
taaaatactt aggaataaac ctacctaagg aggtaaaagg cccatagtct aaaaactata    300
ggatactaac gaaggaaatc aaagatgaca taaacagatc aaaagagatg ccatgatctc    360
ggattggaaa atcaacatt gtaaaaataa ctattactat ccaaagcaat ctatagattc     420
agcacaatcc ctatcaaatt accaatagca ttttttcacag aactagaaca aagatctttt   480
naatttgtat gttaacgcaa aagatcctga aaagcagaag catcttgaga aagaaagcag    540
agttggagaa caggtaccc acttcgactt tacaacaagc tacagtcaaa agatatgcag     600
tactgccaca aacaaaaca gagatagga actgtaagaa gcccaaaaaa actaccacta      660
ttgcattatc g                                                         671

<210> SEQ ID NO 96
<211> LENGTH: 615
<212> TYPE: DNA
<213> ORGANISM: Sus scrofa
<220> FEATURE:
<221> NAME/KEY: modified_base
<222> LOCATION: (580)
<223> OTHER INFORMATION: a, c, t, g, unknown or other
<220> FEATURE:
<221> NAME/KEY: modified_base
<222> LOCATION: (586)
<223> OTHER INFORMATION: a, c, t, g, unknown or other
<220> FEATURE:
<221> NAME/KEY: modified_base
<222> LOCATION: (594)
<223> OTHER INFORMATION: a, c, t, g, unknown or other
<220> FEATURE:
<221> NAME/KEY: modified_base
<222> LOCATION: (602)
<223> OTHER INFORMATION: a, c, t, g, unknown or other

<400> SEQUENCE: 96
gcacgagggc ggtgcagggg acagagagtg cacgggtggc agccggagga ccctgcgtga    60
tggccaagtt tctttcccag gaccaaatta atgagtacaa ggaatgcttc tccctgtacg    120
acaagcagca gcgagggaag attaaggcca ctgacctcct gactgtgatg aggtgcctgg    180
gggccagccc gacgccggtg gaggcacaga ggcacctgca gactcacaag atagacaaaa    240
atggagagct ggatttctct actttcctga ccatcatgca catgcaaatg aaacaagagg    300
atccaaagaa ggaaattctt ttggccatgc tgatggcaga caaggagaag aaaggataca    360
tcatggcatc tgaactgcgg tccaaactca tgaaactggg ggagaagctc acccacaagg    420
aagtggatga tcttttcaag gaagcagata ttgaacctaa tggcaaagtg aagtatgacg    480
aattcatccc acaggtcacc attcccgtgc aggactactg aaatcagaga aggagagagc    540
ctcccctggg cctgagaaac tcaactgatg cattttttaan agaaantgtg tccntcactg    600
gnaggagatg caacc                                                     615

<210> SEQ ID NO 97
```

```
<211> LENGTH: 671
<212> TYPE: DNA
<213> ORGANISM: Sus scrofa

<400> SEQUENCE: 97
tgcagtttac gattcccctt ccttttctt ttatttttt gttaagataa aatcacataa      60
aattcatcat tttaaccaat ttaaagtgta caattcagtg gttttagtat atttaccatg     120
ttgtgcaacc atcaccacta attttgaagc atatttatca cctggtaaaa caaccctgta    180
cccatcaagg agcgactccc cattttttc tcccccaacc tccataaacc atttgtctct     240
atgcacttgc ctattctctg gcatttcgca taaatgaaac tacataatat gtggtcctct    300
atatctgact tctttcactt agtttaaatt ttcagtgttc atccaatgtt gtagcattta    360
tcagtacttc atttctttct gtggttgaat gatattccac tgtgtgtgtg tgtgtgtgtg    420
tgtgtgtgtg tgtgtatagt tcctttatca caaacctgct cctgtgcctg tcttgtgtac    480
ttagagagta gcacccttca tcctgtgttc cagacaaaaa attgggatgt ctcccataat    540
ctttttctct tcatttgccc tcataatcca gtcagactag gtagaaatct tgtcagtcct    600
gtccctctct aaatatctcc tgccctccct tcctccatca tgggccctac cccaggtgag    660
gactccctct t                                                         671

<210> SEQ ID NO 98
<211> LENGTH: 459
<212> TYPE: DNA
<213> ORGANISM: Sus scrofa

<400> SEQUENCE: 98
gcaggtttaa acgaattcgc ccttatccaa gaaaaagcta ataagcacta tcacagagaa     60
tacaggcaga tgtacagaac tgaagatttg aaaggctagg atggcaagaa aagctggcaa    120
cttctatgtg cccaaggaac ccaaattggc atttgtcatc aggatcagaa gtatcaatgg    180
tgtgagttca aaagtccaaa aagtgttgca gccttttttt tctctgtcag atcttcaatg    240
gcacttgtgt gaagctcaac gaggcttcga ttaacatgct gagaattgtg gaaccatatg    300
tcacatgggg gtacccaaac ctgaagtcag taaatgaatt gatctgaaag catttacggc    360
aaaacgtaag aatcgaactg ccctgacaca taatgcattg attgcccaat ctttaggtaa    420
atatggcatc atctaagggc gaattcgcgg ccgctaaat                           459

<210> SEQ ID NO 99
<211> LENGTH: 461
<212> TYPE: DNA
<213> ORGANISM: Sus scrofa

<400> SEQUENCE: 99
caatttctgc aggtttaaac gaattcgccc ttcaaggcag cagaggggtt ggggttggga     60
gcagctacct ggagaaaaag ggacattaaa aatagagaga tttaggagtt cccatcatgg    120
ctcagtggaa acgaatctga caatctgaca agtatccatg aggatgcagt ctcgatccct    180
agcctcgctc agtgggttaa agatccctaa aaagacaaaa acgagagaga aagagacatt    240
tagcaaatgg tgctaggaca actaggtatc cataggcaaa agaatgaatt tggacctcta    300
tctcataccc tatactaaaa ttaactcaaa atagatcaca gatctaaatg taagcgttaa    360
aactataaag ctctgtaaat taccatgacc ttggattaaa cagaagtttc ttagatatga    420
catcaagtaa ggagttaagg gcgaattcgc ggccgctaaa t                        461
```

```
<210> SEQ ID NO 100
<211> LENGTH: 966
<212> TYPE: DNA
<213> ORGANISM: Sus scrofa
<220> FEATURE:
<221> NAME/KEY: modified_base
<222> LOCATION: (875)
<223> OTHER INFORMATION: a, c, t, g, unknown or other

<400> SEQUENCE: 100
gggtactccc aaggtgaggt ttcctaaggc cccaggggt gaggacttgt attaaactca      60 atgattttt ttttataata tatataatta attgaagagc catcataaat tttaactacc    120
atactcaaca agttaaatac tgtgcagtta aaaatagaaa actaagagcc agataagaag    180
aaatttaaat aaaaattaaa catggtaatt tcttgcaacc tcagtgttaa caataattat    240 taccttaat tatgttttc tctactttaa gaatgaaccc gttacgttcc aagaagtgct      300
ttctggcatt aaaatcttag gttcttgcct gaccacagtc tttcagcata aaatgtgcct    360
cgatgaatgt tgcatgtgaa tgctgggtga tatccaaata attattacca aacaggttta    420
gcctaggaaa gactgacctc acttgctcaa aaatctggtt aaagaatggg gagggacgtt    480
ttatttctct tggtgatctg tttatttgca tctaagattc aagtatgaat ggattaatcc    540
agccactgta tatgggcttc aattgaactt tcaactctct gaaaatgata acagtgtaat    600
taggataaaa gatcctttaa aaaggtaaag atattaggca gactagctat gtaagtcaat    660
ttttaaaaaa attttacttt tcttcaatat gaacatacac caaatacaga tggtttggta    720
catcatagag tgtgaatcac atcctttgt agctttgata tctcagggac acttattttg     780
tggaagcaaa gttctttagt ttatccagag gttgttagta gatctgaatg ttcagaattc    840
taagatatca tgctcttaat attatttgga atcanaccct agagtgatag ggtacttggt    900
gaactactct caggattatc atgggtgtcc ctttgacagt aaaactggta agctcataca    960
catatc                                                                966

<210> SEQ ID NO 101
<211> LENGTH: 732
<212> TYPE: DNA
<213> ORGANISM: Sus scrofa

<400> SEQUENCE: 101
gcccttaata caattcctct gtgtgtgtgt gtgtgtgtgt gtgtgtgaga gagagagaga     60
cagagagaga ggttttggt ttttgggtt tttttaccca ttcatctgtc aatacacact     120
taggttgttt ccatgttttg ctattttaaa taatgctgca aaatcttggg ggtacagata    180 tcttttgaa actgtgattt ttttttcctt tggatataca cttagaagga gaattgctag    240
atcttatggt aattctaggt ttaatatctt gaggaatctc catcccttt tctatagcta     300 ttgccccaat cccaccaaca atgcacaggg tccctttgc tctgtgtcct caccaacgct    360
catctcgtct ttttgatgcc aactcttcta acaagtatga ggtaacacct cactgtgatt    420
ttaaattgca tttccctgat gactggtcat gtggagtacc ttttcatgta cctgtcagcc    480
tattctattt ctaaaccagt cctgagagac atttcaagat aacacaaatg cacacaggac    540
tgaggtgggc attgaaaagg tcatttattg ctgaactgtg agacactgcc ctcacagaaa    600
tgaactgact cccaagttgt gctttagtga ttctccatct cctacgcttc ctcaaagcta    660
attgggcctg ttctgactga tagttttaca ttccaccagg ttacagtcaa ctcttgacgg    720
cctaaaacca at                                                         732
```

<210> SEQ ID NO 102
<211> LENGTH: 521
<212> TYPE: DNA
<213> ORGANISM: Sus scrofa

<400> SEQUENCE: 102

| | | | | | |
|---|---|---|---|---|---|
| ctagtcctgc | aggtttaaac | gaattcgccc | tttataagaa | atattaatag | acataaaagg | 60 |
| agaaattgat | gagaatacaa | tgaatgctgt | gggtgcagcc | ctaaaaaaat | caaaatcagt | 120 |
| aaatcatata | tatataaata | atgtatatca | aaatcatata | tataaaaata | atggaataca | 180 |
| ataatagtag | gagactttaa | cacccaactc | acttcaatgg | aagacagatc | ttccatattc | 240 |
| cagacagaaa | atcaacaaag | caacagagat | cctaaatgac | acaataaaac | agttagactt | 300 |
| aattgatatt | ttcaagacat | tacatacaaa | aaaatcagaa | tacacgttct | tttcaagtgc | 360 |
| acagggaaca | atctctagga | ctgactacat | actggggccc | aaaactaacc | tcaacaaatt | 420 |
| taagagtata | gaaatacttt | caagcagctt | ctctgaccac | aatggcatga | aatgagaaat | 480 |
| caactgcagg | aaaagaaagg | gcgaattcgc | ggccgctaaa | t | | 521 |

<210> SEQ ID NO 103
<211> LENGTH: 679
<212> TYPE: DNA
<213> ORGANISM: Sus scrofa
<220> FEATURE:
<221> NAME/KEY: modified_base
<222> LOCATION: (392)
<223> OTHER INFORMATION: a, c, t, g, unknown or other
<220> FEATURE:
<221> NAME/KEY: modified_base
<222> LOCATION: (425)
<223> OTHER INFORMATION: a, c, t, g, unknown or other
<220> FEATURE:
<221> NAME/KEY: modified_base
<222> LOCATION: (482)
<223> OTHER INFORMATION: a, c, t, g, unknown or other
<220> FEATURE:
<221> NAME/KEY: modified_base
<222> LOCATION: (496)
<223> OTHER INFORMATION: a, c, t, g, unknown or other

<400> SEQUENCE: 103

| | | | | | |
|---|---|---|---|---|---|
| tgcagtttac | gattcccctt | acccagctca | cctcttcctg | ggagaggctc | tttagcaaga | 60 |
| tggagagggc | aaaatagagg | tgttctcagc | ataagagtac | accaaagtgg | gtgggagaag | 120 |
| aaaactttt | tggttttgtg | gatgtacctt | tctgaggctg | gacatggcga | gctgttttct | 180 |
| ttccttttct | ccttctcctta | cacactcctg | aagtctcctt | accaactcta | ggaggaggaa | 240 |
| aatctgacag | aatcaagccc | ctgggttgat | ggaagtgtgt | gtgtgtgtgt | atccttgggg | 300 |
| tcagagcaga | aaatccccag | tgccctcaac | tcccagacag | tggctgactg | tggcagggat | 360 |
| attaacccat | tcctgagaga | cacaggctct | angattccct | gaaggctttg | tccacgcttc | 420 |
| tgtangctgt | tcggcccagt | gtctaagatg | ccccactcgg | cctttcccca | cttcactcag | 480 |
| gntcaaactg | catggntggc | tggaaaattc | tccaggatct | ccagctcctc | attattttct | 540 |
| ctccaagcca | ctcccaata | aatccctggg | ggttgatccc | tacccttgggg | acgcttcttg | 600 |
| aggcctggaa | acccaaagag | gtgtacattt | tcacacccca | gcccccaacc | aattttgag | 660 |
| agaggaaggt | tttcacagg | | | | | 679 |

<210> SEQ ID NO 104
<211> LENGTH: 890
<212> TYPE: DNA
<213> ORGANISM: Sus scrofa

<400> SEQUENCE: 104

```
ccctgattct gggtaataca gctttcgcca tcccactgca tttccaggaa tattttagca      60
aaccaaatgg gttaagttgc ccagtgagtc tgcctgttaa tctggatctg gatttcttac     120
accaccttcc ctcctgtccc ccgacagtgc acgtcccaga gccttgtagt gcctctaccc     180
acaggaacct cttctagaca ttcctctggg ctcctcaacc caaacagacc ttcccaagcg     240
aatcatccaa ggacatctta catatatgaa ggtgggtaca cagagaagcc atcttaagca     300
ctggcagatg cttactaaat gtctgaataa atgaattact aaacagaagg aggtgggtca     360
tgccagggcc aaaaatggct caatgaatga atgaataaat aaaagagact agagaccagg     420
tcccttggc ctgctagcct ggtcctcacc tgtctcctgg tttgaggccg cagggctcac      480
ccacagcagg aggaggaaaa ccagccacat ggctccaggc ttcgagcgga gacagcgttt     540
cagggatcac agccaggatt tggaataccc acccacccca ggaagctcat ttggtatctg     600
caccccctacg ggaggagcca gctgacacct gggctgtcat tggcaagggc agggtgtggc   660
accaagacag agccacagtg tccaacagct tggatagctt cccaggcaag gtaccccaga     720
ggaaaagaaa aaacaaaaa tctcccttca tgagttccag gcttgggaga gaaaataaac      780
aaccaaatgg tcgcggcagg gattggaatt tacaagtcta cctccccttc acatataggt     840
tggggcgtcg gagagacaag gtgaccattc acacgttacc tttgaaagcc                890
```

<210> SEQ ID NO 105
<211> LENGTH: 919
<212> TYPE: DNA
<213> ORGANISM: Sus scrofa

<400> SEQUENCE: 105

```
gcttggcaaa tgagcccttc acaccaggtg ccacaagctt ggcccttctc aggaaccact      60
tctcccagca ccccttgagt tctgaggaac aacacctcct tggggggcag cttcctccag     120
caccccagag aatggtctcc tggtgaaagc tgttggcatg gcacctctca aggatgacat     180
cccctgacac tctctcaggg cacttctgca gcttcagaga atttctccac cacccaggta     240
gtctggttct caggcttggg gaatctgact ctcttctaca tttgttcctt ccctgaggct     300
ccatctacac tcctagggat ggtgactgct gcctatatct gctattccag tgctctttaa     360
agttctccga actccttatg atgcagtctc ccattacttc aaccccccat tacagttaac     420
aactctttat atgaaatagg ccctatgcaa attacatgcc agtttaaaag tgacttagga     480
tagttacctc tcaaccttta gaagactatg ttctactaaa ttacgacggg tcccgagtag     540
agtataaggt actgtaagta acttgtgtgt actctgctat catccttctt gtgtggtttc     600
ctgccgtccc aggggcacac ccggtgatat atggacattt ctcaggtagg gtacgatcag     660
agctgggagt gctgactgac ggcacaatca ctaaaattga agatccaaga caaatctgtt     720
acttaatctg ccgcccacag agagcccatc ctacaccgcg atggaggaga acacgatcac     780
accagctgtc ctagaaataa tcagattatg tccgctggac catggggag accccgataa      840
agcttgtcct gtaataaacc acacgtccca cgctacatct aactactaaa cccactggga     900
taacaatttt ataaagttt                                                  919
```

<210> SEQ ID NO 106
<211> LENGTH: 898
<212> TYPE: DNA
<213> ORGANISM: Sus scrofa -continued

<400> SEQUENCE: 106

```
ccgtcgaaat cgcccttatt catgattatc taggaagtca ttgcacctct ggtaaaaaag       60
aagaaacatg ataaagtatg acttgacttt attttccaaa gagggagac ttttttttgtt     120
ttcttctcaa agacatcctc tatgtgagga tgaagaaggg ccaagtattt tttataaaga     180
cagtgatttt gagcaactgt aaattgtcag ccacctttct tctttggtgt atggtgtctt     240
ctttactagc ctggtcctaa ggtaacaaca tttattagct cttttttcaa ggatgtctgc     300
ctaagattta actctcattt tttcctttcc tatcactccc aaacaggctg aaattggctt     360
ttgtgctttt agccagttgt ttatttagga agtaattttc aaaagcctgt taggtacaaa     420
gccctctgaa ggttataagg acaaacccag gtttaggtat gatccgaggg agtttaatgt     480
tactgaaata aatgaggcag atcactggcc tgtgacgatc tactgcctag aattgttttt     540
cttcctccac tagcactggt cagaatggaa tacacaactg gaagtatctg gggaactaga     600
tctgagtggt gcatatgcag agcgggaata tacccatgaa ctccggttaa ttaaagtagg     660
atgtgttatt tactaataaa agatgtggtt actcgcttaa gtttctctat ggcgagagag     720
gatgtgacaa ctgacagatt acaatcctct tttcttcttg tggtaagagg ggcgcagact     780
ttagttgcca acatatgtgg tgagtgttgt gttatttgcc gagccgccca cagaagaatt     840
agagctgatt tcattccctc cggggagtta tagtatgtat gttgctccca cgttgtac      898
```

<210> SEQ ID NO 107
<211> LENGTH: 893
<212> TYPE: DNA
<213> ORGANISM: Sus scrofa
<220> FEATURE:
<221> NAME/KEY: modified_base
<222> LOCATION: (666)
<223> OTHER INFORMATION: a, c, t, g, unknown or other

<400> SEQUENCE: 107

```
gcggtcgaaa atccgccctt ggcagggttt ctcaacctct aagccagata attctttact       60
gtgatggact gtcctgtgta ttgtaccatg tttagtgtaa ttcctggcct atttaccctc     120
caggtgccct tcttctcagt tatgaagata aaaaatgtct ccagacattg tcaaatatct     180
gtagtgggtg caagatcctc cctggttgaa aaccactgcc ttaggaggtc tttaaggcta     240
ggctggtttg gggaagcagc agtaactatc tcccagtctg tactgagaac ctgcctatgg     300
atgtagcttt ctaaaagcat tgttatcttt tggagtaaaa gttaagtcct aattccaaga     360
actcatggta tagagctgtc tgtcattctc attgatttac ttcctctctg aatgctaaag     420
ggccccttttt ataatcattg ttatacagat ggtagtgaag gatctaacct gactcatatg    480
tcaaagaatg gactctcctt gtcagtggtc tccctgcttt cacgtagctt gtgttggaag    540
tgtgggtatg ctcatacatg catgtgtgtg aatgtttgca ctcagctttg tacatactgt    600
atcatgtgac agatttcagg gttatgaaga ctaaggtttg gagaactatc tggggaaaac    660
tgggtnatag tcagccagga ccaatcagat actcattttc ttcttcctca tgtgacccga    720
cagtccttct ggaaatggtc ttgttgcttc ttccttatgg tggtacgtgt agattaaatg    780
gtcattgtgg ctgatacagg tagggaacag ttagaaagga tggtcagctg agaaattcag    840
ttccaactat atagtccatt actggccaac atcagaacac aaagtcagat ggt           893
```

<210> SEQ ID NO 108
<211> LENGTH: 527
<212> TYPE: DNA
<213> ORGANISM: Sus scrofa

<400> SEQUENCE: 108

```
ccctcccgcg gccctggcat tggctatatg gtatcctgac agaggtgggg gcacaggtca      60
ggggggtccc ttagagaggg gtcttgctag tcttcacagg cttacaagaa cttccaagtc     120
aaggagtagg accacagcag tggctaatga aagggaagat ggggcatggg aggctttacc     180
ttctcagttc tgagttttca tttatttttt tttctatttt tttgtttatt tgtttgtttg     240
ttttttaaga gctgcgtctg cagcatatgg aagttcccag gccagggggt tgaatcagag     300
ctttagctac tcgcctacac cacagccaca gcaatgccag atccaagccg cgcctgtgac     360
ctacaccaca gctcacagca acacaggatc cttaacccac tgagtgaggc cagggattga     420
acccacgtcc tcatggatat taatcgggat cattaccact aagccatgac aggaactcta     480
gttctgagtt ttcttgccgt caaagggcga attcgcggcc gctaaat                   527
```

<210> SEQ ID NO 109
<211> LENGTH: 678
<212> TYPE: DNA
<213> ORGANISM: Sus scrofa

<400> SEQUENCE: 109

```
tagtctgcag gtttaacgaa ttgcccttga caagaaaacc ttgccatgat tgtcagcaga      60
agagaaggag caatgtagaa agagacacta ggacagagag aagcaatggg caaaggaggg     120
agggaggagg ggacagacag gtcactgtgc aggtacattt gtgtacacat actcagcctt     180
tcagtgaagg tttagcctct tgggggcag gataatgtgc ctggagaagg cagagacatt      240
tcttggtgga gagggtccta ggacatcaaa ggagatcaag ttagatggct ttggtctttt     300
caatgaagtg tcatagagaa aggagagaac gagagaggag gggaagggag aaacctattt     360
ctctcaaata ccaactcttc acagtcaaat ccttagctct ctgcaaggtc agttcattcc     420
aacaaagctt gaacagcaag aataaggctg gggatattct ttagaacaag gctcgatcaa     480
gaccccaaat atctgtgcct tacaacttca gtaagatggt tttggcttac aaaaaatttt     540
taagagcaga taaatcattt tatattaagt caggggttct taaaatgtgg cccagagacc     600
acctggatca gagtcaccct ggacacgtgt tgaaatgcag attcctggat cccgcccaag     660
ggcaattcgt aaactgca                                                    678
```

<210> SEQ ID NO 110
<211> LENGTH: 372
<212> TYPE: DNA
<213> ORGANISM: Sus scrofa

<400> SEQUENCE: 110

```
tgaggtttaa cgaattcgcc ctctaaaaaa gtccccctt aaagttacag cagtgttatt       60
tgggttaaag cccaaggact ttctaacagc tctgcagatc aatccatgca tttgttcata     120
ccagctagga agcgtgtcac ctgtaattag ttactattaa tacatagtag gtgagtcact     180
tcttttttaat aaattagagc tgcaggtgag tcacttttct ttttaacaaa ttatagctga    240
ttcataatca ctctcgctca ctcgaaagct gaaattgttc tcttaagaag agaaaatggt     300
gggattatag tcaagtccca gaattgcact caaactaaaa taaattcaag ggcgaattcg     360
cggccgctaa at                                                          372
```

<210> SEQ ID NO 111
<211> LENGTH: 470
<212> TYPE: DNA

<213> ORGANISM: Sus scrofa

<400> SEQUENCE: 111

```
ttcgcccttc ccacctctgc tgaggggaca gcagcatctt ctctggtcca ccagactcag      60
agcatggaga ccaccagaga aacccacagc agcgccatcg cagctgtgag ctcctcgaca     120
cctttatctt ccacaagtgg acaccctctt acagaaggcg cttcccggga gacatcccct     180
tcggggggacc caacctcttc atccgcgtcc agacccaccc ccacacctgc aacaacatca    240
gccgtgtcga cagcacctgc ttctacagat ggcacttccc ccacttccag cctaagcaac     300
acaccccccaa caacatcacg gccgctcaca tccccagtta caaccaacac cactgtggga    360
ggcccagggg acacgtcccc acccggcaca agaaccatca ctccaggaac ctcatcagtc     420
tcaacgacaa ctggaccaaa gggcgaattc gtttaaacct gcaggactag                470
```

<210> SEQ ID NO 112
<211> LENGTH: 681
<212> TYPE: DNA
<213> ORGANISM: Sus scrofa
<220> FEATURE:
<221> NAME/KEY: modified_base
<222> LOCATION: (613)
<223> OTHER INFORMATION: a, c, t, g, unknown or other
<220> FEATURE:
<221> NAME/KEY: modified_base
<222> LOCATION: (624)
<223> OTHER INFORMATION: a, c, t, g, unknown or other
<220> FEATURE:
<221> NAME/KEY: modified_base
<222> LOCATION: (667)
<223> OTHER INFORMATION: a, c, t, g, unknown or other

<400> SEQUENCE: 112

```
tgggccccat ctgttccatt tttcactgtg ttcacacagc actgccctag aacaatgtca      60
ggcatatagg agacactctt tacagagttg tttcactaac aaatgtatgg ataaatgaat    120
gcatgaatgt gtgctgcaaa acaaatgcag tgactgaaga tcaggggact tgccttctag    180
acccaactgc cctatttatg ggccaggaga cccgacacaa gctttggagg caggaatcat    240
gacttcatca ttctagtgtc tcgggtgctt ggcatgagta gaaattcagc acgtgaacaa    300
ataactccat agtctttcct attcttaatt tccccaaacc cagtgtcaaa ctcaaactgt    360
cattttagtt gagggcatct atattgagtg tagatatctc tacagatctt aaaaatgcat    420
tcgtggaaaa gagcagaagc cagcaaccgc cccccccccc cccacctcat atgagcgtgg    480
ccatgaccgt ggaggcctca tgcgcaaata cggatgccca gttcctgcag ccactttgga    540
gtctcaagga aatgttgagt atttaacctc tatgaagtgc caacaattgt gctcattttc    600
acccactcct tgnctctgtg ctgngaaagg acacacagt gactagagtc tgcttgcatg      660
aatcagnctg gcagagtgca a                                              681
```

<210> SEQ ID NO 113
<211> LENGTH: 754
<212> TYPE: DNA
<213> ORGANISM: Sus scrofa

<400> SEQUENCE: 113

```
ttcgccctta gatctgccca tatgtgcatc atccatcatc cagtggccag tttgggacct     60
ggctggcaga ctgccccttt cctttggtgt gctgtttagg acagataca ggcatgcgca    120
gtttggacat gagcccagga gtcccttat aactgtacag aatcaaattc tggagccccc    180
tcctcctcac aatctccttg gtactttctg gttcccagag gcccccttca ggttctctgg    240
```

| | |
|---|---|
| ccttcaaggg ctttagcttc cctgctctac cctacacttc ctatgacggc aactgcctct | 300 |
| gaccacgcac agagaaaaag gagaggtggg gaaagcagat tctctggtca gagagatgag | 360 |
| ttctctctct tggagcttta ggtgcttatc cagctgttgt ggctactgct acaggtttgt | 420 |
| tggggaactg aggtggaaga gaatgaaaaa aaaaaaaaaa acaacagaaa atgtaggaag | 480 |
| catcctccac tcactctaac ccataggagc cgttttgct tctttgatca gaagcagagg | 540 |
| gcttctttgg cactccttct gaccacagat ccaagtccgc tgtcctagtc caggcctgga | 600 |
| gatgctagag gagaaaaaag gaaaactcaa tgctggtttg atgttactcc aggttctggt | 660 |
| tgtcttccct atccacctgc tcccatttac ttcgagaaag tatcaaatct ctttccctca | 720 |
| gaaccaaaca aggcgaattc tgcaactgca gtag | 754 |

<210> SEQ ID NO 114
<211> LENGTH: 417
<212> TYPE: DNA
<213> ORGANISM: Sus scrofa

<400> SEQUENCE: 114

| | |
|---|---|
| atttagcggc cgcgaattcg ccctttttgat taaaaaaata ctcttggaat ctttaagtaa | 60 |
| ctatagcaag ttgtaggata caaggttaat gttacaaaag taaattacat tcctctatac | 120 |
| cagtaatgaa caaatagaat ttaaaattaa aaacatatca ccattggagt tcccatcgtg | 180 |
| gctcagcagt taacaaaccc aattagcatc catgaggatg caagttctat ccctggcctc | 240 |
| actcagtggg ttaaggatcc gatgttgcta tgatccctac cttgggaacc tcaatatgcc | 300 |
| acaggcgcag ccctaaaaaa agaaaaaaaa gtatagttgt cagatttagc aataaaaata | 360 |
| caggaattcc agttaaattt gaacttcaga taaagggcga attcgcggcc gctaaat | 417 |

<210> SEQ ID NO 115
<211> LENGTH: 470
<212> TYPE: DNA
<213> ORGANISM: Sus scrofa

<400> SEQUENCE: 115

| | |
|---|---|
| tcgcccttat gctcacgaat gaaagaatat agaaattttc tttaacatct tctctgacca | 60 |
| taatggcatg aaactagaaa tcaaccacag gaaagaaat aagaaaaact gactacatta | 120 |
| agactaaaca acatgctact aaaaaaccaa tgggtcaatg aggaaatcaa aagggaaatt | 180 |
| taaaaatatc tcgagacaat gaaaatacaa ccattcaaaa tctttgggat gccccaaaag | 240 |
| cagttcttgg agggaattc atagtgatac aggccttcct taaaaaagga gaaaaatctc | 300 |
| aaatcaacaa tttaacctac cacctaaaag aattacaaaa agaagaacaa atgttaaaag | 360 |
| tcagaaggaa ggaaattata aagatcagag aggaaatcaa tcaaatagag atttgaaaaa | 420 |
| acaatagaga aaaaaatcag taaaaaaggg cgaattcgcg ccgctaaat | 470 |

<210> SEQ ID NO 116
<211> LENGTH: 462
<212> TYPE: DNA
<213> ORGANISM: Sus scrofa

<400> SEQUENCE: 116

| | |
|---|---|
| atttagcggc cgcgaattcg cccttccagg tgggcctttc aaagctcagc attcagggtc | 60 |
| ctccagcagc cagcaaggac agacagaggg ctgtgtggag ggccttgcaa gtgttactgc | 120 |
| tgtcagagcc taggctcagt gtgggcaggg actaaaactt aaatgtgagg atgaggagga | 180 |

```
agcagatgag gacaaaatca tgggaagact gaaggtgcca gggatgggga ttggggatcc      240
atcgtttgat tttaggatga ggttgtagca gggtccctcc taataaggct gagttaagca      300
aggcccctgc attgggctga tgattccatt cagtgggagc tattgtgtaa tgaaagctac      360
cacgtgcccc tgccaaggac caggcactat agaaggtcca aagatggaga acatgtgcc       420 tgtcctcaag gagcctcaag gcgaattcg cggccgctaa at                         462

<210> SEQ ID NO 117
<211> LENGTH: 487
<212> TYPE: DNA
<213> ORGANISM: Sus scrofa

<400> SEQUENCE: 117
catatgcagt ttacgaattg cccttcagtc cctttgtttg gcctttgtgt ggcccaaaca       60 ccagccccc cttcaccct caggagcaga gcttcccctt catcacttga gcccctcct        120 gtgcagtggc ctgacaccag catgtagcac accccactg cgggtccagt cacgaggag        180 tcccccccca ccccatcgct gtcaatccta ttgcctgtgt cttttgcagc gtgagagtca      240
tggcaagcag atcttgcact cctcgtggcc aggaactgtg tgtagcagga gcctggccca      300
ccgagcccac accccacttg gtaaactgtt gagtgcggag cagtggacag agaacgtgga      360
gttgtgcaga tctgggtttg aaacccagac cagacgttta gtctttatgt ctgtaaaatg      420
gtcctcctct cctaagtggg tatccacggt cagatccttc tgaagggcga attcgcggcc      480
gctaaat                                                               487

<210> SEQ ID NO 118
<211> LENGTH: 726
<212> TYPE: DNA
<213> ORGANISM: Sus scrofa

<400> SEQUENCE: 118
acgtgcaggg tttaaacgaa attcgccctt tttcatgaac aggaacccaa ggtacaaagt       60
gggagcagct gctcaaggtc acacagtggt gagactgtcc aggttttgt atctccatgg      120 ccttcctgaa ccaaagcagc acccacacag acagcccctg tgatcaaaac ccagagctca     180
tttctttctg cctcctgcct ccaaggggtt gatgacaaca ggggtgctgc tatcttatag      240
cctctggtac tgcaaggaca accttgactg cccactgaca aatccagtcc tgctccctcc      300
ccagtcccct gcatcacatt tttctactca ttgacttaac ataggccgtc aaataaatgt      360
tgtcaatcta aataaaaagg taaatgaga taagctcaaa attgtcaaaa agatgagttt      420
attcagaaat tgcagaggaa ttacaattta ggatacacat gtgcaggaat gtaaagagga      480
aagaattcag ttagagttta ttaaaataaa aaacaaacag agaccagatt tgaaaataca      540
agccagtcca atgatacaaa gctcaattca gctcatttta tgagaccaat ctgacttggg      600
tcatttctta ttcatttctc gtggaaatca taagaaaaat atcacaagaa tgagatgaag      660
caacccctgg ccaactctgt taagaaaatg aaaatagtat cagttttctt aaaccaaaaa      720
agggga                                                                726

<210> SEQ ID NO 119
<211> LENGTH: 371
<212> TYPE: DNA
<213> ORGANISM: Sus scrofa

<400> SEQUENCE: 119
gcaggtttaa cgaattcgcc cttagaatga gagagtaaaa gttttccact ggtctctgga       60
```

```
tttggagccc tggtatttcc attctgttgt tcattcattc attcagttag tcacttagca    120
aatatttatt gagcacctac tctatggctg gcattgttct aggtcgtaag ggcatagcaa    180
tgaacaaata ataaaaagac ctgctacaat tagaaaatac attagatagt tatagatgct    240
aaagagaaaa aataaatcag ggaaggcaaa taggaagtgt gagtgaaggt gaaactttag    300
acaagttagc caagaaaggc actgctgaga gggtggcatt aatagaagg gcgaattcgc     360 ggccgctaaa t                                                         371

<210> SEQ ID NO 120
<211> LENGTH: 501
<212> TYPE: DNA
<213> ORGANISM: Sus scrofa

<400> SEQUENCE: 120
aactgagtta cgattcccct ttagatctct agaacctcgc tccctccact gcatccccac     60
tgcttcttca tgttcttcaa acacgccagg ctcgccccg actctgagac tctgcacatg    120
ttctgttctc tttgcctaga ataccttccc ccagacaccc acaggtcgct cctcacctcc    180
ttcaagtctc tattaaatgc caccctctca gcagtgcctt tcttggctaa cttgtctaaa    240
gtttcacctt cactcacact tcctatttgc cttccctgat ttattttttc tctttagcat    300
ctataactat ctaatgtatt ttctaattgt agcaggtctt tttattattt gttcattgct    360
atgcccttac gacctagaac aatgccagcc atagagtagg tgctcaataa atatttgcta    420
agtgactaac tgaatgaatg aatgaacaac agaatggaaa taccagggct ccaaataagg    480
gcgaattcgc ggccgctaaa t                                              501

<210> SEQ ID NO 121
<211> LENGTH: 403
<212> TYPE: DNA
<213> ORGANISM: Sus scrofa

<400> SEQUENCE: 121
ctagtcctgc aggtttaaac gaattcgccc ttcagccata aaaagaaca aataatgcc       60 atttgcagca acatggatgc aactagagat tctcatacta agtaagttag aaaaaggaag    120
acaaatgcca tacatagata tcacttatat gtagaatcta aatgtggca caaatgaacc    180 tatctacaga acagaaacag actcacagac acggagagca gacctgtggc tgccaagagg    240 gaggggagg gagcgggatg gactgggaat ttggggttag tagatgcaaa ctattacatt    300
tagaatggat aagcaatgat gtctgctgta tagcacaggg aactatatcc aatcacttgt    360
gatagaagat aatatgagaa gggcgaattc gcggccgcta aat                      403

<210> SEQ ID NO 122
<211> LENGTH: 1042
<212> TYPE: DNA
<213> ORGANISM: Sus scrofa

<400> SEQUENCE: 122
ttcgccctta tgtcagcatt ttctccaagg atctgctcat taagatctgg aatgaccctc     60
tcttcaatgt gcaggacatc aacagtgctc tctataggaa ggtcaagctg ctcaatcaag    120
tccgggtaag accctgaaaa ggtctagtcc tagattaccc tctgttcata gcagcttccc    180
aagatcacca catttctctt tgtcaccatg gcagagctgt aaccatctca tcattgtccc    240
tttctctgtg tacttcctct tgccattttc gaggtatctg tccagttaga gtctcaaacc    300
```

-continued

```
cggcaaggcc actagaaagc aatagataac acttgatggc aaaagcagga tttctccctt      360
tgatgaaaat attacgcaac agagaatagg gtagcagggg ggcaatttgg aatctggttt      420
tctcagtggt tcccagccgt gtgtgtgatt tggcagactg acctagcaga aaggccttcc      480
ctgaccttga agcaagttgt tgagttacag cagagaggat ctggctctgg ctgcaggatg      540
caaagcttcc agaccgccag aatttaaagg tactactggt ctttctaatg gttgcctctc      600 tccttttta ctccctccaa ctctcttccc atcaccacaa tgccctcctc tccagctgct       660
gcggatccag ctgtatcaca tgaagaacat gtttaagaca tgccgactgg ccaaagagta     720
agttgtgtgg aggccagagg cctctggctg aattaatgtc tctggaggaa acatgcccca    780
ccacggggcc cttgttctgt gaacaaacaa gtacgtcgat cttgaaaaaa ttccccaaat    840
accaatgaaa ttctacacag gaacctgcta ttcctctccc cgaagggaac ttgcggtatc    900
tccacagcac cccctgcctt taaatggcca ataccgccag gataagcact ctcctcaacc    960
ttgaaacgag cccggccggc gcgaggaccc ccaacagcaa cctccctccc ctgaccccca    1020
tcttcaacac accacccacc cg                                              1042
```

```
<210> SEQ ID NO 123
<211> LENGTH: 924
<212> TYPE: DNA
<213> ORGANISM: Sus scrofa
<220> FEATURE:
<221> NAME/KEY: modified_base
<222> LOCATION: (586)
<223> OTHER INFORMATION: a, c, t, g, unknown or other
<220> FEATURE:
<221> NAME/KEY: modified_base
<222> LOCATION: (744)
<223> OTHER INFORMATION: a, c, t, g, unknown or other
<220> FEATURE:
<221> NAME/KEY: modified_base
<222> LOCATION: (797)
<223> OTHER INFORMATION: a, c, t, g, unknown or other
<220> FEATURE:
<221> NAME/KEY: modified_base
<222> LOCATION: (828)..(829)
<223> OTHER INFORMATION: a, c, t, g, unknown or other
<220> FEATURE:
<221> NAME/KEY: modified_base
<222> LOCATION: (852)
<223> OTHER INFORMATION: a, c, t, g, unknown or other
<220> FEATURE:
<221> NAME/KEY: modified_base
<222> LOCATION: (854)..(858)
<223> OTHER INFORMATION: a, c, t, g, unknown or other
<220> FEATURE:
<221> NAME/KEY: modified_base
<222> LOCATION: (861)..(862)
<223> OTHER INFORMATION: a, c, t, g, unknown or other
<220> FEATURE:
<221> NAME/KEY: modified_base
<222> LOCATION: (864)
<223> OTHER INFORMATION: a, c, t, g, unknown or other

<400> SEQUENCE: 123
tcctgcaggt ttaaacgaat tcggccttga atgttttttc cataattgta gtaatggggt       60
atacatactt ttttatatgt aaacgtctta ctttggaaca attttagatt tacggaaaag    120
ttgcaaagat agtgagttct tacatatccc tcagtttgtt ttctctaatg ttaccatctt    180 atattttcg aaactaagaa actaatgcta gtatattaat tttaaccaaa ctccagtttt     240
catcagtttt gccagtacta tccttttcct gttctagggt ccagtcctgg aaagcacact    300
acatttagtc atcatgtctc cttaggctct tctggtctgt aacagttaac tcagcttttc    360 cctgttttc acgcgcttga caatgttgag gaggtatttg ggagacagtc cctcaaactg    420
```

```
ggtttgcatt atgtttctct caacaccgag tggtgatgtg cccatctcgt catagggtg      480 cataacatcc acaagacagc cctggtgacg ataacctcta tcacttggtg aaggtaatgt     540
tggccagctt tctccactgt aaagctgcta ctactctctc tccatngctc ttctttaaag    600
tgaatcacta attccagtcc agactcatgg gagggggggcg ttaaacccac ctccctggaa    660
gcggaaaagt gcaaagatag tgagtttaca tagattacat agattggaat tctcttggga    720
agatttgtct cttctccctc attntattat ttattccaat cttataagta tggataatgt    780
gtactggtct ctctctnttg ttcataagac atagtgtata aggggttnnt cgtgtaaccc    840
agcatggcct tncnnnnntt nntnatttag tcttatggca attcttgggc tgctccctcc    900
gcatatgagg gttccaagct aggg                                           924

<210> SEQ ID NO 124
<211> LENGTH: 1384
<212> TYPE: DNA
<213> ORGANISM: Sus scrofa

<400> SEQUENCE: 124
cctgtcgaaa tcgcccttg tgtgagagaa tctcccagaa agcaagcaga acatggactt     60
ttgtgctcaa agccagttct gggtggaaaa gcctcagaaa taaatataaa aaataaaaca    120
aggagttctc atcatggctc agtggttagc aaacctgact aggaaccatg aggactcggg    180
tttgatccct gaccttgctc agtgggttaa ggatccggcg ttgccatgag ctgtgctgta    240
ggtcacaggc gcggctcgga tcctgcgttg ctgtggctgt ggcgtaggct ggcggctata    300
gttccgattg gaccoctagc ctgggagcct ccatatgttg ccggtgcggc cctaaaaaga    360
caaaaaaaaa ccaaaaaata aaaaaataaa actaaaaatt aagagctaaa aaggaagatt    420
tcctttcatg gcctaagctg taatttctaa aaggtgaaag ctaaggtcct catctgagac    480
ttctgaactg caaacttgtg tctctgtgtc ccctcaggg atgtggtttg gctcattgga     540
actctaggaa aaagaaaaaa tctccaaatc aaagctgtct tcccacgagc tttcttagat    600
gtgaagagtg ttggggttag aaccttcctt cacatcggct ggaacaaact ggtatctgct    660
gtactccagc cactgggcgt tggagcatgt aaacttccct gcccccattc ttgaatccat    720
gtggattcca gaaccacgg taacctgcac tggaaaggga gctagagaaa acctaagcag     780
aaggatctga gggagtgtgg ttcctgtgca gcttctcaca tgactcaccc ctccctctgc    840
ggtagggttc cctctcagga gttaagcccc cacctttgct agataagagg acactctttt    900
tctcactctg tctattctca tttttctgga ctctcctctg cacctgtctg tctacgtaca    960
ggaggcccca ggaatatcac cattatagtt gaagatccca ttgcaggttt gggagccagt   1020
cctcctcctc gtccaccacc atcctcctcc ttctgctcct ctgtgaccat cttgcctagt   1080
tcaagaactt ccttttccat tctggtgtca attcacgtct ggttagtctg tcctgtagc    1140 ggtgtttgga cctttttgta aactgatacc agtattttgc atggtatgtt ttctgcccac   1200
cacttccaga tgcctcattc agtctctcag cagcttctgg gaggtagact tatccatctt   1260
gtgttgccca aagataaaac tgaggtgtgc ttttttgtgta attcatcata atgaatcaat   1320
cagtggcaga atgtttctta caactgagta ctgtgaatta ccttattttc cttgagttaa   1380
cacc                                                                1384

<210> SEQ ID NO 125
<211> LENGTH: 1089
<212> TYPE: DNA
```

<213> ORGANISM: Sus scrofa

<400> SEQUENCE: 125

```
tcattttctg caggttctaa cgaattcgcc cttgtggaaa ggttgcattt gtgccatata      60
ttagattcca gatataagtg atatcatatg gtatatgtct ttctctttct gatttatttc     120
acttagtatg agaatctcta gtttcatcca tgttgctgca aatggcatta ttttggtctt     180
ctttatggct gagtagtatt ccattgcaga tacataccac atcttctcaa tccattcatc     240
tgccaatgga catttaggtt gtttccatgt cttggctatt gaaataccac atagttctta     300
actactgtag atatatatta tattgaaatt gagtagacat actcctcctc ctttcttctt     360
cttcgtaata gttttggcta ttcttgttcc tttgcccttta catataaatt ttagaataat     420
cttgtccata aaacaaaaaa aattttttgc tgggattttg ataggacttg cattaagtct     480
gcatataaat ttggagataa ctgacatcta tagatacctg acatctatac tatgtagggt     540
catccaagcc atgaacagaa tatatcttca ttcttgacat ccgctccagt tctgcacatc     600
atgaactagt acttgctgta tacaaagcct gtacatattg agtctgactc cacactaatg     660
ggttctgggt ttccccccat cgattgtaag tggtatagta ttccaaatta ccggtgtcca     720
tatgcacatt gctgcataac agatatacaa gagacagttg tgtgtgagtc taatatccag     780
accccctggg gagactcatt aatcccagga gggttctaaa accatagatt ccatggggat     840
atttcacata tactgagata tgtacaaact aaataatgcg agtgtatgag aattacgtca     900
aaataatctg ggtagggtag tgggtgcgga tatggattaa acgcatctga atatgaggtg     960
gataattact ttaagctgca taatggagtg cctgggggggg ggtcaaaatt ctacactcca    1020
aaccttgggt ttgaatggga ccataccacc aataataaat gattcccaaa tgttatgccc    1080
gattaccaa                                                            1089
```

<210> SEQ ID NO 126
<211> LENGTH: 819
<212> TYPE: DNA
<213> ORGANISM: Sus scrofa

<400> SEQUENCE: 126

```
gcgggcgcga attcgccctt ctctggttca gttgttcacc tatgcctttg ggttcaggat      60
ttttaatcct caatatgtta tcttttcatc ctggtgtaat tggtgcctca tgactgtaaa     120
tggctgccac ggctccaggc atcacatctc attaaaaaca gtaaaagggg agaagaggag     180
tgcccgcaag ctcctcctct tcccttgtcc cttttataag aaagcaagac tccagaagtt     240
ctccagcata tttccacctg tgttttattg acgagaacta tatcactgat cacaaaagga     300
aaaggtagg gaaagtaaga tttaactttt ctggtgtcta tagcagaggg tgataggggtg     360
tgggtaggaa tggctatgga gtctgtttta agccctcatt gtctcttgtt tctttttttgt     420
ttgtttgttt gcttttttttt tttttttttt tagggctgca ccggcgacat atggaagttc     480
ctaggctagg atcgaatcgg ggctatagct gccagcccac gccacagcca cagcaactcg     540
ggatctgagc caagtctgtg acctacacta aaactcacag caatgccaga tccccaaccc     600
actgagtgag gccagggatc gaacccgtgt cctcatggat actagtcaga ttcatttctg     660
ttgagccatg actcaaactc ccattcattg tatcttgtaa agcagacttt ctgccacatg     720
cagacattga acagaaacct cacagggcca agggcataac tggtaccaga ctgtaatgaa     780
gcattaaggg cgaattcgtt taaacctgca ggaaatgac                            819
```

<210> SEQ ID NO 127
<211> LENGTH: 421
<212> TYPE: DNA
<213> ORGANISM: Sus scrofa

<400> SEQUENCE: 127

| | | | | | | |
|---|---|---|---|---|---|---|
| gcccttttgca | ggtatcttta | tggttataaa | gcattttac | ctgtttgagc | tcattttact | 60 |
| ttcccagctg | tttgggtagg | tgttatctga | caaaaagtct | ttgttgacca | aactttagtt | 120 |
| ggtctctgaa | ccttctccta | gactcatctg | tggcattcat | cataaaatcc | agtttcagca | 180 |
| agagccctga | caagccagtt | tagccagagt | gtcccatcaa | tatctggtca | ccctcaatgt | 240 |
| ctggtcaggc | tgtgacttgc | cttgggtggc | agagctggga | ttcaggttca | ggtatcctaa | 300 |
| tatccagctg | gagcctgggt | taccacagtg | gcctctggag | aatgtctgc | acctctggct | 360 |
| ttccttgcat | tggaaagtgg | gaagttagct | gtgttaaagg | gcgaattcgc | ggccgctaaa | 420 |
| t | | | | | | 421 |

<210> SEQ ID NO 128
<211> LENGTH: 976
<212> TYPE: DNA
<213> ORGANISM: Sus scrofa

<400> SEQUENCE: 128

| | | | | | | |
|---|---|---|---|---|---|---|
| ttgccctttc | ccagagcagg | aacagtcggc | tcagggttgc | ctgaggagac | agcaccccctt | 60 |
| cctagcagct | gatggactag | ggacccagg | ggtgtggaga | cccttactttt | tcaccctgcc | 120 |
| caggtgctgg | ggggtctgg | aggcgcttag | ttccacgctc | agcaggtcgg | gagggtccat | 180 |
| ggggtttccc | agatagagtc | tgtgaggaga | gaactgagtc | agaggtgggg | aagagtgtgg | 240 |
| tgttggccat | gacaccctgg | agaaggtgct | gggcctgtcc | ctgtagggtc | aggcagaaga | 300 |
| cagaaccatt | tcatccaagc | cctttgcaag | catggttctg | cggcacagga | cttccccctc | 360 |
| ccaggagctc | ccttctgtag | atctagctgt | gactgggagg | ggtaccatgt | ggagggagag | 420 |
| ggggcagaga | aagaacgaac | tgatcgcagg | ttgaaaagcc | tgggactgta | ggggctccaa | 480 |
| gaataccta | caagggcaga | gctggccctc | tacaactccc | acggcacccc | aacccacgcc | 540 |
| tggcagccac | cacctgctgg | cacactctct | tgtctcccac | caggcctgtg | gcatctgggc | 600 |
| cacactgccc | cagtcaggat | cgtaggaggc | atccttctgt | cccactgcca | ggaggggag | 660 |
| taggggctgg | gccactgcct | cactcccaat | tcacctgcaa | cccttgtgct | gactgttagg | 720 |
| atctatagga | cttagtcact | ggggctgatt | gaagctggga | ggaatggggc | tgggctggcc | 780 |
| accgcacgcc | aggagagggc | agagggcacc | ggcctcctgg | aagggcgtct | gtgctcgctg | 840 |
| ccctcacctg | gctcttagga | ggcagccatg | ggcacccctcc | cagggcttag | tgctctggtg | 900 |
| tgcgggggca | gggatgcagg | gctgctgcac | caagtccctc | agggcagaag | tggtcagaag | 960 |
| tagagaaggg | cgaact | | | | | 976 |

<210> SEQ ID NO 129
<211> LENGTH: 707
<212> TYPE: DNA
<213> ORGANISM: Sus scrofa

<400> SEQUENCE: 129

| | | | | | | |
|---|---|---|---|---|---|---|
| atttagcggc | cgcgaattcg | cccttgtaca | atgctgtgtc | aactaggtct | caataaaact | 60 |
| ggagggaaaa | catcagaaaa | aagagaatca | ctagaaaaat | gaaacatata | acccaaagac | 120 |
| tgtaaaatac | taaccacaaa | attttaaata | atacacttat | tttatttta | ttttttagt | 180 |

```
tatcaattgg tagggtataa ctgcaactat ttttatgatt ataagtacac aatgattgcc    240
tagagtatct tttctgatta aaataaatt attacataga tacccttcat ctaactttta     300
atttattcta attcaattat acagagcaga ggttggcaaa cattttctgg agggtaccac    360
agagtctctg tcacagctac tcaattctgc cattgtaaca tgaaagcagc cactgacaat    420
atgaaaacaa atggccatgg ctgtgttcca ataaacttta tttacaaaaa taggcatcag    480
tagtatttga tctgtgggcc attgtgagcc aatccttcac atttcagtca aacatttgtg    540
aaatttatca atttccctga aagcatcttc aaatcactat ctcctgaaac aaactgctcg    600
tttttttcct tgtgaaattt tttcaaaaaa ttttttgttt ccagtgaata gtctataact    660
gccgcccttg cttcccaccc tcaagggcga attcgcggcc gctaaat                  707

<210> SEQ ID NO 130
<211> LENGTH: 380
<212> TYPE: DNA
<213> ORGANISM: Sus scrofa

<400> SEQUENCE: 130
tttttcttgt ttaaatggat ggtgaaagac aaataccgta ctgtggcttt gatgtaacca     60
atgctaatct cttctaacaa caagttcaac ggattgagaa acttgttaag actgcaccta    120
cttctccgca caaacttgtt catcagcgtg aaggggctcc cttcttgtc cactggagca     180 ggagactcta atcacctcag cccacagtta acaagttctt taaataaagg ttcaaagaga    240
cacagcccca tttgacaaga ttgaaaaccg gtactaccaa gccaaggttt tctccaacgg    300
agagggtatt gggaagcatg cgctctccca catgccgcca gtgggcctgt aaataaaggg    360
cgaattcgcg gccgctaaat                                                380

<210> SEQ ID NO 131
<211> LENGTH: 1298
<212> TYPE: DNA
<213> ORGANISM: Sus scrofa

<400> SEQUENCE: 131
ttcgcccttc tcctctggac cccttctggg atcaggatca gagccaagcc cacctcccct     60
tgttataggt gaccaaagca agagccaggt ctagaagaaa ggattcccctt tatcactgct    120 gggagtcctg acaccaagtc ataaaaaatg ctttgctact agaggagggg gagctgggag    180
tacagtgtat gtatcagaaa gaaagacctc cttggaaaca acatcccagg catggaagca    240
gcatcctccc agcaagggtc aaacataacc ccaagatggc cagtgctacg tgtatcatgc    300
tgtccaccgg tctccttcca aggctcaggg ggtagaggta cctgcagccc agagaggacc    360
aggccagccc ttttcccagc ctgctctggc cctatctccc ttcccctcc aagaacagcc     420 cagagtctcc atggcaacag gagagcacag tccctgatca aaaacaggct tctcctgcag    480
gtgcctgtca gcatcctggg acaggcaaga tgtgaagcac ctcctgggaa accaggacct    540
gggttaaaaa tcacctatgg ctgccccagc actactgggg actagtccct ggaaacctca    600 gcaccccac tcccagtcc tggccaaggt tgtccacaaa tggctgacaa aggtggatga      660
aacatactgc tcaaaatacc accccacgca cttctctctg ggtgttcctg ggagcctctg    720
gccttgagga aaaacacaca cccttgttt ccccctcccc cacctactac aggaagcaga    780
ggctccaggg atcaggcccg gccaaggacc tgcatgcaca tggatttcaa aactcctgtc    840
ctccttaacc agtttgtgaa aacagaatat caaagtgctg tcagccatcc cagcctccaa    900
ataagagcct cctggaaaaa ggtcagtcat cactggtctc acagcctaga cagagcctcg    960
```

```
caagcttggc tcacagaata tctagtgtcc tctctctgtc cactgcctgg tactgcaaga    1020
agcactgagt ctgaagaagg gggctcccgg attggactaa gagcttccac aagaaagaat    1080
cacaaaaaga gcacagatat aagagagcca agaaccaagc taaaggaaaa cagaaccagc    1140
ctgagaccca cacatacgaa cccagaccca aggaacacc cacgaacaga gcccatca       1200 cccggagaca tggagacgga gcaggacaaa caaacacact tcaagcactg aggaagcaag    1260
gcggcaaagg gcgaattcgt taaacctgca ggacatga                            1298

<210> SEQ ID NO 132
<211> LENGTH: 1422
<212> TYPE: DNA
<213> ORGANISM: Sus scrofa

<400> SEQUENCE: 132
tccagccctg ggaaagggaa ataattaacc tggagtatag cttttgatct actactgaca      60
gacattaata ggatttataa aattcatggc gggcaaagga ttagagaaaa aagactttc     120 atatactgct gatgggatta taaattacta gggtcatttc agaaagtaat ctgttctatt    180
aaaattaaaa atgcatctaa cttttggccc aataatccac tttggggaat atatacgaca    240 gaataaaat taccagcatg taagaataaa tgtacaatgg tatttttaca gaattttttt     300
gttttagggg aaaaaaactg ggaaaatgca attacagtgt acttattatg ctgcacttat    360
ttctcttgat agaaagtagc tgcaaatatg gaaaattaaa aatgtacac accatctatt     420 gattattgta tgactgtatg agtgcagaga aagtctgga aggtactaca caactcttaa     480
aactaagtac cagaaagtag ggctcttggg tttgttgtaa tgagtttgct tcaccagggg    540
ccagatagtg agtaaatcca acatggatgc cgaatccaga atctccaga atacggtatg     600 atgcgtgggg tataattctt agcagaaaga tttgattcga accctaagtc cgttccttac    660
taagttatgc tgccttttct gggggacac ccatccctgc ctgcccaact gaaaatcctc     720
ttcttcctgg tgttccagcc tgacccctcc tgaccctgtt ccaggaggaa gttacttcct    780
gcacaaaagc ctcccactcc ctaaagctgg atttagtcac agcacttgct gtgctgaatt    840
acaattcagt gggtctccct gcaatgctct attggactat agactcctca aaggcaggga    900
atgtgatttc gttcattcat ttattcattc tttcttgaca tccctgttcc ccccccgcct    960
cccctgccaa ggcacagtcc ctataattag agctgaggga ctgggagcag catccttcat   1020
ggttatgtaa atttacatca aaacgtgggg ttggcgaagg gcaaatactc ttttaccatt   1080
ggaaagtcaa ggctatcttt gcaaacaata tctcttatgt aagttttatg agatatttg    1140 gcaagaaact aatcctcgta gttcaagaca tattttttaa aaaagacatt aggagaaaaa   1200
cccaagtgaa gactgaagtg ggaacttctc tccatctatc ctcaagaccg gatgtctttc   1260
tccccagccg gcagcagaaa tggagcagag gaggagtgt ctttccctga gtcccagagg    1320
ctgtactgtt gacactggac agaaggagac tcgtgggaa ggatggagag gtggtccctg    1380
gagagaatgg aaaagggata agaaccccca gaaacgcctg gc                      1422

<210> SEQ ID NO 133
<211> LENGTH: 1019
<212> TYPE: DNA
<213> ORGANISM: Sus scrofa

<400> SEQUENCE: 133
atatcctgca ggtttaaacg aattcgccct tcacaagtct cttctccagt ccatgatttt     60
```

```
ctcttctgag gagatgttca tttgtgctgg atattagatt ccagttataa gtgatatcat      120
atggtatttg tctttatctt tctggctcat ttcactcagt atgagattct ctagttccat      180
ccatgttgct gcaaatggca ttatgtcatc ctttttatg gctgagtagt attccattgt        240
gtatatatac cacttcttcc gaatccaatc ctctgtcgat ggacatttgg attgtttcca      300
tgtcctggct attgtgaata gtgctgcaat gaacatgtgg gtgcatgtgt ctcttttaag      360
tagagctttg tccggataga tgcccaagag tgggattgca gggtcatatg gaagttctat      420
gtatagattt ctaaggtatc tccaaactgt tctccatagt ggctgtacca gtttacattc      480
ccaccagcag tgcaggaggg ttcccttttc tcccaaccgc tccagtgttt gttatttgtg      540
gacttactga tggccattct tactggtgtg aggtggtagc tcatggtagt tttgatttgc      600
atttctctga taatcaggat gttgagcatt ttttcatgag cttgttggcc atctgtatct      660
ctttcttgag gaaatgtcta ttcaggtcct ttgcccatt ttcacttggg ttgttggctg      720
ttgagttgta aaagttgctt atatattcta gagattaagc ccttatcagc tgcatcattt      780
caaactattt tctcccattc tgtaagttgc cttttgttt tattttggt ttcctgtgct        840 gtgcaaaagc ttgtcagttc gattaggtgt cattggttta cttttgcttt tatttctgtt      900
gctttcggag gctgacctga gaaaacattt gtaaggttga tgtcagagaa tgttttgcct      960
atgttatctt ccaggagttt gattgtgtct tgtcaagggc gaattcgcgg ccgctaaat     1019

<210> SEQ ID NO 134
<211> LENGTH: 801
<212> TYPE: DNA
<213> ORGANISM: Sus scrofa

<400> SEQUENCE: 134
attacctgca ggtttaaacg aattcgccct tagagacaat ccacatatct tttacccct      60 tttctgcaat ggcaatgtta caaaactata atacaacatc acaaacagga tattaacatt     120
aaaagagaaa agaacattgc catggcaagg attcctcctg ttgtactttc atagccacat    180
tcacatccct cctgccccat cctcccctta acctctagca accactactc tgtttcatca    240
tttcaaggac attatataaa tggaatcatg cagaatgttt ggagattggc tgttttccac    300
tcagcaaaat tctctggaga ttcatctagg ttgttgcaag tatcaatagt ttattccttt    360
taattctgag tagtattcta aggtatgggt gtactatagt ttgttttact atttagctat    420
agaatgatat ctgggttgtt ccagttctt gactaataaa gcttctatta gcattcatgt      480
acaggttttg tatgaatata tattttaatt tcttggagat gaatgtgcaa ggatgaaatt    540
ggtgggctgt aggatagttg catgttttag tcttataaga aactaacaaa ctgttttcca    600
gggtggctgt accactttac actcccacct gcaatgaatg aatgacagtc tctgcatcct    660
tgccaacatt taacattgtt actattttt actttagtga ttctgataga tatgaagtta    720
caccttgggg tttaaatttg cattttccta atggctaatg atattgaaca agggcgaatt    780
cgtttaaacc tgcagaaaaa g                                              801

<210> SEQ ID NO 135
<211> LENGTH: 1502
<212> TYPE: DNA
<213> ORGANISM: Sus scrofa
<220> FEATURE:
<221> NAME/KEY: modified_base
<222> LOCATION: (1198)..(1199)
<223> OTHER INFORMATION: a, c, t, g, unknown or other
<220> FEATURE:
<221> NAME/KEY: modified_base
```

```
<222> LOCATION: (1376)
<223> OTHER INFORMATION: a, c, t, g, unknown or other
<220> FEATURE:
<221> NAME/KEY: modified_base
<222> LOCATION: (1456)
<223> OTHER INFORMATION: a, c, t, g, unknown or other
<220> FEATURE:
<221> NAME/KEY: modified_base
<222> LOCATION: (1498)
<223> OTHER INFORMATION: a, c, t, g, unknown or other

<400> SEQUENCE: 135
aatttcttaa atacattttg attttttcctc ctttaaagag ctcactcagc tacctcacag     60
ctctccctga ccatactcta ccttcccccct gtgagcccctt gacattctcg ctaaaccttc    120
tgttcgagca catctcacac agtccttgcaa aggtagtgtt ttccccaaga gaataaacaa    180
gtaaatgaat gaatgtaagg aattgcctgt tctacgtaga ggcacgtgga cagatgaaat    240
gaccttcaaa gggtccttcc tgacgaggat tgcctttgtt gcagcagtgg cctttcctgt    300
cctctttagc caccctaggc tcagtattcc ctctgcaaaa acccagtgat attcccaaag    360
acccagcacc agcccttcaa aattaagcca gaagaaccca tgttgaggtc ttaggcagac    420
aggaggccct gaccggttca gctcacattg ggtcctgtag tcagataaat ttggtctgtt    480 ttcctcttttg ccacatggct gtccataata actgtcctct atatttttac taccaaagga    540
gcaggtctga tttcctccaa ccaaaagagc ctgaacccac ccagttatga gatgaatatg    600
aaaccaacta accctggggg ctctctagtc tcatcgcatg atttttcttt aaggtatctc    660
tgctgttttc ccccagatca gggatccaca ggggactcta aattctatgg gtgtccaccc    720
cctcagagtc tttgtggctt caactattca taatagttgg gttcaacaaa tagacacaac    780
tctttctaga gagtgagaga gctacctggg aaacattttg ttcttgataa cgttttttcct    840 ctctgcctgt cattgggaac aagaatgatc aaaagtacat tgtggaacat gggatgggat    900
tgttctgagc ttgctcgatt acctcccctc ttagctctct tatttcttgt cttgctggca    960
agtatctgca gtgattactt tcccaagtct tgtagtgatg aaaatgactt catctcccctt   1020 ttcttccctc agctttgtct gcaactgttt ctgttttgtt ttgtccagca gtcattatca   1080
gagtagttaa cattctaaat atccttcact ttattattaa actgccagct ttttctttgc   1140
aaggactaaa ccgagagata aaatgatatt tatatgccct aaaaatacccc aaggtatnnt   1200 ttaaaaatga aaaagttacg tctacaaggt aagctgagag aagaatgata aggccatgtg   1260
aaagaaagct gaagctgata gaatatctaa atggtgtcta atcacagaaa aacagcttac   1320
agttcaaaat cttcaccggc tctaagggc cttattgatt gttacaacat atgggntgtg    1380
tgcacaggaa gccaagctaa cttctaagca ggtcctcagc ttcccttcca acaattaagt   1440
aattaattaa tcaatnttgg tctttggtcc tctacggcca cactggtgct atagagtnat   1500
cg                                                                  1502

<210> SEQ ID NO 136
<211> LENGTH: 229
<212> TYPE: DNA
<213> ORGANISM: Sus scrofa

<400> SEQUENCE: 136 tcaattaccct gcaggtttaa acgaattcgc ccttacacca gatacttaac ccactgagtg     60
aggccaggat caagcccaca tcctcacaga ctctatgctg ggttcttaac ccactgagcc    120
acaatgtgaa ctcctatagc aatttttaaaa ataaatgcaa attaaatttc tacctttaaa    180
``` tttttttatct ttaacatttg tcccaagggc gaattcgcgg ccgctaaat         229

<210> SEQ ID NO 137
<211> LENGTH: 1273
<212> TYPE: DNA
<213> ORGANISM: Sus scrofa

<400> SEQUENCE: 137
ataagaacca gggccgtggg aggggacact cttgtggccg cgtggtaaag aatttctctg    60
tcctcacaca gaggggagaa ggtcttttc ttttataggg taaaccctaa aaggcggggt   120
gtgaagaggc gggaccatgt tgtgagaagg gaattcgggg ggcgcttttt tcttatatcc   180
ccgaaagggc agaaagggga gtgttctcca aagggaaaa aagtgggga cacccagggt    240
ttttcccatc acacggtttg taaaaacgcc gccccggaga ttttaaatgc gacccctaat   300
agagggaat tgaatttagc gggccgggaa tttgcccttt ttattcaagt ggaaggaaac    360
ttttttaacct ccaccaatga acaaggggtg ttttttttgtc cactttttcca agaaaaaaga   420
aagaaaattg aaggcaatgg acaagaattt tccccaaatt tggaattttt cctccccata   480
aaattttccg atgttactgg catcagatac cgactctcta ggctaaaagc agcataagtc   540
agtgtctaat gtagcacgtt attatttaac tgttttaggc tgaatgcact aaaaagtttc   600
ttctaatatt ccaaggaaca ctaggacctc tagatgctac agccactact tttaggataa   660
atacgtagaa aagaaatgag ttcaacttat agaacagatc tttgtgagag agacagagac   720
agagagatag gagaaaagca gcaaaccggc tgaggatttt tatcttcccct tctctacaca   780
gacctctgga cactgacccc tctggggtgt ttggaatggt gaacagaaca gactcaattc    840
tacatttaaa aaggaggagg agacgggaga aatacatcct acagacgtct gcacaaacaa   900
aacggagtgt gtagttagcc ctggctgaga ctccgcaaac tccgctcccc ccctcacagc   960
tgcaaactgt tctcacgctc actgtgcgca gcctctactg atgccccact gcccgccgcg  1020
ggggctctcg gacaggcagg cagagttctc ggccctgcca ccccaccggt cctgaggaca   1080
gaggaaatgg tcagtggggc gtgcagaggc gaggccagcg ccccccaccta ccaggccggc  1140
ccatgccgat cttctccagg tcctcattct tgacgtactc aaagtgggac aggcgggtca   1200
acgtcgaggt cgtcacggag ccgcacgata tactcttgca tctgcacctc ggacagcagc   1260
tccaaagggc gat                                                      1273

<210> SEQ ID NO 138
<211> LENGTH: 1113
<212> TYPE: DNA
<213> ORGANISM: Sus scrofa

<400> SEQUENCE: 138
ttcagtcctg tgtccttatc tcttcttact tagtacattt tcctaaaaca gtctcattca    60
tttgcagtgc tttaactgtc acctctgcac taacaacctc cagcttagac atctctgccg   120
atccacatga ctagcttctg ctgtaaggct acctgttcta caggccaagt acaacctgac   180
ccaaaatgaa tttatttct gtcataagat tgcccttcct cctgatattt ttaatattaa    240
cctttggcat tgccaactat tcagtctccc aagccagaaa cttgggaatc acaccaaaat   300
gttttgtaag aatccgatac ttggagttcc cgtcgtggcg cagtggttaa cgaatccgac   360
taggaaccat gaggttgcgg gttcgatccc tgcccttgct cagtgggtta acgatccggc   420
gttgccgtga gctgtggtgt aggttgcaga cgcggctcgg atctcgcgtt gctgtggctc   480
tggctaggcc aatggctaca gctccgattg gaccectagc ctgggaatct ccatatgccg   540

| | | | | |
|---|---|---|---|---|
| cgggagcggc | ccaagaaata | gcaaaaagac | caaaataaat | aaataaataa | aaataaataa | 600 |
| ataaataaat | aaataaataa | aaatgtaggc | atttctgtgt | gtctcagcgg | gttaagaacc | 660 |
| tgatgtagtc | cccacgagga | tgccggttcg | atccctggtc | tggcttagtg | agtttcagat | 720 |
| ctggtgagct | cagatccggt | gtttctgtgg | ctgtggtgta | gcctgcaagc | tgcagctcca | 780 |
| attcaaccct | tggctgagga | acttccgtaa | gctgcaagtg | aagctgtcaa | agaaaacaa | 840 |
| attggatcta | tgtaataatc | atcagtggaa | gccaaagcca | ttagagaaat | gtcaaagggg | 900 |
| gacttttata | atgcacctac | caatgggtgc | atctggctga | caaatgccaa | acagtggaaa | 960 |
| ggacccaccg | gacatgcctc | tctcctttag | aaacacagga | agcccacctc | ctcccagaaa | 1020 |
| atcttacaca | aaaaggaccc | ttactctaca | atccaggaat | ccacggacaa | aggaactcac | 1080 |
| caggttccac | taaccctctc | aacgctaacc | gcc | | | 1113 |

<210> SEQ ID NO 139
<211> LENGTH: 946
<212> TYPE: DNA
<213> ORGANISM: Sus scrofa

<400> SEQUENCE: 139

| | | | | | | |
|---|---|---|---|---|---|---|
| cgcccttagc | cctgatggga | actcccacta | gtcaggttct | taaccatga | gccccaatag | 60 |
| gaactccctc | aactaaattt | tagctaaccc | aatccagcaa | cacatcaaaa | agatcacaca | 120 |
| ggagttcccg | tcgtggcgca | gtggttaacg | aatccgacta | ggaaccatga | ggttgcgggt | 180 |
| tcagtccctg | gccttgctca | gtgggttaac | gatccggcgt | tgccgtgagc | tgtggtgtag | 240 |
| gttgcagacg | aggctcggat | cctgcgttgc | tgtggctctg | atgtaggctg | gtggctacag | 300 |
| ctccgattca | accctagcc | tgggaacctc | catatgccac | gggagcggcc | caagaaatag | 360 |
| caacaacaac | aacaacaaca | acaacaaaag | acaaagaca | aaagacaaa | aaaaaaaaa | 420 |
| aaagatcac | acacaacaac | aaagtaggat | ttatatcaag | ttcagaagga | tggttcaaca | 480 |
| tatgcaaatc | aactgtctta | caccacatta | acaaaactca | aaacaacat | gatcctctca | 540 |
| atagatgcat | aaaaagtatt | tgacaaaatc | caccatccac | tgatgataaa | aattcttacc | 600 |
| aaagtcagta | tagagggaac | atatcttaac | ataataaaag | ccatttatga | caaacccact | 660 |
| gccaatataa | tactcaaaag | aaaaaagcta | aaagcctttc | tgcctcaatt | tgcaccaaaa | 720 |
| caagaagccc | actctcacta | ctttttattca | ggatagattg | gaagtcctag | ccatacaatc | 780 |
| agaaaaacaa | aaaaataaag | gtatccaaat | gggaatcccc | tccgggctca | tgttaacaaa | 840 |
| ttgaaaggaa | caagaagtgc | aaattgaacc | tggcatgctc | agggggcaagg | atccgattgc | 900 |
| agaacggggg | aaggccaaaa | cgcccaaacc | gcttgcgggt | cgggga | | 946 |

<210> SEQ ID NO 140
<211> LENGTH: 1045
<212> TYPE: DNA
<213> ORGANISM: Sus scrofa

<400> SEQUENCE: 140

| | | | | | | |
|---|---|---|---|---|---|---|
| ttcgcccttt | agccagagct | cattaagtat | agggaaagct | gcctgacagt | acgtacagtc | 60 |
| aaaacaagca | aaaggcagtg | agttccccat | cactagaagg | gctcagccgg | gctgggcggc | 120 |
| acttggtggg | actgctgtag | tgtgtctcaa | acttttttatt | tccagactac | cacccacata | 180 |
| aaaatacagt | tcatgttata | attctgtaca | tatgcacaca | gttttttttaa | agttctagtg | 240 |
| ctgacccact | ccaccggcgt | gaggcccaac | tgggcagtga | tcagcataag | cctagggaaa | 300 |

```
gcattgcact agttggccag aaggtcttat caggtctggg attctgtggc tgtcctctca    360
aggaatttaa actcctgttg ataaccacct gagaaaaatt catttaggaa gataaatctt    420
catcttaaaa actcacaaaa catttactct tttattataa actaataccg ttgaatgtat    480
caacaagcaa aaagagtaaa agtcactgcc actcagagaa tgccaatagt aatatttgga    540
tatatttaat gctaggctta ttttttttt cattgtgtat agctctttta aaattttga    600 gatcacatga tcacatggct taaaccattt tgtaaacatt ttacttcaca ctgttttatg    660 aactttttt tttggccact cctgcagcat gcagaagttc tcaggcctgg tatagaaacc    720
cccacagcag taaccagagg catagcaggg acaacgctga atccttaacc cactgatcct    780
tcaggaaact cctctcttat gaattttcc ctcactgctg tatattcttc cacaaagtta    840
tttttagtga atgtgttgta ttccactgca ctaatgcatc cataggaact taaccaaatt    900
ctggtgatta ccactaggc agtttccagt ttttcctgtg gacataagtc tttgattact    960
tttccttcct ttagataaat tctgagaagt ggattttgaa gaatggaagt aaaatattaa   1020
aagggcgaat tcgcggccgc taaat                                         1045
```

<210> SEQ ID NO 141
<211> LENGTH: 604
<212> TYPE: DNA
<213> ORGANISM: Sus scrofa

<400> SEQUENCE: 141

```
ctagtcctgc aggtttaaac gaattcgccc tttctttatt tagctgtccc acttcaaaac     60
cccatgccat gttccgggaa tacctcatta tgtgagtcct gataggctct ccttccacta    120
agagaaattt caggtattcc tcttcccagc agcccctggc agcaagatct ggacacagag    180
ctaggctgag ctaattcatt ctaatcttcc aaggactcat accattcccc aaaaccctca    240
ccccagaatt ctgccactgg aaactttgtc cagtgatctg tgttttagg agaatttccc     300 caacttattt acaaatataa tcttgtgtgt gtgtgtgtgt gtgtgtgtgt gtgtgtgtgt    360
gtgtgtcttt tgcctttcc tagtgccgct cctactgcat gtggaggttc ccaggctagg    420
ggtctaattg gagctgtagt cgccggccta cgccaccgcc acagccacag ccacagccac    480
agccacatgg gatcctagct gcttctgcaa cctatatcac agctcaaggc aacactggat    540
ccttaaaccc actgagcaag gccagggatc gaacccgcaa agggcgaatt cgcggccgct    600
aaat                                                                604
```

<210> SEQ ID NO 142
<211> LENGTH: 261
<212> TYPE: DNA
<213> ORGANISM: Sus scrofa

<400> SEQUENCE: 142

```
gaattcgccc ttaatgtat atcatatccc tagcccttat ttatcttaaa actggaagaa     60
ccggaagatt gtacctttca gctcccttcc ttcacttctc ctttcttgca cccctcatcc    120
tcctacctct cttgtacccc gtgaacctcc tacctcatc tctggtgacc ataaatttga    180
tctctttctg tgaatttatc tgttttgaa gtatggttgt cccacaacac tgtattaagg    240
gcgaattcgc ggccgctaaa t                                              261
```

<210> SEQ ID NO 143
<211> LENGTH: 402
<212> TYPE: DNA
<213> ORGANISM: Sus scrofa

<400> SEQUENCE: 143

```
gtttaacgaa ttcgcccttc tacacagatg acatgacagt atatacagaa aaccctaagg    60
attccactca aaaactattc aaattgatca atgaattcag caaagtagca ggatacaaaa   120
ttaacattca gaaattggtt gcatttctgt atacaaacag ggaaatatta gaaaaggaat   180
ataaaaaata ccttttaaaa ccatacccct aaaaatatac ctaggaataa acctgaccaa   240
agaggtaaaa gtcttataca ctgagaactg taaaacaata atcaaggaaa ttgaagagga   300
ttcaaagaaa tggaaaaata cgccatgttc ctggatttga agaattaata ttattaaaat   360
gggcatacta cccaaagaag ggcgaattcg cggccgctaa at                      402
```

<210> SEQ ID NO 144
<211> LENGTH: 472
<212> TYPE: DNA
<213> ORGANISM: Sus scrofa

<400> SEQUENCE: 144

```
ttcgcccttt aatactccag acttgactgt gccttttctt agagaaaaca atcaacaaa     60
accccccacaa ttttttattat gcaagtacaa tatgttttgt gtttaggaca cagaagttaa 120
cagaaaaaaa atcacctgta ttctaatccc cagagacaaa tcccctttgc acatactctg   180
ctaaattctc ttttatgcat aggacactc atatatcaat aaaggatca aatcataact    240
aatgtttgat aacctctcca ttactttaac tgtgaacata ttccttgta cattgtattc    300
acattctgat ttgatatatt attttatgtc ttaaatagtg tgttttaata tattttaaat  360
agaatgtttt taaatatttt taaatatttt aaatagaata gtgactgtta aactgaaggc  420
ttactatgtc aggcactgtg ctaaataaag ggcgaattcg cggccgctaa at          472
```

<210> SEQ ID NO 145
<211> LENGTH: 441
<212> TYPE: DNA
<213> ORGANISM: Sus scrofa

<400> SEQUENCE: 145

```
tgggtgatca cgtgacagtc ctgtggtttt ctctggtgga cattccagca tccagctgtg    60
acggcggcca ggaccatgat ttaaatgacg gtgttctctg tgcccagatt agcaaagcat   120
aaggtggagc atgatgcaag tcacaggaag accgagtctg gagttctagc agtgtcagac   180
ggaattggta aaggcctcgg cttttccacc tagctattca aacaaagcat gaaaccaagt   240
ttaaaatgct caaacaatca gccaacaatt gaatgttgtg tcatatacgt gaagccatca   300
gcattccact ctctccagag gaatataaca gaatgcagag agtttacagt aaagcgtcct   360
caatcaaaaa caactcgtca catcctagac ctgcctattt taaatttgtt ttgggggctg   420
tgggtttctt ctggtggtaa a                                              441
```

<210> SEQ ID NO 146
<211> LENGTH: 578
<212> TYPE: DNA
<213> ORGANISM: Sus scrofa
<220> FEATURE:
<221> NAME/KEY: modified_base
<222> LOCATION: (94)
<223> OTHER INFORMATION: a, c, t, g, unknown or other

<400> SEQUENCE: 146

```
agcgctgctc ccagggcgta gggatgaaaa gggcacacag ctggagacag agagagagag    60
```

```
gaccggtcac ccccggggtg tggggatggg gacnctcccc ttttttttag atcacaagct    120
cacgcttgct acacgagact cccccacagt gaccggtccc tattactacc atggtcccat    180
agacctctct tttttacgta gccgcaagcc gcgctgcccc tctatgccct tcctgcaacc    240
gccacaagga ctgcaacaaa gatactttg ggtggttcaa acaacaacaa aacacctctt    300
tttagtgctc ctgcggggcg gcatcttctt tgataaccac catcaaaacc ttttttttc    360 ttactcggtt attattcgac cgatacacca tgcgcgtaca gtataggagt ggtgctagag    420
gaccgatcga cgtgatccac gttatactga cagtacaagc aacgaggatt aagtaacaca    480
cggacccact ctgaccgcct acgacaaacc accaaccact cccaacaagc gagccgcacc    540
acacggatta gacgactttc gacatcctcc tgttcgtt                           578
```

<210> SEQ ID NO 147
<211> LENGTH: 1196
<212> TYPE: DNA
<213> ORGANISM: Sus scrofa
<220> FEATURE:
<221> NAME/KEY: modified_base
<222> LOCATION: (737)
<223> OTHER INFORMATION: a, c, t, g, unknown or other
<220> FEATURE:
<221> NAME/KEY: modified_base
<222> LOCATION: (916)
<223> OTHER INFORMATION: a, c, t, g, unknown or other
<220> FEATURE:
<221> NAME/KEY: modified_base
<222> LOCATION: (975)
<223> OTHER INFORMATION: a, c, t, g, unknown or other

<400> SEQUENCE: 147

```
ttaattatct gcaggtttaa acgaattcgc cctttttaaa aaattaatgt tataaattgc     60
catgagaaag aaacagcaga ttcaatagga aaattctcca tgaaaacgta aagggctgaa    120
aatagctaag gaaattccaa ggatagtctt gctctaacag atatcaaaat atattctaaa    180
gctatcataa ttaaggtagt gtggcatttg tgtaggaaaa gacaaattag gatcaatgaa    240
acaaaatgga aagtccataa ataaatccaa acatataagg aaacttgata taccacagag    300
gtggtaacac aaatcagtag ggtattgata cattatttag tacatgatta tttagtactg    360
gctatccata taaaaaaaat agattcacat cccaaatcaa tacaaaaata aattccaggt    420
agattaaaga cctaaatgtg aaaaataaaa ttttattact cttgtgactt aaattgtgtt    480
cccccaaaag atctgttcaa gtcctaacct ttgatacctg tgaatgtgac cttcatgaaa    540
atagagtttt tgcagatgaa gtcaaggtga gatgaggttg tactagagta gggtggaccc    600
taaatccaat atgactagtg aacttataaa aagaggagac gaatcataca aggaaaaccc    660
cttgtgacaa tagaaggaaa gattggagtg attctcctat aaaccaagga atgccaagga    720
ttgccaccaa ccactanaac ctggaagagg caaggaaggc tcctcatttg caccaccaaa    780
gagagcacag ccctgccaac acctgatttc agacctctat cttccagaac cataaaagaa    840
tataattttc atgtttaaaa gcatccaaag taatgataat ttgttacagc agccctatta    900
aatacataca ggtacnttta gaagaaaatt aagtttaaga atcagcatag agaaagggtt    960
cttttctttt ctttncttg cattgctgct gcatatgaag tccgggcagg atgaccccat   1020
gactgctgtg cgaatctatt gtgttcccac tcagaatcta catcagagca acagagatta   1080
tgctataata gttgctagaa cgaggctcag aatcttacag tagatagctt aaaactacac   1140
tacacaggga caccgcgcca tctgaaagac gggcgccgat gaatgacctc cccccc       1196
```

<210> SEQ ID NO 148
<211> LENGTH: 1244
<212> TYPE: DNA
<213> ORGANISM: Sus scrofa
<220> FEATURE:
<221> NAME/KEY: modified_base
<222> LOCATION: (1128)
<223> OTHER INFORMATION: a, c, t, g, unknown or other

<400> SEQUENCE: 148

```
gaatttagcg gccgcgaatt cgcccttctt cttgggtcag ggacagctat ttctcaccag      60
ggatggacct cttgcaaaca cccaacctgc acctgccttt ccagccttga cctccccacc     120
agcacactct cttccactct gtgaggaatc ttgtgcttca ccgttggggg aagctgagta     180
gcaagagtga aaaaaaaaag agcaaaaagt gttggagaga gacagacttg ggttctaatt     240
ccggttctgg tcctggttag ctgcaaaatc ctggaaaagt tacttaacct ctgagccact     300
cagagacact taggtagtta tctgcataca aataatctat ttacatgtat gaggcagaac     360
aaccaatagg ccgttggcag tgaacaaaag caaaacagaa ttttaaaag agaggagagg     420
aaaacattca tctgggaact aagattttga tgctatattt tctttgtcag ttgagaagca     480
ggtggctggg ccattggccc taagcaggct ggctgggcct tggaaagcag caatttgcat     540
tgtggattct cagggaagct tgagagttta gcatgaggta tagggggga cagaccctgt     600
gagatcctcc aggcccctca tttaggggtc atctctactc cctcatggga atctctccta     660
gtaaccacct cctgggttag aactgtgacg gctatgtggg tcaatacccca caaaggtcgg     720
aacagtagag tcgagtctgc tataatgctt gtctcagaaa tgctaatttg ttccaatgca     780
tttgatagat gagggaacaa tttgaaccta ctgcaaattt cacatttgct gatgaatgat     840
ttcatcttca agaaacacta gctgaaagca gaaaactgca cccagtcgca ccaagccacc     900
taggaataca aaaaacaaaa cagaacaaaa caaaaaacgc acacgtagcc aggccacaga     960
catcagagtt atcccagctc atcacatcct tccacatctg gtatcagata actgatacca    1020
tctaccctcc accgtcacac agctacccag gtccaggagc caacatccct tccaacaccc    1080
acttccagga gccaacttca gatctttctt gaagcaaagt gccatacnta ttgttgtact    1140
aatgtatttc ttaatcattt gatgtgcaaa accctgctac cattttaact aggtgaattt    1200
ttgtgtgtca tgacaccagt taagggcgaa ttcgttaaac cctg                     1244
```

<210> SEQ ID NO 149
<211> LENGTH: 962
<212> TYPE: DNA
<213> ORGANISM: Sus scrofa

<400> SEQUENCE: 149

```
atgacaatat gtgctcataa aatagagtga gtaaaactgc tttgtgaact ataaagacta      60
ttgttgctct cacatgaact actacttccc ctagctgcat ctactacatg gaacttgttc     120
catttgactt ttttgtttgt ttttggccat gcttatgaca tgtggaagtt cccaggccag     180
ggaccaaacc catgccacag cagtaatcag agctgctgca agtgacaagg ccagatccct     240
aacccgctgt gctacaaaag aactccccaa tttgatttca taatcagaaa tcaccatcac     300
tattctctct tttaagacct gacctgtggc tcagcggtaa caaacctgac tagtatccat     360
gaggttatgg gtttgatccc tggcctcact cagtgggtta aggatctggc gttgccatga     420
gctgtggtat aggtcacaga cgtgactcgg agcccacatt gctgtggctg tggcagcag     480
ctgtagctct gattagacac ctagcctggg aacctccaca tgcctcggtg cagccctaaa     540
```

```
aagacagaca gacagacaga cagaaagaaa gaaagaaaga aagaaagaaa gaaagaaaga       600
aagaaagaaa gaaagtaaag aaagatagag agaaaagaat aactactatt tactcagttt       660
cctatgttcc aattactgtt atgtattttt tatacatata tgttgagtag cagtcctgag       720
agttgggtat taatattctt gttttctaat caggaaagca gagttcaagc aggtcaggta       780
atttggccaa agtcactcag aaccagaatt caaatatgga tccttgaagc ctcttgtcat       840
ggcttgtctg ctatactgca cattaattaa cctcttctca actttgtctc tagttccttt       900
ctgtccacag ggtatgattc acctcaagtc acttttatct ttagagggcg aattctcgaa       960
cg                                                                     962

<210> SEQ ID NO 150
<211> LENGTH: 550
<212> TYPE: DNA
<213> ORGANISM: Sus scrofa

<400> SEQUENCE: 150
aatgtggcac acgtcacagc tgtggctcca gttccatccc tggcccgcga acttacatat        60
cccatgggtg tggccgaatt ttataaaact gatttactta tcataaaagt taggaagcta       120
ttttaaaagt aagaaaaaaa aaatgcctgt aatcccactg ctcagagaag caaagttagc       180
atttctgcct tcttcctccc tcaggtattt tgttgaagtt cttttatttt attttatttt       240 ttttttttttt gtctttagtg attttgggga tgctgccatt tcttgggccg ctcctgcggc      300
atatggaagt tcccaggctt ggggtctaat cgaagctgta gccgccagcc tacgccagag       360
ccacagcaac gcgggatcca agccgcgtct gcaacctaca ccacagctca cggcaacgcc       420
ggatcgttaa cccactgagc aagggcaggg atcgaacccg caacctcatg gttcctagtc       480
ggattcgtta accactgcgc cacgcgggga actccctgaa atccattttt aaaaaagata       540
atgcaggtaa                                                             550

<210> SEQ ID NO 151
<211> LENGTH: 1296
<212> TYPE: DNA
<213> ORGANISM: Sus scrofa
<220> FEATURE:
<221> NAME/KEY: modified_base
<222> LOCATION: (1068)
<223> OTHER INFORMATION: a, c, t, g, unknown or other
<220> FEATURE:
<221> NAME/KEY: modified_base
<222> LOCATION: (1134)..(1135)
<223> OTHER INFORMATION: a, c, t, g, unknown or other

<400> SEQUENCE: 151
tgcaggttta aacgaattcg cccttatttc gcccaccccg gggaggccca gcagggtagg        60
ggtccctgca gagcctcacc tgcctcattg gggagaagga cctgcatctc ttcgagaagc       120
taggagatgg ctcctttggc gtggtgcgca ggggcgagtg ggacgccccg tcggggaaga       180
cggtgagctc tctgggtcct gtgatgcgtg cagaggggca ggctcctgag aggccctgcc       240
ctgccctgcc ccttaaggtg gatctgttcc tctgttggga tgtgaagggg ctggggaca        300 ggtcaagagt agctctccct ggagtccatg ctcaggttta actgcatata tacacttctt       360
ttttcaatta caaaactaat ttactggagt tcccactatg acacagtggg ttaagggtcc       420
agtgttgctg cagctgtggc acaggtcaca gctgtggctc cagttccatc cctggcctgg       480
gaacttacat atcccaaggg tgtggctgaa aaaaaaaaaa aaactgattt acttatcata       540
aaagttagga agctatttta aaagtaagaa aaaaaaaat gcctgtaatc ccactgctca       600
```

```
gagaagcaaa gttagcattt ctgccttctt cctccctcag gtattttgtt gaagttcttt      660
tagacggaaa ttttggacac aacttttttaa ctctcgccct ttcgtcttaa tgtattctat     720
ttaaacagtt ttcctcagag ggctagacag catgtgtgca gtaaagcaca cagttcttga     780
gtgtaccact cagtgcattt tcacatatgc atgggcccgt gtgaccacgg cccaggtcag     840
gatacagaga gcaccccccag cccccaaaa gcgccctcag gtctcttcta ctgagtatcc     900
ctttccttca agggaagcca ctattttgat tcctgtcacc atagatgttt tatggtatta     960
cattttaaag cattttcctt ctatgccaca acattttttt attgtgacat tttaacattc     1020
catcatcata ccggtcatct cttgccttct ggttaccact taacctgngc atgtcctcag     1080 gaagggggaga cccagctcat ggcccttgtg ggtcagccgc tgccctccct cagnncagcc    1140
acggcacctg ggacacgctc aaccacctgg atgaacaaag ctgaagcaaa aatgttgagc     1200
ccactggaaa ggaacagctg gccaaatgtg ttggggggggg ctgttctaat tcctgaccccc   1260 gttccgcaca gaggttattt aaagcctaaa ccaggg                               1296

<210> SEQ ID NO 152
<211> LENGTH: 1026
<212> TYPE: DNA
<213> ORGANISM: Sus scrofa

<400> SEQUENCE: 152
atcgaaccca aaacctcatg gttcctagtc agatttgttt ccgttgtgcc tcgacaggaa      60
ctcctgtgct atattttaga ttccacatat aaatgatagc acatggtatt tatctttctc     120
tttctgattt acttcactta gtatgagagt ttccagttgc atccatgttg ctgcaaatgg     180
cattatttca ttttaatga ctgagtagta ttccattgca tttttatacc aaattttcat     240 tttttttaatt ttataatgat ttttatttt tccattatag ctggtttata gtgttctgtc    300
aaatttctac tgtacagcaa ggtgactcag tcacacatac acatatacat tcttttttcct   360 cacattatcc tgctctacca taagtgacta gatatagttc ccagtgctat atataacagg    420
atctccttgc ttatccattc caaaggcaat agtttgcatc tgttaatccc aaattcccag    480
tccatctcac tccctccccc accacctccc ccactccctc ccccttagca accagaagtc    540
tgttctccat gtctattatt ttctttttctg tggaaaggtt catttgtgcc atatattaga   600
ttccagatat aagtgatatc atatcatata agtggtattt gtctttctct ttctgactta   660
cttcacttag tatgagagtt cctagttcca tccatcaagt tgctgcaaat ggctttattt    720
tgttctttac ataccaaatt ttcttaatca ttcatctgtt gatggacatt taggttgctt    780
ccatgtcttg gctatggtga atagtgctgc tatgaacata gggttggatg tatcttttag    840
aattgtggtt tgtccggata tatgcccagg agtgggattg ctgggtcata tggtagtttt    900
atattgtttt ccgtggaacc tctatactgt tctccatagt ggttgtatca gtctgcattc    960
ccaccaacaa tgtacagggg ttccctttttt tctacaccct caagggcgaa ttcgcggccg   1020
ctaaat                                                                1026

<210> SEQ ID NO 153
<211> LENGTH: 1830
<212> TYPE: DNA
<213> ORGANISM: Sus scrofa

<400> SEQUENCE: 153
gctggcagct gagggctgac ctccagggga actgggagtg gggagctggt gggggatacc      60
```

```
tggatgcctt ccccacaccc caccttttcc tatccccca cctaaccctg cctccctgtt      120
ggggacctcc cttccatcgc agaaccaacc tacgaccctg tgagtgaaga ccaagacccc     180
ctgtcaagtg acttgaagag gctgagcctg cggaagccag ggctgccccg tgggctgtgg     240
ctagcgaagc cctcagcccg ggtgccgggt accaaggcag gccgtggcag cggtgagatc     300
acgctcattg acttcagcga ggagcctgta gccccggccc ctcgcccctg tgcaccctca     360
ctggcgcagc tggacatgga cgcctgttcc ttgctggata agaccccgcc gcagagcccc     420
acgcgggcac tgccccggcc cctgcatccc acgcctgtgg tggactggga tgcacgcccg     480 ctgccccac ctcccgccta tgatgacgtg cccaagatg aggatgactt tgaggtctgc       540
tccatcaaca gcaccctggt gggtgcagag gtctctgctg gtccagcca gggtgagacc      600 aattatgcct tcgtgcctga gccggcacag ctcctccctc ccctggagga caatctgttc     660
ctcccacccc agggtggggg caagccaccc aactcagccc agacagcaga gatcttccag     720
gcactgcagc aggagtgcat gcggcaacta caggtccctg ccagctctct tgtcccctt g   780 cccagccctg ggctgatga caagcccag gtgcccctc gggtaccat ccccccaagg         840 cccacacgcc ctcgtggtga gctgtctcca gccccctcaa gtgaggagga gatggggcgg     900
tggcctggac ctgcctcccc tccccgggtg cctccgcggg agccctgtc cccacaaggc      960 tcaaggaccc ctagtcccct ggtgccacct ggcagctccc cgctgccacc ccggctctca     1020
agctcacctg ggaagaccat gcccaccacc caaagctttg cctcaaaccc caagtatgcc    1080 acaccccag gtgatccagg cacctggccc ccgggccgg ccctgcctc ttaccccatt        1140 gtccgagatg gcaagaaggt cagcagcacc cactactacc tgctacctga gcgcccaccc    1200
taccttggag cggctaccag cgcttcttac gtgagggccc aaagccctga aaaggcaaac    1260
ccaatgcctg gtgccccggc tgctgccccc ttcccaacac cccaaacccc tggtgccccc    1320
caatggccac tgtttcaacc caatgccaac agggcggccc cagaaacccc aagggcaaac    1380
tttctccacc aacaagacac aaacccagg ggcccccgcc ccccagccc cgtgggggc      1440 ccctggttcc cctttgccaa aaaaggggtc cccctcggg ggaaagggcc cagaaggtct     1500
ggtatgctcc ctcacaaaca aaccccata tggtcagaat cttgggccct cgctcctcac    1560
ggtgaggaag aggcgtcggg ggccccacac aggaaccaac caacaaaggg cgccgtcgct   1620
tcggtatgac cgggggggtgg cctatgccca ccaccaacgc gcaggtgtga ggagtggcac  1680
cacagaagag aggccgaggg cccgtctaag aacacagcgc ggggagggga gagaggcgtc   1740
tcatatttaa agagacaaac cctctccctc tcttgttata tgagacacaa aaagaggtgt    1800 aatattttc gcaaccaccc ccgcaaccca                                      1830
```

<210> SEQ ID NO 154
<211> LENGTH: 1301
<212> TYPE: DNA
<213> ORGANISM: Sus scrofa
<220> FEATURE:
<221> NAME/KEY: modified_base
<222> LOCATION: (1121)
<223> OTHER INFORMATION: a, c, t, g, unknown or other
<220> FEATURE:
<221> NAME/KEY: modified_base
<222> LOCATION: (1165)
<223> OTHER INFORMATION: a, c, t, g, unknown or other
<220> FEATURE:
<221> NAME/KEY: modified_base
<222> LOCATION: (1210)
<223> OTHER INFORMATION: a, c, t, g, unknown or other
<220> FEATURE:
<221> NAME/KEY: modified_base
<222> LOCATION: (1222)
<223> OTHER INFORMATION: a, c, t, g, unknown or other
<220> FEATURE:
<221> NAME/KEY: modified_base
<222> LOCATION: (1225)
<223> OTHER INFORMATION: a, c, t, g, unknown or other

<400> SEQUENCE: 154

| | | | | | |
|---|---|---|---|---|---|
| ctgcagttta | cgaatcgccc | ttgagctcca | agacatggaa | ctactggtgg ctcccggcag | 60 |
| gaatggctca | gaaggaaacc | tggaaactct | gattccacac | cctccggcaa ggagaccaaa | 120 |
| taaattgaaa | taagcctcca | tctccaatac | tgtcagcagc | ccagtaactg aggggccacc | 180 |
| accctgtgca | gctcctgggt | ggtgataggc | tgtagcaagt | gcaggcagtg gggatccaca | 240 |
| gtcacagagg | gtcccagagt | gagggctctc | ctgttccccc | tctctcagag aacctctgac | 300 |
| ttgtctatca | gtctgggaga | ggcctcttca | acttgctact | gagggcaccc agattctcca | 360 |
| caggccatct | gcaccacgct | gccccacccc | aggaaaactt | ctctatgctt cgggacaccc | 420 |
| aaaaggagaa | aaaccctgaa | taagaggtcc | taacaggaaa | aatcaatcaa attgaggcca | 480 |
| tggcttggca | aagagcagga | gagagggaa | ggaaggaagc | aggaacttca atcagaaga | 540 |
| ctccgagtta | aggttgccac | ttgccagccc | aggggacgtg | agaaaaaaac ctttagctca | 600 |
| gtgtcttcga | tggcaaaatt | agtcagatgg | aaaggagcta | tttcatgggt tgtggtgacg | 660 |
| ataaaacaaa | gtagtatctg | gtataaaagt | aggataatta | taacatctta tttgagaaag | 720 |
| ggaccactgt | attttagagc | tggaagactg | ggggcaggag | ggtgatggag gcagaatgga | 780 |
| aagggcacct | ctgttggatc | agagacactc | ccatcatcct | acgattaccc agctctaaaa | 840 |
| agccacccgc | agtctccctg | agggttttgc | aagggccagc | ttggtttatt cagaatgtgg | 900 |
| cttctcgcat | gaaccgacgc | caaacgccag | ctccaccatg | gggcagggc cctgctctcg | 960 |
| ggcactgcag | ctgcatggct | ccttgcgcag | caatctcctc | catgccttg gtttctgggc | 1020 |
| tcagctctgg | aggcagaggc | tgccctggca | gagtttgact | tgcctgcaat ttatgacttc | 1080 |
| attgccagga | gaggccaaga | agcagctggg | cttatgtgct | ncaataatgg tttactactg | 1140 |
| ggttccaagt | gctgccgaat | gcttncaaga | gcacgccgtg | gagtgggcca gccgctctcc | 1200 |
| caggccaggn | ctgaggactc | cnagncatct | ctctcctatt | tcaggctttg cactctgccg | 1260 |
| gctgaatcat | gccagcaaca | ttagtcctgg | tgtgtccctt | t | 1301 |

<210> SEQ ID NO 155
<211> LENGTH: 845
<212> TYPE: DNA
<213> ORGANISM: Sus scrofa

<400> SEQUENCE: 155

| | | | | | |
|---|---|---|---|---|---|
| atttagcggc | cgcgaattcg | cccttctcct | gctgcaagag | ttataaatga ctgacaaccc | 60 |
| agctgctgcc | cctctgcatc | taccattacc | tttgcctaga | gatcattcct cccctccccc | 120 |
| caccctgggc | tactcccaac | caatgcctga | gcgcagtgag | ggcataatgc aggcacatcc | 180 |
| cccaaaccat | gggacttctc | caatgggtta | ctggctggag | gacaccctat tgccctgatg | 240 |
| ggaaccttct | cagaactggg | ctgaaaccta | agactcttct | taccaagtcc tccttccttc | 300 |
| tttccctgcc | ctgtgtggta | tgaaggctgc | tctcacccct | tctggttccc tcctgtggt | 360 |
| agccagtctc | caaggaggcg | cccagcgatc | tctcccacct | tccatgcag ccctttccca | 420 |
| cactgtacca | gggtcggtct | gtgtgaccag | tagactacgg | cacaagtgat agaatgtcac | 480 |
| ttctgagata | aaataagaaa | aggcagtgca | gcttctgtct | tggtagatct ctccccctc | 540 |

```
tcaggtcact cactacgcgg gaggccagct gccgtgttgt tgagatgctc cagcctgtga    600
agcaaggagc tcaagccccc agccaacagc cacccgagtg agcttggaag cctttagctg    660
actgctgcct ggttgacagc tcacctgcaa cctaccagga ggccctgagc cagaatcacc    720
tagctaagtc tctccagatt ctcaacccctt agaaactgct tgaaataaca ggtttgttgt    780
tttaagccac taggttttgg agtaatctgt tctgaagtaa aagggcgaat tcgcggccgc    840
taaat                                                                 845
```

<210> SEQ ID NO 156
<211> LENGTH: 386
<212> TYPE: DNA
<213> ORGANISM: Sus scrofa

<400> SEQUENCE: 156

```
ctagtcctgc aggtttaaac gaattcgccc ttgtggcaaa gtgggaagct gaacccaaat     60
ataaggttga aatctgcctt cctgactttc gattggctgg aaattaaccct ctcacccaag    120 gcaccagcag cgtctgtcag tggcaaagat ggagaacaga gagatggatg ggacgtggg     180 ttcccaaggg aggaggtggc tcagtctctg acacaacagt tctcaacctt gccatgtgcg    240
ccactggctg tgaaggtcgc atgtaatttg ttactgctaa ttgctacaaa tgttttttctc    300 ttagagtgta ttcaggattg cgcctgtaat tacattgctt tcacttgctt agtgatgagc    360
caagggcgaa ttcgcggccg ctaaat                                         386
```

<210> SEQ ID NO 157
<211> LENGTH: 1753
<212> TYPE: DNA
<213> ORGANISM: Sus scrofa

<400> SEQUENCE: 157

```
gcaggactta aacgaattcg cccttgcctt tggttgctgg tcccttgaca gtggtgtgga     60
cctgtgggga gatgggggga acaggctgct cctggttgca gggccccagg tggtggaagt    120
tatcctcaag gaggtggggg cagcacacag agcctctggc agtagtaaga cggggcattt    180
gcattcccag gggtgtgaag gcaatgggtg gcccttggtg gtagggctcc ttgcagtgaa    240
ccctaaaggt gacgggccac aggtggtgcc tgttcatagg acctttagtg gtggtgagct    300
gagcccactt caagagtcca agatggctgc aaaggtttgt acctgccccc atagcctgag    360
caagaggcat gtgcagagaa agatgttact atggaagtct tgcttcccct cctctcaccc    420
ttcccagcaa gggcaccttg cttctcctgc aggttcaggc ctcctcccat gctcccttgg    480
ctgtggtgta tttctctcca gtgctctctg gctgtttccg cacagccaac cctagtcctc    540
ttcccagaat tgacctctgt agcctgagtc tcagcaccca tcctgcccga gtgtcttagg    600
ctgtgggcct cagcagtaga accaatggtc tgtgcagctc tctctctgct tttccctcct    660
ctgaccagct gctgtacttt tctctgaggg tttgaggctt ccctcttttc ctggctgatc    720
tccctgtcag ttaggtggcc ttccagtgag gagtcctttc ctctttcaca gctccctctc    780
tggtcctttc ttgattcctt tttcttttttt cccttctctc tctcttttttt ccttttttatt    840 cttccagtaa tgtggagggt ttcttgcccc atttggaggt ctgaggtctt ctgccagtgt    900
ttagtagatg ttctgtgcaa attgttctac atgtcagtgg gttttttttg cttcttaggg    960
tcacactcgt ggcatatgga agtttggaag ttcctgggct aggagttgaa tcgaagctgc   1020
agttggtggc ctatgccaca gccacagcaa tgccagatcc ataccgtgtc tgtgacttac   1080
accacagctg atggcgtgcc agatgcttaa tccactgagt gaggccagga atccaacctg   1140
```

```
catcctcacg gatactagtt gggtttgtaa cccactgagc cacaacagga acccaaatc      1200 atggctaggt ttttcctgat ctaaagaaaa agtctcatcc acatcgtgtc ctccatatcc      1260
ccatcttgtt taactgaaag catcctgaaa aaggggtcta cattctccac ttccttttta      1320
tcatctactc cttacatctc ctccacctct atcacctcac caaaaatcct ttcccccaaa      1380
gttaccccca aactcctccc taagcaccaa gaccaatttc cttctcagtt cctattcatt      1440
tctgtaaaat ttggcaccgt ccattcaaca tacatttatt gagcatctac ctcagtattc      1500
tctccttgac cttcccttg acactggcac aggattgccc ccctgggagc tgaaggatgc      1560
ttctccccgc ccccgtccct gcccaacaca ttccctgtcc cttctgtacc ctttgcctct      1620
tctctcctca gctcccagat gaagtcaggc ttctgggggc atctccttct ctctcctttc      1680
acactttctc tctggctaaa ctgcatctac tttcacactt tacaaataca taactctacc      1740
tatggagacc tgc                                                         1753

<210> SEQ ID NO 158
<211> LENGTH: 1815
<212> TYPE: DNA
<213> ORGANISM: Sus scrofa

<400> SEQUENCE: 158
attactgcag tttaacgaat tcgcccttgt atcattaagc ctgagaattt agacttgtaa        60
ctaaagtgca aggccctgtg tatgtccccg taacccagca agggacccat caccatcccc       120
accccacatc tgagaaaact gaggttcacg gagatgaaca tgcactctcg tcattaatga       180
gtcacagaag gtcagggttg ggtgatcact gcaacccttg gggaatgata actgccttga       240
atcacacttg ccctggtgac acagggagtc acatagctgg aattcaagac taggtctgcc       300
tagctccaaa gtcaaagtaa ggaattaaca tgctctgagg gcttattcta tgccagtggg       360
cgctcacatc ctaaacggtg atttccctaa ggcagatgca gagctaagcc tttaagaatg       420
gacttgctgt ggagttcctg ttgtggctgg ctccgtggta atgtacccag caagtatcca       480
tgaggatgcg gttcgatcct tggccttgct cagtgggtta aggacccagc attgctgtgg       540
gctgtggtgt aggttgcaga catggctcag atcctacgtt gctgacactg tggtacaggc       600
tggccgctgc atctccaatt cgactcctag cctgggaact tccatatgct gcaggtgcag       660
ccctaaaaag acaaaaaaaa aaaaaaaaa atggacttgc tgtccaactg caaggagagt       720
gattagttgg catccactgg ctattagaca agaccatgct cttctcgcag cacccctcagg      780 ccaatgacca agcaaggcag tggggcaagg acttggctag ttctagcccc aatggactcc       840
tctaagagac agtctgcatc ccagagcacc ccagagaaga ggtagggact ttgtggcttt       900
gtcagctgtg tcggctccct ttttccaatcc tgtgccctcc cttttccttt cacagatgtt       960
attccccaat aaatttttctg tttcactcca tctcagcatt cacttccaga aggatctgac      1020
cgtggatacc cacttaggag aggaggacca ttttacagac ataaagacta accgtctggt      1080
ctgggtttca aacccagatc tgcacaactc cacgttctct gtccactgct ccgcactcaa      1140
cagtttacca agtggggtgt gggctcggtg ggccaggctc ctgctacaca cagttcctgg      1200
ccacgaggag tgcaagatct gcttgccatg actctcacgc tgcaaaagac acaggcaata      1260
ggattgacag cgatggggtg ggggggggact cctccgtgac tggacccgca gtggggtgt      1320 gctacatgct ggtgtcaggc cactgcacag gaggggctc aagtgatgaa ggggaagctc      1380
tgctccctga ggggtgaaag ggggggctgc tgtttgggcc acccaaaggc caaaaaaagg      1440
```

```
gccctgtcat tcttccagaa ttaagtttca aacccctttt tcctaaaaag gccctgcatt      1500 tttccccca  aatagaccca tcctcctctc caatttccc   ccgaggcaaa agggagtaa      1560 atggctgcct aaaaaaacat tccaggccct gggcccccc   aaaaaaaaaa gcctttcttg     1620
gtaaaaaagc caagggaag  gggccggatt accattagcc cccaaaataa aggataccct     1680 cccccaacttt aaaaaacact cccccggaa  aataaaaaag ggccttcaaa aaaatccccc    1740 cgcggggcc  acaaccaac  agggaatga  gggggggccc tcttcacctt gggaaaaaca     1800
aaaactccct tattt                                                      1815

<210> SEQ ID NO 159
<211> LENGTH: 496
<212> TYPE: DNA
<213> ORGANISM: Sus scrofa

<400> SEQUENCE: 159
atatcctgca ggtttaacga attcgccctt tataacctcc acatatagct ccatcctctt       60
tgacccaggg tgaagaggac ccagctctat ggattcactc cctttcttc  ggcttgggag     120 ggactggggc agctgttgag cgagtgcctg tggaagtgtg agcagtggaa gttgtaagag     180
cctgggaggt ggttgagggt agagatgctg ctgtgcttgt cttgctgtct gtcttctgca     240
aggtggtgat tgttcctagg caggcaggga gagaagacag gagtgagtct aacagtcagg     300
gggtagcaga gttaaacaga gtcatagact ttagaacctg gaagagacag ctagaaaact     360
gtcttctagt cacaccaaaa ccactgcctg aggagaagca gctgccacct ggggtaaaga     420
ggatggtgag gctatcaccc accaaacccc aactgatttc ataaccttct gaagggcgaa     480
ttcgcggccg ctaaat                                                     496

<210> SEQ ID NO 160
<211> LENGTH: 1336
<212> TYPE: DNA
<213> ORGANISM: Sus scrofa
<220> FEATURE:
<221> NAME/KEY: modified_base
<222> LOCATION: (1327)
<223> OTHER INFORMATION: a, c, t, g, unknown or other

<400> SEQUENCE: 160
ttagatcact gccttgctgg gcgccctctg gccacagcgg tagtgaagaa atccatgggg       60
ggttccagga ctcggagtga gcaatgcccc acctcagtgc aagcccaggt atcctcacct     120
tccccagatt caggctcctc ctctggaagg acttctttaa acaatccctt tttaggtgat     180
accacacacc tgtcaccatt aggagtcaac agccatcata attcactgat atcatcacag     240
ataaggagag accaggaaaa ttggcagaaa tatcctgctg taacttgcct ctctgaaaat     300
gtgccagact tgtcccaggc tcagatcact ctgcatgtgg catgccaaga actcagagca     360
gatcagtcac cactccttaa attagccctc ctgaggtagg gttataagag cctagactgt     420
gaatagacca tacactcagt gacagtgtca cagctgagca atagctcaca ccttctaagt     480
cttgactctt acttttgagt ttcagcccca tcccttaaaa agtatgcagt gttgagcaag     540
tcactcagcc tctccaaatc tcactttcct catctgtgaa acagggtgc  tgttaactga     600 gagaagctat gacgcactat acaaatatga ggtatcaaaa ctttagttat ttatagcatc     660
aaaatatgtc cggtggaaaa aaatacacct ggtgagagaa atatgaaaga aattcctatt     720
cccaccagtg tgggtcagtt aatcacaagt caattgacac tcgagaactg gcaataaaga     780
caatgtctcc tgcagaatct gcctatgggg tagaagtgcc ttggcaacgg gcattcctta     840
```

| | |
|---|---|
| ttatagaaac cattcagcag agcagaccca ctgacagagc tctcgaacac tcttcttagc | 900 |
| cgcaaccaga ggaaagtcag ccagcaccaa atagcctccc tctgaggaca caggcttcag | 960 |
| gacccaagtt tctttatcgg atgtaagggg atgacaggga caagtccagc caccagtatc | 1020 |
| catggctctg ataaaacaag tagacccagg cccttaggat ccaagcagct gccttccagg | 1080 |
| acaggcaatc cagccatttt ctaaagctat ctctgctgca gaggcgattg agaaactct | 1140 |
| ccttcctggt ccccatagca gaaaatcagc ccatcagtgg agtggtggaa gccaagcatc | 1200 |
| aggatgggaa atgaaggaat tgagaagagc ggttaagagg cagctgcaat agttaagagt | 1260 |
| aatgaggata acacagcaaa atgaacaggt gaccataggg gaagaaataa ttgggaggaa | 1320 |
| ttatagntga tgccaa | 1336 |

<210> SEQ ID NO 161
<211> LENGTH: 1125
<212> TYPE: DNA
<213> ORGANISM: Sus scrofa

<400> SEQUENCE: 161

| | |
|---|---|
| atttagcggc cgcgaattcg ccctttattt taaatgataa ccttgctggg tagagtattc | 60 |
| taggctgcaa attgttctct tttaaaactt tgaatatatc ttgccagtct cttctggcct | 120 |
| gtagcttttc tgcagagaaa tcagctgata gccttatggg ggtcaccta tagttaactc | 180 |
| tttatttta ttttgctgcc tttagaatct tcttctttag cttttgacat ttttattatg | 240 |
| tctttgtgta agtatgtttg ggttcaactt gtttgggct ctctatgatt cctgtacctg | 300 |
| gatatccatt tcatctttag acttggaaag ttttcagcca taatttcttc aactgtgttt | 360 |
| ccagtgcttt tttgttcttc ttctccttct ggaatcacta ttattcatag attggcatgc | 420 |
| cttatattag cccataggtc tcttatattg ctttcgcttt tttttttttt ttcatttggt | 480 |
| tttctgtctg ctgtcctgat tgggtgattt ccattattct atcttccaag tcatttattt | 540 |
| gttcctctgt attattcatt cctctgttca gtgcctttaa ctcagctttc atctctgcag | 600 |
| attaattttc taacttctct tggctcctcc taacagtttt tagttccttt ttaaagtaat | 660 |
| ctgcattact gttaatatca gttttttaatt ccttcagtat tttcattacc tccttttttg | 720 |
| aatttgctct ctgttagagt acagaggtct gtttcattat ttgctccttc agggggaattc | 780 |
| ttttaactga gagtagttcc tatgcttctt cattttgctt atatttttct tactctgtga | 840 |
| atttaaggaa aacaatgatc tctggttttg aaggctgttt atatgtggga gcatccctgg | 900 |
| gtagcttttg agggcttact tttttttttt tttgacatga ggggtgcttt tgttttggat | 960 |
| gttttctgtc tctttcttta gtctgtgtaa gctgttatcc tcttcatagg ggatgtgcca | 1020 |
| gtgtacagcc tgtgcatgcc cccggggagg caggggcaat gggtaacacc aataggcctt | 1080 |
| tggttgctgg tccattgaag ggcgaattcg ttaaactgca gtata | 1125 |

<210> SEQ ID NO 162
<211> LENGTH: 427
<212> TYPE: DNA
<213> ORGANISM: Sus scrofa

<400> SEQUENCE: 162

| | |
|---|---|
| tgcctgcagg tttaaacgaa ttcgcccttt ggtccgttgt cgttgagact gatgaggttc | 60 |
| ctggagtgat ggttcttgtg ccgggtgggg acgtgtcccc tgggcctccc acagtggtgt | 120 |
| tggttgtaac tggggatgtg accacccgtg atgttgttgg gggtgtgttg cttaggctgg | 180 |

| | |
|---|---|
| aagtggggga agtgccatct gtagaagcag gtgctgtcga cacggctgat gttgttgcag | 240 |
| gtgtgggggt gggtctggac gcggatgaag aggttgggtc ccccgaaggg gatgtctccc | 300 |
| gggaagcgcc ttctgtaaga gggtgtccac ttgtggaaga taaaggtgtc gaggagctca | 360 |
| cagctgcgat ggcgctgctg tgggtttctc tggtggtctc caaagggcga attcgcggcc | 420 |
| gctaaat | 427 |

<210> SEQ ID NO 163
<211> LENGTH: 2628
<212> TYPE: DNA
<213> ORGANISM: Sus scrofa

<400> SEQUENCE: 163

| | |
|---|---|
| cgcccttggt cttgccaccc taagtaggga acccaaggcc atttgtgtgt atctatttca | 60 |
| gaatcaacac atcccctat cctcactggg atgcagactt ggtgcctctc acaaaggaag | 120 |
| aaggaacttc caggaactct tgctcacgta cagcttggtc tgcacatccc aggatcaagg | 180 |
| atgaagactg ttgtcttctc agaaattctt ggtgaccaaa gcctggcatt tctgagatgt | 240 |
| tcctgggctg tgagtggctt caggcttctg cccctctgtg ataagggctg gggagctgga | 300 |
| gatgttccaa gctgcccctc ggggatgatg atggatgaga tggctggtgg agcaccagct | 360 |
| gtaggaactg tgatgggtga caatggcagg ggagtggtgg tggctgtgct ttgtattcct | 420 |
| gctgttatct tagaggaaac agaaactgtt gtatctgctg gggttttttc ctccattgtt | 480 |
| cctagaactc gaagatgagg aaagatgcta actcaaaatg cccttaggat aactgatctc | 540 |
| atgatagctc cagcacctgg aaagatggcc agcatccagg aattattgca tggacatctg | 600 |
| ttgcatgaat gagctcaggt gtgcccactc cctggttcct tcagctgagg ttagaaagaa | 660 |
| ggtgaaatgg cacctatttc tcctatgact atcatggggg tcccagggcc aggaggaggc | 720 |
| caacatgatg gccacagcct gggaggtgtg aacactcctg tggcagaagg tagccagact | 780 |
| cctgagggcc atcgaggcca ggagggtgtg cctacatcaa aaggggccag gagagacaag | 840 |
| ctgcaaaact tagacggtgg aggctggaga tgggaggaga ggaaggcttg ggggaaagag | 900 |
| acttagagct atgctgctga gcagatgatg gtcaaagctg agttgagatg cttcttgact | 960 |
| tggttctaga gcatctggag ttatcaccag ggttaccttg gtgcagccac accagatgct | 1020 |
| gggagaaatt gggtcaaatg acctgtggtg atagtcaagg tgaagaaatg gttggccaag | 1080 |
| aggcattgct tggggtgtga ctttggtggg tacagtagga agggagagag aagattctgc | 1140 |
| tttggagcca actgtgaagg gtggattcta aattattttc ctcagtgttg ttgacatcat | 1200 |
| tttttcatgg tcagctcaaa ggaagtggta ccatttactg atgaggaaaa ggaggggagg | 1260 |
| cctgagaaag cctgtaatga cgtcagtgac ttttctgata ccctggttcc ctcagaacac | 1320 |
| aggtcagctg cgcttttgact tgggggagaa aggatgaaa tgggaaaacg atatggttgt | 1380 |
| aactgttgtg atttggggggt tgtttggtt gttttagctg tgattccaga cagacacagt | 1440 |
| gcttttgata ccccctaaca aagtcctttc taagaccgac atggacaagt caacagagac | 1500 |
| aaggccacag ggtggttaag agtgtgggtt ccacaactta cagatataga aaacaaacat | 1560 |
| tttgtaacta aggggaagg ggggaaaaat taggcgtttg ggtttagcag atacaaacta | 1620 |
| ctatatgcaa aatagataag cacagagaac tgtattcagt atattgtaat aagccataat | 1680 |
| ggaaaagaag atgaaaaaga ataagtatat atatatatat atatataaat atatactgaa | 1740 |
| tcactctgct gtacaccaga aactaataca acattgtaaa tcaactatac ttcaattttt | 1800 |
| ttgtcttttt ttttttttt ttttttttt ttggcctttt agggccgcac tgatgcagca | 1860 |

-continued

```
tgtggaggtt cccaggctag gggtacaatc ggagctgcag ctgccagcct acgccacagc    1920
cacagcaatg ccagatctct gacccactga gcaaggccag ggatcaaacc cgcatcctca    1980
cggacgctat ttgggttcgt taaccttgga gccacgacag gaactccaac tatacttcaa    2040
ttaaaaagaa aaaagactc tgagttccag agtcaaactg actaatgttt gctgtgtgac    2100
ttgggcaagt tacttgacct ctctgaggct tggggttttt atctatgaaa gtgagatgat    2160
ggtagataat agtcatacca atggggtagt ggatgtaaaa tacttaactc agtatctaag    2220
ctcagtaaac agcactctgt gctgtctgtt atcttggtct ctacaaagtg ctaagatcct    2280
ggcaaaggca gccatccttc caactgtgtc cttattaagg tagaagctct cctggctggt    2340 gttttttccag ttaaatatac ccctcccaga tctccactgc tcccaccagg caagccaca    2400 gcacctttcg ccgggacaca gtccccagcc agctcctaac tggttttggt ttcactcttg    2460
ccccccttcc aatccatttc cttccacagt atccagagca gcaaagtgca aacctggtca    2520
catcactcct ttacctaaaa ccacttactg tctgcccatt ttagctcctt aaaatccaca    2580
atccattcca cagcttacaa gacaagggcg aattcgcggc cgctaaat                2628
```

<210> SEQ ID NO 164
<211> LENGTH: 2460
<212> TYPE: DNA
<213> ORGANISM: Sus scrofa

<400> SEQUENCE: 164

```
ttcggttgct ccacctggag ataatgagca tctcgtccca ggtgtggaga gcagagtcca      60
gcgtccagcc atgggcttgg tgtctgaggc tgtccctgga ggggcatgcc agccccaggg     120
ggcctgtggg tgttggggga gagcaccagc agcagggtcc gggtgccagg cactccccac     180
cctgcctcct tggcctcggc cagcctgggg gtggagggtg gggaggcgtt tctctccttg     240 gaatggcccct attttggat gggctttgtc ccttcctggg tgttgtcctc tcttcttcct     300
tcctttcttg cccttcccac ccagagggca gggtggtaaa tcaagggttg cagtgtctgt     360
ggtggccggt cagcagcctt gttgacaatg aggttgggct cccagccctc ccctgccaca     420
cctcttggct ccccaaggat tgctgtgctc ctggggttca acatttagtc tctgaaacag     480
gctgttaggg ggtcatgctg ccccagtggc cacatcacct cacagaggag gatccaggtg     540
ttggagactc cctgctgctt ctagcctccg tctctcctag cccctccgtc tggctgcagt     600
ttagaggaag cctttcttta cactcctgtt tggacaggtg atgtacgggt caggagcatg     660
tagcttggtg ccacaggtat ccgccacagc agcacgaggc tgctatcacc cctgccttag     720
cccagagtct gtacctgtcc tcaggtgtga gtgatcccag cggcagacat aggatccttg     780
tggcctcttg gcttttttggc attcaaagca tccaggaggg cgctctgttc tttcatgctc     840
acctggcctg gctcccaccc caaccccagg ctcagactta ggctgtgtca acagattttg     900
catatgagat cagagccagg ggctggtggt cccatattcc agccacactg ggggctgag      960 ttctcttctt gacccttgt ttaatacaag agtagagctc tcctcccaag gaggtggatg    1020
ggagggacct ggacggggcg gggagcaggg gcctcgatgg tgcctggagg tggtggaagg    1080
cactagagat acgtaagctg gtaatgtgac agcctgggtt gccccaggtg cttccaaacc    1140
catgaagggc tgcttgcagg agatagactg gttggaggc ttgccccaa gcctagtgct     1200 aaggccatag tgttcccttg gacccttaca gctcagaacc tctggaactg agctgaagag    1260
tgagactggg tggccaggag aggatcaggg cttaggcctt gcgggggggag ggaggtgagg    1320
```

```
cagtattgtg aaaagggtgc tggtttcaca gacagacaag tgggtttgaa tcctgggtct   1380
gctgcactct ttctggtaac taggcaactc atgtcacttg tttgaacatg tttccttatt   1440
tgtaaactgt aggaaaagct gtctgaccca ccaaggtggt tcagggtaag gctgtgtgca   1500
aatgccaagc cctgtactgg ggaacctggg ggtcctgggg ggcggttggg aggaggcagg   1560
catgggagcc tactctgatc cggaggcctt agccctcgtg ttcccttctg ccaagatggt   1620
cagatatgat ggcttagaga gcttgatatg aaaagggtcc caatccttgg ggccatccta   1680
caacaccctg gttcaccatg tctcttctgt tgagcagggc tgagaattac tggtggcgtg   1740
ggcagaacac gcggacgctg tgcgtggggc ccttccctcg caacgtggtg acctccgtgg   1800
ctggcctttc agcccaggac atcagccagc ccttgcagaa tagcttcatc cacacagggc   1860
atggcgacag cgaccccgc cactgctggg gctttcccga caagattgat gagtgagtac   1920
cagcagggct cctcctcagg cacgcaggct ctccaggcct ccaaggtcct tgtcctaact   1980
ctgggccaag ggtctctcat ccagcagctt ttccttgtag gcagaactgg ggttggagct   2040
tcaaagggtg ggcccactct ttcttttggt ggaaaggccc cctagcacac tggtcttagg   2100
aaaatggact aggaaacagg cttccaaggt ccttgtccta actctgggcc aagggtctct   2160
catccagcag cttttccttg taggcagaac tggggttgga gcttcaaagg atgggcccac   2220
tctttctttt ggtggaaagg cccccctagca cactggtctt aggaaaatgg actaggaaac   2280
aggctttgga agtagttagg taggaaagtt tctcatgact cccagcattt aggcagcttc   2340
ccttttccgg ctggtagtac cagagtccca gagctgctgg ctcaggccca ggggcacaag   2400
gcccagaaaa agctccctgt ggggaaactc agaggggaag ggcgaattcg ttaaactgca   2460

<210> SEQ ID NO 165
<211> LENGTH: 1273
<212> TYPE: DNA
<213> ORGANISM: Sus scrofa

<400> SEQUENCE: 165
ttcgctttcc ttcgcagcac tgaagcttgt attttctctt gatattttc ctcagagcta     60 ctaagagttc tctcacatgc taggaccctt atccccagtc ttttctcaga gcatcacgag    120
ctggggcttc catttccctt taacaacaac gccttatcca aaggcgctga aaaattaccc    180
tgctgtcatg gcaggcacga atgggagaac aacacagaca gacttctaag acatggtatg    240
aaggcttcag ggttagtcgc tggtaccaga aattccagaa aaattggact ggagcgttaa    300
cccagctgga ccacatgaag agttggcaag agatttcaag cttctccagg ggagcaaaga    360
tacgtgaacc cgttttagag actggggttgt ctcccaaaca gtaatcagat tcctgtcctg    420
catcccgtga tcccacaggt gtaaaccaca ttccgcact tttttctcct tcctccaggg    480
ctgtgacggc ctctctgggc agtgccaggg agaactggtt gggggggggt gccatgaggg    540
tgtcctgtga gcttggtttg cggctactgg tgtaggacct ggcagggcat ctcccagctg    600
ctctcagcct cctctccaca tcttgaacct tcactactgc caagtcttgg gcctctagga    660
ctccaacact ggctgcttca tcatctgcct ccccaccttc taggccagga gatgttcaac    720
acctctggag tcataatgat ccgcaatggc tccacggtgt cagccagctt tgatggggcg    780
gtgaccatct catgtatcgc tctcgagtta acccagctgg accacatgaa gagttggcaa    840
gagatttcaa gcttctccag gggagcaaag atacgtgaac ccgttttaga gactggggttg   900 tctcccaaac agtaatcaga ttcctgtcct gcatcccgtg atcccacagg tgtaaaccac    960
atgaacaaat atgtgcttgg gggtgagggt acaagtggtg ggggaggtga tgacagttct   1020
```

```
gaattcataa tgcatcatct cgggtggcag ctgtgcatct gttccatatt ttgaaacccc      1080
ctcccataca gtagaactat ttcagcagaa taatatctag atgactgaaa gaaagtcata      1140
tgttacccat gtcccgagtg gctcagaaga atgataaggg tagtgtcggg ttgaaactgt      1200
attttactct gactttcaat cactgctgca ctgagctgct gaactgatat aagagactcc      1260
tatgacctcg aaa                                                         1273
```

<210> SEQ ID NO 166
<211> LENGTH: 2207
<212> TYPE: DNA
<213> ORGANISM: Sus scrofa
<220> FEATURE:
<221> NAME/KEY: modified_base
<222> LOCATION: (1335)
<223> OTHER INFORMATION: a, c, t, g, unknown or other

<400> SEQUENCE: 166

```
atttagcggc cgcgaattcg cccttcagtt gtcgctgaga ctgatgaggt gcctggagtg        60
atggttcttg tgccgggtgg ggacgtgtcc cctgggcctc ccacagtggt gtcggttgta       120
actggggatg tgaccacccg tgatgttgtt ggggtgtgt  tgcttaggct ggaagtgggg       180
gaagtgccat ctgtagaagc aggtgctgtc gacacggctg atgttgttgc aggtgtgggg       240
gtgggtctgg acgcggatga agaggttggg tcccccgaag ggatgtctc  ccggaagcg        300 ccttctgtaa gagggtgtcc acttgtggaa gataaaggtg tcgaggagct cacagctgcg       360
atggcgctgc tgtgggtttc tctggtggtc tccatgctct gagtctggtg gaccagagaa       420
gatgctgctg tccccctcagc agaggtggtg gaagagggtg aggttgactg gggccctggt      480
ccagttgtcg ctgagactga tgaactcacc atagttgatt tgtaagtacc agaatttgaa       540
gtttccctct tttttctttc agttttgttt gttgatgtta cttcttttga gaggttttct       600
tttgtgggag ttatgtagct gatattcgat gggtatttct cctcagtaat agtagttgtc       660
atagtgtttc cacctgtaga ggattaaaga tatgatgatg catatgtttc aatagtgccg       720
ttaaatataa gatacaagga ctcgttgaca agacaggttc cttctgtgaa gttgtagcat       780
taagaacaca atttttggagt tcccactgtg gcacagtggt taatgaacct gactaggaac       840
catgaggttg tgggttcgat ccctggcctc gctcagtggg ttaaggatcc ggcgttgccg       900
tgagctgtgg tgtaggtcgt agatgtggct cagatcccat gttgctgtgg ctctggtgta       960
ggccggcagc tgcagctcca atttgacttc taacctggga aactccatat gccgagggag      1020
cggccctaga aaggaaaaa  aacaaaaaca aaaacaaata aacaaaacaa aacaaaaaaa      1080
acagtatttt ggagttccca tcgtggcgca gtgcttaacg aatccgacta ggaagcatga      1140
ggttgcgggt tcgatgcctg gccttgctca gtgggttaag gatctggcgt tgccgtgagc      1200
tgtggtgtag gttgcagact cggcttggat cccgcgttgc tgtggctctg gtgtaggctg      1260
gcagctacag ctccggttag accctagcc  cgggaaccctc catatgccat gggagtggcc      1320
caagaaatgg caaangaca  aaacaaaca  aacaaacaaa aaaaaacaa  aacaaaacaa      1380 acaaaaaaaa gaacacaatt ttttcccgcg tgtaccactg tatatcatgg tgggtcagaa      1440
taagtggctg caggattacc cctgtctaat atttctacgg ccactgtgta acctcatcat      1500
aaataatact tcagtgaata tctttgtgct aatatgtttt cagtgtcatt cattgtgtgg      1560
tataatggaa atggacccag aacactccta ctctctccat ataagccata tatgaaggc       1620 aagatacaag agcttcagtc tcaaaacagt tttttaatta aaatacacag actgtccttt      1680
```

-continued

| | |
|---|---|
| caagcaatac atacacaaat ttttattaag caggaattgc tgggaaatgt ggacagctgc | 1740 |
| atgcaaatca tgaaaataaa ctcaaaatgg cttaaagagt taagtataag acaagacaca | 1800 |
| atcaaactcc tggaagataa cataggcaaa acattctctg acatcaacct tacaaatgtt | 1860 |
| ttctcaggtc agcctccgaa agcaacagaa ataaaagcaa agtaaaccca atgacaccta | 1920 |
| atcgaactga caagcttttg cacagcacag gaaaccaaaa ataaacaaaa aggcaactta | 1980 |
| cagaatggga gaaatagtt tgaaatgatg cagctgataa gggcttaatc tctagaatat | 2040 |
| ataagcaact tttacaactc aacagccaac aacccaagtg aaaaatgggc aaaggacctg | 2100 |
| aatagacatt tcctcaagaa agagatacag atggacaacc agctcatgaa tatatggtca | 2160 |
| acatcctgat tatcagagga accccaatca gaagtaccat gagtagc | 2207 |

<210> SEQ ID NO 167
<211> LENGTH: 2361
<212> TYPE: DNA
<213> ORGANISM: Sus scrofa
<220> FEATURE:
<221> NAME/KEY: modified_base
<222> LOCATION: (2337)
<223> OTHER INFORMATION: a, c, t, g, unknown or other

<400> SEQUENCE: 167

| | |
|---|---|
| atctgcaggt ttaacgaatt cgccttcct ttcgttgcgc acacacacca cctccaggat | 60 |
| ccaggccctc gtgccaggcc gttctgctca ttaattaatc catagagtca ttcagtatct | 120 |
| ttaaaggagc acccactgtg tgcccagctc tgtgccggtt gccggaaaga gacacccctc | 180 |
| gcttcctgcc cccagagaat aagacctgac ggaataagat cttgcgggca cagctcggtc | 240 |
| cgccctcca ctaacacctc agccgcttgc ttcatgggtc aatccctcca gcacacggac | 300 |
| tccaggtagc cacagctgct ctctgagccc ttccggcctc tcgggtctcc tcgcccggcc | 360 |
| tgactcagcc tgtggagatg atgggccgtg agcacctggt gcaggaagct cggctggggg | 420 |
| agcaggagga atgctacgac gactgggctg cggccatgag gaatatgaca gagctgaatg | 480 |
| agccgctgtt tggtgaagac agagactgtc tctccgaggc ctgcaagaat ggagttgggg | 540 |
| cacgccattc ttcctgaagg gtcacgagta gcattgagca gaagacatct gcagatggtc | 600 |
| atgagaagac agggaaggtc catgcttacc aggaagaaat agagaaggag ttggaggtgt | 660 |
| taggtcagga tgtgcggaac ctgctggcta attacctgat caagaactgc agtgagacct | 720 |
| agtatgagag caacatgtct tacctgaaga tgaaagggga ctattacggc tgcctggcag | 780 |
| aagtggcccc tggagagaag agggcgagtg tcgtggtgtc atctgagaag gcctgttgcg | 840 |
| aagcccatga gaacagcaag gagcacacgc agcccactca tcccattagg ttagacctgg | 900 |
| ctcttgacta cttcgttttc tactgtgaga gccagaacac cctggagcaa gcctgccact | 960 |
| tgcccaagat ggcttttgcc atcttcgagc tcaacactca ccaaggactt ctatctacca | 1020 |
| ggactccacg ctcgttgtga agctcctcct tgataacttc atgctctgga caagcgatca | 1080 |
| gcaagacgac gacggtggac aaggcaacga ttaaggtagc caggcagcgc acgctgatgc | 1140 |
| tactaccgca ggctttatt ttttttcctcc aggagttggg ggtcctgtgg gagagggaaa | 1200 |
| gggagggatg accttcctac ggaaaaacgc atgacctgtc ctatctttga ccgtctctga | 1260 |
| catttcacc aaaataccac tagtggaaag tcaaggctag ctgtgctgat actggaacag | 1320 |
| cagcctcaga ctggcacatg gactgatatg tagattaatg cacatggagc tgtctttaac | 1380 |
| ttattgctag aaaatagggt ttgaagatga aagaaaact tgttttgtt ttttaagatg | 1440 |
| aaaagaaaac ttaaatggag tggccctcac tcagtaagtt ctatggttct agtaaggatt | 1500 |

-continued

| | |
|---|---|
| tttatgtaca tatgttcttg ttttttgagt tttgggtatt tccttcctat ttcatctgtt | 1560 |
| ttagctgtgc atttttttt ccagggtgta ctctaccaga tatgaaacag tttaaatccc | 1620 |
| aatctgatag acttagaaca tatgatatat ctatccttat ggtttaggcc ttgccagttt | 1680 |
| tcagaagttt ctgattagtt gacaatatta atactaaatt gcagtttaca gtatttccac | 1740 |
| attacagcca tatgtaacat cagaccattg attgtgtatt tctttatct ggcttttac | 1800 |
| atccttattc ggctgtatcc aggttggttt tgcagttatc tatctcctag gccaaagggc | 1860 |
| ttgcctgaag agaagcaaag ctgctttagg ttttgtttaa taagtgcttg gcagtagctg | 1920 |
| ttgggttttt gccctttctt cttgagttaa atccaccgta aaaattattg atcactttga | 1980 |
| tagaaatgtt aaagtccaca gaaatagaga aaagtctgta tgtcatctat tgtattgata | 2040 |
| ttatcagaga aatcctgatt tttaagctgc cacagctcct tctttgggga ttacactgcc | 2100 |
| attttccttct tcacttgagt cgtccccact ctacatttg ccaccggcac tcattcggat | 2160 |
| gggttgaaaa gccgttgggt tgtagaagct agtggtcgtt ttgagaaagc gcatgatgca | 2220 |
| gtgtatgaga attcaggtgc taggagcttt ctggtggaaa aattctaaag ctgagttccc | 2280 |
| actgtggctc agcaggttaa gaacatagtg tccttgagga tgtggatttt gatcccntgg | 2340 |
| gcaagctgcg gcgaagggcg a | 2361 |

<210> SEQ ID NO 168
<211> LENGTH: 1939
<212> TYPE: DNA
<213> ORGANISM: Sus scrofa
<220> FEATURE:
<221> NAME/KEY: modified_base
<222> LOCATION: (1891)..(1892)
<223> OTHER INFORMATION: a, c, t, g, unknown or other

<400> SEQUENCE: 168

| | |
|---|---|
| ggcctcggcg ggcaggggag ggctgtgagg gaggggcagg gcacagccaa gcttattcct | 60 |
| ccttcctctg tgccctcagg tgacagagct ggcacctctg ggatcgttgt tggaccggct | 120 |
| gcgcaagcac cagggccact tcctcctagg tactctgagt cgctatgctg tgcaggtggc | 180 |
| tgagggcatg ggctacctgg agtccaagcg ctttattcac cgtgacctgg ccgcccgcaa | 240 |
| cctgctgttg gccacccgtg acctggtcaa gatcggggac ttcgggctga tgcgagcact | 300 |
| accccagaat gacgaccact acgtcatgca ggagcatcgc aaggtgccct tgcctggtg | 360 |
| aggggcagcc gctgctagct tccggggcct ggacccacc ctgccccacc tagtccctgt | 420 |
| acacccaagg cctcagagcc tctggggcct tcttgtccct tctgggcttg ggggtactgt | 480 |
| tcttgagggc ccagccattc acttatccac ccaggacttc ttgagggcct gtgtgccagg | 540 |
| tgctgggaac atgggctaa gtgctatggg gacacatgaa agcttcccgg aggacccagt | 600 |
| attaagctcc tgaagtatca gaagtgagcc aggcagaggc tgcgtagtaa gcatgttcca | 660 |
| ggcagagctg ggggcaggca gggccttgca gactgatgag agtgttcatt tgcacgtggc | 720 |
| gaagtacagg gcgctgtgcc agcccctgtg tgagctgatc acgtgccgag accatcgtgg | 780 |
| tctctgctgt cagaggcacc caaagcagcg tggtctcctt gctttggggt gggaggagtt | 840 |
| ggtccagctc tgcttgtcag aaaccttct aatctaggat gtacggtcac cctaattgac | 900 |
| tgactttaga cctagggtga ccatacatcc tggattatgc ctcatgtcct ggagtcatta | 960 |
| atagcacccc ctttcatact caagcatgct ggtctgaacg gtcaattata aggtcacttt | 1020 |
| ttttgtttgt ttttgttttt cagggccaca cccgcagcat atggaggttc ccaggctagg | 1080 |

| | |
|---|---|
| ggtctaatag gagctacagc tgctggcctc accagatcca agccacgtct caacctacac | 1140 |
| cacagctcat ggcaacgccg gatccttaac ccacttgagc aaggccaggg atcaaacccg | 1200 |
| caacctcatg gttcctagtc ggattcattt ccactgcgcc acaacaggaa ctccaaggtc | 1260 |
| accttttcaa atgcagcccc tgtaagcccc atgaaatgag cagattactg ttattcccat | 1320 |
| tgggcagatg aggaacaggg cttagagagt tcatttctct tggttccacc ccctctgaat | 1380 |
| ggcaaggcca actctccagt cccacgagag atccttgctt ctccatctag gacggcttcc | 1440 |
| tcctcgctcc ttgtgcctca gcctcctctg gagtgcatac cctttgccag cttcactgca | 1500 |
| gtggcatttg tcttcctcac ccaagaggga gcctcatggg gagtgtgggg ggaagccact | 1560 |
| ttgattgttc tcaccegttt tggttctttc ccaggcctta tccaaatttc ccacccacac | 1620 |
| catcctgctg aaatgaccca gtcctagga tcctgcccca aatctggaaa tggtcatcct | 1680 |
| cccacgatta gaaaacagcc taagatctca tccctgcccc cacccaccct tacctctcca | 1740 |
| ggagcctctg cccttcttct tctccctcct cccagcccag gctgagtggg ggtgaagctg | 1800 |
| tctttgagtc tgttgcaccc agagcgagaa gtcctgccct gttcacttca cacccatgtc | 1860 |
| ccagaactta actgtgaatt tgggcatgtg nngcaacaca cgcttggtac agggggcagg | 1920 |
| gggctccgag aggcagctt | 1939 |

<210> SEQ ID NO 169
<211> LENGTH: 528
<212> TYPE: DNA
<213> ORGANISM: Sus scrofa

<400> SEQUENCE: 169

| | |
|---|---|
| tacctactgc ccagccgagc attcttccag agagcttgaa gtcagtgcag ttgtgtctga | 60 |
| gagtgaatgt gacgttctca gagctgctgg tgtaattaac aaggctggcc tgtcccatat | 120 |
| aggttttcac cacatcagga cccttgatgg agggcgggta ctgatctgag acacaaagaa | 180 |
| ggggtcaggg tctggggcag gatatttcct gccttctggg cctcctttct ctctctctag | 240 |
| tcttctcgct tgtgtgaggc attcccaggg ctgggaccca cctccagaag caggaaatat | 300 |
| cctgccccag accctgaccc cttctttgtg tctcagatca gtacccgccc tccatcaagg | 360 |
| gtcctgatgt ggtgaaaacc tatatgggac aggccagcct tgttaattac accagcagct | 420 |
| ctgagaacgt cacattcact ctcagacaca actgcactga cttcaagctc tctggtaaga | 480 |
| atgctcggct ggggcagtta gtggttgagg tctgagtcaa gctttggg | 528 |

<210> SEQ ID NO 170
<211> LENGTH: 2023
<212> TYPE: DNA
<213> ORGANISM: Sus scrofa
<220> FEATURE:
<221> NAME/KEY: modified_base
<222> LOCATION: (660)..(661)
<223> OTHER INFORMATION: a, c, t, g, unknown or other

<400> SEQUENCE: 170

| | |
|---|---|
| cacccccaac cccccccca ccccgccgc cccgaaagcc ctggagcgct gggacgtgag | 60 |
| agggagaggg gggcaagagg attatgatta atcagtctgt tccccacgcg gctgcaaggc | 120 |
| aggcctgcaa gatgacgttt tccctgagat gaagtccagc ttctgtggtc tagagattgc | 180 |
| tttagttgtg aggtaccagg tccagaataa actgcccagg acctggtccc aggtctggga | 240 |
| gaggagcctg agggaggagc caccggcttg ttttcctctg gggaatgagg gtgtgagaag | 300 |
| ggctgatgct gagccccggg aggcagagtg agagctccgg gggaaagagc aaggcctttg | 360 |

```
gagtcaccaa gggcaagctg cttcccagat gaacctcagt ctccccattt gcacaatggg      420
aataataata atgcctatgg gcttagcaca tagaaagttc ttagcaaatg ttggggtccc      480
ataacaacaa aggttagtta gggcaagtgg acagaaaaag agccaaaaag ttatttcaag      540
tgagaatctg ggggtgtcct cagtagagag gccacctcat ggaagtgagg gggtatgatt      600
cttgctgggt ggagagttct ggaaagaaga tggggggagg aggtgggcag gcccagcacn      660
naggacttgt gaggttactg agatcgtcag ctgggctaga tcagcgagct ggtgttgaac      720
ataagcagat aagctcattt tatgcactga ttattcataa gtcagtaaag tcttcaagga      780
tgttggttta aagcctggtc tttctccctg gtcccttctg gactggcctg cacatcatca      840
ctcgcagtct atttactgag ctgaaaagac agaccttcct aatgtccaaa gctgtgaagg      900
gcctgctaca ggttcatgaa ttcaggcaga agacaaggag accagtgggt cagagacaaa      960
ggactttctt aatcaaggtg cacgaggagc ctaaacttca cttttcacatt ggctttcctt     1020 gcccccaaag tccacaggg caaagcagag gcagggccaa gtggattctg ggacacaatg      1080
gatatgcatc atagctgaga aaccctgacc caaggaaacc ccaatctttt aaggggttgc      1140
aagaaaacct gcccaaacct ttccccagag gtagacttta ttacattgga caggaaataa      1200
attagccttc tattcctgtc agagacacga cctctgtctt cctaggctgt tcacatttta      1260
taaatctcct tgaagaaata atgtagaaca aaaggctctc actgcctctg ctcccaagat      1320
ttgcagaaat gcgagagacg gatagagaac tgactcccaa catcagagcc tgggggggtca     1380 ggtgggggtgg ggtgggggtgg ggggaggggca cccaagttca tcaggcccag cttgttggct   1440
ctttcccctg ccttggcttt actggcgtga ctcattcaag tgtcacacat atactccctt     1500 ccccccaggtc tctgtgccca gcacagagtc tgacccctaa tgattctcaa taaatgtttg    1560
tcaaatggat gaataaatga ctgggtcttt atagaaattc tgctttacag tgtgaaaata     1620
gcttaaacat taaagaaatc acaataggaa tgaaactaac atttatcaag tgcttactgc     1680
aggctggcat agttagttcc actataactg gagctggctt catgggtatg tccccgtgca     1740
gccaaacagg atctcaggct taggagggcg ctgagcttgt tttaatgctg tgctgccatt     1800
attctgaact tcttgttctt tttattttttt tttaattttt ttttacaagg ggccccacaa     1860
attatgtagc tagtcctggc tgaactccta cataggcatt cctaaaattc acagtgctct     1920
gtaaaatcct ggaataaaca tcacagggct tgtggataaa atggggttgg ggccccacat      1980
tcaaaaactg tgaagggcga attcgtttga acctgcaaaa aat                       2023
```

<210> SEQ ID NO 171
<211> LENGTH: 382
<212> TYPE: DNA
<213> ORGANISM: Sus scrofa

<400> SEQUENCE: 171

```
aaatggggggg agtagcattg tcaaaatgat actagttgat tatttcttct cttggtctac       60
agatttactg tccagctgaa tagtgacttt gacaagagtc agaaatttgg atgctcgttc      120
aagagaaaat aatagcagag taaatgata tttctatca agtaaatcac aggcctccca       180
acaagccaca ctctcagaaa acaatggag gaaagggatc tcatagaacc atttttattc       240
ctgctgaaga gggattcata cccacagatt ggcttaatat ttaaagaacg cttagctggg      300
ttcttagcaa gtggaagtca gaattatctc aaatgtcctc tgttttaaat tctagctttg      360
gaggaggtga gaaggacacg aa                                               382
```

<210> SEQ ID NO 172
<211> LENGTH: 1961
<212> TYPE: DNA
<213> ORGANISM: Sus scrofa
<220> FEATURE:
<221> NAME/KEY: modified_base
<222> LOCATION: (1900)
<223> OTHER INFORMATION: a, c, t, g, unknown or other

<400> SEQUENCE: 172

| | | | | | |
|---|---|---|---|---|---|
| ggttaacgaa | ttcgcccttt | ggctctctcc | aggcacaaga | tcctaaaacc | agccatacca | 60 |
| atcccatacc | atgtccatag | ttaggccaca | agtcacattc | tgtctgacaa | cccctctgcc | 120 |
| tgccaggggc | tccctggaaa | aggcccagcc | ctgggcctgg | tactggccca | cttttctgtg | 180 |
| tggccaacac | atccttcttg | ccccggatca | agcctggcgt | cctcgccagc | agggcttggt | 240 |
| gacatactcc | agccacaggc | cccaccaggg | actgaagcca | gaggcaggtc | agctgcaggg | 300 |
| tctgctgagg | ctgcccccag | gcctgccttc | tagaggctcc | ttcttgtacc | tcagcagggg | 360 |
| ggcactgagg | gctctgaggt | tgtagggaca | gcgccaggtg | aggaagggac | aggcaaggca | 420 |
| gggttcccag | cctcctgctg | ccttagcctc | actctgccac | tgggagcagc | aggtacagca | 480 |
| ggtccttcag | acctaggcag | ggcatctccc | tgcccttgtg | agatggacag | gctcaagtga | 540 |
| tttcttcagg | gcagagaccc | tctggctttc | cagatatctc | agcgcctaaa | ggagggaaac | 600 |
| aaccagaaag | ccctccatca | acaggggat | agtgcaacaa | tcttgggtgt | gagagggcct | 660 |
| ctcagtgcca | gccaaattct | atcgaaaact | ggcggttcta | ggcaatgatt | ttagaattta | 720 |
| tcatcctaga | atgccttctt | tactttgata | aactgaaaat | aagagaataa | cattataaat | 780 |
| tattatgcac | aatgttagca | gtaactaatc | tgtagttact | gatgcagatt | cataagaata | 840 |
| accatgagat | aatggctaac | ttcagtgacg | gtctcccttg | ggccaaacat | ttgcagtgtg | 900 |
| gtgtcagatg | ccaccctcat | tcactcctct | aaccacttct | gtgaggtagg | cactatcatt | 960 |
| tacacacatt | ttacagatga | ggaccctgag | agatcaggaa | agtagcatta | gctgatgcca | 1020 |
| cgtgggagca | gaaggctggt | cctaactcag | gctgtctgcc | gccagaggac | tctgaaagcc | 1080 |
| cacaccctgc | tggtgcctcc | cgggggatt | tcaccacttt | ctgacttgat | aaaacattca | 1140 |
| tttttatgta | tttatattct | atattccata | tgttatttac | attatatatt | ttgttatata | 1200 |
| taaatatata | aattttata | gcaaagtaat | aggatttttt | aaattagaca | tttcaaaagg | 1260 |
| cattagaacc | ctgttatttt | aaactgaaat | aggaaatgaa | gacgaagcc | atttctgttt | 1320 |
| aaatcagtga | gtcctaccta | tactgctgct | cactggagcc | gctctcagga | agcaagcccc | 1380 |
| tgcacccaag | agaggctcca | gttccttta | ccattactgt | ttctgcaaag | aactgcccat | 1440 |
| cctgggatca | ggcccctccc | tcctcctggc | tggggacccc | tgagtctctg | gccttgacac | 1500 |
| cctcagggac | aggaggtggc | aggtgcaggc | tcacttgtgg | agggtggggc | tgctcacttg | 1560 |
| tggtgggcg | agccgcagga | gcccagcagg | tgacagcccg | cctgctccag | gttccagtcg | 1620 |
| aacatctcca | gcactttgtg | gcactcgcct | cgggccgca | gacccaaccc | aaatagctgc | 1680 |
| tccacctgaa | gagcagaagg | tggtgccatg | ggacacgctg | ggctgcggg | gcgccagaca | 1740 |
| agggcagggc | cgaggagagc | cagggagcgg | ggtcggagg | gggtgagtgg | gaggagagct | 1800 |
| gcagacccga | tcttcagggt | ccctgaaagc | cagagcaggc | aggaggtatg | gtaccttcag | 1860 |
| atactgggca | gccctctgca | cgctccagct | gtggctctgn | caggccgcct | ggcactcctc | 1920 |
| tgtgggtcac | ccatgcacca | tggcctgtag | ctgggcacac | c | | 1961 |

<210> SEQ ID NO 173
<211> LENGTH: 2052
<212> TYPE: DNA
<213> ORGANISM: Sus scrofa
<220> FEATURE:
<221> NAME/KEY: modified_base
<222> LOCATION: (2045)
<223> OTHER INFORMATION: a, c, t, g, unknown or other

<400> SEQUENCE: 173

| | | | | | |
|---|---|---|---|---|---|
| attacctgca | ggtttaaacg | aattcgccct | taatcggcat | ttctgcattc | caggcagagc | 60 |
| cagccttgcc | caaagaggtg | tagacggctg | acttggggtg | ctgtctcaga | ggacaaggaa | 120 |
| ggctccacca | ccaccctgtt | ggccacttgc | tttctgaagc | tgcaattcca | attatggctg | 180 |
| aagccctaag | cctggacttc | agagagaagt | agtgtggtcc | cccgccgccc | ggctcagtcc | 240 |
| ccccatctct | aaatggacaa | gttgatccca | ttgtttcctg | ggtgcaggag | tatcataaag | 300 |
| ttaagaggaa | ttttaagcat | agagcagtga | gccaggatac | aaggaagata | ctactgaaga | 360 |
| gaattaacct | agacaccagg | gccagcttgg | tcttcttttc | ttcccctccc | cccaacttt | 420 |
| tagggacaca | cttagcatat | ggaagttccc | aggctagggg | tgtaattcag | agctgcagct | 480 |
| gctggccata | gccacggcca | cgcaggatct | gagctgcatc | tgtgacctac | agcacagctc | 540 |
| atggcaatgc | tggatcccca | cccaccgagc | gagtccaggg | attgaaccca | cattctcatg | 600 |
| tatactagtg | ggattcgttt | ctgctgcgcc | acaagaggaa | ctccagcttg | gccttcttaa | 660 |
| tcatttttct | gagtctcttc | ttgctcatga | gttcttcta | ttaacattct | gtgtgttttg | 720 |
| tttggtaata | ttctctaggc | tacagttttc | tacctgtaga | ggagaaaaaa | ggcattccag | 780 |
| gttagaccaa | agtaagagtt | ggacatcttg | tcgacctaac | acagctaact | tcccactttc | 840 |
| caatgcaagg | aaagccagag | gtgcagagca | ttctccagag | gccactgtgg | taacccaggc | 900 |
| tccagctgga | tattaggata | cctgaacctg | aatcccagct | ctgccaccca | aggcaagtca | 960 |
| cagcctgacc | agacattgag | ggtgaccaga | tattgatggg | acactctggc | taaactggct | 1020 |
| tgtcagggct | cttgctgaaa | ctggatttta | tgatgaatgc | cacagatgag | tctaggagaa | 1080 |
| ggttcagaga | ccaactaaag | tttggtcaac | aaagactttt | tgtcagataa | cacctaccca | 1140 |
| aacagctggg | aaagtaaaat | gagctcaaac | aggtaaaaat | gctttataac | cataaagata | 1200 |
| cctgcagagg | gcacttggcc | ccttatttca | tcctgatatc | atccctgaag | aaagtgagag | 1260 |
| aagcaggcgg | tggggaagga | aaagaatttc | taggagttcc | cactgtggcc | cagtgggtta | 1320 |
| aggaccccat | gttgtctcag | tgaggatgtg | ggttcaatcc | ttggcctggc | tcaaagggtt | 1380 |
| aaggatctgg | tcttgtcaca | gcatagattg | cagctgctgc | tcgggtctgg | cgttgctgtg | 1440 |
| ctgtggctgt | ggcataggtc | acagctgcag | ctctgattca | accctggcc | cgggaacttc | 1500 |
| cgtataccac | aggtgtggcc | taaaaagaaa | ataaataaat | aattttaaa | aaggatttc | 1560 |
| caggcccgtc | tgcatactga | cgccttcct | gcatcccttt | tggatttag | gatgtggcaa | 1620 |
| gagcgaatct | aattcacctt | ctccttgccc | tcctccagtt | tcattcttat | ttcccacttg | 1680 |
| agcccagcta | cttctcagct | tgcctatttt | ctaaagttgg | gatgcctctc | ttcatctgtt | 1740 |
| tgtgcttcct | tctccctcc | caaggcatct | gatggggcca | gtgcagggtg | agcgagaggg | 1800 |
| gagcagatgg | gtggataccc | tgagtcctgt | ctggtggata | cctcctaggc | ctgcagactg | 1860 |
| ctgggcttac | ccaggggcag | gaaactgaaa | ccaagtttaa | gtgaacattc | tgtgggaggt | 1920 |
| cagagagctc | aggctggact | tcaggtacaa | gtatgttgaa | gcgaagataa | agtatgatc | 1980 |
| ttttcacatg | gaaggaagac | acagacgcgg | ttggacaggc | taagccctgg | gtctaggtag | 2040 |

```
cttanaagaa aa                                                          2052
```

<210> SEQ ID NO 174
<211> LENGTH: 1674
<212> TYPE: DNA
<213> ORGANISM: Sus scrofa

<400> SEQUENCE: 174

```
gtttaacgaa attcgccctt tgatatgagt attgcactcc tgctttccta tcatttccat       60
ttgcatgaaa tatcttttcc atcccctcac ttcagtttat atgtgtcctt tgccctctta      120
taggcagcat atcataggct ctttttttt taatccagtt ctgcaaatct atgtcttttg       180
attggagcat tcggtccatt gacatttaag gtaattattg ttaaatatgt atttactgcc      240
cttttaaacc ctgtttccca gttgattcta tgtttcttct ttgtttcttt cttttctttt      300
tttggtggga tgatttcctt ttattttatg cttgtgtcct cttcttttta gtttttatga      360
atgcattgtt tggttttgat ttgtaattgc cctcttttt tcaagtatat taacctttc       420
ctatttctgc ttgctttagg ttgatagtca tataggctca aacacgttct aaaaaagagg      480
ctagattttct tactctcctt ccccacattt tgatgtcctt ttttttgtctt catgtttatc    540
cttttgctgt tccttgtgtt tattattgct ttcacaaata ggtgggcttt cccccttttt      600
aatctgtata ctggctaatt taagtgattg cttttcagtt tgtgatttcc tccatctcat      660
attttcttgc ttgtttccta tttagagacc tttcagtatt tcttttagag tgaatttagt      720
atcgatgtat tctcttagtt ttctgttttgt ttgagaaatt cttatttttt ctttctattt    780
taaatgataa tcttgttgag tagagtagtc taggctgcaa attttttccct tttagaactt     840
tgaatacatc ttgccaccat cttctggcct gtagcatttc tgcagataaa tcaactgata     900
gcctttggg ggttcccta taattaagtc tttgttttc tcttgctgcc tttagaatcc        960
tcctcttatc ttgaactttt gccgttttta ttacaatatg tcttggttc agcttgtttg     1020
gggccctctc ttcttcctgt atcttgatat gtttccttct ttagatttgg aaaggtttca    1080
gacacaattt cttcaaatat attttcaatc ccccttcttt tccatcttct cctggaattc    1140
ctattatgtg tagtttggct cccttttata tatcccatag gtctcttata ttgctttcat    1200
tttttttat tttgttttct gtctgctgtc ctgattgggt gattttcatt attctatctt    1260
ctaagtctct tatttgtgat tccacgttat tcattctgct cttcaatgtc tttaagtcag    1320
acttcatctc tgcaaatgaa attcctaatt tttcttggct cctccctata gtttctagtc    1380
ctccccctt ttttttgcat tttagggctg cacccgcagc atataggagt tcccaggcta     1440
ggggtcatat tgaagctaca gctgctgggc tacaccacag ccacagcaat gcaggatccg     1500
aaccacatct gtgacctaca ccacagctca cagcaatgct gggtccataa cccactgagt    1560
gaggccaggg attgaacctg catgctcatg catactagtt ggattcagtt ctactgcacc    1620
acaatgggaa ctccctctga tttcttttta agggcgaatt cgcggccgct aaat          1674
```

<210> SEQ ID NO 175
<211> LENGTH: 655
<212> TYPE: DNA
<213> ORGANISM: Sus scrofa
<220> FEATURE:
<221> NAME/KEY: modified_base
<222> LOCATION: (95)
<223> OTHER INFORMATION: a, c, t, g, unknown or other

<400> SEQUENCE: 175

```
aattgtgtgt aaatgtatcc tgttttaatt tagagccatc accccttcaa ctctggtgtg       60
```

| tgcacatacg tgttctgtag gtgtgtcttc cttgngtgtc tgtgtgagca cctgagcatg | 120 |
| aaacttggcg ccttcttcgg aatcctcttt ggggctctgg gcgccctctt gctgatgggg | 180 |
| gtcgccttgt tcgtgttcct gcacttcaga tacttctctg ggaccattta ctccctggac | 240 |
| ggagacctga ggcctgaaag ctgaggcctt gccccacaca ggtggctctg tcctaggata | 300 |
| cctcagggcc cacccagtc ccacccgcac acactttttc aggcgccttg gtttggtcca | 360 |
| gattggaaag agaaaagtga ctgatggcag ttcaggattc ttcaagaaga atgaaaaaca | 420 |
| ggaatgaata aaacagtca taaaaacaag gccatacctt atcagtataa tagacacagg | 480 |
| ctgacaggaa gaggccatat aggcctgcta cataaatggt aggttctcac acagacacac | 540 |
| aaagaagaca cacctacaga acacgtatgt gcacacacca gagttgaagg ggtgatggct | 600 |
| ctaaattaaa aaccagaata catttacaca caaaactctc tggtttactt caaaa | 655 |

<210> SEQ ID NO 176
<211> LENGTH: 3312
<212> TYPE: DNA
<213> ORGANISM: Sus scrofa
<220> FEATURE:
<221> NAME/KEY: modified_base
<222> LOCATION: (2900)
<223> OTHER INFORMATION: a, c, t, g, unknown or other
<220> FEATURE:
<221> NAME/KEY: modified_base
<222> LOCATION: (3158)
<223> OTHER INFORMATION: a, c, t, g, unknown or other

<400> SEQUENCE: 176

| ttcgcccctt tgtacttcat acaagagaga tcctcttgga tcgtcctcag cgcccttgct | 60 |
| ccattgccta acatacaccc aaacctcagg gccacagacc cagaggacct ggcagtaaat | 120 |
| gccactcctg ctgtgtctag atccctctgg attgtgaccc tgtgggagca ggggctatat | 180 |
| cttgttcatc tcagcatctc tggtgtcagg ctgaccctgg ttcacagagc aacagggctg | 240 |
| ttggattgcc aggctgaccc tgagttctgt tgccttcact gtaccctggg cagagggctt | 300 |
| gctgggctt cctggctctg ctccccttct cccttagcc tggccctgtg gcttcagctg | 360 |
| gttcctctcc ccaaggagcc agggagaaga agaggacctt actctcccca gctaggtttt | 420 |
| gctccaggac tgtttccgtt tcttctgct ctaaccttct ggctgaattc ccccacccctt | 480 |
| ttctcgttca aatgcctcct ggattacttt ctctagaata tcacctggac tatgtatcaa | 540 |
| ggctcaggtt tcaatgaga ggtctggcag ctggttatgg atccaggctg ggaaccatca | 600 |
| cccagaaggc atccttgagg gacctcacct gtttcccaat ctacctgcag gatccttaac | 660 |
| ccaccacca ttttagctt acctgagtaa tgatcttatt ctgtggtagg ttttacctct | 720 |
| gccattagac tgtcagcttt agagatttaa tagaccctca gtgtccaaga atacgcccac | 780 |
| atcttagcta attcacattc attgacttcc tgctgtaaaa ggaagttcag agcagtgtag | 840 |
| caaaacatgc caggcctgat tcaagctaaa ggaaatgaac ttgaatacac aatctctatg | 900 |
| gtacttgtaa taggaaataa cccaagggtc caacgtaatt aaattatgat ggcagtccac | 960 |
| tcaatggaat attattcaga cttttaaaat atgtgtatga agcattttgt aatgaaaaga | 1020 |
| aatgtttagg tttagagcca cctgataaag taggaattca actttatgag ttattcctgg | 1080 |
| agaagtggct agaaatttat caatgtatta agagggtttt tttaggagtt cccgttgtgg | 1140 |
| ctcagtgggt taagaaccag acacagtgtc tgtgaggatg tgggttcaat ccctggcctc | 1200 |
| gctcagtggg ttaaggatct ggcattgcca caagcttctg tgtcacagat gtggcttgaa | 1260 |

```
tcccgtgttg ctgtggctgt ggcataggcc tgcagctgca gctccaattc aacccctagc    1320
ctgggaacat ccatatgcta caggtgcagc cctaaaaaga aaaaaatgcg aaaaaagaaa    1380
aaaagagggg ttttcaaac atattgatga tgtttttctt ctctctgctt ttaagtattt    1440
tccatatgat gaacatgtct tatcttcata atgggaaaaa aaacagcaat ggagaacttt    1500 tttttttta cttttttatta ttttttaata gttatttcct caatacaatt ttttctactg    1560
tacagcattg tgacccagtt atacatacat gtacacattc tattttctca caatatcatg    1620
ctccatcata agtgactaga cagagttccc aatgcaacag agcaggatct cattgctaat    1680
ccattccaaa ggcaatagtt tgtatctatt aaccccaagc tccccaacca ccccactccc    1740 tcccctcct ccttggcaat gacaagtcta ttctccaagt tcatgatttt cttttctgtg    1800
gaaaggttca tttgtgccgt gtattagatt ccagatataa gtgatactag tgatatcata    1860
tagtatttgt ctttctcttt ctgacttaac ttcactcagt gtgagagtct ctagttctat    1920
ccatgttgct gcaaatggca ttattttgtt ctttttatg gctgagaagt attccgttgt    1980
gtatatacac tacatcttcc taatccaatc atctgtcaat ggacattggg gttgtttcca    2040
tgtcttggct attgtgaata gagctgcaat gaacatgtgg gtgctgtgtc ttttttaagg    2100 aaattttgt ccgcatatat acccaagagt gggattactg ggtcatatgg tagtgaaatt    2160 tattttaaa gattctgtaa ggactaggct gggctctctg tcagaccct gtgttagagg    2220 tctctatggg ccaccctgtc tgagaaagca ggccatcatc gttcaggcct catcatgaaa    2280
cactaactga gtgttgtcta tggacagaag tctaggctag aggcagcagt tctgacaggg    2340
tactcagggt gagcaaagac aacctaataa ccatgggagg cacagcgcag agcagaatga    2400
gcactggagc tgtgggaaca aggcctacat ctgtcacaga ccaactgtgt gacctgggac    2460
actgccttct ctccagccct gtgctttgtc tgtggtagaa tgaggagtgt ggattgcatg    2520
attgtcaagg tctcttccag ttttaaaatt atgttgagat tctttttgc tttccaattt    2580 gcaaagggaa gcctacccat agtcacagct agtgaatctg ggcccctggg tgctggattt    2640
ttgactgagc actttgctaa tttccaggct ggagtcttct tcaagttgag tgaatggata    2700
catttagatt cctgggcctc atgtcaatcc tgcaccttca cctctgcctc tctacccagc    2760
atggcctctc ctcttgggga ccccaggcct ggaagatgtt gcttaggcag gcattagctc    2820
ccctctgcct cagaggaaaa atgagaagag aaatgaacta attggcgtga aaatgcaggg    2880
cactttagaa gaaggggcn ttgaaaactc aatcctgggg agaaatgaac aaggcccctt    2940
ttgttttggc cccttttgtg gtgggccccc aaaacaaccc aagccccccc cccccccttt    3000 ccaaccccc ttcccaaggg aaaggccaaa aaaagccctt ttcccccccc ccttttccca    3060
aattccaaac cttttggaaa accccccccc ccccttcccc ttggggggc cagagtgggg    3120 gcccctggg aaccacccca aacccaatgg tttaaagnaa acaaacccc cccaaatttg    3180 ggggggggt tccccaagt tcccaccggg aagggaaaat tccccccccc cccccaacc    3240 cccccaattc ggctttggtc caaaatcccc taaatttgcc cctgggggc ccctttttt    3300 gcaaagcgtg ta                                                        3312
```

<210> SEQ ID NO 177
<211> LENGTH: 3765
<212> TYPE: DNA
<213> ORGANISM: Sus scrofa

<400> SEQUENCE: 177

```
ctgcaggttt aacgattcgc ccttgataaa ccatagagat ttaccctggc ttagaaaagt       60
```

-continued

```
gctattggcc ttgcacttt ttttaacatc accctgacac ccccagtccc actcacagac    120 taacccact tcagaggctg gcactatttt tattgagcac ctattaagca gtcggcactt    180
tcacagacct tatcttgtac catacaatgg actaggattt attagaattt tacagtcaag    240
gaaactgagg ctcagagagg ttaggtaact ttcccaaagg catagaagga gatggtaccg    300
gaacccaaat gctgatctgg gtgacccag atcccacaca gcaaccagct gcataaacac    360
ccagtgtggt tgaggagtgt gagagtcaaa accacgtgac tccccagaac ctctcctgct    420
gcccagaggg ataagcttgt acattctggc cactctgaga aatcccctta gagagtcctt    480
ctgccaccct ctgcctgcac tgagcaaagt gaccatccct ctaggtttct ctggagcagt    540
ccattcatgc tcattgctcc catgtatggc taacagcatc ccttttcact ctcaaatgtg    600
tgccaggaca gatcctagat tataagggtg tcggctcacc actgagggat gctcagccat    660
gcctctgacc atgtgctcag cctttttctc agcatgggca gtagctcctc caactaaacc    720
tccacatggt ttcctgaatc ttcccttggc ctcttcttct ccagcctgga gagtcccaga    780
ggccttctgg caggctgcac gctgctgtgc aaagggcatg agctttggaa cccagagttt    840
tgggttctct actggctacc cctggtgaat tattttgttt gtttgaacct tagtttcttc    900
atccataaaa tgggcataat aaaacataaa ttttaaggtg gttgtaaggc ttcaatgaga    960 aaagaatgt aaagcacttg gcaaagatgg ctgtttctcc ttttgctggt tgaagaagct    1020
ggagaatagg gatgcaaaag agggcactgc aatgggattc tctctcctag tcagtggaaa    1080
gtaatgctgc tgaaacacat gttccttgaa taaatgctaa ggccttaata attaggcacc    1140
cataatggta gaggttactg actctgactc cgcagagaaa agaacccagg ttatccatgc    1200
tgaattagca gtgcctgact gtgggtaaca aaattgatct tcagttcttc ttaatatttt    1260
tttcagtttt ttgatttct gtaccatgta tgcatgtgtg tatgatttta tactcagagg    1320
aaaacaacca ttatggaaac agacccctttg caataactgt agtttttagc aggttaggct    1380
atttattcag ggttgatgga ttctgattcc ccagatggtc agtggaggag tctggaagga    1440
aacccaggct tctaggttcc cagttgtaaa acacagaaa agtttgcaca catccttttg    1500
tacagaaaat aactactctg tcccccaacc tgggccctca cctggttctc ctaggggctc    1560
tggggctgag actgagtggg gactgcccct aggaagggcc agtgcaactg cgggcagaaa    1620
aggctgctgt ggagggagca cttggtcttc tgctcggggc cagcccctcc cttccttgac    1680
acccagagac tccctggccc tggtctctgc acatctctcc caggaaggag tcagtgaggg    1740
cctgggggca gggggcatgg tagagggaca gtcacagaag gaaagaggcc caagtgggt    1800 tcaggcactc agtaggaatt taatgaataa atgaatgagc aaatgaatga atcaaaggat    1860
aggcaaacag ggaaccaaac ccttcagagt tagtatggca gctcagctgc ctgtgtcagt    1920
ttgagacagc tctaaagggc cagccaggtc tcaggttcct caaggatct gatgaggcca    1980 ctgctgtaac tgcctcgaaa ctcagctccc tctgcccaac cctgcctttc ccacccctca    2040
cagggggttc caacagcacg ccccaggtaa ccacccgcac aggagtctcc ctcttggggt    2100
gtttcctggg aaactcaacc taagacaatg ccccaactgt cacacaaagg aggaagtaga    2160
atttataata aagcatgttc cctgtatgtg actgctcagg tgtgaatgca ccaggacctt    2220
gcagtacctg ggggcttgta agacacacag atctcagttc ctacctcaga cctgctggaa    2280
tcccaacctg cacctgagct ccgtccctg gggatgcatg tgcatggagt ccgaacacat    2340
cgctaagaga catcacatgg gtcaggtgtg attataaatg tgcactgaca cgtatgaatc    2400
```

```
tacagtcact caaagacaag tggtggtgct gtcggtggtg agattttcta aactggtgaa    2460
taacgctatg taaaatgcca aataaaacac ataaaattcc ctcaattcac ccagtagttg    2520
aactcctgga aaattctgtg tatcttaaaa ttgtgcaaaa aaccctcctt caccatgaag    2580
aatagaggac atttcctcat tgtgcattac tgccctgtgg agggtaggag atccctggcc    2640
cttgactttt acaccggtgg cctctggcac agtgaccact gaaaacaccc ggtacttccc    2700
aaactgtccc ctaggggtca ttactgtcct cactgctccc caagagaaaa ccctgggctt    2760
agaactttac atgctattca tccactcctc ccataacct taggaggtaa gtgttactat    2820
tccctctcct tcactaagaa aatcaagctc agagatgctg agcaacttgt ccatattcac    2880
gcagctagta actggggggag caaagttgaa cccaggtctg cctgtcacca agtccatgt    2940 ttctccctat aggttgcttt gcaggtgttt agtctatcaa gagttgtata gttaacacgg    3000
catgaccagg tttgcttata acacaaaata aaccettcat ctggatgcag gcaactata    3060 ggaacctgag gctgagagca gctgggcttc cccggggaac ccccacctga atgccttca    3120 gagcctgggt gggaagatgt catcataggc caggcagtcc cctccttccc tgagcctcat    3180
tgctttgtga cccacaggtg gcttgaggtg tgcaccaggc aaaaccatga tcctccattt    3240
ctaggctaag agacagccaa ggatgcttga gctgaacctc acatgttcac agttcttcag    3300
gcatttctgc cacactattg aacacactgg ccaaataaag ttgaaatttt caaaaaagc    3360 accctaagtg gctgtccacc cccatatacc acaaagagac ccccaaagac accagcaggc    3420
ccagatcagg gaggtgtcag tgagagtgtc tctgtgggtc cctcccaccc cccactcctg    3480
acctcaggtg tggagtggag attgccctga tatctagctc agatgccatg ccttccacct    3540
ggaattaact tgaccctgag tgaggctctg aaggacagct acattgggca ggtataagtg    3600
ggagccgaca gagtcacgga ggggccaaga tgggagcaag aaggctctcc ccagccacct    3660
ggtgcaggag ggctgagagg cactctctct gtaaatctat gcaccatgtt ggtagaatcc    3720
tgttccactt ctagagtgaa gggcgaattc gttaaacctg cagta                   3765
```

<210> SEQ ID NO 178
<211> LENGTH: 2723
<212> TYPE: DNA
<213> ORGANISM: Sus scrofa

<400> SEQUENCE: 178

```
tgcgaggtcc caacgaaatt cgccctttt ccccatcatg ggaactaccc aggtgagttc     60
tccctcttct ctcaccagat gactgccaca catctgcctc cagctctggc ccttctctcc   120
attctctcca ttgtggtggg agtggtcctt atgctcagag ctgatcatgc ctctgtcctg   180
cctgcaatcc ttccatgcct gcacactgct ctcaggataa agtccaaatt tctcgttatg   240
gcttacaaat ccctccagga catgtgctct gcctggctgt cagcctcatc ttgcattctg   300
cagtcttcca actcaactct gtcctgagcc agccaggctg tccgccaaac aagtgggagc   360
acatcaatca agactccttt tggtggtcac attctctctt aatcacttgc ccccctttcc   420
aaactggact agacccttc cagtcctccc aagacagtta gaacactggg gtttcactca   480
catttacctc tctctcagaa tggccacatg gctgaccct tctccttcca atctctactc   540
agtgtcacct ccagagagag gccttccttt atgcatcat gctaccaccc accctgtca   600 ctctatcaca tttcatttct agcatttata actacctgta gactttttaa tttgcttgtt   660
tattacctat tccacactaa aatataagct ccctgagagc agtaatctta tatcttattt   720
acctctgaac cccaaccteg gaacaaggcc ctgacacaca aaaaggactc aatacatctt   780
```

| | | | |
|---|---|---|---|
| caaggtaaaa tagtttttat ttttaaaaac gcaatctgaa gactccttac agaaattaaa | | | 840 |
| ggcctcgaat ccccgcaaag cacagctatc cttgactgcc tcctccttta ggaagtgctt | | | 900 |
| ttcattctct gacctctgtg gtcccaggcc gtcctggctc ttctctcact ctgactggtc | | | 960 |
| ctttgtgtac ttgtttcccg tttcctcctc ctcttcattc ccctcccaac tttgagctgt | | | 1020 |
| cctccacacc cgagtcttag ttctctccag catacgacac aaccccctcag tagcatctgg | | | 1080 |
| gtctctgtgt ggagtggaca gttcacccgt ccatacctct gaccctaagt cctcccacca | | | 1140 |
| cctgtagcct gcaaggtccc acttggaatt ccttttgtgc ctttaaactg tgtaatgaca | | | 1200 |
| gtcttccagc tcggagcagt gaattcctga ggattttgta atctctgcaa acataccatg | | | 1260 |
| tcaaaacctc attacaataa atcagttcta ctctaataaa aaattttttt aaaaaacctc | | | 1320 |
| attacagtat ctttacgcag ttgtatacca tgtggcccttg gaaggaatg agagagctct | | | 1380 |
| atatgtattg atttggaaca gtttctacaa catggaaaaa aacaatatgt gcagtcgtgt | | | 1440 |
| gcagggcggt gctatccagg agaaatataa tgcaaaccac acatgcaatt ttaaattttc | | | 1500 |
| taatagccac attaaagtaa aaagcaggtg aaattaattt taacgataca gtttatttaa | | | 1560 |
| ctcagtaatg tgcaaacagg atcatttcaa catatcaata tgaaaaatta ttaatgagat | | | 1620 |
| atttaatgtt ttttctcata ctatggcttt gaaattcagt gtactttata cttactatac | | | 1680 |
| atctcaattt ggtcttgcca gctttcaggt gctcagtaac catgtgtggc tgttggctgc | | | 1740 |
| cctattggac cctgcaggtg tccccccttga agagtatgtg catggccagc acacagcaca | | | 1800 |
| tgccagagaa gcatatgctc tatgggatat tggtgactgg ctgtgggtca caggatatgt | | | 1860 |
| tgaagttacc tctctgaagt gcatattcta gatccttttcc gtgcccctgc ttagacttct | | | 1920 |
| ttttcaaaag gactgccatt ctgcacaaag actctgccat ttttgcccag aggccatgtc | | | 1980 |
| gctcccaaga aggaaaccag ctcctctcat tccaactcta ctttcaccat cctttgtgca | | | 2040 |
| ggccctctag ataaacttgg tcaaaaccag tcagtcagtc catcagtcat tgaacattca | | | 2100 |
| ttgtgtgttt gctatgtgcc agttgcttgc caggccctgg aacgtgacgt aaacctgctc | | | 2160 |
| ctgccgtcat ggagctccca ggccagtggg taatctctct gcatccttcc tcacccaccc | | | 2220 |
| cttccttctc acccgcagct ccctccttcc tctccctggg cctcagatct ctctcctggc | | | 2280 |
| acccatgggc aatgacaggg ggctcaaacc acacccctttt gagcttggtt tccatttcac | | | 2340 |
| aggtcagcct ggtcttggtc ttcctgggga gttttctgtg cattagtcac tgtgctcaga | | | 2400 |
| gagcacagga tggcaagatg ctgaggtcat gaggaggaca ggaggaagtc tgtcaaggca | | | 2460 |
| aggacttggc ctgggggtct gctctggaat gaccaagtcc aggctgtcct ggagagacag | | | 2520 |
| cagagacctc caggtctagt tgagactgga tctgggtgtg gggtccagca gggcacacag | | | 2580 |
| ccagaggagg gaagtactgg ctctgaggtg tcctgtcctg cactgcctct ctcctcccct | | | 2640 |
| tcaagcctcc atacctcctg ctcagcaccg tggctcaggc cctcagatct gctccctggg | | | 2700 |
| gccaagggca attcgtaaac tgc | | | 2723 |

<210> SEQ ID NO 179
<211> LENGTH: 729
<212> TYPE: DNA
<213> ORGANISM: Sus scrofa
<220> FEATURE:
<221> NAME/KEY: modified_base
<222> LOCATION: (716)
<223> OTHER INFORMATION: a, c, t, g, unknown or other

<400> SEQUENCE: 179

```
ctagtcctgc aggtttaaac gaattcgccc ttaggcactc atatcttctt ttcctctgtc    60
cctttttctc tgatccccett tctctcgatt acagagggaa ccaccctaca ttttcaggcg   120
ctgtgaggta ccatggcatt tccagactcc ttgcagcttg gattctctgg cactgccctc   180
cacctcctgc ccccaccctg ctcacctgca ttggggcccc tcgggtaggt gctggcactg   240
gcctccattc tcacagtagc ccctactgca cggggacaca caggtgaagc ctctctccgg   300
gctgaaaacc aggttgtagt ccttgtagcc gttacattgg aagtaatttt tcagtgtgct   360
cacattcact gtcagatagg acacaagcaa aatggaaacc aatggattta caccaaatct   420
atacctttc tgtcaagaat tccattttag gcactcatcc tgagaaatag ttggaaatac    480
acaaaacta catatattca tggaaatccg tagcagcatg gtttataaga gcaacaataa    540
gcagaagtgg ctttgttttt tttttaggg ccacactagt ggcatatgga agttcccagg    600
ctaggggttg aattggagat gcagctgcca gccaaagcca cagccacagc cacagcaatg   660
ccagatctga gctgcatctg caacctatac cacagcttgc tgaagggcga attcgncgcc   720
gctaaattc                                                          729

<210> SEQ ID NO 180
<211> LENGTH: 2840
<212> TYPE: DNA
<213> ORGANISM: Sus scrofa

<400> SEQUENCE: 180
atttagcggc cgcgaattcg cccttgatcc caaggcactt ggcacataat gatctgagag    60
cactcatcat cttgctgcaa tatcataatc ccctgggaca tagacattgt tcaacttgta   120
tcccctcttc agggcttgac acaaagaagg tacccaatga attcttactg agttattgat   180
tctccatgtt ggcaaacaaa cctgggtcga cttttagta ttttccctta ccatctttc     240
actaaaccta ggagatgctg gcagagctgg caggctgatg aggagtgaga aaaacagcaa   300
gaaaccctag ggtttaggga actgtgtgtt tgacaagaaa agtaccttgg gtctcctgac   360
ccctgagaa accccagat acttccatat cccacttaca aaaatatttt ttgaaatgtg     420
ttagctctgc tttcgtccac caaaaaatga cttttttgg ccatgcctgc agcattctca    480
agttcccaga ccaggaatca aacccaagcc acagcaggga caatgccaga tccctaaccc   540
actgtgccac cagggaactc ccccagtgac atttttttta atggggtaaa aaatgcccat   600
gatctataaa taggaatgac tttgtagcaa aagaacaaat tgtttccaca aaggggggtgg  660
gtcagaaaag aagacagttg tacacacaga actgttctgt gtataatgta aactactgat   720
tggtagggac aggcaggaac atgaagaaat agaatgtatt atgattataa tttattgggt   780
gcttatcatg gcccatgcac ttagcaaaat gttttaccta tgtgacctca cttaatcctc   840
acaaccattc tataaatact ctcccccagt ttacaggctc agaaaggtta agaaactttc   900
ccaagaatag aatccaggtc taatagcaat gcccaaaggt aacttaatac tttgcccatt   960
ctatatcaca tttgactgat tttttaaaaat tgcagctaaa tagaatttaa ttcctgcctt  1020
gatgaacagt gtacacaaaa cacatttgga tctgaaggct aaagtcctcc caagcctcag  1080
gacccaccat gtaggccagc tttgagcccc agatactgag agcaacccag acccatcctg  1140
aatggtcttt gttttgttt ttgtcttttt gctatttctt gggccgctcc ctcggcatat   1200
ggaggttccc aggcgagggg tcggatcgga gctgtagctg ccggcctatg ccagagccac  1260
agcaacgtgg gatccgagcc atgtctgtga ccttcactac agctcacagc agcaccggat   1320
ccttaaccca ctgagcaagg gcagggaccg aacccgcaac ctcatggttc ctagtcggat  1380
```

```
tcgttaacca ctgtgccacg acgggaactt ctggtctttg ttttaataa acccaagctg   1440 ttagcatcct ttcttatgat ttatctcttt tcctaaagtt cagatgatat ggcaaagcac   1500
aaaaggctaa atgtcttgat ccagtaaatt cctaaaaacc agtaagaaat ggattattaa   1560
tttaactttt tagtaggtca gggctatcaa taggtatctc atagaaagga aatataaata   1620
gcacaacatt ttttaaaaaa acgttcattc attcattaga gggatgcaga ttaaaaacta   1680
cagacacacc attttccacc tgtcagacta tcaaaagtca gaaagttctg gtaccatgtg   1740
gaaagctctc acatactctg gtggctgtga tactgggaac agcctcctcc atggggagaa   1800
agttggcagg atcccttatt actacacact ctgactcagg agcaccagtt ctgggaactc   1860
atccttcaga ttgccttcca aatgaagtat aacccacatc tgccatttat tgctgaaatg   1920
gctgtaactg cagaggactg gaaaccacca aatatccatc aaaagaggcc tggttaaata   1980
ggttatagta catccatatc catgcaaccc taaacaagaa tggggaagat cttccagtat   2040
ggctacagag ctcttcaaaa tactgtaggt gtggagttcc cgtcgtggaa cagtagaacg   2100
aatccgacta ggaacgatga ggttgagggt tcgatccctg ccttgctca gtgggttaag    2160 gatctggcgt tgccctgagc tgtgatgtac gtcgcagacg cggcttggat cctgtgtttc   2220
tgtggctgtg gtgcagccgg cagttgtagc tccgatttga cccctcgcct gcgaccctcc   2280
ataagctgtg ggtgcggccc tataaagcaa aaataaataa attaattact ataaacagaa   2340
tactgtagat gaaaaaaaaa ataagaaaca tacgagaaac tgatgagaaa cagcctctgg   2400
agaggggagc tagcagctgg agtgggatat gtcactgtat agttttttggt acttttttgaa   2460 ttttgaatca catgaattat tagaaaaaga aaatacttat acatattcag gcctttcatg   2520
ttatggctta actccagtta attgtgctag tgtactctgt catgcagtat atcctgcctc   2580
agggaaactc cagagcgaaa acctggggat tctgagtcca tgactccatc aggccctctg   2640
ccagcccctt acgataaact aggcatgcaa tcccctccct ctgtctatac aggtggtgct   2700
acagagcctg ctgtccagga caaatggcag tgggctgggg agcccaggag cctcaggtga   2760
ctggacaaga aggaaagaaa caggcagaca caagtaagta acataaaaga aagggcgaat   2820
tcgcggccgt aaattcatct                                              2840
```

<210> SEQ ID NO 181
<211> LENGTH: 726
<212> TYPE: DNA
<213> ORGANISM: Sus scrofa
<220> FEATURE:
<221> NAME/KEY: modified_base
<222> LOCATION: (641)
<223> OTHER INFORMATION: a, c, t, g, unknown or other
<220> FEATURE:
<221> NAME/KEY: modified_base
<222> LOCATION: (651)
<223> OTHER INFORMATION: a, c, t, g, unknown or other

<400> SEQUENCE: 181

```
ttgaaagtcc tattttttct atgttggtgg cccaaaattg gtatctgccc tactcaccta     60
ccacagctcc acccacctcc caacacacac attaggacag aggggctgaa tgacaacatc    120
ccttcaattc ccacttccct tccctcaaca cagagaccga cctcccaccc tctcccacac    180
tcacctccag ggaggaattg cccacccgat cgttctggtt atataaacac tggctctctg    240
cctggcaagt gcagaccacc attcttggct tgagtacaga tgacaagtca tccttggcac    300
ttcttgccag aatctccaga ggacatggtt tcagtgactg tggtgtccat agcaacgtcc    360
```

```
cattctctgc ccccagggaa gacagatcat tttgagagct gggagcctca tctcctctgc      420
tgcctgacac atcctggcat ctaataccc  aagtgctgat gctggacgtc ccccacccct      480
gtcagaccac ccctccaatc ttactaggca tttccttgag caaggctagt ttctagtttc      540
tgttggatca cactccaacc tggaggggca ccagcccaac taagtgattc tagggtagaa      600
ctccatgaat gaaaaggtgg gttgccaacc tccgggttgg nagtgtgatc naacagaaac      660
taggaactag cctttgctca ggaaatgcct agtaggatgg aggggtggtc tgacaggggt      720
ggggga                                                                726
```

<210> SEQ ID NO 182
<211> LENGTH: 1913
<212> TYPE: DNA
<213> ORGANISM: Sus scrofa

<400> SEQUENCE: 182

```
aacccccaca gcagtaacca gaggcatacc agggacaacg ctgaatcctt aacccactga       60
tccttcagga aactcctctc ttatgaattt ttccctcact gctgtatatt cttccacaaa      120
gttattttta gtgaatgtgt tgtattccac tgcactaatg catccatagg aacttaacca      180
aattctggtg attatccact aggcagtttc cagttttttcc tgtggacata agtctttgat      240
tacttttcct tcctttagat aaattctgag aagtggattt tgaagaatgg aagtaaaata      300
ttaagatttt cattttgtat taataaattc ctttccggaa atataccaat ttataatccc      360
aagagcaatt atgaatgtgt gtctgtgtac tcatcaatcc tggttattgt catttatttt      420
aaatctttac aaatgtgatt ttttaaaaaa tgatatcttg ttttgatttt gcatttcttt      480
aaatactatg ggaattcaag atgtctccaa ggagaaaaaa ctcaaaagcc aaaactcaaa      540
agcctgcaac caagataaga attgcccgac ccttatcatc ccacctggct cattgtaatt      600
gttacaatgt tcctcaggac ctccccaccc cagcaacttg gcctattcct tcctgccccc      660
tactaggtat gtgggtatgt ggcccactct ttaccctgca cctataggggg caacatatgc      720 ccccaaccaa gcagcaagtg taacagaaga ccccacccct cccagccaa  tcagcaggtc      780 tacaggtgta tagcaagacc actcctcgca ctcctttgtc tttgggctgt aaaaacagac      840
tggacaatgt gaccagagtg ggctctcctg gattaccagg aagtcagccc actgtgttga      900
cagtgtctct tgcctcaata aacttgtctt ttctacacct tgctttaaat ctggaacatt      960 cttttttccac ccacgtgcag agaccacaac aaatactcgt gggattgaaa atctctgtgt     1020
atttctttgt ttattcatgt cctttgcccc catctttatt ttattttaaa gtagtatcgt     1080
ggggcgttcc tgtcatggca cagcagaaac gaatccaact aggaaccatg aggttgcgag     1140
ttcgatccct ggcctcactc agcagcttaa ggatccagtt ttgctgtgag ttatggtgta     1200
gttcgcagat gcagcttgga tcctgcgttg ctgtggctgt ggtgtaggct ggcagctgta     1260
gctcgatttg accccagcc tgggaacctc catatgccac aggtgcggcc ctaaaaatca     1320
aaaaaattta aaagtaaat aaattttaa aaaaataaag tagtattgtg actttgtaat      1380
aaaaatatat tatataatat ttaatatgca acagtaaat atatatgtat aaacatattt      1440
aatatataaa catgtaacat tttatatta aggatatctt tcaactatgt tgcaaacatt      1500 ttttctttc aagttgattt atgcctttca ttttacagac agagttaact ttcttttaaa     1560
atactgtcaa atgcttttga aagccaaaac tgatgatgtt tggattttgc atgttattct     1620
tttctcctca ctgccctctt tgccgctttc ctccctacca tgcacgctcc agaagcagat     1680
aagtgagaac tccttatggt tggtgaggct tatctcattt tccaatctct tatttttctct    1740
```

```
gccgctgtct aggtcatggt caggttatga ctatataatt aaacagaagg gtcataagag    1800
aaaatccaac tgtgaatatt ctatgtcctg gattactcat ccctataatc cccaactgta    1860
aactgaggtt tctagtccca ctctccttaa gggcgaattc gcggccgcta aat           1913
```

<210> SEQ ID NO 183
<211> LENGTH: 4479
<212> TYPE: DNA
<213> ORGANISM: Sus scrofa
<220> FEATURE:
<221> NAME/KEY: modified_base
<222> LOCATION: (4236)
<223> OTHER INFORMATION: a, c, t, g, unknown or other
<220> FEATURE:
<221> NAME/KEY: modified_base
<222> LOCATION: (4298)
<223> OTHER INFORMATION: a, c, t, g, unknown or other

<400> SEQUENCE: 183

```
ttgttctata gtgtcttttc tggggtgggt atcaggaaaa tgctggccta aagaatgag     60 ttagaaagtg ctcttcctct tttatttact ggaaaagttt gagaaggttt gatgttagtt    120 cttcttaag tgttctttag aattcaccaa tgaagccatc aggtccagtg gttttctta    180 ctggttcaat ctccttacaa gtttatagat ctctagattt tctgcttctt catgatttag    240
tcttggtatt ttgtttattc atttctagga aacatacctta gattatttca tctaggttat    300
gcaatttgtt ggtatataac tgctcatagt aatctcataa ccttttaat ttctgtagaa     360 tcagtagtaa tattcctatt tccatttctg gttttaataa cttgagtctt ttttcttag     420 tccatctagc taaagttttg tcaattttgg atcttttcac agaaccaatt tttggtttga    480
ttctctctat tattttccta ctctctattt catttatctt tgttctaatc tttattattt    540
cctttcttct gttaggaatg tctattttat cttcaaaaaa ccaagttaag ttatattctt    600
aattttatct tttattcagc tttccttctc tttttctgtt ttttgctgtt gttgttgttt    660 tgtttttgt tttggctgc actcacagca tgtggaagtt tgatcccgag ccagggatca     720
aacctgtgcc acaaagaaa tgatggcatt tgcagcaaca tggatgggcc tagaaatatc    780
atgctaagtg gttagacagt gagacatcaa catcatatgc tatcacttac atgtggaatc    840
taaaaaggga cacagtgaac ttcttttgcag aacagacgct aactcacaga cttgaaaaca    900
gttggtttct ggagttcccg tcgtggctca gtggttacga atccgactag gaaccatgaa    960
gttgcaggta tgatctctgg cttttgctcag tgggttaagg atcaagcatt ggcgtgagct    1020
gtggtgttag tcacagatgc cgctcagatc tggcattgct gtagctgtag cataggccag    1080
cggctgcagc tccaattgga cccctagcct gggaatctcc atgtgccgtg ggagcagccc    1140
tggaaaaaca caaagacaa aaaagaaag aagaaagaa agaaagaaag aaagagagag     1200
agagaggaaa gaaagaaaaa caaaaaaaaa aaaaacctgt gcctcagcag taaccagagc    1260
cccagcagtg aaaacgctgg atccttaacc cactgagcca ccagggaact cctccttttt    1320
cttttttctt tttgattttt ctagaccacc ttttcactga ggtttccagc tttatgcaga    1380
aaatattcag tctacagtgt cctgatctaa gattgtttcc tttctccatg cagccattaa    1440
aatgccaaac tctagatctc agaaatctcc aaattgtatg agagcactta cttatcatct    1500
tagttttcaa ctccttcact cctgagcgtc tccctttctt tcttcggatc tcagctcagc    1560
attcagaaaa tatttattac acattatctg gcatttgcat gttctctagt taaaggtttg    1620
tctcttctgc catattgctg ggagtagagc tgtactactt ttatgaacaa acaaatacaa    1680
```

```
atctttactt taaaaaactt ggactgtgca atcatgaaac ttttgctgct aatattgatt    1740
ttaacagagg tgatgcaggc tccaaaagta tattaattgc caagaatcta taataagttt    1800
attagtaagt ttggcatgta actagcttct atctggtgac tcaaagccca gaagacagag    1860
cgttgctttt atttatgttc ttaggaagag gaaataagct taataataat ttcatggtgt    1920
atgtcttcca atctaaacct tagttagaaa aacgaagttt atgactttac tgaggaggga    1980
gcaggtatag gacttaaagt cctagaaaca aatctattca taattctgaa taaaaaagtc    2040
cccttttaaag ttacagcagt gttatttggg ttaaagccca aggactttct aacagctctg    2100
cagatcaatc catgcatttg ttcataccag ctaggaagcg tgtcacctgt aattagttac    2160
tattaataca tagtaggtga gtcacttctt tttaataaat tagagctgca ggtgagtcac    2220
ttttcttttt aacaaattat agctgattca taatcactct cgctcactcg aaagctgaaa    2280
ttgttctctt aagaagagaa aatggtggga ttatagtcaa gtcccagaat tgcactcaaa    2340
ctaaaataaa ttcttctctg ggagttgtct ctctggggat gacctccctc caactagttg    2400
tgatcacgga gcttaaaatt tgtttaagaa cagccaggga gctaataaaa gccaaaaaaa    2460
ttaattccta agggaaaaaa aaagacaaga ttttgtggtt tcctctttgt ttcaaagact    2520
caagggtctt aaagtttggg aggatggtat ggtctcctgg ctgactgagg cttcatctgt    2580
agctagtttg agtgcagtca agcaattcaa atagaacagg ttggcattta aacactctgc    2640
ctggcaagta catgggaaaa gaaagggtat gatcaattaa attaacatca tgctatgatg    2700
tgaccagggc tagaatgtgt gtactcattc actagatttc tgctagattg ggacaaatgt    2760
taaagataaa aaatttaaag gtagaaattt aatttgcatt tattttttaaa attgctatag    2820
gagttcacat tgtggctcag tgggttaaga acccagcata gagtctgtga ggatgtgggc    2880
ttgatcctgg cctcactcag tgggttaagt atctggtgtt gccacaagct acagtgcaat    2940
tcgaagatgc agacctggcg ttgctgtggc tgtggcatag gccagcagct gaagctctga    3000
tttgacgcct ggcctgagaa cttccatatg ctgcaggtgt ggctgtaaaa agaagtataa    3060
tttaatttaa tttaaataaa aatgcaataa ttcaggttga aagagttaac actctttccc    3120
accccagacc ttaaaatagt ttaaaattag tctttccacc actgtggcct gtgtttaatc    3180
catggtctgg gactgagatt ccatatcaac tgttgcacac catggccaga aaaaaaagaa    3240
aaaagtcttg aataaattat taaagcagtg catgcatcta gtcaggtcag gcattctata    3300
cacaaagtca caacatttcc cttttcttgc tcttcaaaga aggtcctgat atgtcagcaa    3360
aaatcttagg tatttgagat ggggtacaag agagaaatga gggaggaaag aagatcacaa    3420
gattatcaca aggggttaaa attgaaggat ttttagagat ggcattagga gaggagttga    3480
gagggaaaac tgattgagat atgcattggg ttaaggaaaa ttaaaaggct gtgagaaacg    3540
tgtttgagaa atgtgtgtat aggatatgca aaaatctgaa tttttttaaat ttatttttta    3600
ttgttatttc ccccaacaca cttttttttt tcccactgta caacatgggg acccagttac    3660
atatacatgt atacataatt tttctcccat tgtcgtgctg tgttttaagt atctagacat    3720
agttttcagt gctacacagc aggatctcat tgtaaatcca ttccatgagc aatagtttgc    3780
atccatggac cccaagctcc cactccctcc ccctctcccc aggcaaccac aagtctattc    3840
tccaagtttg ggattttctt ttctgtggaa aggttcattt gtgctgtata ttagatacca    3900
gatatgagtg atatcatatg gtatttgtct ttctctttct gactgacttc acttagtatg    3960
agagtctcta gttccatcca tgttgctgca aatggcatta tttcgttctt ttttatggct    4020
gagtagtatt ctactgtgtt tatgtacatc ttcctaatcc aatcgtctgt caatggacat    4080
```

| | |
|---|---|
| ttgggttttt tccagctctt gactattgtg aatagagcca caatgaacat gcgggtgcat | 4140 |
| gtgtccttt taaggaaagt tttgtctgga tgtatgccca agagtgggat tgctggatca | 4200 |
| tatggtagtt ctatgtatag atttctaagg tacctncata ctgttctcca tagtgactgt | 4260 |
| accagcttac attcccacca acactgaagg aaggttcnct tttctcccac cagttccagt | 4320 |
| gttgtatttg tgactactga tgccatctta ctgtgggggg tagccacgga gttgattcat | 4380 |
| tcttgaacag gagtagcttt tatagctgtg ccttttttt tctgagacgc atcaggcttg | 4440 |
| ccattactgg tgtgcttgag taaggttatt caataactt | 4479 |

<210> SEQ ID NO 184
<211> LENGTH: 4479
<212> TYPE: DNA
<213> ORGANISM: Sus scrofa
<220> FEATURE:
<221> NAME/KEY: modified_base
<222> LOCATION: (4236)
<223> OTHER INFORMATION: a, c, t, g, unknown or other
<220> FEATURE:
<221> NAME/KEY: modified_base
<222> LOCATION: (4298)
<223> OTHER INFORMATION: a, c, t, g, unknown or other

<400> SEQUENCE: 184

| | |
|---|---|
| ttgttctata gtgtcttttc tggggtgggt atcaggaaaa tgctggccta aaagaatgag | 60 |
| ttagaaagtg ctcttcctct tttatttact ggaaaagttt gagaaggttt gatgttagtt | 120 |
| cttcttaag tgttctttag aattcaccaa tgaagccatc aggtccagtg gttttcttta | 180 |
| ctggttcaat ctccttacaa gtttatagat ctctagattt tctgcttctt catgatttag | 240 |
| tcttggtatt ttgtttattc atttctagga aacatacccta gattatttca tctaggttat | 300 |
| gcaatttgtt ggtatataac tgctcatagt aatctcataa ccttttaat ttctgtagaa | 360 |
| tcagtagtaa tattcctatt tccatttctg gttttaataa cttgagtctt tttttcttag | 420 |
| tccatctagc taaaagtttg tcaattttgg atcttttcac agaaccaatt tttggtttga | 480 |
| ttctctctat tattttcta ctctctattt catttatctt tgttctaatc tttatttatt | 540 |
| cctttcttct gttaggaatg tctatttat cttcaaaaaa ccaagttaag ttatattctt | 600 |
| aattttatct tttattcagc tttcctttct ttttctgtt ttttgctgtt gttgttgttt | 660 |
| tgttttttgt ttttggctgc actcacagca tgtggaagtt tgatcccgag ccagggatca | 720 |
| aacctgtgcc acaaagaaa tgatggcatt tgcagcaaca tggatgggcc tagaaatatc | 780 |
| atgctaagtg gttagacagt gagacatcaa catcatatgc tatcacttac atgtggaatc | 840 |
| taaaagggga cacagtgaac ttcttttgcag aacagacgct aactcacaga cttgaaaaca | 900 |
| gttggtttct ggagttcccg tcgtggctca gtggttacga atccgactag gaaccatgaa | 960 |
| gttgcaggta tgatctctgg cttttgctcag tgggttaagg atcaagcatt ggcgtgagct | 1020 |
| gtggtgttag tcacagatgc cgctcagatc tggcattgct gtagctgtag cataggccag | 1080 |
| cggctgcagc tccaattgga cccctagcct gggaatctcc atgtgccgtg ggagcagccc | 1140 |
| tggaaaaaca caaagacaa aaaagaaag aaagaaagaa agaaagaaag aaagagagag | 1200 |
| agagaggaaa gaaagaaaaa caaaaaaaaa aaaacctgt gcctcagcag taaccagagc | 1260 |
| cccagcagtg aaaacgctgg atccttaacc cactgagcca ccagggaact cctcctttt | 1320 |
| ctttttcttt ttgattttt ctagaccacc ttttcactga ggtttccagc tttatgcaga | 1380 |
| aaatattcag tctacagtgt cctgatctaa gattgtttcc tttctccatg cagccattaa | 1440 |

```
aatgccaaac tctagatctc agaaatctcc aaattgtatg agagcactta cttatcatct   1500
tagttttcaa ctccttcact cctgagcgtc tcccttctt tcttcggatc tcagctcagc    1560
attcagaaaa tatttattac acattatctg gcatttgcat gttctctagt taaaggtttg   1620
tctcttctgc catattgctg ggagtagagc tgtactactt ttatgaacaa acaaatacaa   1680
atctttactt taaaaaactt ggactgtgca atcatgaaac ttttgctgct aatattgatt   1740
ttaacagagg tgatgcaggc tccaaaagta tattaattgc caagaatcta taataagttt   1800
attagtaagt ttggcatgta actagcttct atctggtgac tcaaagccca aagacagag    1860 cgttgctttt atttatgttc ttaggaagag gaaataagct taataataat ttcatggtgt   1920
atgtcttcca atctaaacct tagttagaaa aacgaagttt atgactttac tgaggaggga   1980
gcaggtatag gacttaaagt cctagaaaca atctattca taattctgaa taaaaaagtc    2040 cccttaaag ttacagcagt gttatttggg ttaaagccca aggactttct aacagctctg    2100
cagatcaatc catgcatttg ttcataccag ctaggaagcg tgtcacctgt aattagttac   2160
tattaataca tagtaggtga gtcacttctt tttaataaat tagagctgca ggtgagtcac   2220
ttttcttttt aacaaattat agctgattca taatcactct cgctcactcg aaagctgaaa   2280
ttgttctctt aagaagagaa atggtgggaa ttatagtcaa gtcccagaat tgcactcaaa   2340
ctaaaataaa ttcttctctg ggagttgtct ctctggggat gacctccctc caactagttg   2400
tgatcacgga gcttaaaatt tgtttaagaa cagccaggga gctaataaaa gccaaaaaaa   2460
ttaattccta agggaaaaaa aaagacaaga ttttgtggtt tcctctttgt ttcaaagact   2520
caagggtctt aaagtttggg aggatggtat ggtctcctgg ctgactgagg cttcatctgt   2580
agctagtttg agtgcagtca agcaattcaa atagaacagg ttggcattta aacactctgc   2640
ctggcaagta catgggaaaa gaaagggtat gatcaattaa attaacatca tgctatgatg   2700
tgaccagggc tagaatgtgt gtactcattc actagatttc tgctagattg ggacaaatgt   2760
taaagataaa aaatttaaag gtagaaattt aatttgcatt tatttttaaa attgctatag   2820
gagttcacat tgtggctcag tgggttaaga acccagcata gagtctgtga ggatgtgggc   2880
ttgatcctgg cctcactcag tgggttaagt atctggtgtt gccacaagct acagtgcaat   2940
tcgaagatgc agacctggcg ttgctgtggc tgtggcatag gccagcagct gaagctctga   3000
tttgacgcct ggcctgagaa cttccatatg ctgcaggtgt ggctgtaaaa agaagtataa   3060 tttaattta ttaaataaa aatgcaataa ttcaggttga aagagttaac actcttccc     3120 accccagacc ttaaaatagt ttaaaattag tctttccacc actgtggcct gtgtttaatc   3180
catggtctgg gactgagatt ccatatcaac tgttgcacac catggccaga aaaaaaagaa   3240
aaaagtcttg aataaattat taaagcagtg catgcatcta gtcaggtcag gcattctata   3300
cacaaagtca caacatttcc cttttcttgc tcttcaaaga aggtcctgat atgtcagcaa   3360
aaatcttagg tatttgagat ggggtacaag agagaaatga gggaggaaag aagatcacaa   3420
gattatcaca aggggttaaa attgaaggat ttttagagat ggcattagga gaggagttga   3480
gagggaaaac tgattgagat atgcattggg ttaaggaaaa ttaaaaggct gtgagaaacg   3540
tgtttgagaa atgtgtgtat aggatatgca aaaatctgaa ttttttaaat ttatttttta   3600
ttgttatttc ccccaacaca cttttttttt tcccactgta caacatgggg acccagttac   3660
atatacatgt atacataatt tttctcccat tgtcgtgctg tgttttaagt atctagacat   3720
agttttcagt gctacacagc aggatctcat tgtaaatcca ttccatgagc aatagtttgc   3780
atccatggac cccaagctcc cactccctcc ccctctcccc aggcaaccac aagtctattc   3840
```

-continued

| | |
|---|---|
| tccaagtttg ggattttctt ttctgtggaa aggttcattt gtgctgtata ttagatacca | 3900 |
| gatatgagtg atatcatatg gtatttgtct ttctctttct gactgacttc acttagtatg | 3960 |
| agagtctcta gttccatcca tgttgctgca aatggcatta tttcgttctt ttttatggct | 4020 |
| gagtagtatt ctactgtgtt tatgtacatc ttcctaatcc aatcgtctgt caatggacat | 4080 |
| ttgggttttt tccagctctt gactattgtg aatagagcca caatgaacat gcgggtgcat | 4140 |
| gtgtcctttt taaggaaagt tttgtctgga tgtatgccca agagtgggat tgctggatca | 4200 |
| tatggtagtt ctatgtatag atttctaagg tacctncata ctgttctcca tagtgactgt | 4260 |
| accagcttac attcccacca acactgaagg aaggttcnct tttctcccac cagttccagt | 4320 |
| gttgtatttg tgactactga tgccatctta ctgtgggggg tagccacgga gttgattcat | 4380 |
| tcttgaacag gagtagcttt tatagctgtg ccttttttt tctgagacgc atcaggcttg | 4440 |
| ccattactgg tgtgcttgag taaggttatt caataactt | 4479 |

<210> SEQ ID NO 185
<211> LENGTH: 3564
<212> TYPE: DNA
<213> ORGANISM: Sus scrofa

<400> SEQUENCE: 185

| | |
|---|---|
| aaaagaataa aatcttatca tttgcaacca cactgatggc cctagaaggt attcctctaa | 60 |
| gtgaaataaa tcagacaaat acctatgatt ttacttattt gtggaatcta aaaatcacca | 120 |
| aaaaaaagag caaccaggag ttcccatcgt ggtgcagcgg ttaacgaatc cgactaggaa | 180 |
| ccatgaggtt gagggttcgg tccctgccct tgctcagtgg gttaacgatc cggcattgcc | 240 |
| gtgagctgtg gtgtaggttg cagatgcggc tcggatcccg cgttgttgtg gctctggcgt | 300 |
| aggccggcgg ctacagctct gattcgaccc ctagcctggg aacctccgta tgccgcggga | 360 |
| gcggcccaag aaatagcaaa aagccaaaaa aaaaaaaaa aaaaaaaaaa acagaaacag | 420 |
| agtcacagac acagtgaaca acaggtggc tgccagaatg gaggggtgta ggggggatgag | 480 |
| agaaatagat gcgagagatg gtataaacta gttacaaaat aaatgagtcc taggaatgaa | 540 |
| atgtatagtg tggggaatat catcaatagt catgtaacat ctttgaatag tgacagatag | 600 |
| tcttgtttta aggatcattt tgaaatgtat aaaaataatg aatcacaatg ttgtgcacta | 660 |
| ggaactaata cagtgttgtg ggacaaccat acttcaaaaa cagataaatt cacagaaaga | 720 |
| gatcaaattt atggtcacca gagatgtagg taggaggttc acggggtaca agagaggtag | 780 |
| gaggatgagg ggtgcaagaa aggagaagtg aaggaaggga gctgaaaggt acaatcttcc | 840 |
| ggttcttcca gttttaagat aaataagggc taggatatg atatacatta ttataaatat | 900 |
| aattaatgct gctgtatgct gtatatgaaa gttaagagaa taaatcctga gttctcatca | 960 |
| caaggaaaaa atattttttc tttctcttta gtatctgtac gagatgatga atatctgtac | 1020 |
| gagatgtggt aaccattttt ataagtcaaa tcatcatgct atacactcta aacttgtaca | 1080 |
| atgctgtgtc aactaggtct caataaaact ggagggaaaa catcagaaaa aagagaatca | 1140 |
| ctagaaaaat gaaacatata acccaaagac tgtaaaatac taaccacaaa attttaaata | 1200 |
| atacacttat tttatttta ttttttagt tatcaattgg tagggtataa ctgcaactat | 1260 |
| ttttatgatt ataagtacac aatgattgcc tagagtatct tttctgatta aaaataaatt | 1320 |
| attacataga taccccttcat ctaactttta atttattcta attcaattat acagagcaga | 1380 |
| ggttggcaaa cattttctgg agggtaccac agagtctctg tcacagctac tcaattctgc | 1440 |

```
cattgtaaca tgaaagcagc cactgacaat atgaaaacaa atggccatgg ctgtgttcca   1500
ataaacttta tttacaaaaa taggcatcag tagtatttga tctgtgggcc attgtgagcc   1560
aatccttcac atttcagtca aacatttgtg aaatttatca atttccctga aagcatcttc   1620
aaatcactat ctcctgaaac aaactgctcg ttttttttcct tgtgaaattt tttcaaaaaa   1680 tttttttgttt ccagtgaata gtctataact gccgcccttg cttcccaccc tcaatccctc   1740
cttcccagat cctagtcaga aaggagtaga ggaggggaag ctccctcctg gacgtgatgt   1800
gactccaagg ccaaaaactt ttgcacaccg aatgggagga aatctttgca acaaaatga   1860 ctaacaagcg cttcatctcc aaagtatata aacatctcat acagctttat attaaataaa   1920
aatcaaccca accaaaaaat ggttagaaga ccttttttaga catttctcca agaagacat   1980 acagatggcc aaaaaaaaaa aaaaaaaaaa aagcacctga agagatgctc aacatcacta   2040
attagagaaa tgcaatcaaa actgcaatga gatatcacct cacaccagtc agaatggccc   2100
tcattaaaaa gtctacatgg ataagcaatg agatcctgct atacagccct gggaactata   2160
tctagtcact tattatggag catgataatg tgagaaagaa taatgtatac atgtatgtgt   2220
gactgggtca tcttgctata cagtagaaaa ctgacagaac actgtaaacc agctataatg   2280
gaaaaaataa aaatcatcat aaaaaaaaag tctacaaata ggagttccca ttgtggctca   2340
gcagtaatga acccaactaa tacctgtgag gatgcaagtt tgatccctgt cctcgttcag   2400
tgggttacag atccagagtt gccctgagct atggtgcagg ttgcagatgc agctcggatc   2460
tggcacgggc tgtggcctgc agccacagct ccaactcaac tcctagccag caacttcca   2520 tatgccgcag gtgcagcctt aaaaagacca aaaaaaaaaa aaaaaaagg tctacaaaca   2580 ataaatcctg gagaaggggt atggagaaaa gggaaccctc ctacattgct ggtgggaatg   2640
tagattggtg gaaccactat ggaaagcagt gtagaagtac cttaagaaac taaatataaa   2700
actaccatat gatccagcaa tcccactcct gggcatatat ctggagaaaa ctgtaattca   2760
aaaagatata tatacccta tattcaaaga agcactattt acaatagcca agtatgtaag   2820
caacctaaat gcccatcagc agaggaatgg ataaagaaga tatggtacat atatacaatg   2880
gaatactact aagccataaa aaagaatgaa gtaatgccat ttgtaggaac atggatcaac   2940
ctaaagatta tcatactaag tgaaataagt cagacaaata tcatatgaga tcactaagaa   3000
gaagaatcta ataaaaatga cataaaagaa tttattcaaa cagaaacaga ctcaaagatt   3060
ttgaaaccaa ttttacggtt accaagagg aaacactgaa ggggagggat tgatcgggag   3120
gttagaactg gcatatacac acaactatat acaaaatcta ttggtaacaa ggacctacta   3180
tatagctcaa ggaaatctat tcaatattct gggatagcct atatggaaaa gaatctataa   3240
aagaacgaat atatgtatat gtatgcctga gctactttgc tgtacacctg aaattaacat   3300
aatattgtga atcacttata ctccaagaaa atttatttta aaaagcaat gagggagttc   3360 ccatcatggc tcagccatta gtgaacccaa atagcatcca tgaagataca ggtttgatcc   3420
ctggcctcgc tcagtgggtt aaggatctgg cattgccatg agctgtggca caggtcacag   3480
acttggctag gatcctgcgt tgctgtggct ctggcatggc ccggaggcta cacttctgaa   3540
agggcgaatt cgcggccgct aaat                                         3564
```

<210> SEQ ID NO 186
<211> LENGTH: 4331
<212> TYPE: DNA
<213> ORGANISM: Sus scrofa

<400> SEQUENCE: 186

```
gtttaacgaa ttcgcccttc agcttctgct cttgagtttt gttttcttgt tggcctcagc      60
tcacccctca gatctcactc ttggccctgc ttctctggct gtgagcacct gcgtcacact     120
gacccagtgg ctgtgctata gtcagcaaca ctatccaccc gcctggcctt acactcccta     180
agacctgaca ggtgtgtgcc tctggtgaag ggacttgcag actgtcctta ctgtcaggac     240
tacacaggcc tcaccttgcg ctctctctgc cagagagccc tctcttttct ttgcctggct     300
aatccctaca atcttaaaga gacagctaag gtgtcacctc ctacaggaag gcccctgagg     360
tatgtgcttc cctgtcaggc tggctcagct gggaacacca ggaggacaga gactgtcgtt     420
ccaggcttag gcagagtcga aacttagaag atatttgttc actgaaaaga aaatcactaa     480
ctgtgattta tgtggtgctt agcctcacaa cttcctgggc ccaccacaca taatatcttt     540
tgaagaatag cttctttgat tgtatttatg tactgtgggg caggggtggt gttgtgacaa     600
ccatgaaaat gcactgctca aatcctgctg tgcaagagtt ataaatgact gacaacccag     660
ctgctgcccc tctgcatcta ccattacctt tgcctagaga tcattcctcc cctcccccca     720
ccctgggcta ctcccaacca atgcctgagc gcagtgaggg cataatgcag gcacatcccc     780
caaaccatgg gacttctcca atgggttact ggctggagga caccctattg ccctgatggg     840
aaccttctca gaactgggct gaaacctaag actcttctta ccaagtcctc cttccttctt     900
tccctgccct gtgtggtatg aaggctgctc tcaccctctc tggttccctc cctgtggtag     960
ccagtctcca aggaggcgcc cagcgatctc tcccaccttc ccatgcagcc ctttcccaca    1020
ctgtaccagg gtcggtctgt gtgaccagta gactacggca caagtgatag aatgtcactt    1080
ctgagataaa ataagaaaag gcagtgcagc ttctgtcttg gtagatctct ccccctctc     1140
aggtcactca ctacgcggga ggccagctgc cgtgttgttg agatgctcca gcctgtgaag    1200
caaggagctc aagcccccag ccaacagcca cccgagtgag cttggaagcc tttagctgac    1260
tgctgcctgg ttgacagctc acctgcaacc taccaggagg ccctgagcca gaatcaccta    1320
gctaagtctc tccagattct caacccttag aaactgcttg aaataacagg tttgttgttt    1380
taagccacta ggttttggag taatctgttc tgaagtaata gataactaat acacttcttt    1440
tctttcagag gtgtttcctc ctgttcatct tttgtatgtc taatcctatc atagcatcag    1500
cttttcagag gactaaaaca acacaggtgt cgacagatga caagcaacaa tggaagacac    1560
ttctaatcac atatcatttt agttagtcct cacaataacc ctacgagata ctattttttg    1620
tccccatttt atagatgagg aaaccaaggc acagaaatgt taactccttt gaatgtggag    1680
agagaatcta gaaaagtaga aagagctgcg gttaccacag gaggttctag ttccaactca    1740
gctgtataac tctggacaag ccgtttcact cctctggcct cagtttcctc atgtctacca    1800
tgagggtact gaaataacca gtatttgagg tcccttctaa ggaaaacaat aaagtatctc    1860
taggattcta agaattagac taacaaaact aacgtgtact aaaaaaggaa aaaaatctaa    1920
caagtaatag gcaagatcat atactcggac acatccacat gtgtacatgt tcaaatacac    1980
gtggtccaaa tgtcaactgg gatcatcctt tccttggagt ctacagatga ggttggatca    2040
aatcctgtcc cacctctctc gagttcagtg ctcttcccag acaatgagaa ccctctggcg    2100
gtgagggggtt ggcagagacg ctcttgtgcc agcttcccct cctctgaccc cctgctccaa    2160
tttcctgcct ggtggcttct tgggctctac cctgcacaaa gcaggtctgc ttttctctct    2220
gtgccaacca aaatgtgaga cacagccttc ctctccttca tcctggcccc atgcccact     2280
gccctgaggt gccccttga ggcagaacac tgactgtggt ctcgaggtca ctggccactc    2340
```

```
tactcagcaa acagttgggc tgtcacagag gggcaggaag tcttcctgtc acctgcccca  2400
ggcctgctcc cagctcctca cccccagcta cccaggcttc cccttcctgc tgcacagagt  2460
ggccagataa aatacagatg tttggttaag tttgaatttc acatgaacaa caaataatct  2520
ttagtataag tatgtcccaa atactgcatg agatatattt tttaaattag ctgttattca  2580
cgcaaaattc aaattttact agacattcca taatttagt tgtgaaatcc ggcttcctct   2640
cctttctaa ggcttttcct cgccgctccc tctaagacca cccctgacac tccagattct   2700
cttcactgta taaatcagag caattctggt ctccccagac ctcatcccca aactcaccccc 2760
aggtgcatgc ctatgtttct gaatccctca aggacagctg ctcctttaat agctcagtgc  2820
acctgcagtt ttttgttttt ttttttttctt gaattccttc aacttgttct ttttttttt  2880
tttttgctat ttcttgggcc actcccgcag catatgagaa ttcccaggct aggggtcgaa  2940
tcagagctgt agccaccagc ctatgccaga gccacagcaa tgcgggatcc gagccgcatc  3000
tgcaacctac accacagctc acggccacac cagaacatta acccactgag caagggcagg  3060
gaccaaaccc acaacctcat ggttcctagt cggattcgtt aaccactgtg ccacgacagg  3120
aactcctcaa cttgatcttc taaatagcac tttcatcttc tgttgctggt ataggagtca  3180
tcttaaacat aaaaaggctt cccaagctat catcaaggca tagaagagct gtcagatcct  3240
tgacaagcca acaacatgg ataaagaaag aatttgccag caaaagctgg tcaacaagga   3300
cagcaagaaa ggggacccaa gagcctgaac tgggtgggga ggcctgatgg gagggagagg  3360
ctggggacaa gaacacagtt ctctacttcc cagaaaccat ccccagcact agcccagtgt  3420
tagctatctg atggtattca ggagtatggg agaaaataaa tttgggaaat tcttaacat   3480
tatttatttc acagccttga ataggccaat acacactgtg atttccccag agcagggtga  3540
agtctgcagc caaatacaat tggccttaag agtccctgtt tttggaaagt tgttcatgca  3600
agcgtgttcc gcttaacagc ctaacactcc tctctccgtt aattctgatt ctaggctcac  3660
caggcttctt agtttgagtc ttcagacacg cagaagttgt aaaggaaatg ccctgtcatc  3720
agacacgagt actgtaatcc ctggaaaggg acggcccca ctgaagatga gcagactaga   3780
acagggagaa ataaatcaac agacatcggc attctgccac tttgggagtt ctatcttgta  3840
ttttcagtta actaactggc attccggttt agatattagg tgtcctccac tgggtatagt  3900
tagcaggaca catttcccca caggctggag cactgacaag accttactct agctgctgg   3960
gctgagagga tgggaccagc aaaagtgatc agtaggttcc ttgtcacttc ccatggagta  4020
cttttttcaa ccctagaatt atgggcttta ggaaatgtgg gtcttttata aacattaaat  4080
ttgctgaggg ccaaagggg tcatcatgag ttgaccatct tagcaatggc caaaggccag   4140
ctagtggcct gaggtgtatg aggaaggaga gacatgagaa agaggggtag gatgacaagg  4200
aagaggagcg ataagtcagg gaggttcaca atcagacacg gacaggcgat ctagtaggca  4260
cccagccctg cagtgggaga ggagcggtgt ggaaagcagg aagtagaaaa agggcgattc  4320
gtaaactgca g                                                      4331
```

<210> SEQ ID NO 187
<211> LENGTH: 5460
<212> TYPE: DNA
<213> ORGANISM: Sus scrofa
<220> FEATURE:
<221> NAME/KEY: modified_base
<222> LOCATION: (1405)
<223> OTHER INFORMATION: a, c, t, g, unknown or other

<400> SEQUENCE: 187

-continued

| | | | | | |
|---|---|---|---|---|---|
| ccccaatgag | tcgcgttacg | gcgcgttgca | tctttctggt | tatctttggt | tccgcctccg | 60 |
| agcttcccgg | atgcggtgga | tctacatata | tctgatgttc | cacaatctcg | tatctgtgga | 120 |
| ttcaccgtgt | attacatccg | acttttccca | agtttcctag | gtccgcattt | atttgcggcg | 180 |
| aattgacatt | cccactttt | cgggcctccc | tccatatagt | tgtatagtcc | tccccctct | 240 |
| tctgttgcat | tttagggctg | caccccgcag | catataggag | ttcccaggtt | aggggtcata | 300 |
| ttgaagctac | agctgctggg | ttacaccaca | gccacagcaa | tgcaggatcc | gaaccacatc | 360 |
| tgtgacctac | accacagctc | acagcaatgc | tgggtccata | acccactgag | tgaggccagg | 420 |
| gattgaacct | gcatgctcat | gcatactagt | tggattcagt | tctactgcac | cacaatggga | 480 |
| actccctctg | atttcttttt | aaagtaatct | gcattactgt | tgatatctgt | tcttatttcc | 540 |
| ttcagtattt | tcattacctc | cttttgaac | ttgatacctg | ttagactgcc | gaggtctgtt | 600 |
| tccttgtttg | ctccttcagg | ggaatcctgt | tcttttaact | gggaatggtt | cctatgcttc | 660 |
| ttcattttgc | ttatattttt | cttactctgt | gaatttaggg | aaaacaatta | tctactgtag | 720 |
| tcttggaggg | ctatttatat | acaggagtgc | ttctgggtag | cttgtgaggg | cttactattt | 780 |
| ttttgctgtg | agagctgctt | ttggtttgga | tgcttgctgt | ctcagtgtgt | gcagactgtt | 840 |
| atccccttaa | taggggtgt | gcagatgcat | ggcctgcctg | tgctgaggtg | ggtgcagagg | 900 |
| gacgccctgc | atgtggtacc | tgattaccac | gtccttggca | gtggtgggga | tccatgggga | 960 |
| ggtgggagat | gcaggctgtt | cctggttgca | gagccctctg | tggtggcagt | gactctgagg | 1020 |
| gaagtagggc | ccacacccag | agcccttggt | gtggccacag | caggatgtgt | atattcacag | 1080 |
| ggaggtgaga | acaatagttg | gtgtttggtt | gcagagccct | ccacggcagt | gacccctgag | 1140 |
| gtgactgggg | ctacaggtga | tgcctgttct | tgggacccctt | agtggtggca | ggccttagcc | 1200 |
| acctctggaa | tttgagatga | ctgcagtggt | ttgcacctac | tcctatagtc | cacataagag | 1260 |
| gcaccctgct | gcctgagagc | ccgttttgtgt | gtagagaaaa | ttcccatgct | ggtcctgccc | 1320 |
| ctctgcctct | taccctccca | aaaagtggtg | ccttgcttct | ctcatggtcc | caggcttcct | 1380 |
| cacactgtgt | cacaccactc | cctancccac | tcaggctgtt | tccacacagc | taactctagt | 1440 |
| cctctccccg | gatagcccga | gtgtcggtgc | ccagcccctt | ccccaatgtc | tcagggctgt | 1500 |
| agtgtgctag | gtggtggtac | aggtggtctc | tgccatttgc | tctctgcctt | gcctcttca | 1560 |
| gacccgctgc | tgctctttc | tctgaggcgt | gagcctcccc | ctctgtccca | gctgatctcc | 1620 |
| ctatcagtta | ggtggcttcc | caggcccag | atttcttcc | tctttaacag | ctccctctta | 1680 |
| ggagttctgg | tcctgtcctg | attcctttt | tttctctttt | ctctctcttt | tccccctct | 1740 |
| tgttctaccc | agttatttgg | agggtttctt | gccctttgg | cagtctgagg | tcttaggcca | 1800 |
| gttcagtaga | tgttcagtga | aaattgttcc | acatgtagat | ggttattttt | gatgtgtttg | 1860 |
| tggagaaggt | gagttccacg | tcctactcct | ccaccattct | gaccctgctc | cctgtgttta | 1920 |
| tttgtattga | agtatagttg | atttacagtg | tgtattaatt | tctgctgtac | accaaagtga | 1980 |
| tcccattata | tttatgtgta | tacacacaca | tactctttt | aaaatgtcct | tttccattat | 2040 |
| gatttatcat | aggacattga | atatagttct | ctgtgctgta | cagtaggact | tgttgatat | 2100 |
| atgtgtttaa | atgattaatt | gtttattcaa | gagggggatg | ttacagtggt | gatggttcat | 2160 |
| caggaaggat | gcataggggag | gacatcccct | tctgggagag | gatcagggt | ccttggaccc | 2220 |
| aggcatggcc | acccagggcc | caccagctct | ttgggattag | agtggagctg | ccttacttcc | 2280 |
| aggctttaca | ctcttgatca | tgtgataggc | tcccctggga | atgctggtag | aatggagatt | 2340 |

```
ccagttcagg aggtccaggg tagggcccgg cttctacatt tctagcaggt tcccagatgg   2400
tgctaacact gctcttccta cctcatgcca ccctttaagt agcaaggata atgatacctt   2460
aggataaagg gtgaacacac aagatgcagc ctgtggtgag gctagtgatg atgggactag   2520 agatgttttcc ctcagaattt ggtctagtgg tttgtaaagc tccaccttgt ctctccctca   2580
caaagggcag cagcaattct ctctacctgg tgccagagcc atagaggagg aaaccatgca   2640
ttctgggagc catcctggtg gtggcagcaa gaaccaaggg agaaaactcc aaacagacag   2700
cttcagagaa gatagttggg acagtgaaaa tgtccctacc tgaagagtgc atatattttt   2760
gtttagcttt ttatcctgga acagttcatt caccctctta agtagaatga ccctcatat   2820 tccatcccca gctccaacaa ttatcaactc atggcctatc tctttcaacc atctggacta   2880
ttctcaacag gtcacttcat tcagaagtat ttttaaacaa agctccaaaa tataagccct   2940
ctctttaaaa acataggttt tggagttcct gttgtggctc agtggttaac gaatccaact   3000
gggaaccatg aggttgtggg ttcgatccct ggccttgctc agtgggttaa ggatccagcg   3060
ttgccgtgag ctgtggtgta ggttgcagac gtggcttgga tcccacgttg ctgtggctct   3120
ggcataggcc ggcggctgca gctccgattt gaccccttggc ctgggaacct ccatatgccg   3180
cagaagcggc cctagaaaag gcaaaaagac aaaacaaaaa caaaacaaa aacaaaaaa   3240 caaaaaaaaa taggtttttt ttaaacaagg cagacaaatc tttctgaaaa gccatttagc   3300
aatatctata atttgtcaca aaacaaaaat gttaacaaaa taatgtgtta atagagaatt   3360
tttatattta attttgatag aatgaaaaaa tgcagtgttt aagtatcctt tgagaaaatg   3420
aatttaaaga tacagaaaac tgtttgtggg agttcccatt gtggcacagc acgctaatta   3480
tccagcttgt ctctctgagg gtgccggttt gatccctggc ctggcacagt gggttaagga   3540
tccagtgttg ctacatctgt ggctcagatt tgatccctgg cccagaaact tccatatgcc   3600
acgaggttgg ctgaaaaaga ggacggctta tggtatcaaa cgttaagtaa aaaaggcagg   3660
tatataacag tacaagccaa attaccttat ttttataaaa ccacaataaa gacaatatat   3720
atgcacagga aaaaaaaaac tggaagaaaa tacatcaaaa tttcgagtgg ctttctgggt   3780
aattttaatt ttctcatgct tttctgaagg tcttagttca acaatgcaca catatgacaa   3840
tcataaaaac aacattaaaa aatacagtga ggggagttcc catcgtggcg cagtggttaa   3900
cgaatccgac taggaaccat gaggttgcgg gttcggtccc tgcccttgct cagtgggtta   3960
acgatccggc gttgccatga gctgtggtgt aagttgcaga cgcggctcgg atcctgcgtt   4020
gctgtggctc tggcgtaggc cggtggctac agctccgatt cgaccctag cctgggaacc   4080 tccatatgcc acgggagcgg cccaagaaat agcaacaaca acaacaacaa caacaacaac   4140
aacaaaagac aaaaaaaata aaataaaaat aaataaataa aataaaatac agtgagggta   4200
ggggcttccc aaagggcacc tgcatccttc tcagagtttt ccttgagccc ccagcatcct   4260
tccaggtagc ccagagtttc tttccttggt tacaggtagg ctccttcaaa gccccccactt   4320 ggtccctttt cctggcattt aatcctaggt ggccgctgtt tggctccaga tgttgggtaa   4380
actgttcttt ccctcgaagc ttttctggaa tgagccccctt taagcaccca agaacctggg   4440
ccaggacctt ttggacctaa ttgatttatt gggcaatgtc tatacaatct tatccctctg   4500
tccccttatc atgacattta gcccaagaga ctgtaatgtc acatattgcc aataggtggt   4560 gctcccaac acaaaagcac tcttgcccag gcgttatgaa gatagatttc aggcatcgtg   4620
gtttacacaa taatttcttg agatggtgtg cggacatagc attgctatgt aagggcacgg   4680
agacaaattt accacctacc atttcctcta ccgtcaccac caagaatagc cattccaaca   4740
```

```
ccaaaaatgt aggaagacaa aacgatctca gaataaagat agtccttgca attttaagaa    4800
aaacccagtt tcttggttct tatcatttca ccacaagcca gtgaaaattc gaccctagtc    4860
cagcactggc cctggactgg ctttcaggaa cccctgcttt acccaaggat tccaggaatt    4920
agtggtccct ctattcccaa agttcagatt tctgtaaaag ttaatttgct tcagattaag    4980 aacacccttta ttttcccagt gtgcagtaag gcacatatgc tagatcttcc ctccacttgt    5040
aattgcactg gagaggcaag ccactttaa gcacagccat ctctcttcaa aacacaggtc    5100
caaccacatt attcctctgc tgctgcttct ctgccatctc cctttgtcta taaattaggt    5160
aactcagcat ttcacaccag cggcttcatg atccaggcct gcctcactca ccaggatcac    5220
acgaaagctc cctgcaacca ctccagatgc ttaacagaag gactggtgct agccttgcca    5280
actttagtac ccaggacagg ccagtttgtc tccacacctt tacatgtgca gttccccaca    5340
cccgccatgc tttcatactg cctcaccttc ccggcacatg cctgttcttc tccatcaggt    5400
cagcacagtg tcaccttctc tggggagcca cctccaaggg cgaattcgcg gccgctaaat    5460
```

<210> SEQ ID NO 188
<211> LENGTH: 3594
<212> TYPE: DNA
<213> ORGANISM: Sus scrofa

<400> SEQUENCE: 188

```
atcgcccttt tatctgcaac tgttttcata tatagctgaa taatctgtgg cttaagattt      60
attgtttagg agttccgtcc tggctcagtg gttaacgaat ctgactagga accatgaagt     120
tgcaggttgg atccctggcc ttgctcagtg ggttaaggat ccagtgttgc ctgagctgtg     180
gtgtaggtcg aagatgtggc ttggatccca cgttgctgtg gctgtggtgt aggccagcgg     240
ctacatctct gatgagaccc ctagcctggg aacctccata tgctgtggga gtggccctag     300
aaaaggcaaa aagacaaaaa aaaaaaaaag atttattgtt taaatggtgg tgaaagacaa     360
atacagtact gtggctttga tgtaaccaat gctaatctct tctaacaaca agttcaacgg     420
attgagaaac ttgttaagac tgcacctact tctccgcaca aacttgttca tcagcgtgaa     480
ggggctccct ttcttgtcca ctggagcagg agactctaat cacctcagcc cacagttaac     540 aagttctttta aataaaggtt caagagacac cagcccatt tgacaagatt gaaaaccggt     600
actaccaagc caaggttttc tccaacggag agggtattgg gaagcatgcg ctctcccaca     660
tgccgccagt gggcctgtaa ataggcacga cttttccaca aagaaatttg gcaggatgtt     720
ttaatgacac gaagactttt ataacagcgt taaccagtaa ttccacgtac agaaatttat     780
gttgaggaaa tgagctgaaa taatgaaaat aaaacaaaat atcatacaga aagataatca     840
tcaaagcttt atttctaaca gcaacacact ggaaagagcc aaagtgtcca acagtaagtt     900
aattatggga atgtcatttc atgtaaaaag gcgatgtcca atgttccata ggagcatag      960 actttctctc tctctctctg tccctccgtc tctctctgtc tctatctctg tccctctctc    1020
tctctcaccc ccccccccac acacaccaca taccagcagc acatggaaca agcataaaca    1080
aggtttatta aggaaacagt gaaagcaaag aaacagtaaa gtgtgcatga tccctgactc    1140
tcattatctc acagagaggt ggttacgaca ggagccaatg aaggcagtat tctaggagag    1200
agacctgccc caggtgctct ttacagggaa gtggaaatag gaacagtaca agttttcagg    1260
ttgatggaat ggccttgtta ggaaaggggg cctccagagc tcagcaagca gtatttacat    1320
acaacaccca agatcttgct gttgacctta gctggcctaa tccctctgag tcagctcttc    1380
```

```
catgcctgca aaaggaggag gagaaagaac taccagctaa gacagaaaag atctgtttct   1440
tcagattata tgttcaaaga gtaaaagcat gaagaaatgc ttatgatatc aggtaaagtt   1500
ttttaaaagt acacatatta taaactgtgt attttgtaa gcatagaaaa taatcctggg   1560
agttcccgtc gtggctcagt ggttaatgaa tctgattagg aaccatgagg ttgcgggttt   1620
ggtccctggc ctcactcagt gggttaagga tccagcgctg ccctgagcta tcacgtaggt   1680
tgcagaagcg gctcggatcc cgtgttgctg tggctctggc gtaggcttgg cagctacagc   1740
ttcaattaga cccctagcct gggaacctcc atatgcctcg ggagcagccc taaaaaaaag   1800
gcaaaaagaa aaaaaaaaa aaaaaaaga aataatcctg gaaggacacc tgacaatgag   1860
gtcgtctggg ggtgagattt ttatgaagtg agtacttcaa tgatctatat tttgcaattt   1920
ttacatcatg aatatatctt ctttaatcat ttcaatgttg tataactttg tccataagga   1980
ttaagcacag cttttattag acttattctt aggtactcta tattcatcac tgtcacaaac   2040
aatgtcatta aattttttt ttgctggagt tcctgctgtt tcacaatgag atggatggcg   2100
tctctgcagt gccaggacgc agattcgatc cccagccccg gcacagtggg ttaaatgatc   2160
cagcatttcc acagcgacat tgtggctcac aactgtggct tggatctgat ccctggcccg   2220
agtactccat atactgcagg acagccaaaa aagaaaaaaa aaagtttttt tgctgatgta   2280
tagaatgcag ttatttaaaa tttttgacc atatatgtaa aactttgcta ataatttata   2340
aatttagggg gctttctatg taaatggtaa catgatctgc aaataatcac aagcttccat   2400
accgaaaaga acttctctat gctgtcatac ttctgtttag ttttcttatt ttactgcact   2460
gactagacct tcagcctaat gtccagtaga agtaggcatt gctggcattc ggattcattc   2520
tgatgtttaa aggaaatatc gtcaatgttt catctttaat tatgctgttt actatgatgt   2580
ttattgatat tttttaacgg tttaagggag ttatctattt ttagttcttt caattctttc   2640
aggtatatac acaaaagtgg acttgctgca tcatacggta attctatttt taattttttt   2700
ttatggcata tggaagttcc tgggccaggg attgaatcca aggcacagcc aaagacctat   2760
gctacagctg tggcaatact agatcccttta acccactgca ccagggccag gaatccaacc   2820
catgcctctg caatgaccca agccactgca gtcagattct taacccactg cacctcattg   2880
agaactccta ttttaatta tttttatttt ttaattttta actattttaa aagaactgcc   2940
atactcttcc tgccatacgg actataccat tttacattcc caccaagaat gcacaagggt   3000
tccaaactct ccacatcctc acctgcaaac agagaaaatt tactccttcc tttccagttt   3060
ggatgacatt tatttctttt tatagcacaa ttaatttggc tagaactccc agttctatgg   3120
tgaatagaag tgtgaaagcg ggcatccttg cctcgtttct gatcttagag aaaatgtttg   3180
cagtgtctca ccattgagta tatttgctgt aggttgttca tatatgactt tcattatatt   3240
gggtagttcg tttccttcta ctcctagttt gttgaatatt tttatcatga aacagtattg   3300
aattttgtca aatgcttttt ctgcatcaat tgagataatc atgtcattgt tttcccctcg   3360
tcattagtta attggtgtat tactttgatc aggttttgta tgttgaatca tcattgcata   3420
tcaggaatgt ctcatttggt catgctgtat gatcctttta atatgctgat gaatttggct   3480
tcccactatt tgttgagga ttttttcatc attgctcata aggaatattg tcacaaggga   3540
taaaattttt gtttcttata gtgtcttttt ctgggttggg atcaggagaa tcaa           3594
```

<210> SEQ ID NO 189
<211> LENGTH: 4054
<212> TYPE: DNA
<213> ORGANISM: Sus scrofa

<400> SEQUENCE: 189

```
cttgttctttt ttttctgttt tctttctttc tagtcatatg agctgtttgt gtattttggg      60
agattaagct gttgttggtt gcatggtttg caactatttt ctcccattcc ctaggttgtc     120
ttttcattgt tttctttttt tttttaatg gtttcctttg ctgtgcaaaa acttgtaaat     180
ttgtttaggt cccatttatt tatttgtttt tatttccatt gccttgagag actgacctaa     240
gaaaacatct gtaaggttga tgccagagaa tgttttgcct atgttgttgt ctaggagttt     300
tatggtgtct tatgtttaag tctttaagcc attttgaatt tgttttttgtg tgtgctgtga     360
ggatgtgttc tagtttcatt gatttacatg ctgctgtcca gttttccaag tactgcttcc     420
taaagagagt ttttctcatt ttatattctt gccttctttg tcaaagatta attgaccccta    480
ggtgtctggg cttatttctg ggttctctgt tcaattgatc tatatgtctg tttttatacc     540
agtaccatac tgtcttgatt actatagctt gtaatattg tctggagtct gggagagtta     600
tgcctcctgc tttgatttgg ttttttcctt aggcttgctt tggtaattct gggtctttta     660
tgattccata taaaatttcg aattatttga catagttcta tgaaaatatc ataggtaatt     720
tgatagggat cacagtaaat ctttagattt ctttgggtag tatgcccatt ttaataatat     780
taattcttca aatccaggaa catggcgtat ttttccattt ctttgaatcc tcttcaattt     840
ccttgattat tgttttacag ttctcagtgt ataagacttt tacctctttg gtcaggttta     900
ttcctaggta tatttttgag ggtatggttt taaaaggtat tttttatatt ccttttctaa     960
tatttccctg tttgtataca gaaatgcaac caatttctga atgttaattt tgtatcctgc    1020
tactttgctg aattcattga tcaatttgaa tagttttga gtggaatcct tagggttttc    1080
tgtatatact gtcatgtcat ctgtgtagag taacaatttt acctcttctt ttcccacttg    1140
gaaaccttt atttctttg tttgtcttat tgctgtgggt agaacttcca gtgctgtgtt    1200
gaataaaagt ggtgagagtg ggcatccttg tcttgttgca gattttagtg ggaacgcttc    1260
aacttttctt gttaagtctt atattagctg tgagtttgtc ataaatggct tttattatgt    1320
taagatatgt tccctccata cccactttgt ctgattttgg tattaggatg atagtggctt    1380
cataggatgt ctgtgggagt gttaagagtt tttatcataa acggatgttg gattttttt    1440
ttttttttgt cttttttgcct tttttctagg gacgcttctg cggcatatgg aggttcccag    1500
gctagggtc aaattggagc tgtagccact ggcctacatc agagccacag cagtgcagga    1560
tccgagccat gtctgtgacc tacaccacag ctcatggcaa cgctggatcc ttaacccact    1620
gagcaaggcc agggatcgaa cccataacct cacggttcct agtcggattc gttaaccact    1680
gcgccatgat gggaactccg gatgttggat ttttgtcaaa tgccttctct gtatctattg    1740
agatgatcat gtggttttg acttctcttt tgttaatgtg gtgtatgatg ttgactgatt    1800
tgcatatgtt gaaccatcct tgtgaacttg ggatgaattc cactaggttg ggtatatgg    1860
tcttttttgat gtgttttttg attcgttagc taaacttttg ttgagaattt ttgcatctat    1920
gttcatcaaa gatattggcc tgtattttcc ttttggtag taactttgtc tgattttggt    1980
attaggatga tagtggcttc ataggatgtc tgtgggagtg ttccttcttc agtcttttgg    2040
aaaagtttaa gaaagatgga tacgggtatc tttgtatgct tggtagaatt cacctgtgaa    2100
gccatctgat attggacttt tgtttgtagg gagtgttttt atgacatttc atttcattca    2160
tttcattcaa tttcgtttct agtgattggt ctacagatga tctatttctt cttgattcag    2220
ttttgatggg ctgtatgttt ctagaagttg tccatttctt ctaagttgtc acatttgttg    2280
```

```
gcatataatt gttctcttat gggcttttgt atttctgcag tgtcatttct tttttgttt      2340 atttggttct ctctctcttc ttggcgagta tggccagagg ttttcaggt ttttttaccc      2400 tttcaaagaa ccagctcttg gttttattga tttttttttt tttttttttt tttttttttt    2460 ttttttggc tatttcttgg gccgctactg cggcacatgg aggttccag gctaggggtc      2520 caatcggagc tgcagccacc ggcctacgcc agagccacag caacgcggga tccgagccgc    2580
atctgcaacc tacaccacag ctcacggcaa cgccggatca tcaacccact gagcaagggc    2640
agggaccgaa cccgcaacct catggttcct agtcggattc gttaaccact gcaccacaac    2700
gggaactcct gattttttt tctaatgttt tttcaatctc tatttgattg atttcctttc     2760
tgatatttat aatttccttc cttccactga ctttagggtt ttttgttct tcttttcta      2820 attcttttag gtggtgggtt agattgttga ttagaggttt ttcttatttt ttgaggaagg    2880
cctgtatttt atgatatcta ggacctgttt ttatgacatc ccatagatgt tgtatggtta   2940
tgttttcatt atcatttgtc tccagatatt ttgtaatttt ctttttattt ttctctttga    3000
cccattggtt tttttagtag catgttgttt agccttcatg taatcagttt tttctcattt    3060
cttttcctgc agttgattc tcatttcatg ccattgtggt cagagaagct gcttgaaagt    3120
atttctatac tcttaaattt gttgaggtta gttttgggcc ccagtatgta gtcagtccta    3180
gagattgttc cctgtgcact tgaaaagaac gtgtattctg attttttgt atgtaatgtc     3240 ttgaaaatat caattaagtc taactgtttt attgtgtcat ttaggatctc tgttgctttg    3300 ttgatttct gtctggaata tggaagatct gtcttccatt gaagtgagtt gggtgttaaa     3360
gtctcctact attattgtat tccattattt ttatatatat gatttttata tacattattt    3420
atatatatat gatttactga ttttgatttt tttagggctg cacccacagc attcatttta    3480
ttctcatcaa tttctccttt tatgtctatt aatatttctt atatgtattt gggtgcccct    3540
ataatagggg catatatatt gatgagttaa tagcctcttc ttgaattgat ccttttatca    3600
ttaaatagtg tccttctttg tctttcttat ggcttcttaa aacagaagtc cattttgtct    3660
gatatgagta ttgcaactcc tgcttttccta tcatttccat ttgcatgaaa tatcttttcc   3720
atcccctcac ttcagtttat atgtgtcctt tgccctctta taggcagcat atcataggct    3780 ctttttttt taatccagtt ctgcaaatct atgtcttttg attggagcat tcggtccatt     3840
gacatttaag gtaattattg ttaaatatgt atttactgcc ctttaaaacc ctgtttccca    3900
gttgattcta tgtttcttct ttgtttcttt cttttctttt tttggtggga tgatttcctt    3960
ttattttatg cttgtgtcct cttctttta gttttatga atgcattgtt tggttttgat     4020
ttgtaattgc cctcaagggc gaattcgtta aacc                                4054
```

<210> SEQ ID NO 190
<211> LENGTH: 5588
<212> TYPE: DNA
<213> ORGANISM: Sus scrofa
<220> FEATURE:
<221> NAME/KEY: modified_base
<222> LOCATION: (5490)
<223> OTHER INFORMATION: a, c, t, g, unknown or other
<220> FEATURE:
<221> NAME/KEY: modified_base
<222> LOCATION: (5564)
<223> OTHER INFORMATION: a, c, t, g, unknown or other

<400> SEQUENCE: 190

```
actgcagttt acgattcccc tttgctgtga ctgaactcac caggactgga tccatgatac        60
tacactgaga tgtacctgga aggttcccac gtacatcagc agacctaagg ccttacccag       120
```

```
acatggcagt gggaccctgg ctcacatatg cctgggtgta cgtgtaaggg ggtgggggtg    180
tcttccctgt cccaggatgt ccttggactt ccctggcat gtgtgttgtg tttcagtaaa    240
ttgtgacctg atcacccatc ctcacgtact gtgtgcttcc atcctacctt aacatactca    300
gtgttgccca gggacacatt cttatgatgc agggagggat tttgtgcacc ctcactgctg    360
ccttccacct ttatgctcct ctggttcttg gtttggaccc tgattatagc acttagtgtg    420
gctggcctag gagcctgctg aaacatgagc tccttcagag caggaattgc acatgcttat    480
ctcggtatcc cctgaacctc tcagagcatc tggcctgaag taggatcaca gagagtgcct    540
gctgaattga cttgaacttc aaattctcaa cacaaacaat actcaattat tcctcccctg    600
cagctcgaaa gtcatgttat tttaaaaaat taaatgtggc ttattttttc tattgttgta    660
tctaacacaa ctactgttaa tatatatgtt caccctctcc atgtggatga ttctttgtgg    720
attgccacca aaagttacct tacattcaac atttccaaga taaagtatt aatctttctc     780
ctaaacctgc tctgcctgta ccttcctcat cccacttagt gtcagttgca ttcttgagtt    840
gtttaagccc aaatccttag aacaatttct ttctttcttt tcttttcttt ttccccctt    900
tttttttggc tgtcctgtga cagatggtgt tctcaggcca gggaccagat ctgagccaaa    960
gttgtgacct atgccacaga tatggcaacg ctggatcctt taacccacca tgccaggccg   1020
ggaatggaac ctgtgttctg gaactgcaga gaccctttgg attccattgc gccacagtgg   1080
gaactcattt tccttttcaa aaaaatttt taaagttaag catagttgat ctacagtgtt    1140
gtgtcagttt ctgctgtaca gcaaagtggc ccagaactat ttcttattc tctattctt     1200
tcacatttt gtcccgttca cgaagaaatt cagttggctc tgtcatcaaa gtaggcccag    1260
catgtgaccc ctcctcacca tctccacggc tctcacccta gtccaagctg ccatcatctc    1320
tcacctgaat ggctagtatc ctcccagcag gtctctgttt ccaccttacc cctcaacccc   1380
cagtgtagac tcagtacatc agctggaact atcttttat aatgtaaggc agactgtgcc    1440
actcttgctt caaaccctcc catttcatac aggaaaaaag ccatgttctc acaatggcca   1500
gtaaaaccgt acacgatctg cacccctctg ctggcctctt gaacttgctc actgcacctg   1560
agccacactg acttccttgc ttcttgttcc ttgaatgtgt caggccttga atgcatgctt   1620
ctgccttagg acctttgcat gcattgctca gtctacttag aaagcatctc ctccagatat   1680
ccacttggcc aactcctcca ctgctttcag tggatctatg caacacctct cctctgcttt   1740
gatattcttc ataacactga tcacaaccta gcataatata tattttattt atttgtcttg   1800
tatattatgt ttccctcaat tagaatgaac gagtttgcac agtgcagtat ccctagtgtc   1860
taagacagtg cttggcatat gaaaggtgct caggaagtac ttgttaagta aaaagaaaca   1920
aggcaacttg aatattgctc tgaataaggg gaccatatgt attcaattga ccccttcct    1980
ctttcatagt ggggcagaat aagttttata agtaagttg gacaaaaata aatcaaacat    2040
tcatcccggc atatttgctt agcacctaca acggaagaaa gatattttgt gtgccttggg   2100
ggatccaaag atgtctcttc ccacagagag taaagttagt aggggaggc ttctactcgt    2160
gcttagaagc ccagttcatc tagtacctcc ttatggtggc tttctccaaa ttccctaaag   2220
aggtgctagt ttcctaatgt ctttacattt ctgtcttaat acttaacata ctatgtcgtg   2280
atttatttat taaaattttt gggagggtct ttttagggcc acacccatgg catatggagg   2340
ttcccaggct aggggtctaa tcggagctat agctgatggc ctatgccaga gccacagaaa   2400
tgccagaccc aagccttgtc tatgacctac accacagctc atggcaacac cggatcctta   2460
```

```
acccactgag caaggccagg gattgaaccc gcaacctcat ggttcctagt catatttgtt   2520
tctgctgtgc aagacagga actcctattt acatatttgt taaatcatat gtgcttcaag   2580
acaagcacca tgtattattc atctctatag ccacagaacc tagcatagag ggcgctcaaa   2640
tctttgctga atgacttaga taatgggcca cgtgagcaga tgaccatgaa atatggggc    2700 tgggctctaa aaggtaggaa aatgacattc agtatggaag taacagaata taaatttgat   2760
gatattatta agctgcacta taattaggta gaaatagaca gcagtttata taacaccact   2820
gtttataaat ccaatttta aatagttttt cttttctcgt tttgctccta ttcaaagtga    2880
tgcctaataa agtgtcctta catacatata aggcacaca tgttcataca gtgctgatta    2940
ctattattgt tggaagcaaa aatttataaa atatggcatt aggaaggaaa gtgtttaatt   3000
atgcttctgt gtgtgtgtgt gtgtgtgaga gagagagaga gagaaagaga gagagaaggt   3060
gagagagaga gaattactgg agacgaccaa agttagtgga agtaatatta ccaaagcagt   3120
taagagccag aagtgcctgg aaaaaattct ctagttatct cagattccaa ggtgtgtata   3180
tatgaagtaa aaagccacat atttcataaa gacaaagtgg ggtgtggacc taaacaagag   3240
agcctgtcta aggtcacctg taactcagca cagactccaa aggcaaaaat gcaagaccct   3300
gatgaggaca atgtgaggtg gaattttcct gacaaaagac ttcacctgaa gcttctgcca   3360
cagcccgtcc ctccttcttc cttgggaggg agcctggcca ccagtagtg gaaagccggt    3420 gaatggtaac tagccccatt caaatgaggg ggtactttt ttgtatcgat aaataagtgc    3480
attggtgcat catccagtga tccatcatgc atcatcctgg tcactaaaag cttcttttct   3540
caggcccaga ggatgttttt ggagggttcc tttggggcag ggaatgctgg gcaggggaat   3600
ctgtgtctct ggccaagcat ctccccagac agctccttt gtccctggt gcccactgaa     3660 gtgtctcagc tgcttgccac caaccttgca gttagataaa ggatttcat cagctccccg     3720 tctctgccaa gcaaacacat gcctggaacc ccgaagagga gcccttcagt tctttattcc   3780
aggggcataa gtaaaagaat ccaaaccata cagagccagg gagctgatga aaatccttga   3840
tctaactgca ctattcagaa ggcagctttc ctttccagcc agaggaggat gtcaccctca   3900
gacaccgtct tccttcctca tgacacccctc tctctgcaca cccagcacct cagccatttt   3960
gaccaggttg ccagataaga aacaggacac ccagttaaat tagaacaaat agataaacaa   4020
tgaatgcttt ttaaaataca tcaatgtccc atatatttaa tgggacatgc ttatgctaaa   4080
aaattatttg tgcttttatc tgaagttcaa atttaactgg aattcctgta tttttattgc   4140
taaatctgac aactatactt ttttttcttt ttttagggct gcgcctgtgg catattgagg   4200
ttcccaaggt agggatcata gcaacatcgg atccttaacc cactgagtga ggccagggat   4260
agaacttgca tcctcatgga tgctaattgg gtttgttaac tgctgagcca cgatgggaac   4320
tccaatggtg atatgttttt aattttaaat tctatttgtt cattactggt atagaggaat   4380
gtaatttact tttgtaacat taaccttgta tcctacaact tgctatagtt acttaaagat   4440
tccaagagta ttttttaat caattcttac agattttcta cataagtaat catgtcatct    4500
ataaacaagg atggttttat ttcttcttt ccaatctgtg tacttaaata tatatatatt    4560
tttctcattg aactagttag aacttccagt acaatgttga aaagcaatgg taagagggga   4620
cagcattgcc ttactcctga tcttagctga aaagctttga gtttctcacc attgagtatg   4680
atgttagctg taggattttt tgaagattgt atgtgtttta ccaagctaaa gttcccctct   4740
atttctaatc tgctgagagt ttcgatcata aagggggtgtt taattttgtc aaatgctttt   4800
tctgcatcta tggatatgat catgtgattt cctctttagt ctgtggatgt gatagattac   4860
```

```
attagtttat tttaaaatgt tgaaccagga gttcccgtcg tggcgcagtg gttaacgaat    4920
ctgactggga gccatgaggt tgccggttca atccctggcc ttgcttagtg ggttaaggat    4980
ctggcattgc cgtgacctgt ggtgtaggtc gcagacgcag ctcggacccc atgttgctgt    5040
ggctgtggtg taggctggca gcaaaagctt caattggatc cctagcctgg gaacctccat    5100
atgccacggg agcagcccta gaaaatgcaa aagacaaaa aaaataaaat attaaaaaaa    5160
taaataaata aaaaaaataa aatgttgaac cagccctgaa tccctgagat aaatgccact    5220
tggtcatggt gtattattta ttgtttgatt cgatttgcta atattttgtt gaggattttt    5280
gcatctatgt tcatgagaga ttggtgtata gttttacttt cttgtgatgt cttttctag    5340 ttttagtact aggaaaatgc tggtcttaca gactgaggaa gtttccctat atttcagtct    5400
ttagaaagag agttggtaga atttcttcct gaaatatttg gtagaaatca cagtgagccc    5460
atttggatat gtgcttgata attcttggtn aacgaatgct gagattagtg tatgtatttt    5520
acatgggaac ttgatacacc ttggtgcatt tgaggataaa cccnagcttc gtatatattg    5580
gggaaagc                                                             5588
```

<210> SEQ ID NO 191
<211> LENGTH: 2253
<212> TYPE: DNA
<213> ORGANISM: Sus scrofa
<220> FEATURE:
<221> NAME/KEY: modified_base
<222> LOCATION: (1780)
<223> OTHER INFORMATION: a, c, t, g, unknown or other
<220> FEATURE:
<221> NAME/KEY: modified_base
<222> LOCATION: (1782)
<223> OTHER INFORMATION: a, c, t, g, unknown or other
<220> FEATURE:
<221> NAME/KEY: modified_base
<222> LOCATION: (1800)..(1801)
<223> OTHER INFORMATION: a, c, t, g, unknown or other
<220> FEATURE:
<221> NAME/KEY: modified_base
<222> LOCATION: (2217)
<223> OTHER INFORMATION: a, c, t, g, unknown or other
<220> FEATURE:
<221> NAME/KEY: modified_base
<222> LOCATION: (2221)
<223> OTHER INFORMATION: a, c, t, g, unknown or other

<400> SEQUENCE: 191

```
tatactgcag gttcaacgaa tcgcccttct ctggaatatt attcagactt ttaaatatgt      60
gtatgaagca ttttgtaatg aaaagaaatg tttaggttta gagccacctg ataaagtagg     120
aattcaactt tatgagttat tcctggagaa gtggctagaa atttatcaat gtattaagag     180 gggttttta ggagttcccg ttgtggctca gtgggttaag aaccagacac agtgtctgtg      240
aggatgtggg ttcaatccct ggcctcgctc agtgggttaa ggatctggca ttgccatgaa     300
ctgtggttta ggttccaaat ggggttcaga tctggcattg ctgtgttttt ggggtaggcg     360
ggcggttaca gctccgatta gaccctagc ctgggaacct ccatatgctg ggggagcagc      420
ccaagaaatg gcaaaaggcc aaaaaaaaa aaaaaaaaa aaaaaaaaaa aaaaaaaaa        480 aagagccccc tccttgtata agctcccgtg gggaagggac tggtggtttt cctctcttca     540
tgatgctctg cacacagtgg aagcacagga ggacttatct ccagctagga ctctgccggg     600
agaagcaaaa gttaacaggt aataagatct caaagctgga accctgaca tgttgactcc      660 ctcacaattg ctcactgcca tttcaagatg agaaaccaat gctcctgaga cattaaaagc     720
```

```
caggaattta ttgaatgtga gtagcagagc tgaggttcag aggagggctt ctgcttgtaa    780
ccttcagctc ttttagacag agaaagcaag agggacaagg agaggaacac acacagcagc    840
tgtgagcaga gttaaagcat ctgccttctc ctcccaggga cagaacatag actaacagtt    900
agggatgagg agcctctcaa aggtgcgcca ctatgaaccc taggttgtaa tagaactgca    960
ttgatgtggc tgtgttacag gccggcagct gcagctctga tttgacccct agcctgggaa   1020
cttccatatg ctgcaggtgt ggccataaaa agaaaaaaaa atgctgttat gattaaattc   1080
cttgtatata ttttttctaa attttttactt tttatttatt ttattaaaat atggttcatt   1140
tacaatgttt cttcaatttc tgttgcagag tgatgcagtc acacacaatt gcctgtgctg   1200
tacagtagga acccattgcc cctcaattct aaatgttagt ttgtatccac caccccaaa    1260
cttgctgtcc atcccgaatt ttttttttat tgaagtatag ttgatttaca ctgctgtgcc   1320
agtttctgct atacagcaag ttaatccagt taaacacaca cacacacaca cacatatata   1380
ttttcccttt cttgtactat attctatcat agtctgtccc aaagactgga tagttctcta   1440
tgttacacag taggacctca ttgcttatcc attctagatg taatagtttg catctactaa   1500
ctccaaactt cctgtccatg ccactccctc cctcctcccc cttggcaacc acaagtctgt   1560
tttctatttg agtctgtttc tcttttgtag ataggttcat ttgtgccata ttttatttta   1620
ctattttatt ttattatttt attttttgtct ttttagggtt gtacctgcag catatggagg   1680
tttccaggct acgggtagaa ttggagctgt agccaccagc ctacgccaca gccacagcaa   1740
catgggatcg gaggcaagtc tgcaacgtac accatagagn gnagtcatgg agaatctttn   1800
ncactcagag cccgtcctgg accatctctc ctggatccac ctgtcctctt tcctggacca   1860
tctctcctcc tttggcctca caccctcccc tccctgtttt acctccttac catagccccc   1920
tttatcgaac attctaaaga cttgctggaa agggggggaga aatggttttt cctggctgtt   1980
taggccccat ccccagaacc tcctcctgcc aaggccctgt ccccagctca cgtgcacagt   2040
gacgtccatc cccagtcagg gttgtcgggc aggcctcgca gcccttcccg gaaatgcact   2100
tcacattcgg gaagcacggc tcatcacagg ggtccttgga gtggttgcag tagcggccaa   2160
aggtgttccc gtcacacttg cagccggcca tctggaatgg gttgctgatc actacangga   2220
nagatgccca agaatgagtt gctgatcact aaa                                2253
```

<210> SEQ ID NO 192
<211> LENGTH: 7933
<212> TYPE: DNA
<213> ORGANISM: Sus scrofa

<400> SEQUENCE: 192

```
cttgcacaca aaaaagaaa tcgaaaagac ccagccacct gccgtgggga gctcctgttc      60
tggtggagta agatgagtca gcacagatca tctttgtcat gactaagctg tgttgcccct    120
gacggccatc tagacttaca ttcagggacc tcagcctgtt gtcttccctc tgcctgagca    180
gagagatgcc agcctctatg tatcatactg gcaatgcctg ctacctgccc accagctcct    240
ctgggccttg gccagctccc acatgaggct cgttctccag caggtagccc aaagccacac    300
aaacctctgc ccttcacatt ccccctttccc acagaggctc gaaagcctcc tgaggactga    360
taacctgtgc cagtcacctc ctgcacaggt gggagaataa aacagaacca tccacttgga   420
atttacttgc ttctaaacgt agagctctat gccagctatt ttgtgctggt tatctgattc    480
gtctgttttt tttttttttt tttttttttt tttttttttt tttttacggg ccgaaccctc    540
ggcctatgga agttcctaag ctgggggtcg aattggagct atagcttctg acctacgcca    600
```

```
cagccacagc agtgtgggat ccaagcctcc tctgtgacct acaccatagc tcacggcaac    660
gctggatccc tgacccactg agtgaggcca gggatcgaac gcgcatcctc atggatacta    720
gtcggatttg tttctgttgc agcacagcag gaactcctgt ctggtcattt ttttttgaa    780 gctatgattt actaactata caccgggttt ggcattttga cgtattctct ctaatcactg    840
aaacttccta aaagtaggtg ttattattcc tgttttatag ataagaaatt tagacacaga    900
tgttagtttt ttgtacaaat actgtctact gagcaccagt ctgtgcaagg tatgaggcta    960
gaaacagagt tacaggcgat ggggagcgag actgctagtc tctgccctcc tcagtctggt   1020
caagaagcag atattaaaca gaaaaggcaa gcaaataatt ataattgtga taagtgcttt   1080
gaaggaacgt agagagcatt ctagggacta gagcaggagc agttacttga gtggggcagg   1140
ggacatgcag gagctaaggg aggagcagga attagccagg taggggtggg gcaagacagc   1200
tgtgagcaga gcaatggcac atgctaaggc ctggaggtgg ttagaaacct ggcctaatca   1260
aggatctgta ggtgggttcc ccttgtgccc caggggttta atgatctgtg ggtgtctctg   1320
tgcaatctgg gtttggatac ctggcgcagt ggtttaagaa ttagccattg ccgcaggtgt   1380
ggcatagcct gcagctgcga ctcagatttg atccatagcc tgggaacttc catacaccgt   1440
gggtacagct gaaaagaaa agaggtaaaa aagaattta caagaaggcc aaagaaggcc   1500
agagagattg gggccaagcc agacagatga atgtaatgaa gctagaaagc tggggaggag   1560
tcagatcctt cccgttttca aactcttctg gcataagaat atcctggggg agctgatttc   1620
aaggctggct ctggagccca ctctccacca agtctcaccc agagcacctg cactttgact   1680
tatttcccta agttatgctg aggcaggtgg ccagaagagg acacttcaag aagtatagat   1740
gtacatctta tcactcattt gaaggatctg ggacttttcc taaagaggtg aagctattga   1800
gaccaagacc atgtggcagg ctacctggca cagatttgaa cccagtttca tctgattccc   1860
aaaccggggg gacactgtct cttcctaaag ggaaggtggt atcaggtggg tacactgagg   1920
gctggcggaa ggatcctcca gatgagggaa tggtgtcagc cagaatcttt gtggctcaga   1980
agtgggtgag gcaaggcagc cacagagctg ctggcctgag caaagactag atgcaggtct   2040
cctttcccca aaatctcata ggggctttgc atgtttccac cccaagtgct ttttcatctc   2100
agtatcattt tggctttaca aatactgtac cactgtgaag aagagtttat tgggaccatt   2160
ttccatcttt cccaatgaat acactgaagt ttacctagat aaagccactg tgaaagaatt   2220
tcaatctaca agggaacctg aggacatagt gtggaaaatc tcatgtgtat gccctcagga   2280
aaataaaact taaggactga gagactaatt tttcataaat gcctgattaa cagaaaacta   2340
gtaatattgg aattttctta aataacagtg agttaatcag ggattgcttc atatcagcct   2400
tgggcaattc tgcttatggt ttccagagtc atgaagaaga aatgacccag ttatgttggt   2460
cttgcaaaat gaactgcatt gaactttgta tgatgactat tttttttatgt gtacccagga   2520 aattttcaga actgatctct gttttttttt ttttcttagc agactctgaa ttcttccttc   2580
tgtacattcc ctgctcgtaa atacagccta ccccaaaccc ttagccagct tgccagtagc   2640
ttgctgtagt ttgcatatcc tgaattgcac ttcttctgcc attctggaat aaacccatct   2700
ttttgaaaaa tttgagcttg tctcatttta cattttcatt taggtcaata ttccttgggg   2760
tcagagatgg aatccaaagg caatgactgc tgaaggactg tcacccttgg aattcagcca   2820
ggtgcttgaa ctgaacccct tgtactcata atttccatga gttactgatg gcttccagtt   2880
tggtgagtct cccttggtt aaactctctg actttatttg ggatgtattc aaaggctctg   2940
```

```
tccttttttgg caagtgctca tttgttttct tattgggatt atgctagaac tttggtataa    3000
ttcctctgga attcttgaga gcaaaaatga atgaatgaat gaagtaaata atcagtgggc    3060
acatgtcaag caaataaaca ctcctagagc accccccccc ccgcccttgt tatgagagac    3120
tttggtcttg aagcaagatt cccacgagag gataaattgg tcatgacaa gccaggttga    3180 cattaggtca tctgccaacc gcaatatagt ttctgtgcaa caaggacac ctggtcacgg    3240 gtcgaacaac taggacaaag gccctgccag gggggaaaat tttttaaaaa ggaaagaatc    3300
ctatgaaagg cactatgtga aacaaaatac aactcccaac cctgaaacca cctccttgag    3360
gctatttagg aattttcttt tgctctgaag aaaacctctg agatctgtgc ttctagtcat    3420
ctcagtgttc taaaggtggc cctccttcag gaactctggc ttgatttatg ttcaaaaatt    3480
atggtttaga tgcattttcg attaaaggga ccaaccttac taaagataat ttagaacttc    3540
agtggccagc cttagatccc ccccaaactt gttttctat aaatcgaatt ggaagaccaa    3600
ggcaatagaa ctaaacaaac agatgaaata actgttttat ctgataactg gaggcttcta    3660
aaatattcag aattctaaaa ttgcctcttt ataaaatact atttctaagt taacagaagc    3720
acataatcga aagattttt ttctaggttt attttaaat tttttattg agatatagtt    3780 gatgtacaat attatagaag ttactgatgt ataacatagt aattcatgat tttttttttt    3840
tttttgtctt ttctagggcc gctcctgcgg catatggagg ttcccaggct aagggtctaa    3900
tcagagctgt agccaccagc ctacgccaga gccacagcta cacaggatcc aagccgtgtc    3960
tgtgacccac accacagctc atggcaacgc cggatcctta acccactgag caaagccagg    4020
gatcagacct tcaacctcat gtttcctagt cggagttgtt aaccactgag ccatgacggg    4080
aactccagta atttacaatt tttaaaggtt atactctgtt tatagttact gtaagataat    4140
tgactatatt ctctgtgttg tgcagtatat ctttgtagca tatttattt atatgtaata    4200 gttcgtatct actatacaaa ctactcttac ttgcccctac tcctatctct cccctcccc    4260 gcacccctgt aaccattgct ttattctcta tatctgtgag tctgtttcct tttggttata    4320
ttcaggagtt tgttttattt ttcagattcc acatatgagt gatattatac agtatttgtc    4380
tttctctgac ttacttccct tagcatagtt tgttttttgt tgttgttgtt gttttggttt    4440
ttagggccac acctgcagca tatggaggtt cccaggctag aggtctgatc ggagctacag    4500
ttgcctacac cacagccaca ccagatctga gctgtgtctg cgacctacac cacagctcac    4560
agcaacactg gatccttaac ccactgagtg aggcctggga ttgaacctgc aacctcatgg    4620
ttcctagtca gattcatttc ctctgcgcca ctacgggaac tcccttttagc atagattttt    4680 aaaaagcatt tgaggcttct tattcagcag caccagccaa ggtttcccct aatcccattg    4740
ctctacctcc tctatatcca cctttaccct cttctaatct ccttcctata gctgaacgcc    4800
ccttcttttc tagtgctgaa cccttaccaa ctgagcctgt taaaaccctc ctttttattt    4860
ttttaaaaag acatgatgct aaatatataa tttattgtta taaggaaata tatagtacta    4920
atagattata tatttcaata gcataaatga tctctacgtg atatagacgt agagatatag    4980
aaagatattc tatctttctt gatagaagaa acattaaaa ggaaaattag aaggggggtta    5040 ataggatgaa aacaggaaaa tactttttt caaaccattg taaaatataa gaaaataact    5100
gtcttatgta cagccatttt aatgattccc ttgttcattt ttgctgtgaa atgcactgaa    5160
aatctcaaag tgagttatag ttcatgtgtt acaaagatta aaataatgat aaaactagag    5220
aacaaagaaa aaagaggtta ggaagattaa cacaaagtaa acaccaaata aaagtcatta    5280
acattgaaag ggaacatcgc agatactgaa agttattgtt cttaaaatta aatgttttgt    5340
```

```
aaaattttta ttgtagttta taatgttatg tcaattttg ctgtacagca aagtgaccca    5400
gtcatatgtg tgtgtgtata tatatatata taaaatgtat atatatataa tgtgtatata    5460
taatgtatat atatataatg tgtatatata ttatgtgtat atatataatg tgtatatata    5520
tacatttct catattatct tctatcacaa gtgattggat atagttccct gtgctataca    5580
gcagacatca ttgcttatcc attctaaatg taatagtttg catctactaa ccccaaattc    5640
ccagtccatc ccgctccctc ccctccctc ttggcagcca caggtctgct ctccgtgtct    5700
gtgagtctgt ttctgttctg tagataggtt catttgtgcc acatttttaga ttctacatat   5760
aagtgatatc tatgtatggc atttgtcttc ctttttctaa cttacttagt atgagaatct    5820
ctagttgcat ccatgttgct gcaaatggca ttattttgtt cttttttatg gctgagtaat    5880
attccattgt gtatatgtat cacaccttct taatccattc attttttgag ggacatttag    5940
gttgtttcca tatcttggct attgtgaata gttttgttat taacatatgg gttcatgtat    6000
ctttagaatt gtggttttgt ccacatatat gcccaggagt ggaattgctg gatcatacca    6060
tagttttata ctgagttttc tgagaaacct ccacactgtt gtccatagtg gttgtaccag    6120
tttcattccc accaacagcg taagaggatt ttctttctct cacaccctct ccagcatttg    6180
ttattcgtgg acttattaat gatggccatt ctgactgtgt gaggtggcgc ctcatggtag    6240
tttcgatttg cacttctcta ataattagtg atattgagca ttttttcatg tgccttctgg    6300
ccatcagtat gtcttcttg gagaaatgtc tatattcagg ttttctgccc attttcaat    6360
tgggttgttt gcttttttgc tgttgagtaa tatgagttgt ttgtatattt tagagattaa    6420
gcccttgtcc gttgcattgt ttacaactat tttctcccat tctatacgtt gtcttttttt    6480
taaatgtttt cctttgctct gcaaaagctt ttaagtttga ttgggttcca ttggtttatt    6540
tttgttttta tttctattgc cttaggagac tgatctaaaa aaaagcattt gtactgttgt    6600
cagagaatgt tttgcatatg ttctcttcta ggagtttat atcttgtctt atgtttaggt    6660
ctttaagccg ttttgagttt attcttgggg atggtgtgag agtgtggtct agtttcattg    6720
atttacatcc atctgtccag ttttctcagc accactggct gaagagactg tcttttcct    6780
attttatatc cttgcctcct tgttgaaga ttaattgacc ataggtatct gggtttattt    6840
ctgggttctc tattctgttc cattggtctg tattctgtct tgttaccagt accacactgt    6900
cttgattact gtagctttgt aatattgtct gaagtctggg aaagttatgc tttgtttttt    6960
tttccttagg cttgcttggc agttcgaggt cctttatggt tccatataca ttttttggctt   7020
ctttgttcta gttctgtgaa agatatgatg ggtaacttga tagggattgc aataaatctt    7080
tagatttctt taggtagtat ggccatttta atgatgttaa ttcttccaat ctaggagcat    7140
ggaatatctt tccattgctt tgactcctct ttaattttt tgattaatgt tttgtaattc    7200
tcagtgtata agtctttcac ctcctttggtc aggtttattc ctgggtattt aattttttgg   7260
tgtgcaattt taaaggtat tttttatatt ccttttctg atatttcatt ggtagtatgt    7320
cttttattt ttatttttt tttagggcca cacttgcagc atatggagat ttccaggcta    7380
gaggtcaaat cagagttaca gctgctggcc tatgccacag ctacagcaat gcaggatgcg    7440
agcctcaact gcagtctgca ccatagctca tggcaacact agctccttaa cccactgagc    7500
gaggccaggg atcgaacctg caacctcatg gttcctagtt gaattcattt ctgcagcacc    7560
atgacaggta ctccagaagt gcagctgatt tctgaatatt gatcttgttt atcctaccac    7620
tttgctgaaa ttgttgataa gttccagtag tttttgtgtg aagtccttag ggttttcta    7680
```

```
tatgtagtat tgtgttatct gcatatagtg atggttttac tacttctctt ccaatttgga   7740 tacctttat  ttttattttt atttattttt tgtcttttg  ccttttctag tgttgctccc   7800
gtggcatatg gaggttccta gggtagggt  ctaatcggag ctacagccgc cggcctacgc   7860
cagagccaca gcaatgcagg atctgagccg catctgcgac ctacaccaca gctcatgggc   7920 aaaagggcg aat                                                        7933
```

<210> SEQ ID NO 193
<211> LENGTH: 6041
<212> TYPE: DNA
<213> ORGANISM: Sus scrofa

<400> SEQUENCE: 193

```
ttttcagtcc ctgccccaac cccaaaccat ataagggtaa ggggtggaca caacagaaat     60
acagccagag gcccaccctg gtaacaccac catcatgcct tgtgtgtttt aggggagatc    120
aacggaacca gcctccttgg caagaggaat gaccatgtgt cttataactt cacccctgtc    180
ttcctttcac aacttcgggg aaacaagtcc ttgaataaaa gtttgacttc caggtgtaat    240
ggagatgaac aatgcatcta tgatgccctg gccacagaaa atgcaaacct tggagagcac    300
actatgcggc tctttcgaag ctaccagcaa atgaatgcta ccttgagtga gtggcgtgag    360
gctcggggag gtgtgtgcag agttaggggg cagatgagga gcccctcttc caagacaccc    420
cttaagctac acatttttt  cctaaagtta ttcaacattt taatcccctc ctaaacataa    480
cataaatttt tgggggcca  cacccatggc atgtggaagt tcccaagcgg ggaatcgaac    540
ctgccccaca gcagtgaccc aagctgctgc agtgacaatg caggatcctt aacctgttgc    600
accaccaaga gaactcctaa gctacacatt ttttaattta gccgattatt ttgctcatgt    660
tgtccctctg ctcaaatcct cccctgactc cccagctcac tctatcctta tgacaacctt    720
caaatcaaag ccctgtgcac tccagcccca ctgcctctcc acactcttct cctagaactt    780
ctagaacctc gctccctcca ctgcatcccc actgcttctt catgttcttc aaacacgcca    840
ggctcgcccc cgactctgag actctgcaca tgttctgttc tctttgccta gaataccttc    900
ccccagacac ccacaggtcg ctcctcacct ccttcaagtc tctattaaat gccaccctct    960
cagcagtgcc tttcttggct aacttgtcta agtttcacc  ttcactcaca cttcctattt   1020
gccttccctg atttattttt tctctttagc atctataact atctaatgta ttttctaatt   1080
gtagcaggtc tttttattat tgttcattg  ctatgccctt acgacctaga acaatgccag   1140
ccatagagta ggtgctcaat aaatatttgc taagtgacta actgaatgaa tgaatgaaca   1200
acagaatgga ataccaggg  ctccaaatcc agagaccagt ggaaaacttt tactctctca   1260
ttctacttcc tgacaatgta atatccacct agatataacc ctcagtgttt ccagctctcc   1320
tccaaaggta aaattccaca atggcctgaa cagctctgtc ctctgatcac ttcataccat   1380
gccctgcata acttctcac  caggaaagaa cctgaaatga atcttgtttg gggagaaaat   1440
aaagagagag taagatttg  gctgggtggg caatacaaca atgacctgct ctgcatagat   1500
gcaagagcag gtgcatagat tatttcctgc ttctggaggt gggtcccagc cctgggaatg   1560
cctcacacaa gcgagaagac tagagagaga gaaaggaggc ccagaaggca ggaaatatcc   1620
tgccccagac cctgacccct tctttgtgtc tcagatcagt acccgccctc catcaagggt   1680
cctgatgtgg tgaaaaccta tatgggacag gccagccttg ttaattacac cagcagctct   1740
gagaacgtca cattcactct cagacacaac tgcactgact tcaagctctc tggtaagaat   1800
gctcggctgg ggcagttagt ggttgaggtc tgagtcaagc tttgggtaat tttgcgttat   1860
```

-continued

```
tatactctgt gcaacttcat gtcacctttc attggaatat ctaggaccaa cattacccag   1920
gaatgatcca tataaatcaa atagattccc cccagagatt aatagtgatc tggccagcta   1980
gctcgactga ctccaggctg attcaaagat catttcttct cattcttgta atattgcaaa   2040
atcatcttta tgcaatcacc aagttattag aataaatttt tttttgtctt tttgtctttt   2100
taggactgca ctggtggcat atggaggttt ccaggctagg ggtcaaatca gagctgtagc   2160
tgccaaccta caccacagcc acagcaacat gggatcctta acccactgag caaggccagg   2220
gatctaaccc acaacctcat ggttcctagt tggattcgtt tccactgcgc cacaacggga   2280
actcctagaa taaatatagc aattaaaaag tactaattta aaatatttgc acatctatta   2340
aaagaaggat atcatatgga acaagattta aagaaataca ataccttca tttggtaact    2400 ttctcacaat tttgatgttt gtcaaccatg tttacctaac tttgcccctc cttgcctgct   2460
tttctgtact gggcccaagc agtttcactt tccctctcag taatggtgtg gagaccccat   2520
ttcagaacgg gaaccatgat ctgggtcaag agtcaaagca cacaggttac agcttgcctt   2580
ttagggccag ccctaattaa gctggtgact gctcttttgct aagccagagc ccttagggac   2640
cttgctctga gcacctctct gcctctcttt ctctgtgcat aagaagagac agcattgtct   2700
gcaccctgtg ctccatgtgg catgctccct agtgcctaat caatggcatc aggagactca   2760
ctcctccact gggctcctat cctgaagagg gaggtcctgg aagtgactct catctgctcc   2820
cacccatcag ctcttttcaa tccactgttt taaggagact tccctatttt cttgaaaaac   2880
ataagacagg ttgaatcaga agagtcctta ttgatacaca gcagtatttc cctgtagcct   2940
ggggtctggt caaggtcca ggaaatgaga gcaagtgggt gagggatgag gctgctgtga    3000
agctgaggtc agtctggcct gaagtgtagc ctgagtaagt gttgggaaga tcctggcctt   3060
caccctccat ggctcccccc ccccatatc ccatcctagt gcaggtccag gcagggttac    3120
cctttggggg ctttggggag gtgggggggca accaccttca tctcatggag ttctacccta  3180
gaatcactta gttgggctgg tgccacctcc aggttggagc gtgatccaac agaaactaga   3240
aaccagcctt gctcaaggaa atgcctagta agattggagg ggtggtctga caggggtggg   3300
ggacgtccag catcagcact tggggtatta gatgccagga tgtgtcaggc agcagaggag   3360
atgaggctcc cagctctcaa aatgatctgt cttccctggg ggcagagaat gggacgttgc   3420
tatggacacc acagtcactg aaaccatgtc ctctggagat tctggcaaga agtgccaagg   3480
atgacttgtc atctgtactc aagccaagaa tggtggtctg cacttgccaa gcagagagcc   3540
agtgtttata taaccagaac gatcgggtgg gcaattcctc cctggaggtg agtgtgggag   3600
agggtgggag gtcggtctct gtgttgaggg aagggaagtg ggaattgaag ggatgttgtc   3660
attcagcccc tctgtcctaa tgtgtgtgtt gggaggtggg tggagctgtg gtaggtgagt   3720
agggcagata ccaattttgg gccacaaaca taagaaatag gactttcttt agtgcttata   3780
ggtcaactga attttacct cccagctccc atccagccaa gctagcagga aacttccacc     3840
tcagcctttc tttgagttgc tcagtggttt ctagctccat ggttctggaa cgagacaatg    3900
aagtgtgggg tgggaggagg tccatgtggc cctgggggg cctgagtctc catggatcac     3960
agcttcttca tcccatcaga tgtagggaga tgctctgtgg cttctgggcc ttacttggat   4020
acaggaaacc tcctttaaag tggcttaggg tcccatgtgc ctagaagcag tgcacagcca   4080 tttcttggg gcctcatcgt catcttggga agagaggtac aggcccctc tgattttaac     4140 acctgtaaaa tcctattttt cctttttgct ctcttccaac taaacgaagc atctctttgg   4200
```

| | |
|---|---:|
| cagtttagag aaaatccttc tccattcaag tttctagcca agatacttgg cctaagtcca | 4260 |
| tgaatctggc cctatctgcc ttttttttt taatggccat gcccacagtg tatgggtgtg | 4320 |
| accattaaaa aaaaaaaaaa aaaaacactt ctgggccagg gattgaatct gagccacagc | 4380 |
| tccggcaata ccaaatcctt taactcactg tgcctgtctg gagattgaac ccacacctct | 4440 |
| gcagtgaccc aagctgctgc agccagattc ttatctcact gcactacagc aggaactccc | 4500 |
| cctacctgct tcttaaaaaa aaaaaaaaat gttgttgttg tgaaagggga gctggaaaag | 4560 |
| acaggttttg actggcaata ctgcacccca ttcttcaacc ccttacatac acacacaccc | 4620 |
| tccttatgaa acatgaacac agaattctga cttgaaaggg acagaggtgg gggagtccag | 4680 |
| gaggcagaaa aagaaaaaaa aaaatcagaa tggagaaagg agggattaaa atcaatacat | 4740 |
| tattttggat ttcccaagat atcccttctt ggcagtagga agtgttgaag ggctccattt | 4800 |
| cagggagctt tccagagccg tctcagtaga ggagttagag agacccggag cttggtaaag | 4860 |
| tttccgaagg gtttccctcc ctgtgcccctt gctctggtgg ccatgtgctc tttcagaagg | 4920 |
| ttctatcttg gagttcccat tgtggctcag cagaaacgag tctgactagc attcaagagg | 4980 |
| acacagcttc gatccctggc cttgttcaat ggggttaaag atccagcatt gccctgagct | 5040 |
| gtggtgtagg tcgcagctgt agctctgatt ggatccctag cctgggaacc tccatatgtc | 5100 |
| acagatgcag ccctaaaaag acgaaaaaaa aaaagaaaaa gaaagaaaac aaacaaacaa | 5160 |
| acacaagaag aagaaggcgg ctctgtcttc ttcgaagtca gcaagggaag ggagagcagg | 5220 |
| acactacagc ttgtgtggga tacagctctc cagaaagaat agaatatta tttatttcgc | 5280 |
| ccctgcctta ttctagaaag gaattcagtc caggagagaa ggtgtgagag ggaagaggct | 5340 |
| tgaggtccca gggcagggc caggcagagg gctccgggga aatgatggcc cagggaggcc | 5400 |
| acccagcttg gaggatgatc ggcctttggg cagggatgtg gaggcccagg gtctgatcca | 5460 |
| aaaggtgctc agtgatactg acagaagaca aggacctgag tccatgggtt ctcagaccag | 5520 |
| aggagttggt acagctacac ccagaagccc ttgatggttc ggcttcctgg cggcccagtg | 5580 |
| atcagcaacc cattccagat ggccggctgc aagtgtgacg ggaacacctt tggccgctac | 5640 |
| tgcaaccact ccaaggaccc ctgtgatgag ccgtgcttcc cgaatgtgaa gtgcatttcc | 5700 |
| gggaagggct gcgaggcctg cccgacaaca ctgactgggg atggacgtca ctgtgcacgt | 5760 |
| gagctgggga cagggccttg gcaggaggag gttctgggga tggggcctaa acagccaggg | 5820 |
| aaaaccattt ctcccccctt tccagcaagc ctttagaatg ttcgataaag ggggctatgg | 5880 |
| taaggaggta aagaggggag gggagggtat gaggccaaag gaggagagat ggtccaggca | 5940 |
| tgggggaggg gccagagtac agcagtccca aggcaacgat gaagggcgca ttcgcggccg | 6000 |
| ctgcgactag aaggcttgta ggaggctgta ggtcttggcg t | 6041 |

<210> SEQ ID NO 194
<211> LENGTH: 9163
<212> TYPE: DNA
<213> ORGANISM: Sus scrofa

<400> SEQUENCE: 194

| | |
|---|---:|
| ttgtatcaag acaaagatt tcccatatgc tcccatcact atatttttat cctcacaata | 60 |
| atcctgtgag attcagtttt cattcttact ctcctccccc cacccctccc caccagcctt | 120 |
| caaagtcggg agactgaggc ttgtaactgg gattaagtaa cttgtctgta gagcaggatt | 180 |
| ttattccaca catgcctaac tactggaaaa cactgcctcc tgcatgcact catgatctac | 240 |
| cagcactttt gacattaaat ttaatgtagt attcacaacc ctatgaaata ggtatccctg | 300 |

```
gctccatttt acagatgaga aaatgcagcc ttggagctgg gagacttgtc taggtcacaa    360
ggttggcaag cagcagagca aacagcagag aggggacttg aatttggggt ccagagtcca    420
tatgatttcc tctctaccag tttgactgga ggagtaggtc aggagagctg caacattcta    480
gagctgaaag ggaccagggt gggctttgct tgtggtttga aagatgcct ggaaggtaag     540
actgttaggt ggggttttt gagagtccca gagatgaaga ggctatgggt ttgggaggca    600
tgaggaggtt tcatagcaag atgacaacac ggggcaccca agaaaggaag acagtgtgtc    660
agggagctc agtggtcaga tcccacagtt tgggcttcag gctgtgtggg cctcctcctg    720
tggggactga ggaggctcag agaaatattt tgggctttga agtggggaaa agcaagtata    780
ttcctgtaaa agcgtgattt gcatgggcaa gtggactgca ctgaacaggt aatgagagca    840
aatgccacga ctcatcttat ttgcctgtgg gtacccagta ttaaagtagg ttgtgtgggt    900
tgtgtgctct caagtgactc ccaggcagga catggtcagc aagggtgct tcataacccg     960
ctgcgtgctt cgcaacttca cagcttcccc atcctccttt tactctggtc ctcaccacca   1020
tggcaaggcc agtattgtga ccctctttca ctggggagga aatggagcct tggggaggtc   1080
cagtgactgg ccttgctggt aggaagcaga gtcaagattt gaaccagcaa gtcatggaac   1140
tccagagctg gtaggcaaca gacttggagc tggatgccac tctcctgctt tctggccagt   1200
gcttcttcat catccagtgg gagacacagg aggaccaact gagaacctt cttgacaccc    1260
tgggtagagg tgaccaaatg gtcctggccc tcctatgtgt ccttgggtac tttggggtac   1320
tttggggccc ttagatctga agaaagccca tcttaaacca tcagaactct gaaaagaaga   1380
gcttagattc tgttctttc cttccaagag tagggttact agattaaaaa aaaggctatc    1440
catttaaatt tgaatttcag gtaatgtggc tttaaaaata taagtacgcc tcaaatatta   1500
cttgagaaaa acacttacta aaaattatca tttaaacaat cactcaatta ttgccatcat   1560
tatcattatt gtcgttacaa tcatcccttg tttatctgaa attcaaattc aactagtatc   1620
catgaggatg caggttagat ccctggcctc actcggtggg ttgaagatcc agcattgcca   1680
tgagctatgg tgtaagccgc agacatggct tagatccctc gttgctgtgg ctgtggctgt   1740
ggtgtaggct ggcagctgta actctgattt gaaccctagc ccggggttca aatgccgtgg   1800
gtttggcccT aaaagaaca acaacaacaa aaaaaattta actgggcatc ttgtattttt    1860
atttgctaaa tctggcaacc ctcccagggg ggaccttggc ccacttacag agagagctcc   1920
ttcccctggg tagacaggag aggcactctt gtcagttcat aaaagattcc cggggctgta   1980
gcctccccgg acaccaagta cccactggcc cgccactcac acaacccctag agagtcagtc   2040
aagtgagcag aagctagcag agaaatgcta gcagcatctc tctctaaaat gtgtaatttt   2100
gccttacctg gctccctgtt acctgtagaa gatgcctggt acatggtttc tctagttctt   2160
gggttccatc cctcatctca ggcccatgtt caggagaggc ttgagtagag agggaagctt   2220
gcccttttcc tttgctagag ctctggggac tctacccact ccctctctt tggcagcagc    2280
cactatccac actgtttagg aggttccttt ccctacctcc accccctgc ccagctacct    2340
ctaaacataa aaccacagat gtttcttgta tttgaaggat ttctatttcc ctggggaagc   2400
atttgctaga tgagaaaaga attgatagga aagtgataag gattcttttcc aaaacttctg   2460
agcctcgtag tacctgctcc agagttcttg gctcacttgg acttctgcct tctttgctcc   2520
tcctcttct gccttctttg tgcctcctgg atcctggccc cacacattct ctctgatggt    2580
ttcagaccaa taatcagcta gattctgggg cttgcttgcc tcaagtgggc cgtcagagga   2640
```

```
catcagtcag ggtgatccca gttccatggc tgccatgtgg gaccggatct cccgacatta    2700
cctccttctt ccttgcacag agagattaaa aagagggtaa aagctcctca ttcttcctcc    2760
cagagtgccc agggcataaa cacaagagca tgtgttaagt cagtgccctg ggactcatag    2820
ctcatgaagc tggtcttacc caacacaggc cccagcacca atggatcagg ccacgcagat    2880
atgtctgctg tgactccagc ggctgggaca acctcagagg gactcttttg gaccactgac    2940
ctcactgaaa tctctgtgcc aagccatatc cctttggaaa ctcaaaccct gggcacccag    3000
acctctgata gagctttcat cccaggtggc accatttcag aagcagagac ccgggaaacc    3060
aagaccattt ttcctgcagc aaagaccagg gccctcgtga aacaacgcc ttccaagtcc     3120 atggttgtga ccatgcctct ggagacacca gccacccgta gccgcccat gggaagtgaa     3180 atgaccacag ttgagactgt tacaggtaaa gatctcttga aagccgtctt tgacacccttt    3240 tgcactttttg acagctctga agaagcaaag acgatcatgg ttgactactt gacattggtt    3300
tactctgcag aagctaaggc cttgtcctcg gagagcagca cctcctctga caactcagtt    3360
ccagccattg ccccacaagc cctgttaccc aacattactg ctctggctaa agccttggtt    3420
ccctccaaca tcaccatcct caaagtgatc aactgcagtt ttatagaaat agaagcaact    3480
gccaccatcc ctgggacctc agacataaat cacagcccca caggaggaaa ggccctgtct    3540
gctcctgaaa catcagcttt gcctgactcc aatgaagaca catcacactt caccaggacc    3600
acacttcact cagcccctgc tgagatcttg tcaacagcca gtgccacagt atcaaccaca    3660
cctgatagca cactcaccat cagtagcacc actgagactg aaacaacagc agccaaggcc    3720
acccctccca gtggaaagtt gatgacagtc agcactaact tcttggaagg aaactcaacc    3780
ctctctgttg gaacaagcca caccaaggtc tcagaggcag ttacaacatc cacagaagct    3840
tggtcaacag taggcaaagc gacctcccct gctgggttct cggccatggt ctacagcctc    3900
tctgaagtag ccaccatcat gaactccacc ccctcagaga cttctaccac aggcagcaca    3960
ttcagtgggc ctgttcccct tagcaggaac ccgcttcctt ctgcccatct gacgacggcc    4020
agcagtagtc aagtaataaa caccacttta gccaagacca cagcctcagc aaagacctct    4080
aagatggcca gcacagctgc ggggaagccc tcaagagcca cccctaccac tgttccaaga    4140
tggacagatg ttactgcagg taagtggctc cctcttgtgt gatctttggg gatttggagg    4200
ttggagtcta caggatgtct gcatgtttta agagtaggga gaaaagtggg atctggggcc    4260
tactctgagt ccttctctga ggtcacctct ccatgatctt ctagtggttc ttgccagaat    4320
cagtaacaag caagttaagg tagcatatgg aaaaagttca gtgctgggag tatggagaaa    4380
tggtttgaga tcttgtctct gtccttaaca acctgagcga cctgggacag gtccctcacc    4440
ttctctggac ccagtttctc caccagtact gaaggggggtt gcaatgaagt cctttccagc    4500 tctaccettc tatgaagtta actgttatgt aactactgtg tgccggtcaa ggccccacat    4560
tttatttaaa agtcagtcct cctgctctgc aagctcctgt ttttttgttt gtttgttttt    4620
ggttttagtt tttagggctg cacatgtgat atgtggaggt tcccaggcta tgggtcaatt    4680
agagctgtag ctgatggcct ccgccacagc catagccacg ccagatctga actgcatcta    4740
cagctgcgtc tgctacctac accacagctc acggcaacgc cagatcctta actcactgag    4800
cgaggccagg gattgaaccc acaacgtcat ggttcctagt cagattcctt tctgatacac    4860
cacaatggga acacctggaa gctcctgatt tagccagagc cacatagaag acaccattgg    4920
catctggccc aagttgctgc cctctgagca gctgggacgc catgaaagta gagcttgcta    4980 tgtgtgctttt ctggaattag agctacaaat gctgaattaa aacaaataaa taaattgggc    5040
```

```
aaatgtttgg gaatttaaag ctgtatctct gagacaatag acattctcag ggaagaagcc    5100
ccttgtcaga agctgcttga tcagcccagc tcctggccag gctgtagcct ccacctccac    5160
ttgccatccc tctttcctca tgctcattcc tatagttttt tcaacttgcc ctgccttct     5220
gcagaggtga aataaaaata ttcatcataa ccaccttact gagtatcttt tgtattacag    5280
gcagaggtga tataaaaata tttcacaatc agtaagcact ggtactagct gaatattctc    5340
tcggctgcca ggcagtatac catgagcttt gcatgcatta tctcctctaa ctaaaccttc    5400
aaaaccacct tatgaaatgt tgtgttatta ccccacttga caggggagaa aacagatata    5460
aagaaggtta aaaaaaaaag tagcagtgga ttccaaatga aagtctgatt ctgaaactca    5520
cagtctccca ttgagctttc atttcatttt aaaaatctca atttattaat atatcttcct    5580
tatacacata attgatggta tcactttctt gtgaaccctc ttctggacat gaaatatgga    5640
tctggaagca taaaaggaa gatgaaaaat atgacctata tctatatgat atcgatatca    5700
gtatctatct atctatatat atacttttt tttcctaggg ctgcacccga ggcatatgga    5760
ggttcccagg ctaggagtct aatcggagct gtagctgtcg tcctaagcca cagccacagc    5820
aacacaggat ccaagccatt tcttagacct acaccacagc tcatggcaat gccggatcct    5880
taacccaatg agtgagacca gggattgaac cggtactctc atggatacca ctcagattct    5940
taacctgggg agccacaata ggaactccta gataatatct ttcatgcaag gggagtgtgt    6000
gataaacaga tctctgagac aggctttttt ttttttaag caacttatca ggattccatt    6060
ttgttttacc ctaataaatt aaaccagtct tttatggatg acatttaag ttgtttccag     6120
tattttatta tgacaaacag tgctgcagtc aatagtatac ttttcacatc gtgttatttt    6180
ctgtaggata aacttctaga agtgcgcttg ctggatcagt gctaatggta ttctgatagg    6240
aagaaacaac tacacggtgg caggtaaaag caggcaggtt aaggctcaag aaaagacaga    6300
agttgcctac taatcttcta agtggggaag gctggactgg aagacctcca ccaacttaga    6360
gctgggagaa ctggctgagc gcatcccctc agagaggcag cctctctgca acattctcct    6420
gggctggccc ctttcccaac agccccatcc agggcctcca gaccttgagc acattttaga    6480
tccactttcg tttctccttc tcatgttgc tcttttgact tctccaaatg tggacagggc     6540
ctttggccat catttccttc actcttgttg ggaagacact gccatgggcc caattattgg    6600
agagaaggga tcctctttct ctttgcattg agtacatgca agatcctgtg tgaacacaga    6660
cacatttaca cacgagcgtg gccacataca tgcagagtgg ggacagaggc tgggcagcat    6720
tattcacgtc ttgattccca tattttcatc tccctactgt tctcatcttg caggcaggaa    6780
tggaggcttc ctcctcctga ggctgagtgt ggtctcccca gaagacctca ctgaccccac    6840
agtgacagag aggctgatgc agcaggtgag tgggctcttt ttgtgccagg gagcagagaa    6900
gagggagagg ttctcaggga ctctggggaa gatctgcagg atatagaaga acatctgcta    6960
cacttgggag ggtctggtct tatgcagcat taggagtgaa atctaaggat ctgtgcttgg    7020
ctttacttct ttctgttttt cctgagttct gaattcccct tctctgctat ataaaaaaac    7080
tctttcctgg agttcctgtt gtgactcggt gggttaagaa actgactagt atccatgaca    7140
atgcatgttt atgacctggc ctcgctcagc aggttaaggc tctggcgatg ctgtgagctg    7200
cagcgtaggt cacaggtgca gcttggatct ggtgttgctg tggctatggt gtaggccatt    7260
agctgcagct ctgattcgac ccctagtctg ggagctccca tgtgccacag gttcggccct    7320
aaaaaggaaa aatgtctttg ctcactttt tccctcaggc cctaggaaga tcaggccttc     7380
```

```
tggttcctgg gtgaaggcca atgatattaa tgggcagata ggcaggactt ttggttgcaa    7440
gtggcagcaa cctaactcat tgtagcttac acagaaaagg taagacattg cctgagaaac    7500
ctagaagtgg ctctctagct tcagttatgg ctggatacag aagctcaaac agggtcacca    7560
ggattttctc tttctccccc tcttagctct gctcccttca ttcctcagag tctcttcata    7620
tgtaaggaag ggtggctgaa acagcccctag attcacaagg tacttccttc tcccaagatc    7680
tgcatatggt actagggaaa gactgatctc attgacctga aagggccacc tcgactgaca    7740
gcctgacatg aatcacacag actgggaagg agagacccca aaggaaatag ggatactaga    7800
cagaaccgcc cccccccacc accactgatg tatgtgctag atgggaatca agcttatatt    7860
tgtaggagtt tctgtcatgg ctcagtggtt aacgaatccg actaggaacc atgaagttgc    7920
gggttcgatc cctggccttg ctcagtgggt ttaaggatcc agtgttgcct tgagctgtga    7980
tataggttgc agaagcagct aggatcccat gtggctgtgg ctgtggctgt ggctgtggcg    8040
gtggcgtagg ccggcgacta cagctccaat tagaccccta gcctgggaac ctccacatgc    8100
agtaggagcg gcactaggaa aggcaaaaag acacacacac acacacacac acacacacac    8160
acacacacac acaagattat atttgtaaat aagttgggga aattctccta aaacaccaga    8220
tcactggaca aagtttccag tgcagaatt ctggggtgag ggttttgggg aatggtatga    8280
gtccttggaa gattagaatg aattagctca gcctagctct gtgtccagat cttgctgcca    8340
ggggctgctg gaagaggaa tacctgaaat ttctcttagt ggaaggagag cctatcagga    8400
ctcacataat gaggtattcc cggaacatgg catgggtttt tgaagtggga cagctaaata    8460
aagacaaatt cctgttgcac gtgataatcc aagaggcaag tgtgaatcct ggttgaagag    8520
ggaagccagg gccatgccag atatgagccc ccaaactgga aactatttca ggggtcagag    8580
agaagccagg gagataagag cagatcagag gtacaggaac cagaccatgc aggtgctggt    8640
ctcagttctt gttgggagct ggcccctggc atagagctca gggctcagac gaacaacaag    8700 cttttggagcc aggtggatct gcatgtgaat cccagtccct aactgcatga cctttggtaa    8760
gttactctgt gttacttttc ttccttgtaa aagaaggcag atactacttg ctctaaggtt    8820
actgtggggt ttaaatggca tgaaggacta agcccatggc tagcctggaa gaggcacagg    8880
aagtgttgct ggcctcctcc cctgctgtcc cttctggtcc ttgacctgtg gtgagttcag    8940
gggccacatg ggctggaagt gccacctgct cctttgccg accagttcca ccgtgaactg    9000
caggtgctta cgcctcccat ccaagtctcc ctgctgcgcg tcaggagggg ctgaagaaca    9060
tcagctgcga ccaggcacag ccgtgtgcag aagggggcat cgctgcctgt gacctgaacc    9120
tcaccaggac tggaaaccag gggcgaattc gcggccgcta aat    9163
```

<210> SEQ ID NO 195
<211> LENGTH: 819
<212> TYPE: DNA
<213> ORGANISM: Sus scrofa

<400> SEQUENCE: 195

```
agcgtgtgga gttgatcaga gctacagccg acttcgatga attcgtcggc gcgaattcgc      60
ccttaacata taatagacac taactttatt tctctgggag aagcatatat tcatggctgg     120
ggcagcaact ttggcgacaa agactggtgg gaaaacatgt aacaggacag gggaaaagct     180
gggtcaagat gaagcactgt tgtgcctctg gggcacctgc ccccttggtc tccttccaac     240
cctgggcgcc tggggccctg atccctgcca gagaatgatc tggcgccctt cctctgttac     300
ctgagccacc tcaagcgatc tgcacgtaca agatcctaag accaggcata gcagatcccg     360
```

```
tacatgtacc aagttaggcc cacagacacc tgctggtaga ctaccctct gcctgccatg      420 gctaccgtca agaggcccga ggccccgcac gggcactggc ccctataatg atgtagtgac      480
gacgcagtct cctggcggcg gtgcagtcac gcgttcagca ccccccgcgc tagcgtcgag      540
tccagcacac acgagccctg ccaggcgtag cgccagcagc gacctcgtct ctcgtcaccg      600
acgtctccac acgagcagaa cacgaccaga ccgcccagcg cccgagggcg tagccgagtg      660
ccagtctcgt agcgctgcag tcgtcgggga ggtgttgaca ccgacgacca gactcgcacg      720
tcgcgtgcaa ctccccgata cacctaatgc tccacgtaca cgcgaagttg tccacatagt      780
agccatggat gaacatgcag gagtcaatcg agtcggccc                            819

<210> SEQ ID NO 196
<211> LENGTH: 715
<212> TYPE: DNA
<213> ORGANISM: Sus scrofa
<220> FEATURE:
<221> NAME/KEY: modified_base
<222> LOCATION: (11)
<223> OTHER INFORMATION: a, c, t, g, unknown or other
<220> FEATURE:
<221> NAME/KEY: modified_base
<222> LOCATION: (13)
<223> OTHER INFORMATION: a, c, t, g, unknown or other
<220> FEATURE:
<221> NAME/KEY: modified_base
<222> LOCATION: (113)..(114)
<223> OTHER INFORMATION: a, c, t, g, unknown or other

<400> SEQUENCE: 196
cctactgcag ntnacgaatc gccttattct acccaggaac catgcctata tcctcctccc      60
tggaggggaa ctctggggtt attctctcca gggcaggtcc actgctcttt atnnttggca     120
tgaattactc tgcacaaggg cataaaagtc acttctgcca tccagacacc tgtagcatgg     180
agggccaggg tggcctgggc tggctgagtg ttacccaccc tcataacctc tgactaggac     240
ccttctcttc cctatcctgc ttctggatac aggccctgat actctgatgt gccacatgac     300
atgttccaat ctctgcctgc catccacttc ccctcacttc ctgaacgatt ctggattcca     360
ctcacacagt cccaggccac ctgaaaaaag aactccacct gtactcactg acccacctga     420
ctgccaacaa aaaggaggaa cagagacgcc ggcttgctaa catcacacag accaagatgc     480
gcatctaaag caagcagaca agaaaccact aaagcccag cacattcctt tcatagcgac      540
tgaaaaacgc cgatccacca cacgaatcac acaacacact actaaaccca accatacaga     600
aaacgacatc tcgcgcacaa catacccaaa aaaccaacta atcctaccaa ctacacagac     660
acaatcacaa ccacctacac aaaaacccaa cgaaaaaaca caaacacaac aaaaa          715

<210> SEQ ID NO 197
<211> LENGTH: 706
<212> TYPE: DNA
<213> ORGANISM: Sus scrofa
<220> FEATURE:
<221> NAME/KEY: modified_base
<222> LOCATION: (16)
<223> OTHER INFORMATION: a, c, t, g, unknown or other
<220> FEATURE:
<221> NAME/KEY: modified_base
<222> LOCATION: (22)
<223> OTHER INFORMATION: a, c, t, g, unknown or other

<400> SEQUENCE: 197
cacagcaggt tacgantcgc cnttacaaat gtggtatatg catacattgg aatattactc      60
```

```
                                     -continued agcctttaaa aggatggaaa ttctgatata tgctgcaaca tgagtgaacc ttgaaaacat      120
tatgctaagt gaaatatcca ctcacaaaaa gacaaatatt atatgattac acttacacga      180
ggtaccaaga atagtcaagt tcatagagaa aaagtagagc agtggttacc agggactagg      240
ggtggggaag taataggaag ttactgttta ataagtatag ggtttcaata tggaatgatg      300
aaaaagtcct ggagatgggg agtggatatg gctgcacagc aatgtgaatt acctcatacc      360
aatgaaatgt acacttaaaa ttgttaaaac cgctacatgt tatgaatact tttataatac      420
ataaaaacat tgcatgtcga actaaccaaa attcattccc accccgcct caaattcgca       480 acgggcccg taccccctcg tcatcataaa aagcgaatca aaagcagcgc acaaaagtcc       540
tggctatctt ctcgcccacc ccaaagagga agccacgcaa cactggcaca acttacaccc     600
cacaccccga agtcccctcc cactccacac acccacgaca cacacctcct tccaacctcc     660
caacccataa cacgtcccca atctccgcgg gccatacccca gcaccc                   706
```